US012753143B2

(12) United States Patent
Zhang et al.

(10) Patent No.: US 12,753,143 B2

(45) Date of Patent: Oct. 6, 2026

(54) ESTER COMPOUND AND PREPARATION METHOD THEREFOR AND USES THEREOF

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Yao Zhang, Beijing (CN); Kun Yu, Beijing (CN); Ruiyun Mao, Beijing (CN); Qinghua Duan, Beijing (CN); Yong Li, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 1089 days.

(21) Appl. No.: 17/755,075

(22) PCT Filed: Oct. 23, 2020

(86) PCT No.: PCT/CN2020/123197

§ 371 (c)(1),
(2) Date: Apr. 20, 2022

(87) PCT Pub. No.: WO2021/078249

PCT Pub. Date: Apr. 29, 2021

(65) Prior Publication Data

US 2023/0012456 A1 Jan. 12, 2023

(30) Foreign Application Priority Data

Oct. 24, 2019 (CN) ........................ 201911017549.0
Oct. 24, 2019 (CN) ........................ 201911017553.7
Oct. 24, 2019 (CN) ........................ 201911017564.5
Oct. 24, 2019 (CN) ........................ 201911017595.0
Oct. 24, 2019 (CN) ........................ 201911018285.0
Oct. 24, 2019 (CN) ........................ 201911018298.8

(51) Int. Cl.
*C07C 69/708* (2006.01)
*C10M 105/42* (2006.01)

(52) U.S. Cl.
CPC ......... *C07C 69/708* (2013.01); *C10M 105/42* (2013.01); *C10M 2207/30* (2013.01)

(58) Field of Classification Search
USPC .......................................................... 560/186
See application file for complete search history.

(56) References Cited

U.S. PATENT DOCUMENTS

| | | | |
|---|---|---|---|
| 5,282,990 A | 2/1994 | Yoneto et al. |
| 6,051,539 A | 4/2000 | Kodali et al. |
| 6,365,774 B1 | 4/2002 | O'Lenick, Jr. |
| 2008/0167445 A1 | 7/2008 | Podella et al. |
| 2017/0137739 A1 | 5/2017 | Narine et al. |
| 2017/0357191 A1 | 12/2017 | Sasaki et al. |

FOREIGN PATENT DOCUMENTS

| | | |
|---|---|---|
| CN | 1332785 A | 1/2002 |
| CN | 1524935 A | 9/2004 |
| CN | 101583590 A | 11/2009 |
| CN | 102947428 A | 2/2013 |
| CN | 105863598 A | 8/2016 |
| CN | 107312516 A | 11/2017 |
| EP | 2444388 A1 | 4/2012 |
| JP | H1036870 A | 2/1998 |
| JP | 2007152568 A | 6/2007 |
| JP | 2017173695 A | 9/2017 |
| KR | 101816283 B1 | 1/2018 |
| WO | 2010123492 A1 | 10/2010 |
| WO | 2019118860 A1 | 6/2019 |

OTHER PUBLICATIONS

Al-Wahaibi Yahya et al.; "Injection of biosurfactant and chemical surfactant following hot water injection to enhance heavy oil recovery"; Petroleum Science, China University of Petroleum (Beijing), Heidelberg, vol. 13, No. 1; Dec. 10, 2015; ISSN.: 1672-5107; pp. 100-109.
Amely Taufer et al., "Fatty Ester-Based Hydroxy Carbamates—Synthesis and Investigation as Lubricant Additives", «Eur. J. Lipid Sci. Technol; vol. 120, Dec. 31, 2018; ISSN:1438-7697, pp. 2-4.
Yeoh, F. H et al., "One-pot synthesis of palm oil-based polyester polyol for production of biodegradable and biocompatible polyurethane", Journal of Applied Polymer Science, vol. 135, No. 44, Dec. 31, 2018; ISSN:0021-8995, pp. 2-9.
Brajendra K. Sharma et al., "Ester hydroxy derivatives of methyl oleate: Tribological, oxidation and low temperature properties", Bioresource Technology, vol. 99, Jan. 31, 2008, pp. 7334.
Tirthankar Jana et al., "Effect of branching in hyperbranched alkyd on the performance of alkyd polyurethane coating", J. Appl. Polym. Sci., vol. 135, No. 9, Dec. 31, 2018, ISSN:0021-8995 , pp. 3 Figure 1.

(Continued)

*Primary Examiner* — Ana Z Muresan
(74) *Attorney, Agent, or Firm* — NKL Law; Allen Xue

(57) ABSTRACT

An ester compound which can be used as the additive of the lubricating oil or the base oil of the lubricating oil, and a process for preparing the same and use thereof are provided. The ester has excellent viscosity-temperature properties and low-temperature properties and can be used as the base oil of the lubricating oil. In addition, the ester compound has excellent viscosity-temperature properties and low-temperature properties as the viscosity index improver, can significantly reduce the wear scar diameter of the base oil as the anti-wear agent, can significantly reduce the friction coefficient of the base oil as the friction modifier, and exhibits excellent anti-wear and anti-friction properties.

13 Claims, No Drawings

(56) References Cited

OTHER PUBLICATIONS

Latchmi Raghunanan et al., "Engineering Green Lubricants IV: Influence of Structure on the Thermal Behavior of Linear and Branched Aliphatic Fatty Acid-Derived Diesters", ACS Sustainable Chemistry & Engineering, vol. 4, No. 9, Jul. 15, 2016, ISSN:2168-0485, pp. 4869.

Rogers E. Harry-O'Kuru et al., "Lubricity characteristics of seed oils modified by acylation", RSC Green Chemistry Series, vol. 29, Dec. 31, 2015, ISSN:1757-7039, pp. 251-258.

ESTER COMPOUND AND PREPARATION METHOD THEREFOR AND USES THEREOF

TECHNICAL FIELD

The present invention relates to an ester compound, a process for preparing the same and use thereof, in particular to an ester compound that can be used as the additive of the lubricating oil or the base oil of the lubricating oil, and a process for preparing the same and use thereof.

BACKGROUND TECHNOLOGY

Lubricating oil is an indispensable part of mechanical operation and plays the role of reducing friction and wear, protecting machinery, cooling, cleaning, sealing, and prolonging service life. However, due to the serious harm to the natural environment caused by such factors as leakage, overflow, evaporation, or improper treatment of lubricating oil, therefore higher requirements have been placed on the environmental friendliness of lubricating oils. In the prior art, most of base oils and additives that constitute lubricating oils come from petroleum raw materials, and it is difficult to regenerate under the specific time conditions in nature at this stage. At the same time, most of the components of base oils and additives are isoalkanes, naphthenic hydrocarbons, aromatics, and trace metal substances, which leads to poor biodegradability.

Environmentally friendly lubricating oils refer to lubricating oils with excellent biodegradability, reproducibility, and non-toxicity or low toxicity. The degradation rate of Environmentally friendly lubricating oils is typically more than two times higher than that of petroleum base oils. Vegetable oil has the advantages of good lubricating performance, wide source of raw materials, low production cost, and good biodegradability (the biodegradation rate can reach 70%-100%). It is suitable for both boundary lubrication and hydrodynamic lubrication and can be applied in most lubrication conditions. Compared with mineral oil, vegetable oil has better lubricating performance and viscosity-temperature performance, and vegetable oil has a smaller viscosity change in a wide temperature range, which can produce a better friction reduction. Vegetable oil can also have a reduction of 5%-15% in mechanical energy loss, compared with mineral oil. Vegetable oil also has a higher flash point and a lower evaporation loss, which can significantly reduce the escape of organic gases under high-temperature conditions, making it safer to use in open environments. However, the unsaturated double bonds in the vegetable oil molecule are easily oxidized, which leads to the problems such as the increase in oil viscosity, and the formation of acid corrosion.

To this end, many base oils and additives with ester structures have been developed in the prior art.

U.S. Pat. No. 6,051,539 reported that the purpose of improving the antioxidation and low-temperature properties of vegetable oil was achieved by changing the fatty side-chain structure in the triglyceride structure of vegetable oil, including the reactions in two steps: (1) the esterification reaction of isomeric fatty acid (such as 2-ethylhexanoic acid) and methanol or branched polyol to produce a branched fatty acid methyl esters or a polyol ester, and (2) the transesterification reaction of the branched fatty acid methyl ester or the polyol ester with triglyceride under the action of a catalyst to produce a triglyceride partially substituted with a branched-chain fatty acid and a polyol ester partially substituted with a long-chain fatty acid.

However, for environmentally friendly ester base oils and additives, there is a lot of room for improvement in terms of oxidation stability and viscosity stability. Moreover, with the development of environmentally friendly lubricating oils, higher requirements have been placed on the performance of ester base oils and additives.

In addition, the reduction of friction wear is an important means to improve the fuel economy and prolong the equipment life. Studies have shown that low molecule weight alkanes with lower polar alkane and naphthene structures can only physically adsorb on the metal surface with relatively low adsorption energy, so it is difficult for them to play a good lubricating effect. Sulfur, nitrogen, or oxygen-containing compounds and aromatic hydrocarbon substances with higher polarity can adsorb on the metal surface more stably and therefore have a good lubrication effect. However, with the increasingly stringent environmental protection requirements, the removal of sulfur, nitrogen, and aromatic hydrocarbon substances through deep processing and refining processes such as hydrorefining and hydrocracking has become an inevitable trend in the development of oil refining, the lubricating property of oil products decreases synchronously, and the abrasion of engine components is aggravated.

Therefore, the introduction of an appropriate amount of the lubrication performance improver to improve the lubricating performance of oil products has become an effective means to solve the above contradiction. Many ester-structured additives have been developed in the prior art. CN1524935A reports an application method of using modified oil as an anti-wear agent for low-sulfur diesel, comprising: adding 10-2000 ppm of modified oil to the low-sulfur diesel, and the modified oil is obtained by reacting natural oil and alcohol or amine in a molar ratio of 1:0.1-5 at a temperature of 50-200° C. for 1-20 hours. The natural oil can be vegetable oil or animal oil. The alcohol is selected from one or more of $C_1$-$C_{10}$ aliphatic alcohols, $C_2$-$C_{18}$ polyols, and alcohol amines. The amine is selected from one or more of $C_1$-$C_{10}$ aliphatic amines, polyene polyamines with 2-7 nitrogen atoms, $C_5$-$C_6$ cycloalkylamines, and heterocyclic amines. The addition of the modified oil at 10-2000 ppm to diesel with a sulfur content of less than 500 ppm can improve the lubricity of the low-sulfur diesel.

U.S. Pat. No. 5,282,990 reports a method for improving the fuel economy of lubricating oils for internal combustion engines comprising adding an amine/amide and ester/alcohol mixed friction improver to the lubricating oil, for example, by reacting carboxylic acids such as oleic acid or isostearic acid with amines such as diethylenetriamine or tetraethylenepentamine, and glycerol monooleate or glycerol monoricinoleate.

Although the existing ester structure additives can improve the lubricating performance of oil products, there is a lot of room for improvement. In view of this, there is still a need for friction property improvers with better performance in the prior art.

SUMMARY OF THE INVENTION

Based on the above-mentioned technical problems existing in environment-friendly base oils and environment-friendly lubricating oil additives, and in order to further improve the friction performance of lubricating oils, the inventors of the present invention conducted deep research and found that ester compounds with excellent antioxidation properties can be obtained with the specific ester compounds of the present invention, and the ester compounds of the present invention have excellent viscosity-temperature properties and low-temperature properties and can be used as the base oil of the lubricating oil. In addition, the ester compounds of the present invention, have excellent viscosity-temperature properties and low-temperature properties as the viscosity index improver, can significantly reduce the wear scar diameter of the base oil as the anti-wear agent, can significantly reduce the friction coefficient of the base oil as the friction modifier, and exhibits excellent anti-wear and anti-friction properties. Thus, the present invention has been completed.

Specifically, the present invention provides the following technical solutions.

An ester compound, which has a structure as shown in formula (I):

(I)

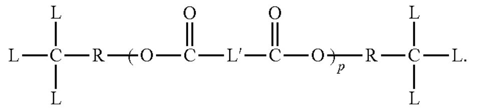

An ester compound, which has a structure as shown in the following formula (VI), (VI)

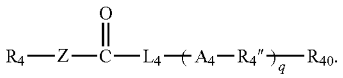

An ester compound, which has a structure as shown in the following formula (X), (X)

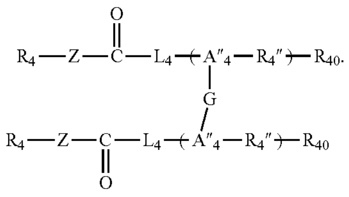

The present invention further provides a preparation process for an ester compound, comprising the following steps:

Step (1): a step of reacting a compound represented by formula (α) and a compound represented by formula (β), (α)

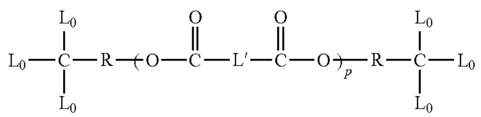

(β)

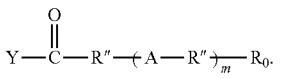

A process for preparing an ester compound, comprising:

(1) epoxidizing at least one olefinic bond in a compound represented by formula (XII), and (2) reacting the product of step (1) with a compound represented by formula (XIII);

(XII)

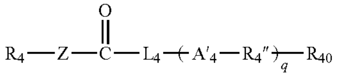

(XIII)

$HG_1—R_1—(G_2)n.$

A process for preparing an ester compound, comprising the following steps:

(1) epoxidizing at least one olefinic bond in a compound represented by formula (XIV), (1') reacting $R'_{4a}$—OH with the product of step (1), (2) reacting the product of step (1') with a compound represented by formula (XV);

(XIV)

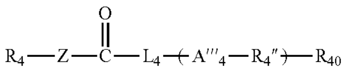

(XV)

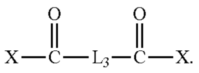

In addition, the present invention also provides the use of the above ester compound of the present invention and the ester compound produced by the above process for preparing the ester compound as lubricating base oil or lubricating oil additive, preferably the lubricating oil additive is a viscosity index improver, an anti-wear agent and/or an anti-friction agent, or a friction property improver.

The present invention also provides a lubricating oil composition comprising the above ester compound of the present invention or the ester compound produced by the above process for preparing the ester compound and a lubrication base oil.

Technical Effect

By such a specific ester compound of the present invention, an ester compound having excellent antioxidation properties can be obtained.

These ester compounds have excellent viscosity-temperature properties and low-temperature properties and are suitable for use as the base oil of the lubricating oil. In addition, the ester compounds of the present invention, have excellent viscosity-temperature properties and low-temperature properties as the viscosity index improver, can significantly reduce the wear scar diameter of the base oil as the anti-wear agent, can significantly reduce the friction coefficient of the base oil as the friction modifier, and exhibits excellent anti-wear and anti-friction properties.

Therefore, the ester compounds of the present invention exhibit excellent low-temperature properties when used as the base oil of the lubricating oil. In addition, when the ester compounds of the present invention are used as the additive of the lubricating oil, various excellent properties can be imparted to the lubricating oil.

DETAILED DESCRIPTION

Reference will now be made in detail to the present embodiments of the present invention, but it should be understood that the scope of the invention is not limited by the embodiments, but is defined by the appended claims.

All publications, patent applications, patents, and other references mentioned in this specification are herein incorporated by reference in their entirety. Unless defined otherwise, all technical and scientific terms used herein have the same meanings as commonly understood by those skilled in the art to which this invention belongs. In case of conflict, the present specification, including definitions, will control.

When the specification derives a material, a substance, a process, a step, a device, an element, and the like with the expression such as "known to those skilled in the art", "prior art", or the analogous term, it is intended that the subject matter so derived encompasses those having been conventionally used in the art at the time of filing this application, but also includes those which may not be so commonly used at present, but will become known in the art as being suitable for a similar purpose.

In the context of this specification, except for what is explicitly stated, any item or matter not mentioned is directly applicable to those known in the art without any changes. Moreover, any of the embodiments described herein can be freely combined with one or more other embodiments described herein, and the resulting technical solutions or technical ideas are regarded as part of the original disclosure or the original record of the present invention, and should not be regarded as new content that has not been disclosed or anticipated in this specification unless those skilled in the art believe that the combination is obviously unreasonable.

In the context of the present specification, the term "single bond" is sometimes used in the definition of a group. The so-called "single bond" means that the group does not exist. For example, assuming the structural formula $-CH_2$-A-$CH_3$, where the A group is defined to be selected from single bond and methyl. In view of this, if A is a single bond, it means that the A group does not exist, and the structural formula is correspondingly simplified to $-CH_2-CH_3$.

In the context of the present specification, the number of a certain group is 0, indicating that this group moiety does not exist, and at this time, the groups attached to both ends of this group moiety are bonded to each other. In addition, in case a group is located at the end, if the number of the group is 0, it means that other groups connected to this group are not substituted by this group. For example, assuming the structural formula $-CH_2-(A)_n-CH_3$, if n is 0, the structural formula is $-CH_2-CH_3$. Assuming the structural formula $-CH_2-(A)_n$, if n is 0, it means that the H in $-CH_2-H$ is not substituted by A, and the structural formula is $-CH_3$.

In the context of the present specification, the expression "number+valence+group" or similar terms refers to a group obtained by removing an amount represented by the number of hydrogen atoms from a basic structure (chain, ring, or combination thereof and the like) to which the group corresponds, and preferably refers to a group obtained by removing an amount represented by the number of hydrogen atoms attached to the carbon atoms contained in the structure (preferably saturated carbon atoms and/or different carbon atoms). For example, "trivalent linear or branched alkyl" refers to a group obtained by removing 3 hydrogen atoms from a linear or branched alkane (i.e., the basic chain to which the linear or branched alkyl corresponds), and "divalent linear or branched heteroalkyl" refers to a group obtained by removing 2 hydrogen atoms from a linear or branched heteroalkane (preferably from the carbon atoms contained in the heteroalkane, or further from different carbon atoms). For example, the divalent propyl can be

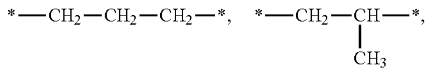

the trivalent propyl can be

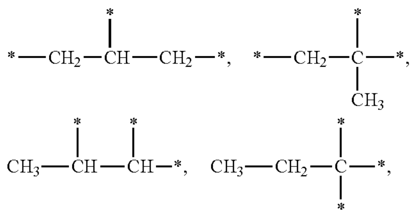

the tetravalent propyl can be

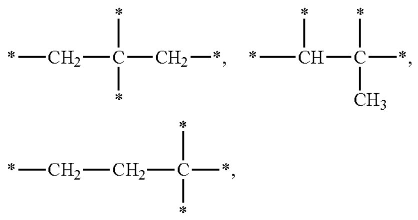

where * represents an attachment end in this group that can be bonded to the other group.

In the context of the present invention, the expression "halogen" refers to fluorine, chlorine, bromine, or iodine.

In the context of the present invention, the term "hydrocarbyl/hydrocarbon group" has the meaning conventionally known in the art, comprising linear or branched alkyl, linear or branched alkenyl, linear or branched alkynyl, cycloalkyl, cycloalkenyl, cycloalkynyl, aryl or a group formed by a combination thereof, preferably linear or branched alkyl, linear or branched alkenyl, cycloalkyl, cycloalkenyl, aryl or a group formed by a combination thereof. In the present invention, the hydrocarbon group may be monovalent, bivalent, trivalent, tetravalent, etc. as required, and the number of hydrogen atoms that can be substituted on the hydrocarbon group is taken as the upper limit thereof. The hydrocarbyl described in the present invention includes $C_{1-17}$ hydrocarbyl and $C_{1-10}$ hydrocarbyl but is not limited thereto. The hydrocarbylene group described in the present invention includes a $C_{2-100}$ hydrocarbylene, a $C_{1-30}$ hydrocarbylene, a $C_{1-20}$ hydrocarbylene, and a $C_{1-10}$ hydrocarbylene, but is not limited thereto.

In the context of the present invention, the linear or branched alkylene represents a group obtained by removing two hydrogen atoms from a linear or branched alkane without violating the valence, and preferably a group obtained by removing each one hydrogen atom attached to two different carbon atoms, and more preferably a group obtained by removing each one hydrogen atom attached to two terminal carbon atoms of an alkane. The alkylene described in the present invention includes $C_{1-50}$alkylene, $C_{2-50}$alkylene, $C_{1-20}$alkylene, $C_{2-20}$alkylene, $C_{1-16}$alkylene, $C_{1-12}$alkylene, $C_{2-16}$alkylene, $C_{1-10}$alkylene, $C_{2-10}$alkylene, $C_{1-8}$alkylene, $C_{1-8}$alkylene, $C_{1-3}$alkylene, but not limited thereto. As specific examples of the alkylene group of the present invention, methylene, ethylene, propylene, butylene, etc. can be mentioned; but it is not limited thereto. In the context of the present invention, the linear or branched alkyl means a group obtained by removing one hydrogen atom from a linear or branched alkane without violating the valence. The alkyl described in the present invention includes $C_{1-10}$ alkyl, $C_{1-6}$ alkyl, $C_{1-8}$ alkyl, $C_{1-15}$ alkyl, $C_{1-11}$ alkyl, $C_{1-10}$ alkyl, $C_{1-3}$ alkyl, but is not limited thereto. As specific examples of the alkyl of the present invention, methyl, ethyl, propyl, butyl, pentyl, hexyl, heptyl, octyl, nonyl, decyl, undecyl, dodecyl, hexadecyl, octadecyl, eicosyl, docosyl, isomers of these groups, and the like can be enumerated; but the alkyl is not limited to these.

In the context of the present specification, the aryl means a group obtained by removing one hydrogen atom from one ring-forming carbon atom of the aromatic hydrocarbon. The aryl described in the present invention includes $C_{6-15}$ aryl and $C_{6-10}$ aryl. Phenyl, a biphenyl group, naphthyl, fluorenyl, phenanthryl, anthracenyl, and the like can be enumerated as the aryl group, but the aryl group is not limited to these.

In the context of the present specification, the arylene group means a group obtained by removing one hydrogen atom from each of two ring-forming carbon atoms of the aromatic hydrocarbon. The arylene group described in the present invention includes $C_{6-20}$ arylene and $C_{6-10}$ arylene. A phenylene group, a biphenylene group, a naphthylene group, a phenanthrylene group, an anthracenylene group, and the like can be enumerated as the arylene group, but the arylene group is not limited to these.

In the context of the present specification, the alkylaryl group means a group obtained by removing one hydrogen atom from an arylalkane, which may be a group obtained by removing one hydrogen atom from the aryl moiety of an arylalkane or may also be a group obtained by removing one hydrogen atom from the alkyl moiety of an arylalkane. Preferred is a group obtained by removing one hydrogen atom from the alkyl moiety of an arylalkane. The alkylaryl group described in the present invention includes $C_{7-15}$ alkylaryl and $C_{7-12}$ alkylaryl. A benzyl group, a phenylethyl group, a phenylpropyl group, a dimethylphenyl group, a naphthalenylmethyl group, a naphthalenylethyl group, and the like can be enumerated as the alkylaryl group, but the alkylaryl group is not limited to these.

In the context of the present specification, the alkylarylene group represents a group obtained by further removing one hydrogen atom from any one of the carbon atoms of the above alkylaryl without violating the valence. Here, the two bonding bonds of the alkylarylene group may be located in the alkyl moiety, or in the aryl moiety, or one in the alkyl moiety and one in the aryl moiety. The alkylarylene group described in the present invention includes $C_{7-15}$ alkylarylene and $C_{7-12}$ alkylarylene. Phenylmethylene, phenylethylene, phenylpropylene, and the like can be enumerated as the alkylarylene group, but the alkylarylene group is not limited to these.

In the context of the present specification, the cycloalkyl group means a group obtained by removing one hydrogen atom from one ring-forming carbon atom of a cycloalkane. The cycloalkyl group described in the present invention includes $C_{3-10}$ cycloalkyl and $C_{3-6}$ cycloalkyl. Cyclopropyl, cyclobutyl, cyclopentyl, cyclohexyl, cycloheptyl, cyclooctyl, cycloheptyl, and cyclooctyl can be enumerated as the cycloalkyl group, but the cycloalkyl group is not limited to these.

In the context of the present specification, the cycloalkylene group represents a group obtained by further removing one hydrogen atom from any one of the carbon atoms of the above cycloalkyl without violating the valence. The cycloalkylene group described in the present invention includes $C_{3-20}$ cycloalkylene and $C_{5-10}$ cycloalkylene. For the cycloalkylene group, cyclopentanediyl, cyclohexanediyl, cycloheptanediyl, and cyclooctanediyl may be enumerated, but the cycloalkylene group is not limited to these.

In the present invention, the substituents that optionally substitute are selected from halogen atoms, hydroxyl, amino, $C_{1-6}$ linear or branched alkyl, $C_{6-10}$ aryl, and $C_{3-10}$ cycloalkyl. The number of substituents that "optionally substitute" can be 0, or 1, 2, 3, 4, 5, 6, 7, or 8, subject to the upper limit of the number of the substituted groups that can be substituted.

In the present invention, each integer can be arbitrarily selected within a predetermined range, for example, 0, 1, 2, 3, 4, 5, 6, 7, 8, or 9.

First Invention

The first invention of the present invention provides an ester compound, which has a structure as shown in formula (I):

(I)

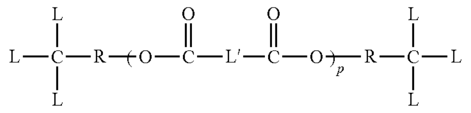

wherein, the L' groups, identical to or different from each other, are each independently selected from a $C_{1-16}$ linear or branched alkylene (preferably a $C_{2-10}$ linear or branched alkylene); the R groups, identical to or different from each other, are each independently selected from a single bond, a $C_{1-50}$ linear or branched alkylene (preferably a $C_{1-20}$ linear or branched alkylene, more preferably a $C_{1-6}$ linear or branched alkylene);

p is an integral number of 0-10 (preferably an integral number of 0-5, more preferably 0, 1, 2, or 3);

the L groups, identical to or different from each other, are each independently selected from a hydrogen atom, an optionally substituted $C_{1-10}$ linear or branched alkyl, a group represented by formula (II), a group represented by formula (III) (preferably selected from an optionally substituted $C_{1-6}$ linear or branched alkyl, a group represented by formula (II), a group represented by formula (III)), wherein at least two L groups are selected from a group represented by formula (III),

—R'—OH, (II)

(III)

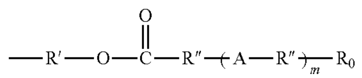

in the formula (II) and the formula (III), the R' group is selected from a single bond, a $C_{1-10}$ linear or branched alkylene (preferably a single bond, a $C_{1-6}$ linear or branched alkylene), and the carbon atoms bonded to L are at most directly bonded to one oxygen atom, the R'' groups, identical to or different from each other, are each independently selected from a single bond, a $C_{1-10}$ hydrocarbylene (preferably a $C_{1-10}$ linear or branched alkylene, more preferably a $C_{1-8}$ linear or branched alkylene, more preferably a $C_{1-6}$ linear or branched alkylene); the $R_0$ group is selected from H, an optionally substituted $C_{1-10}$ hydrocarbyl (preferably an optionally substituted $C_{1-10}$ linear or branched alkyl, more preferably an optionally substituted $C_{1-6}$ linear or branched alkyl); m is an integral number of 1-10 (preferably an integral number of 1-6, more preferably an integral number of 1-5); m A groups, identical to or different from each other, are each independently selected from a group represented by formula (III-A), —C═C—, methylene and ethylene, and at least one A group is selected from a group represented by formula (III-A);

(III-A)

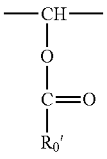

the $R_0'$ groups, at each occurrence, are each independently selected from an optionally substituted $C_{1-17}$ hydrocarbyl (preferably an optionally substituted $C_{1-15}$ linear or branched alkyl, more preferably an optionally substituted $C_{1-11}$ linear or branched alkyl), said substituents that optionally substitute are selected from halogen atoms, hydroxy, amino, $C_{1-6}$ linear or branched alkyl, $C_{6-10}$ aryl, $C_{3-10}$ cycloalkyl.

In one embodiment of the present invention, in the above formula (I), p is 1.

In one embodiment of the present invention, in the above formula (I), when p is not 0, the L groups, identical to or different from each other, are each independently selected from a group represented by formula (III).

In one embodiment of the present invention, in the above formula (I), when none of three L groups connected to one terminal carbon atom is a group represented by formula (III) or formula (II), three L groups connected to the other terminal carbon atom are each independently selected from a group represented by formula (III).

In one embodiment of the present invention, in the above formula (I), of three L groups connected to each terminal carbon atom, if two L groups are not a group represented by formula (III), the remaining one L group is each independently selected from a group represented by formula (III).

In one embodiment of the present invention, in the above formula (I), in case p is not 0, of three L groups connected to each terminal carbon atom, at least one L group is selected from an optionally substituted $C_{1-6}$ linear or branched alkyl.

In one embodiment of the present invention, in the above formula (I), in case p is not 0, of three L groups connected to each terminal carbon atom, there is at least one L group, which is selected from an optionally substituted $C_{1-6}$ linear or branched alkyl, and other L groups, which, identical to or different from each other, are each independently selected from a group represented by formula (III).

In one embodiment of the present invention, the ester compound represented by formula (I) has a structure as shown in the following formula (TV), (IV)

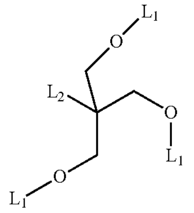

wherein, each $L_1$ group is a hydrogen atom or a group represented by the following formula (III-1)

(III-1)

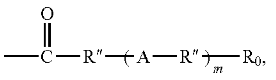

and, at least two $L_1$ groups are a group represented by formula (III-1);

$L_2$ is an optionally substituted $C_{1-10}$ linear or branched alkyl or a group represented by (III-1);

Preferably, $L_1$ is a group represented by formula (III-1), m is 1, 2, or 3, the R" groups, identical to or different from each other, are each independently selected from a single bond, preferably a $C_{1-10}$ linear or branched alkylene, more preferably a $C_{1-8}$ linear or branched alkylene, the $R_0$ group is an optionally substituted $C_{1-10}$ linear or branched alkyl, the A group is selected from a group represented by formula (III-A), the $R^{0'}$ group is independently selected from an optionally substituted $C_{1-11}$ linear or branched alkyl.

In one embodiment of the present invention, the ester compound represented by formula (I) has a structure as shown in the following formula (V), $$L_1\text{-O-L''-O-}L_1 \quad (V)$$

wherein, $L_1$ is a group represented by the following formula (III-1)

(III-1)

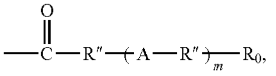

The L" group is a $C_{2-100}$ hydrocarbylene (preferably a $C_{2-50}$ linear or branched alkylene, more preferably a $C_{2-20}$ linear or branched alkylene), Preferably, the L" group is a $C_{2-20}$ linear or branched alkylene, m is 1, 2, or 3, the R" groups, identical to or different from each other, are each independently selected from a single bond, preferably a $C_{1-10}$ linear or branched alkylene, more preferably a $C_{1-8}$ linear or branched alkylene, the $R_0$ group is an optionally substituted $C_{1-10}$ linear or branched alkyl, the A group is selected from a group represented by formula (III-A), the $R_0$' group is independently selected from an optionally substituted $C_{1-11}$ linear or branched alkyl.

In one embodiment of the present invention, the ester compound represented by formula (I) has a structure as shown in the following formula (I-1), (I-1)

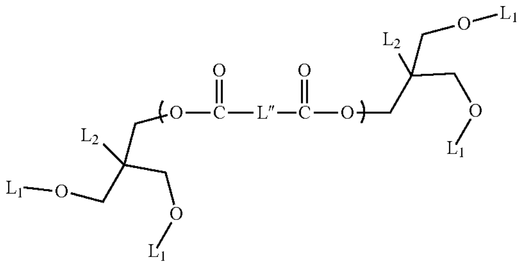

wherein, the L" group is a $C_{2-100}$ hydrocarbylene (preferably a $C_{2-50}$ linear or branched alkylene, more preferably a $C_{2-20}$ linear or branched alkylene), $L_1$ is a hydrogen atom or a group represented by the following formula (III-1)

(III-1)

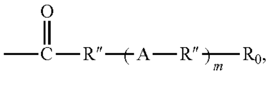

and, at least two $L_1$ groups are a group represented by formula (III-1);

$L_2$ is an optionally substituted $C_{1-10}$ linear or branched alkyl or a group represented by (III-1);

Preferably, the L" group is a $C_{2-20}$ linear or branched alkylene, $L_1$ is a group represented by formula (III-1), m is 1, 2, or 3, the R" groups, identical to or different from each other, are each independently selected from a single bond, preferably a $C_{1-10}$ linear or branched alkylene, more preferably a $C_{1-8}$ linear or branched alkylene, the $R_0$ group is an optionally substituted $C_{1-10}$ linear or branched alkyl, the A group is selected from a group represented by formula (III-A), the $R_0$' group is independently selected from an optionally substituted $C_{1-11}$ linear or branched alkyl.

In one embodiment of the present invention, the ester compound is selected from one or more of the following compounds:

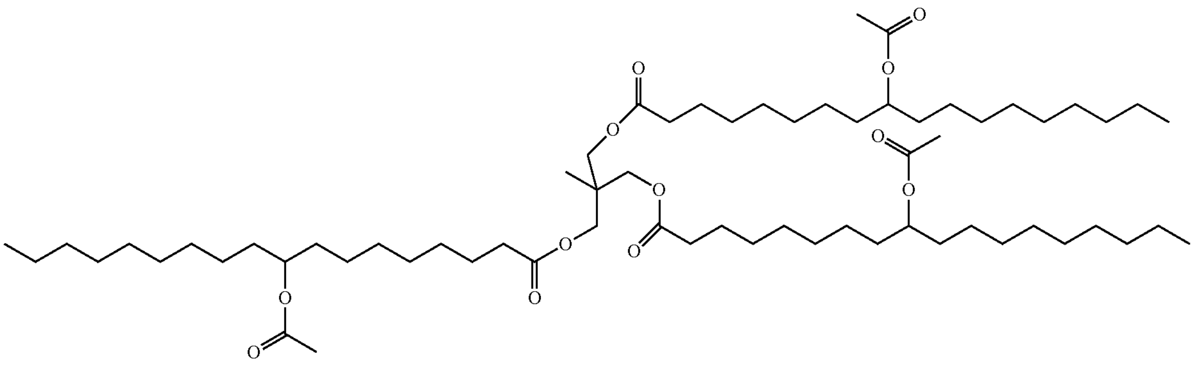

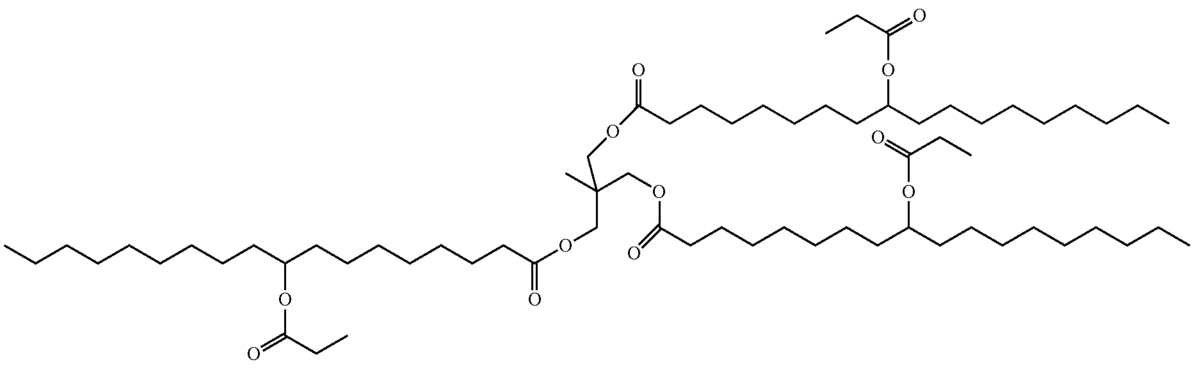

-continued
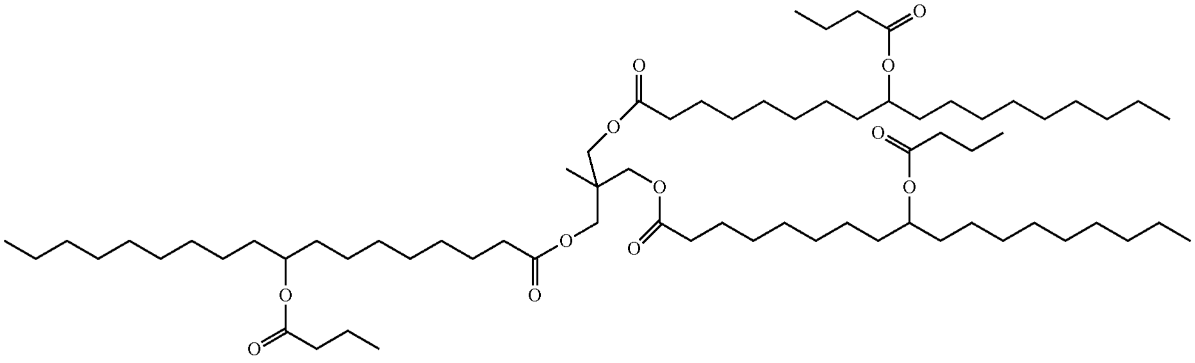
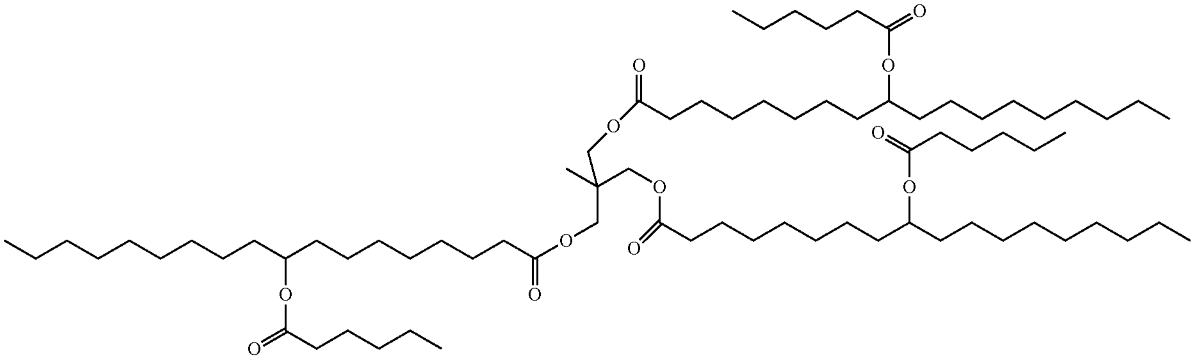
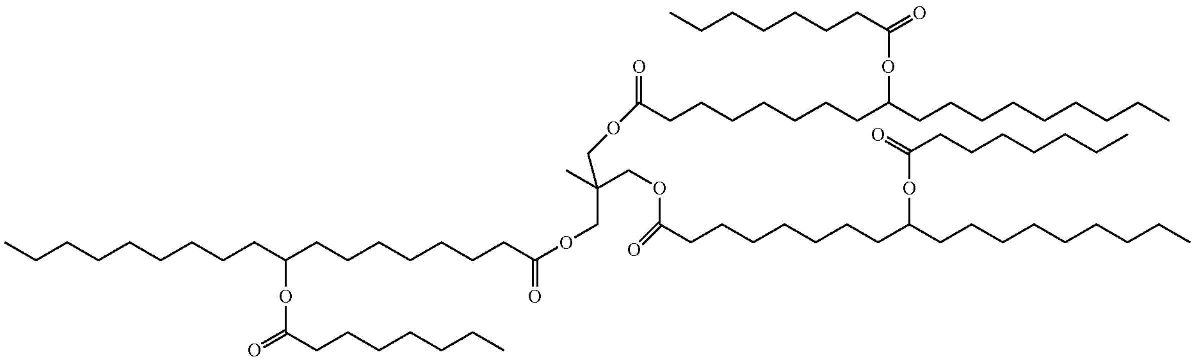
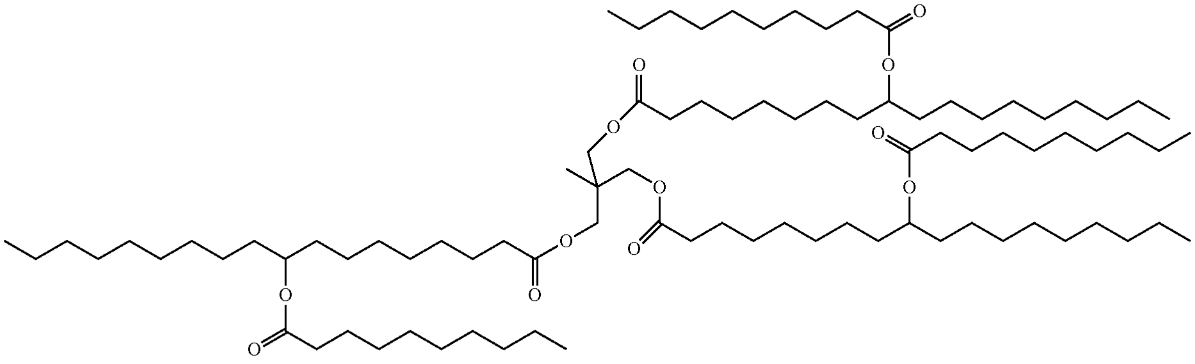

-continued
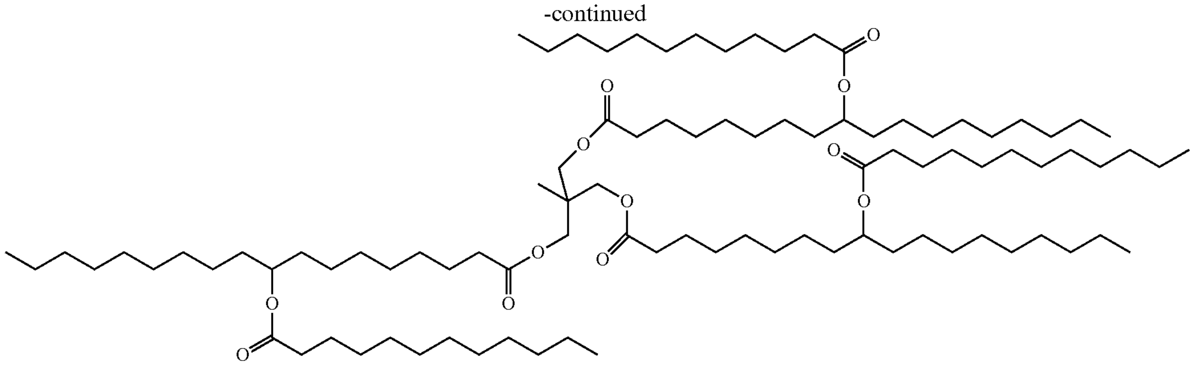
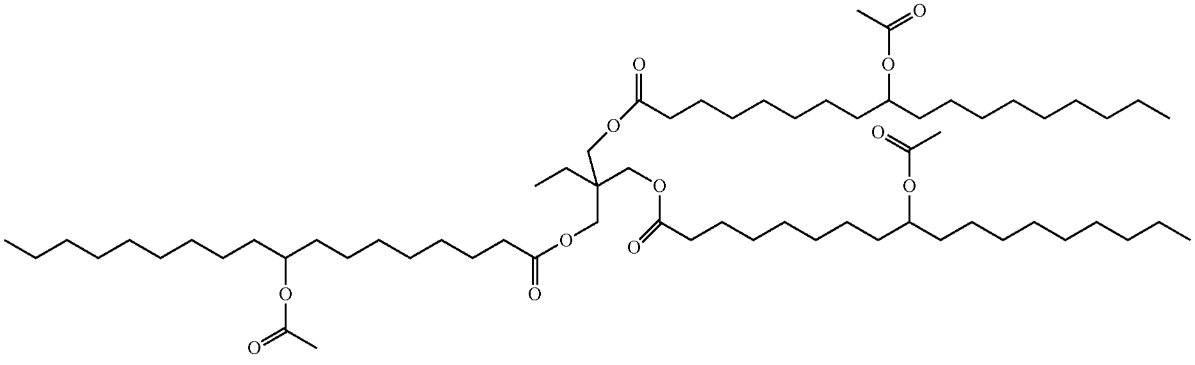
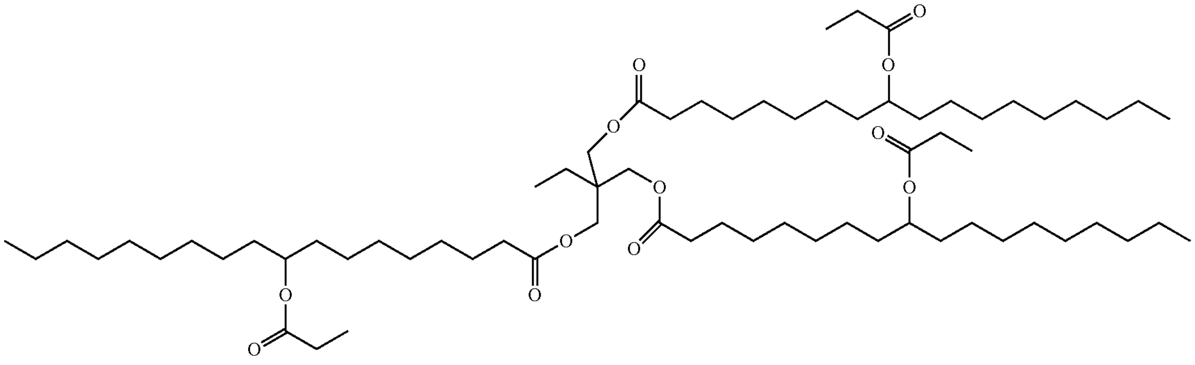
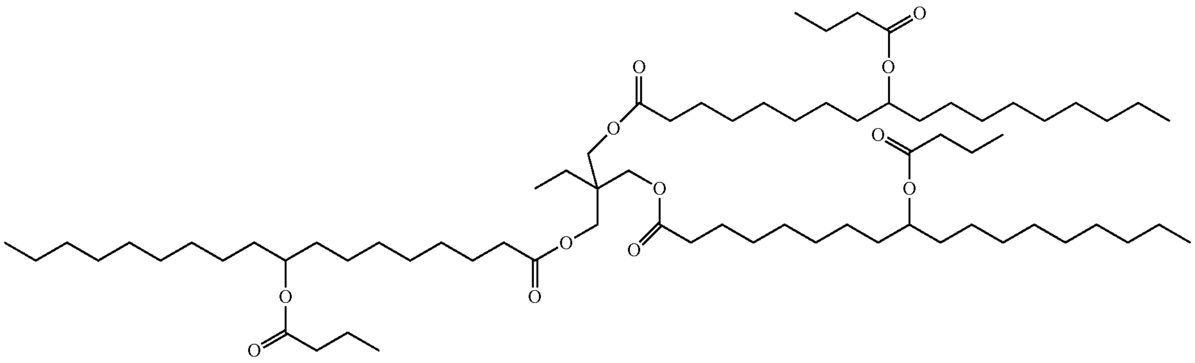

-continued
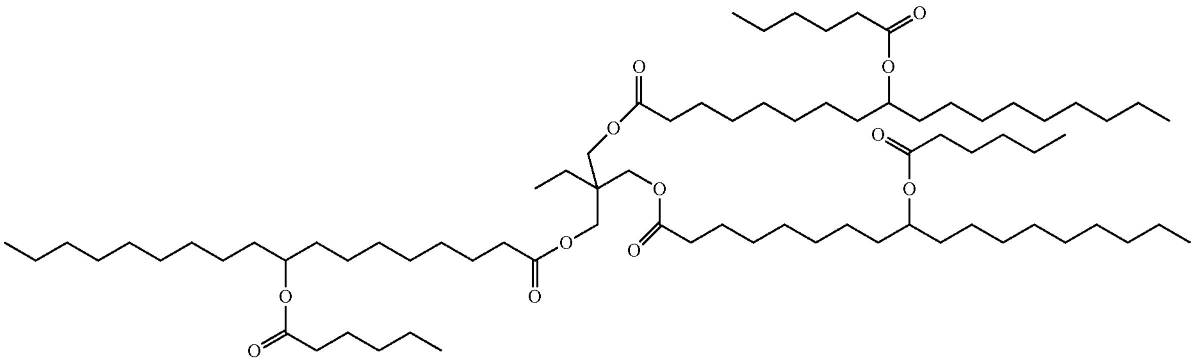
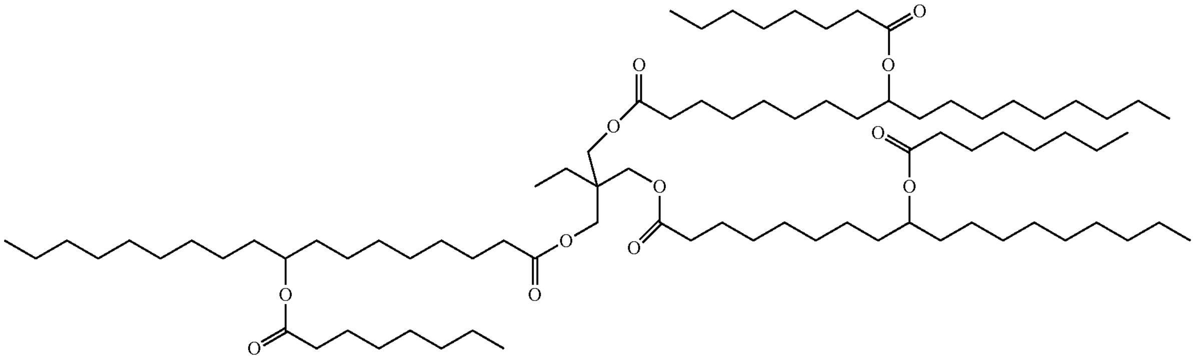
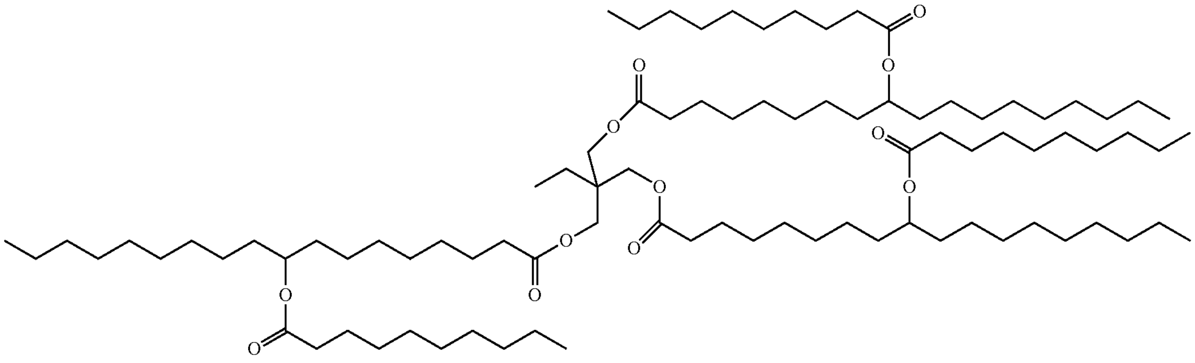
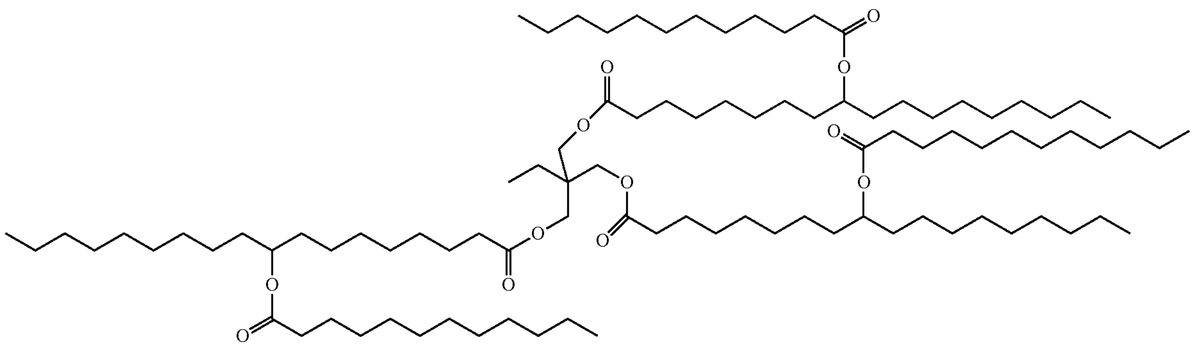

-continued
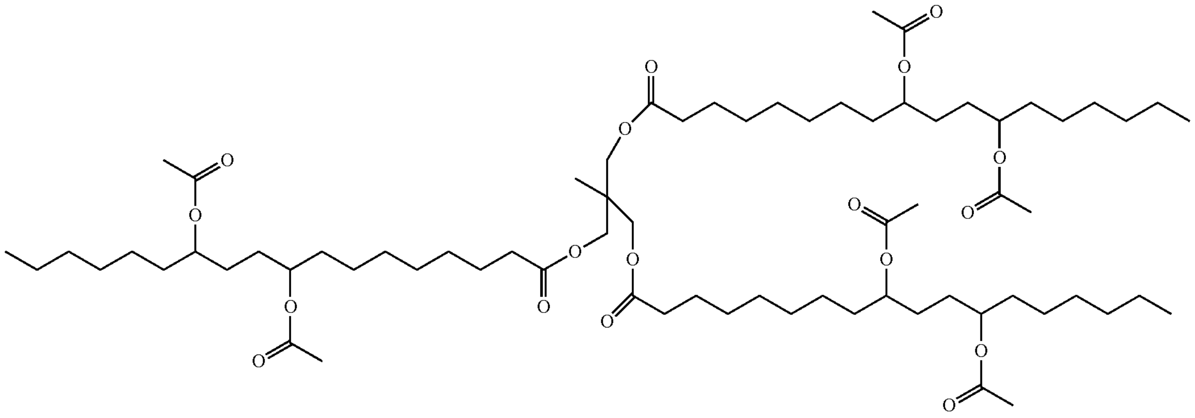
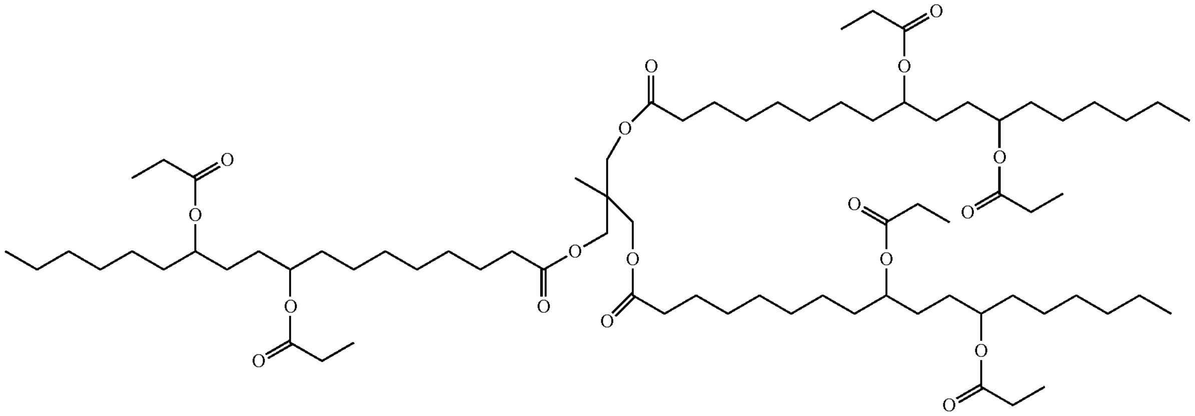
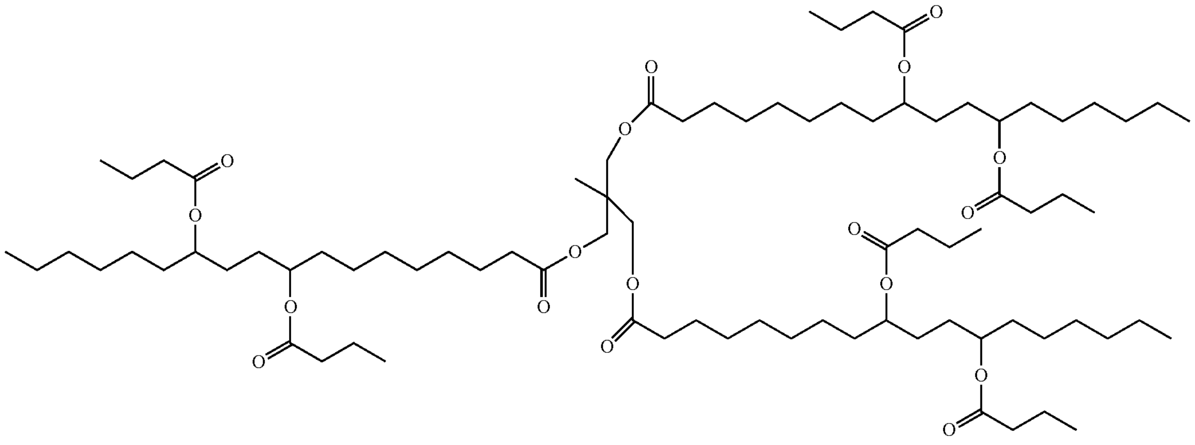
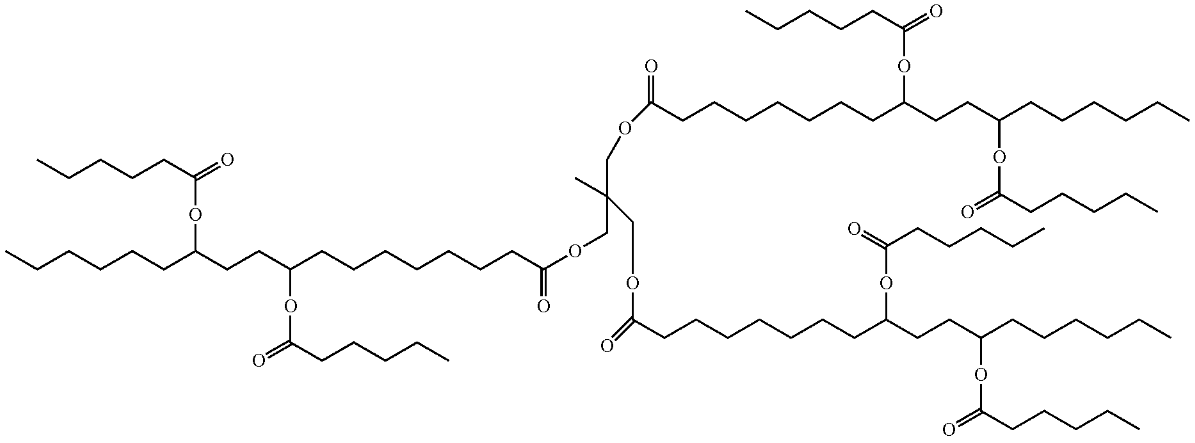

-continued
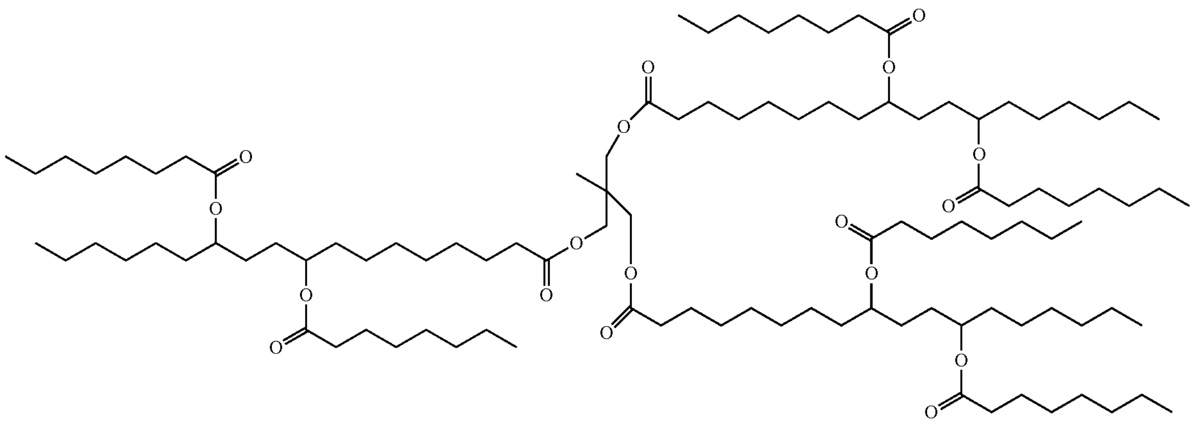
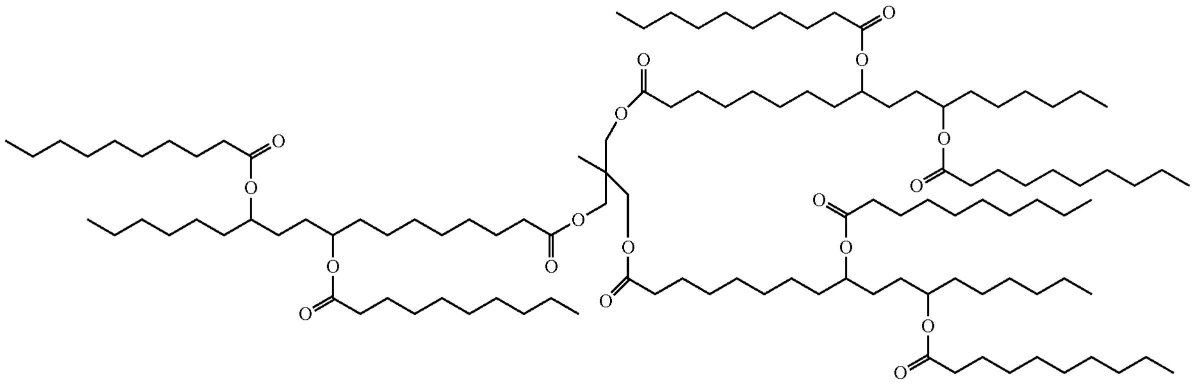
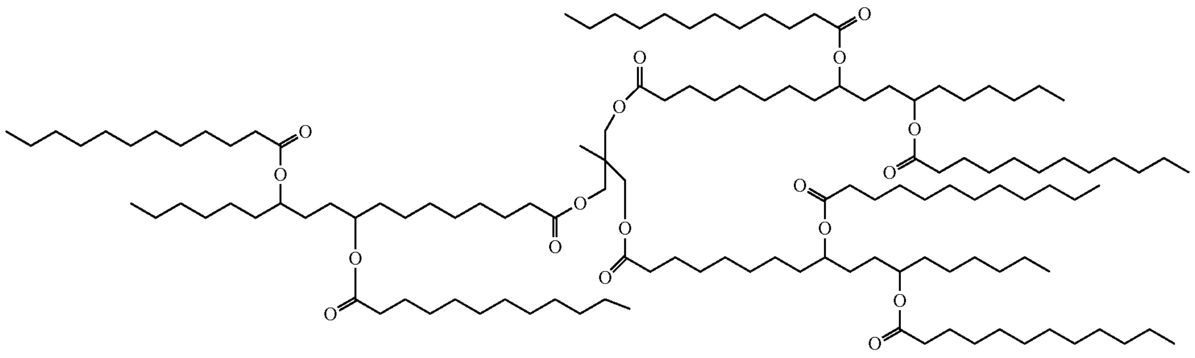
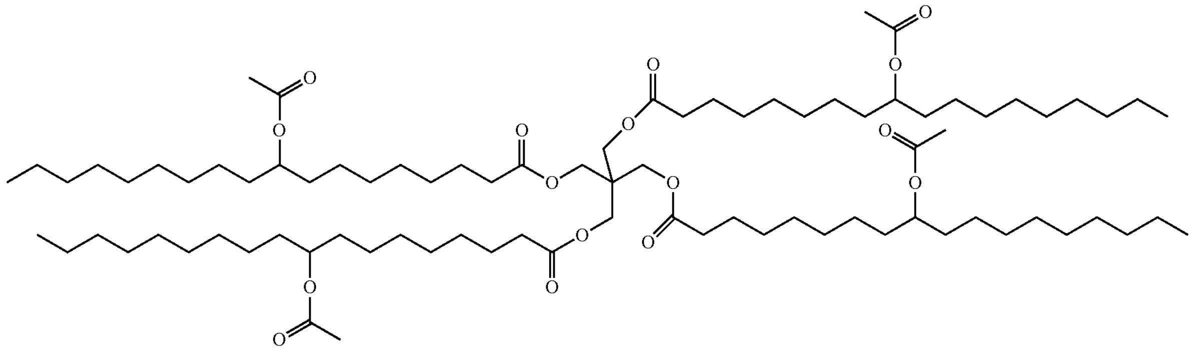

-continued
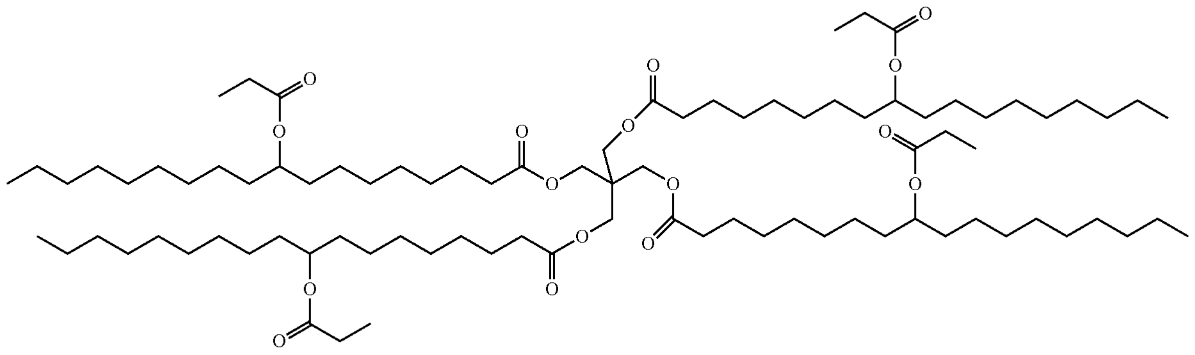
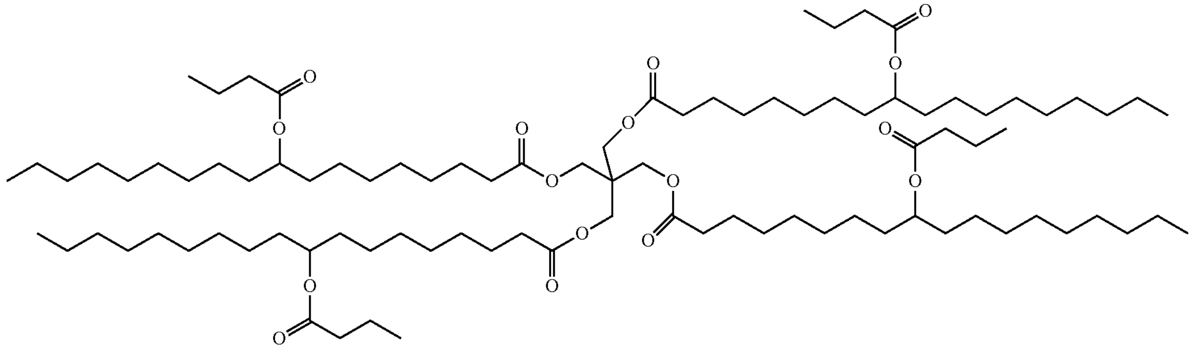
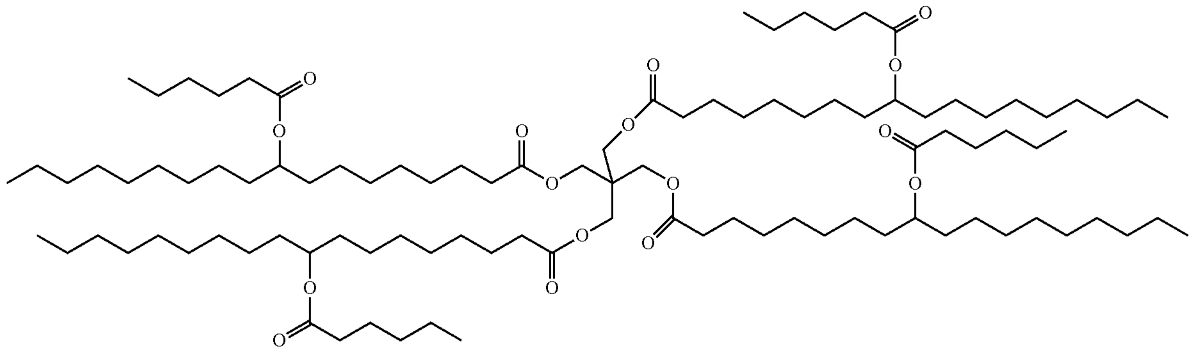
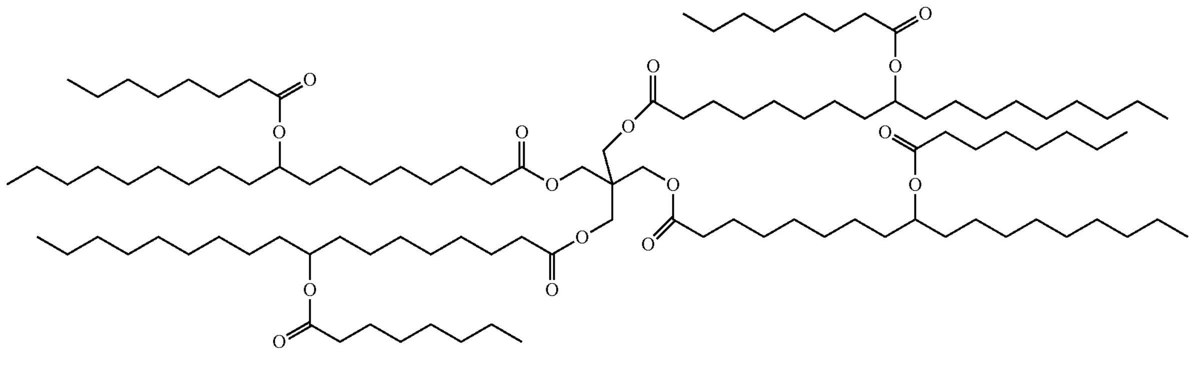

-continued
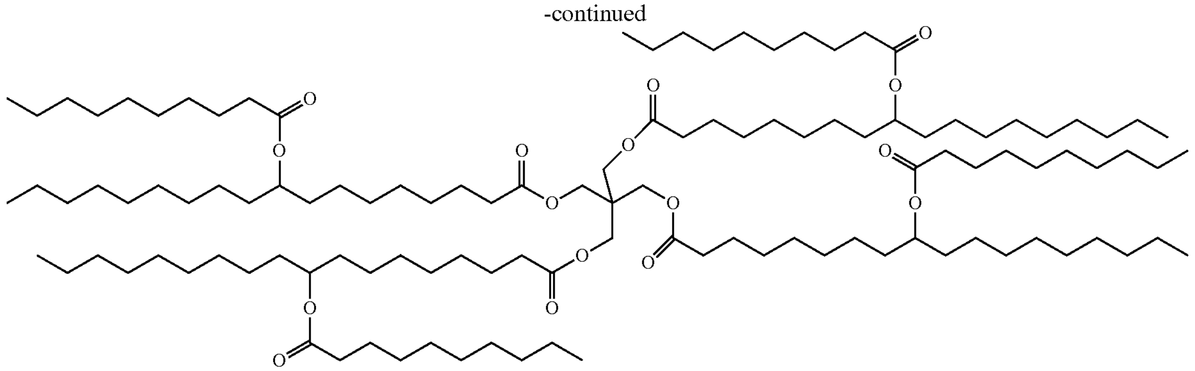
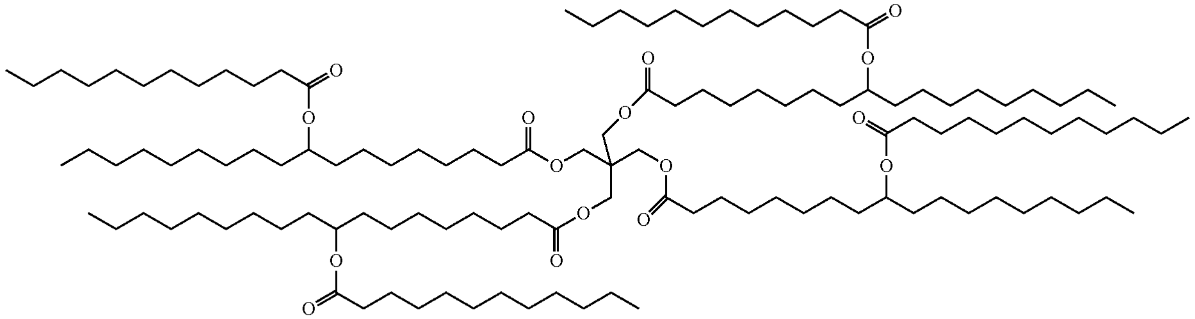
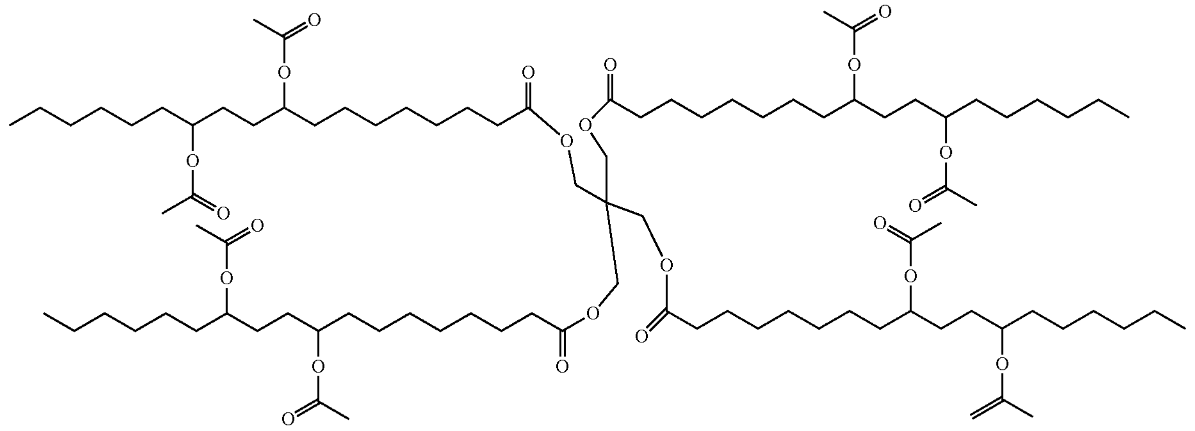
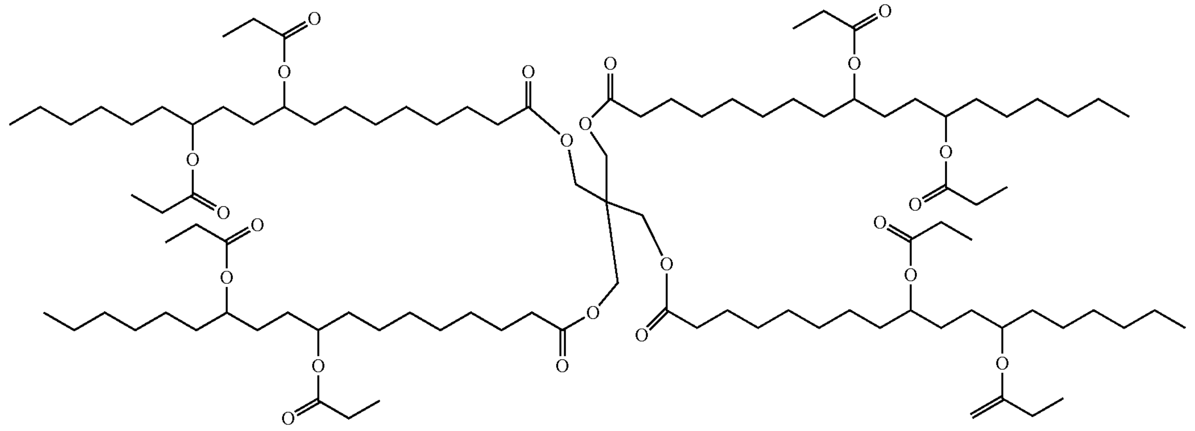

-continued
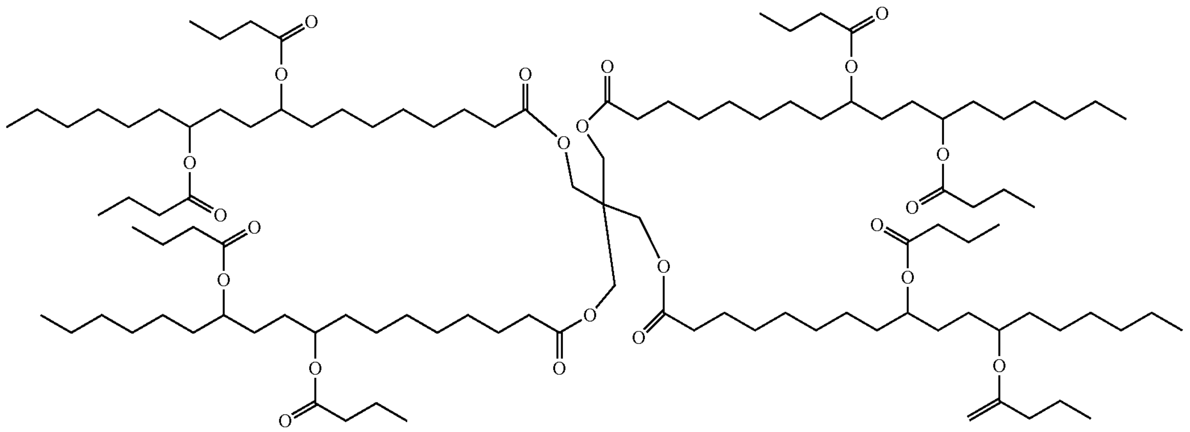
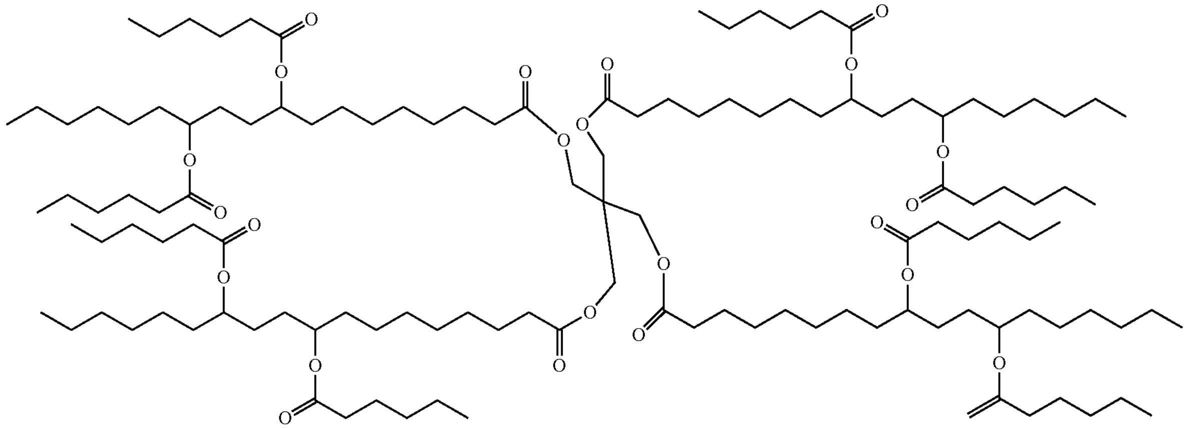
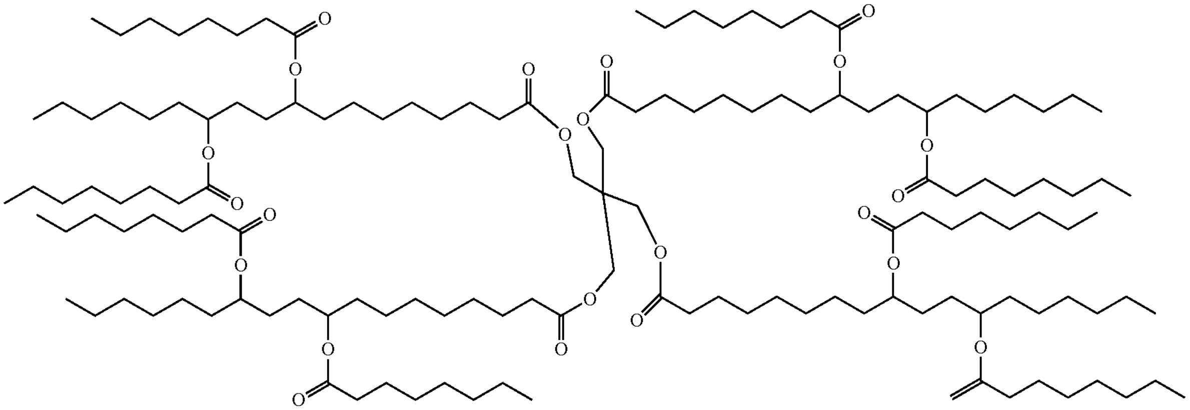
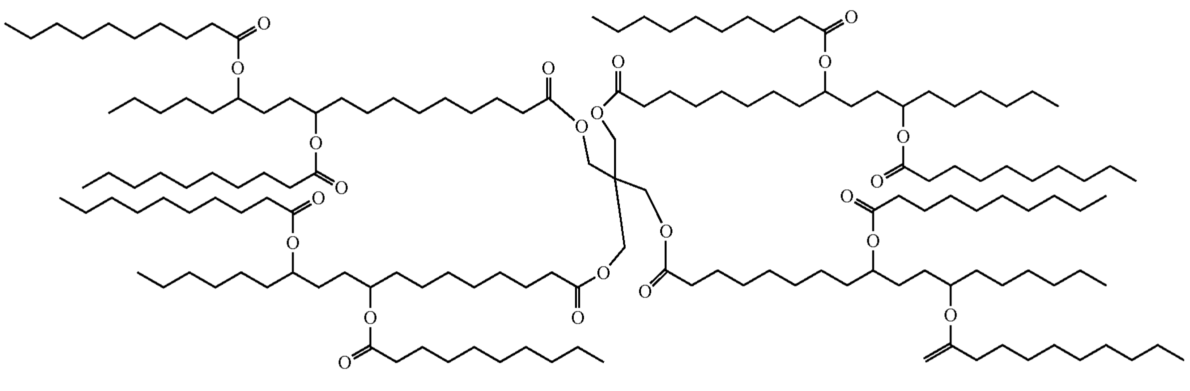

-continued
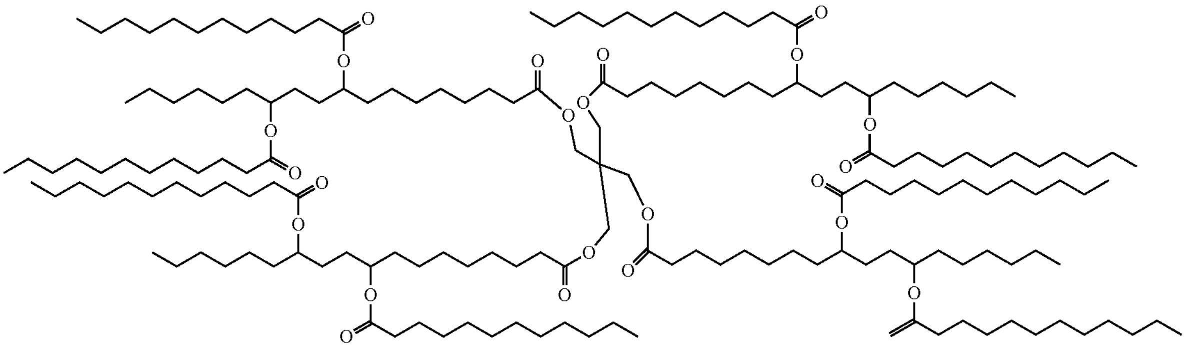
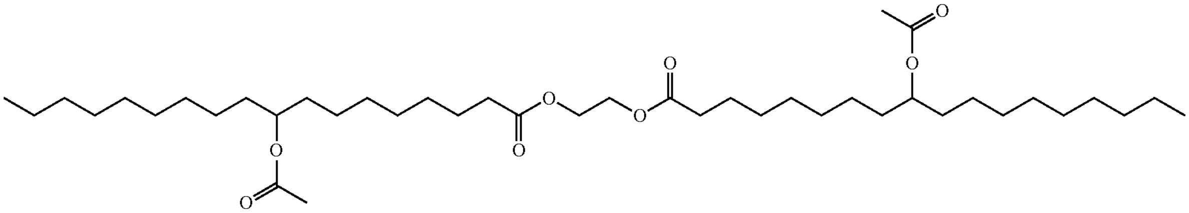
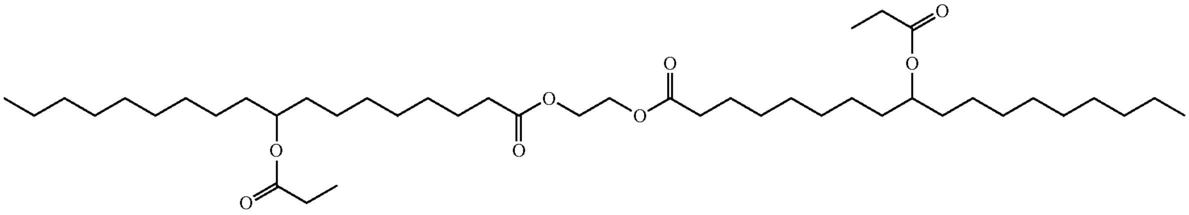
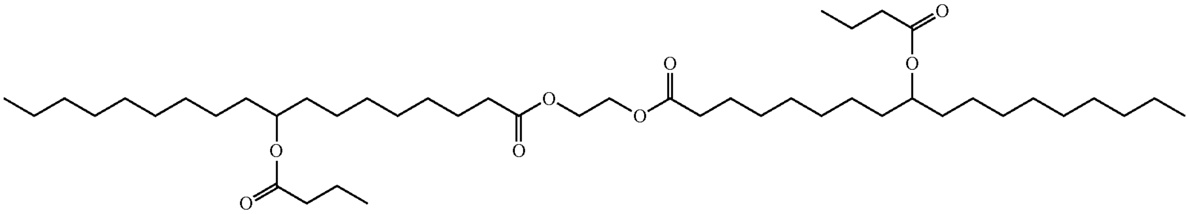
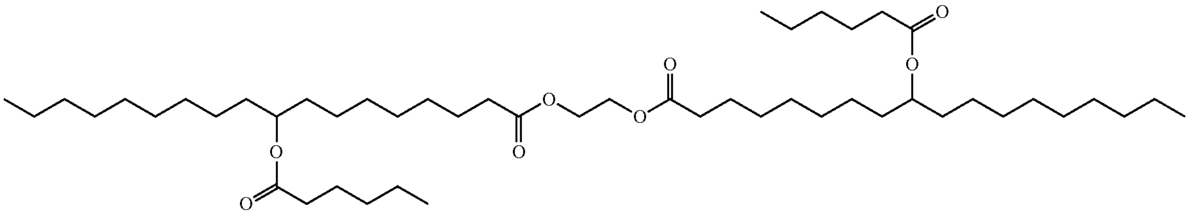
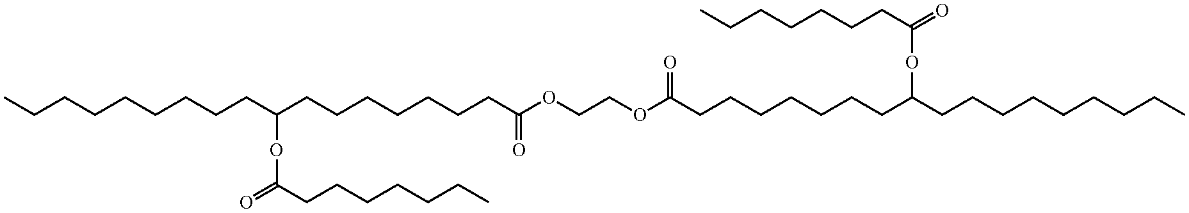
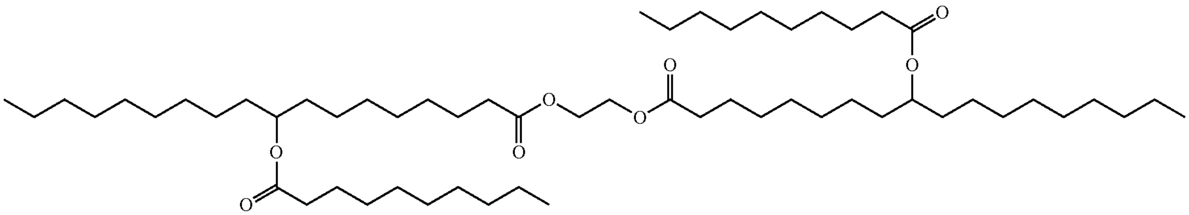

-continued
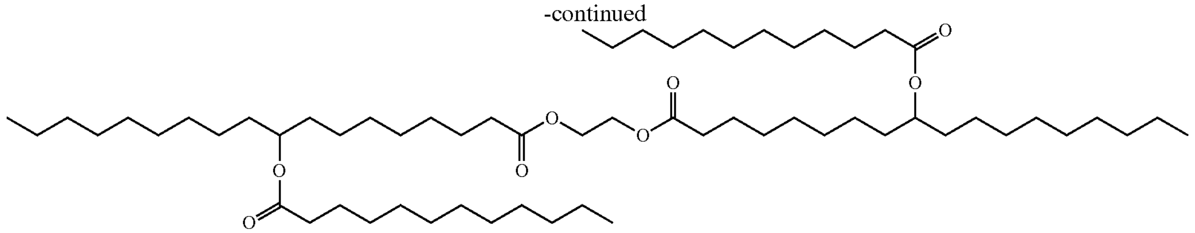
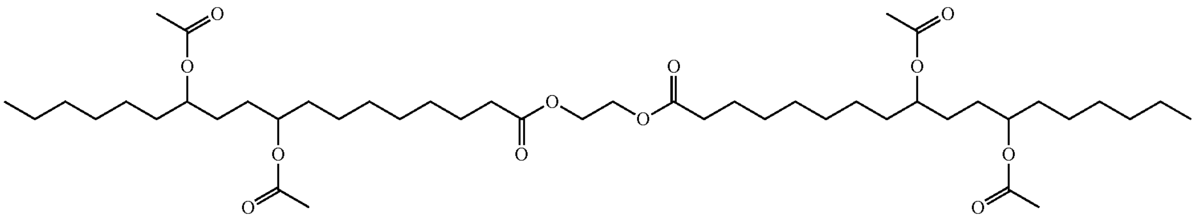
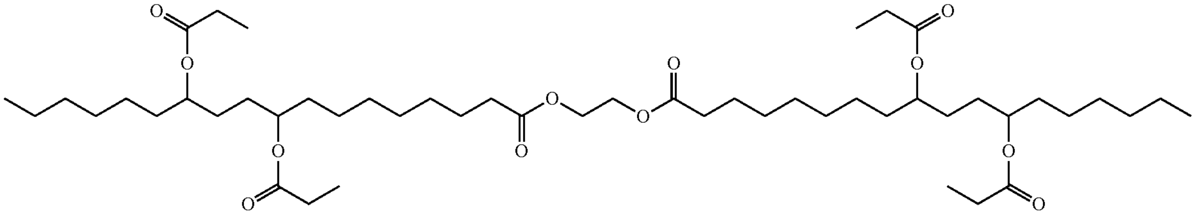
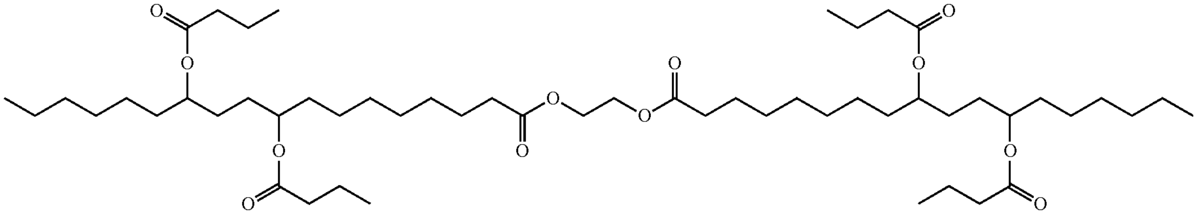
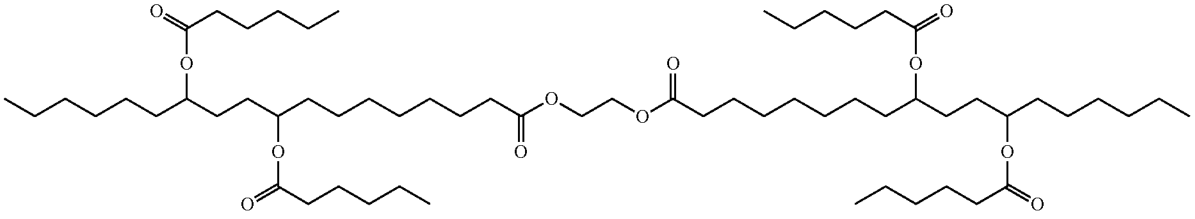
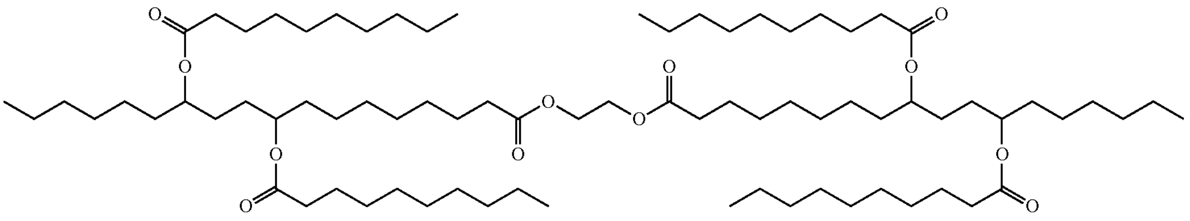
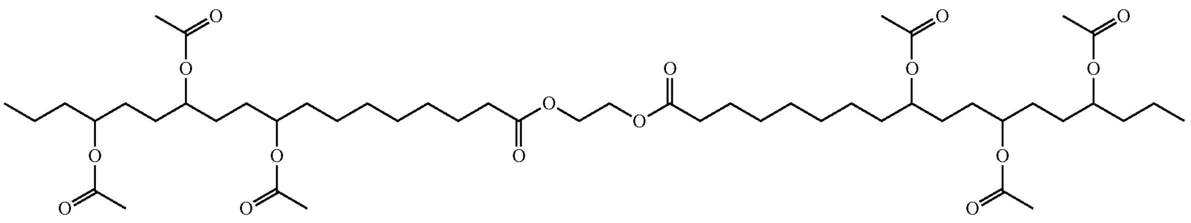

-continued
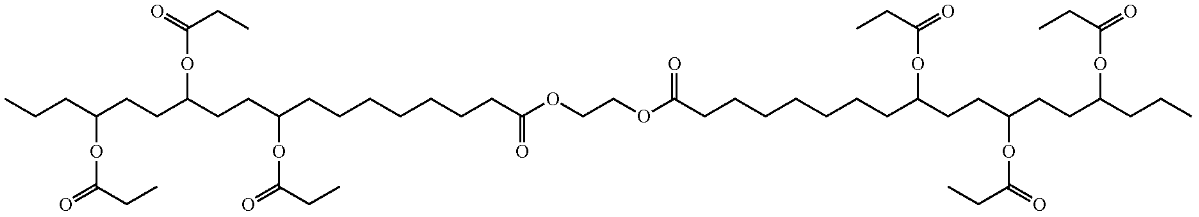
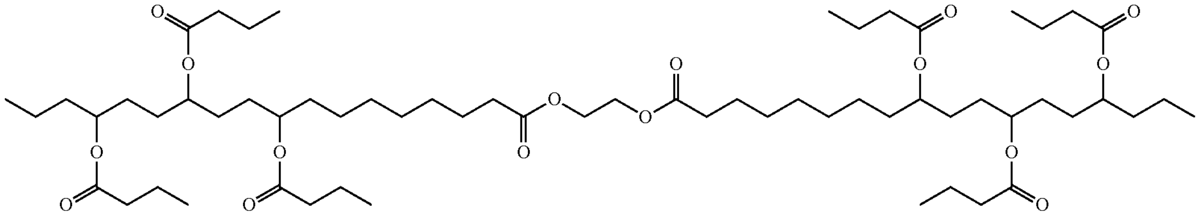
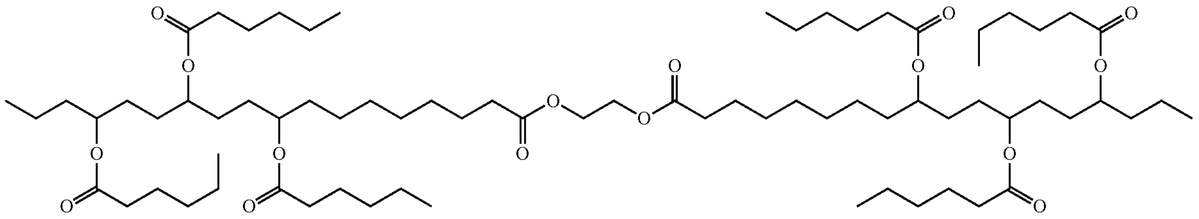
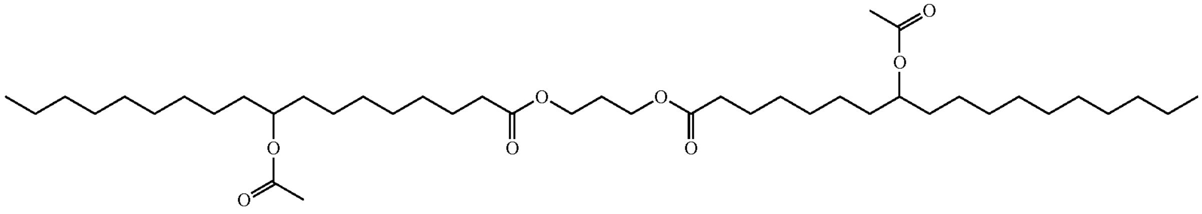
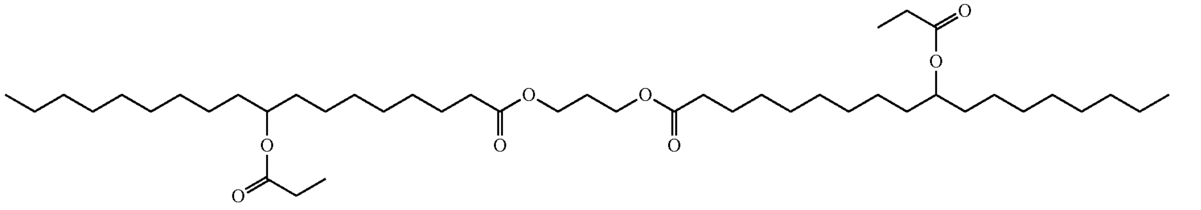
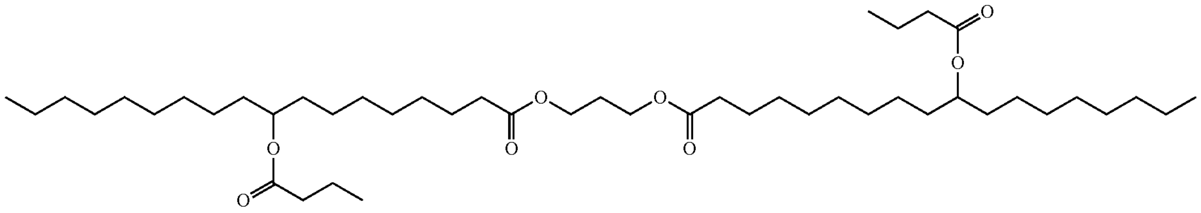
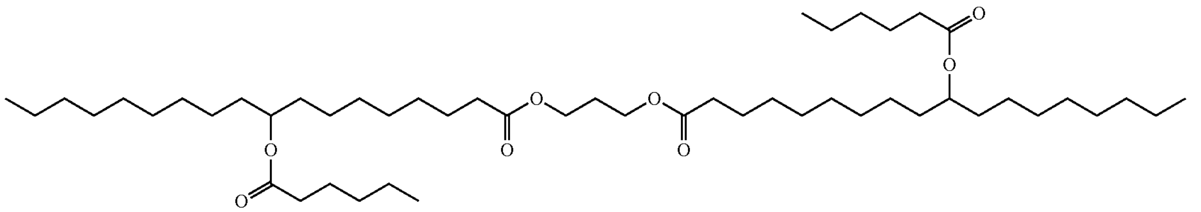
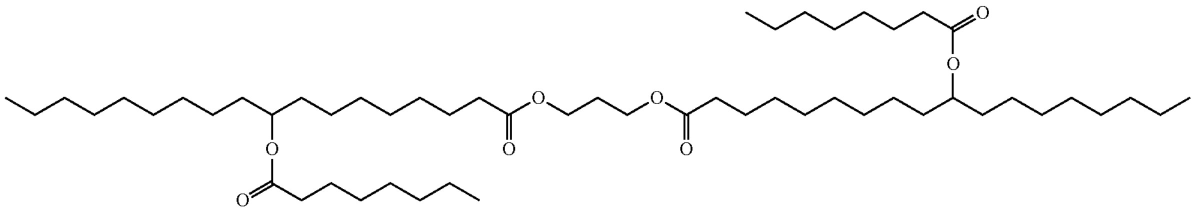

-continued
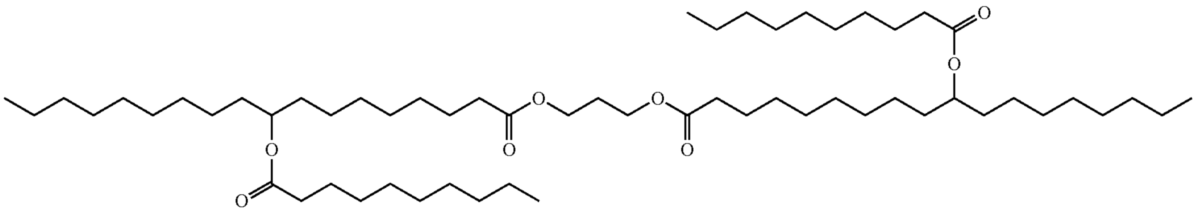
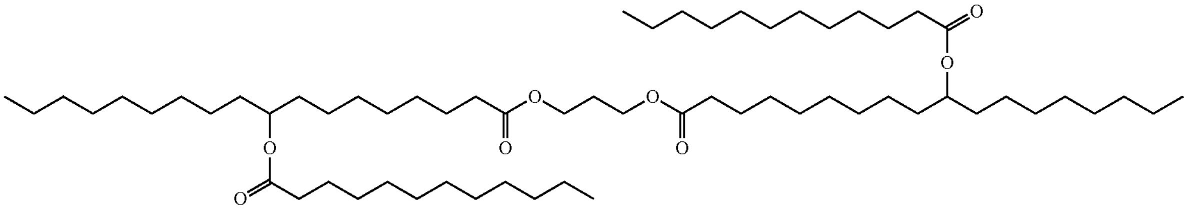
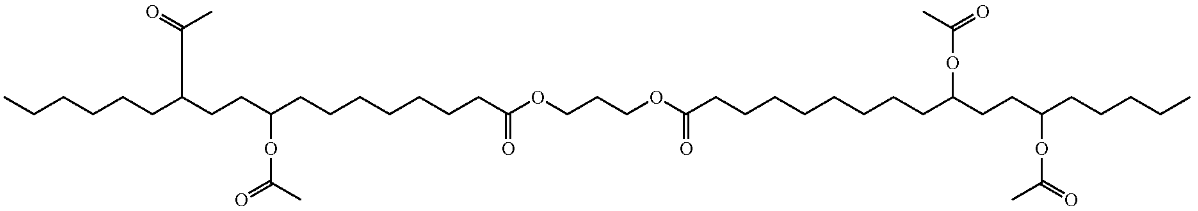
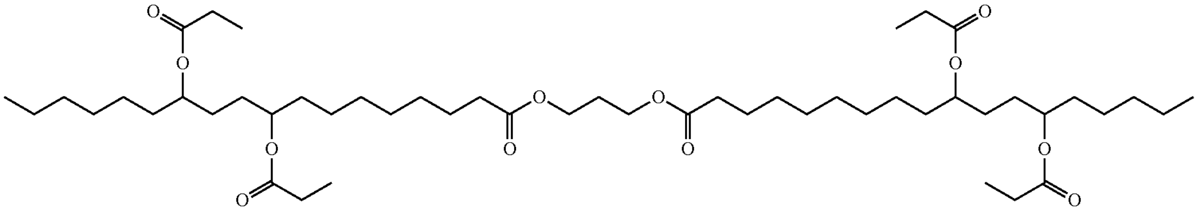
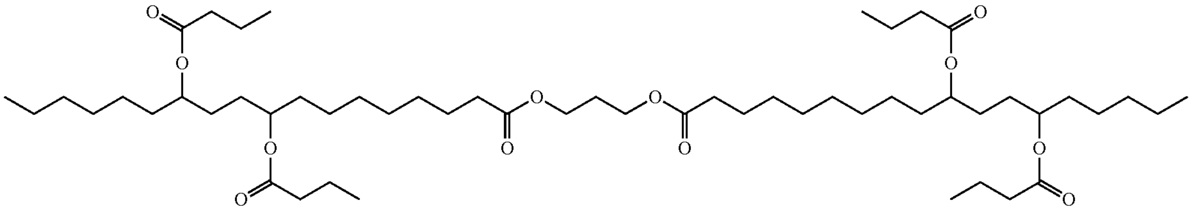
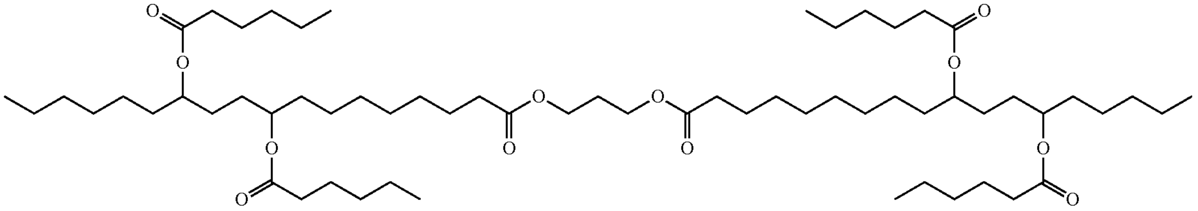
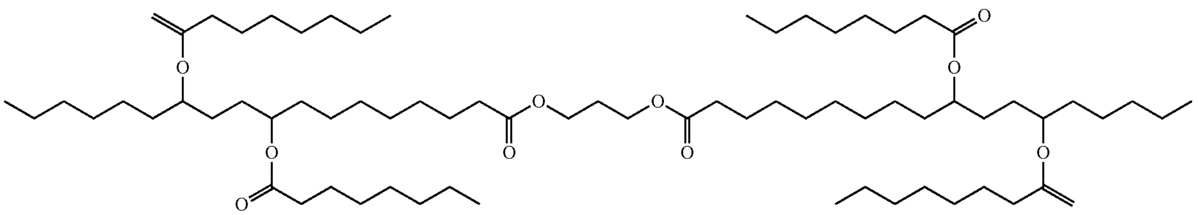
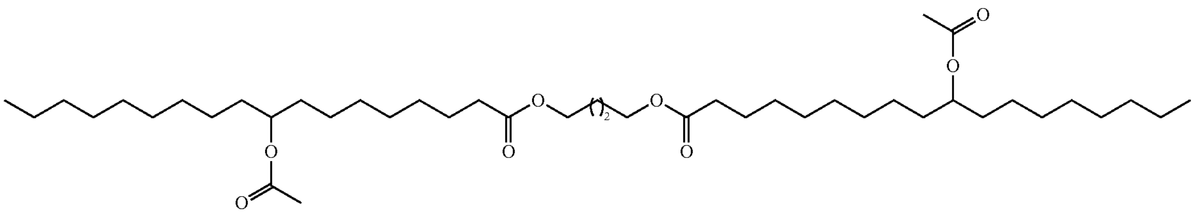

-continued
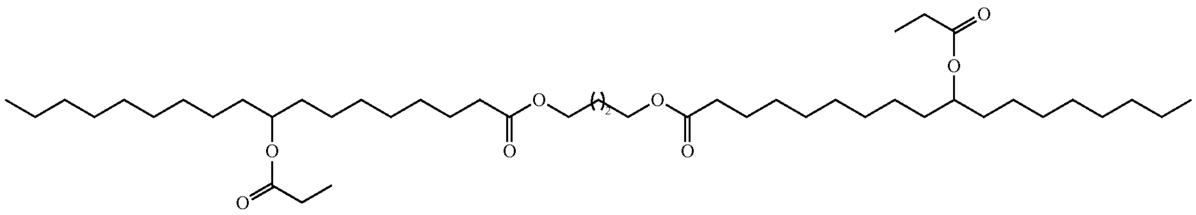
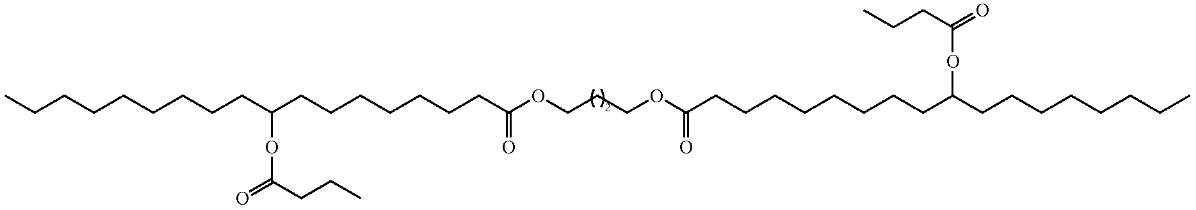
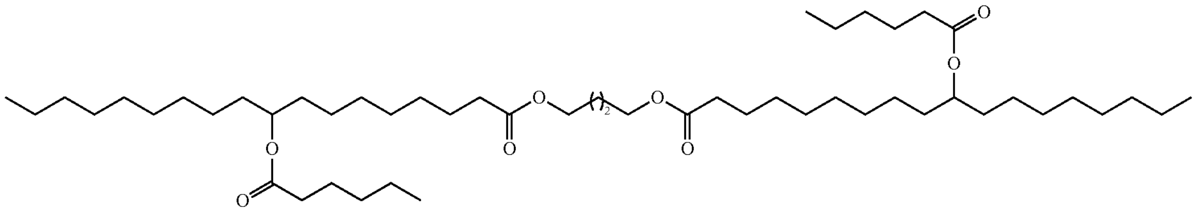
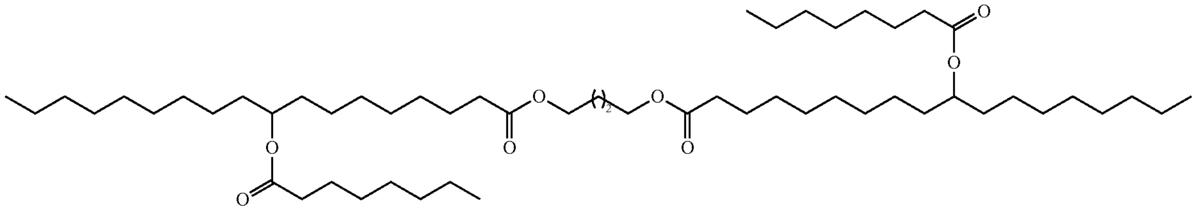
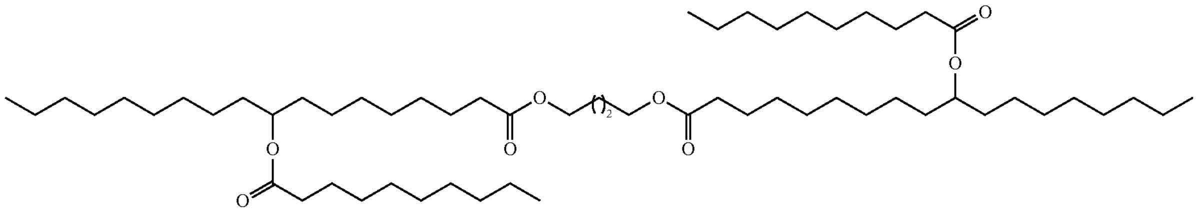
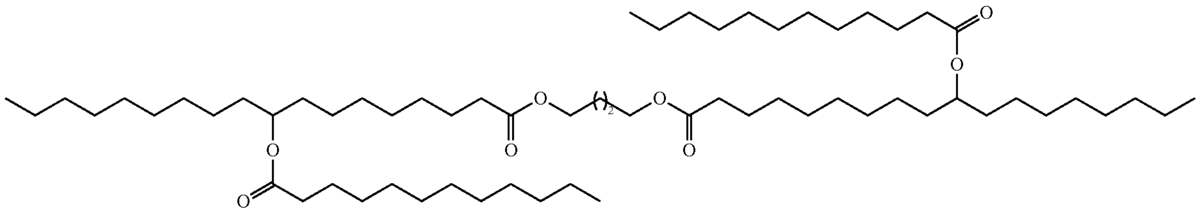
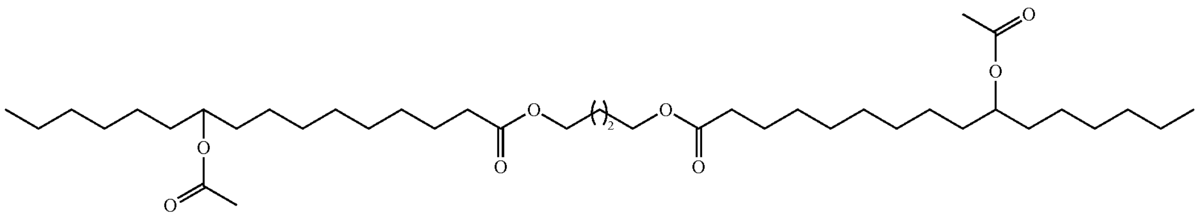
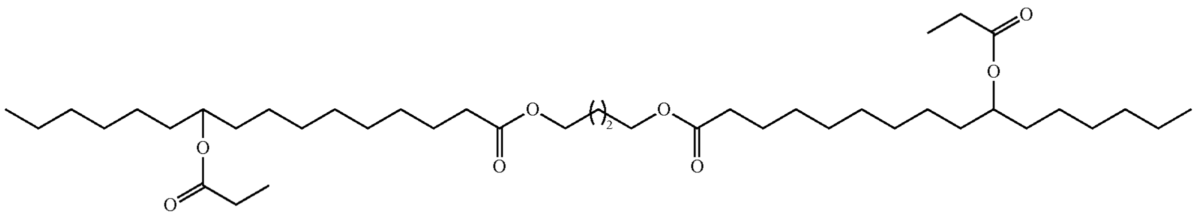

-continued
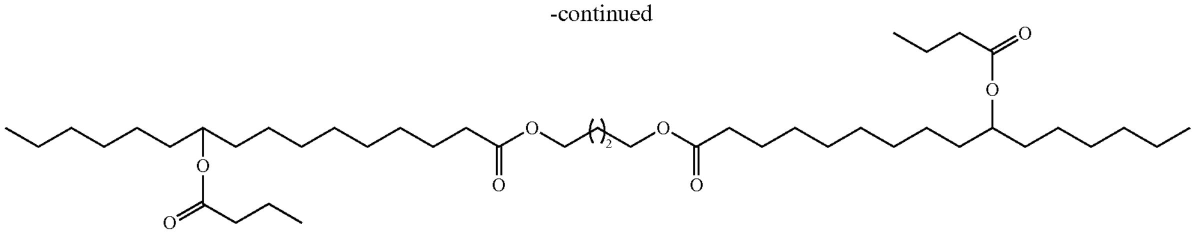
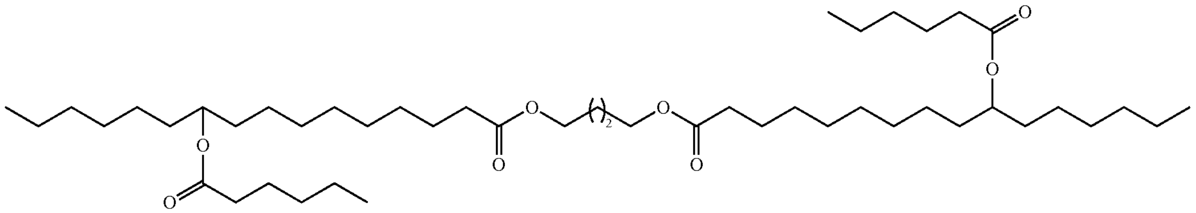
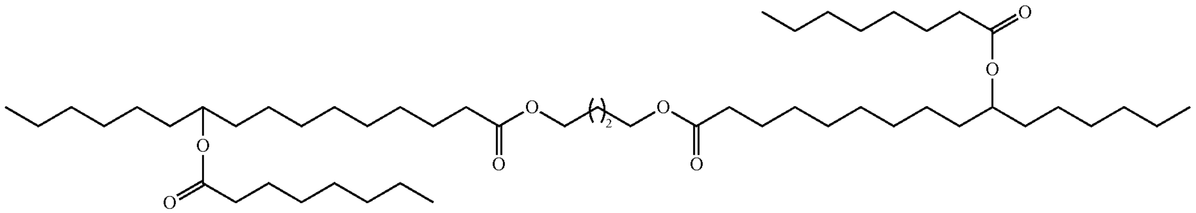
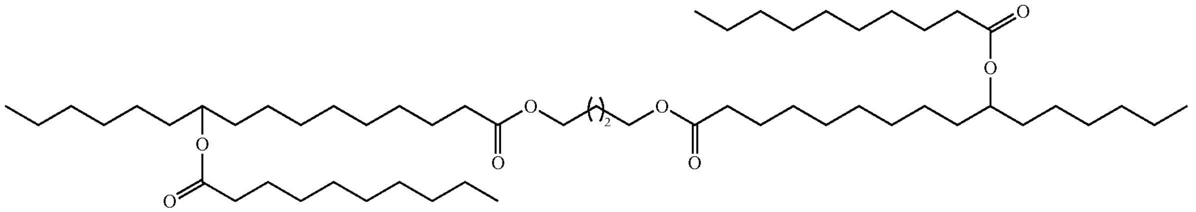
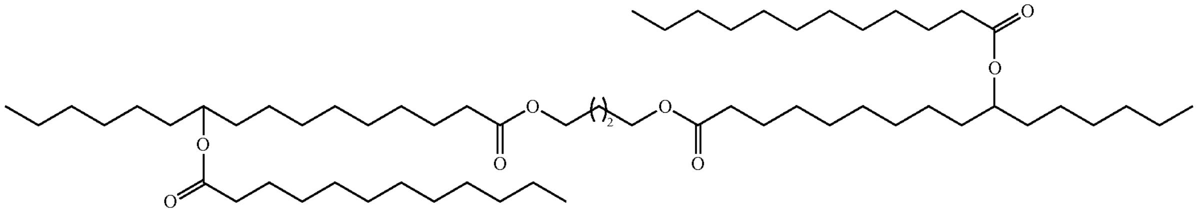
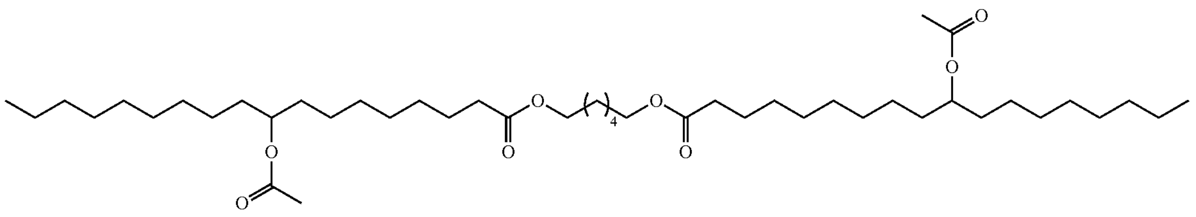
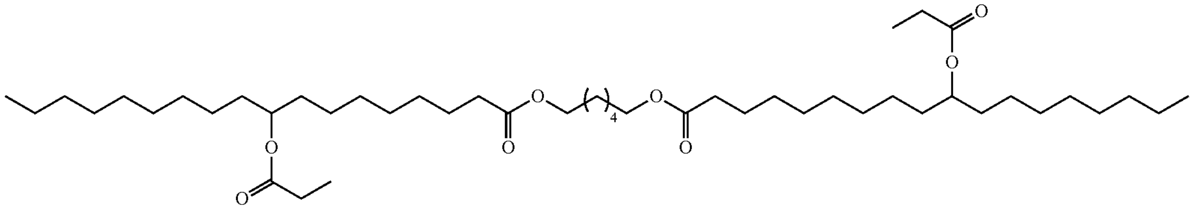

-continued
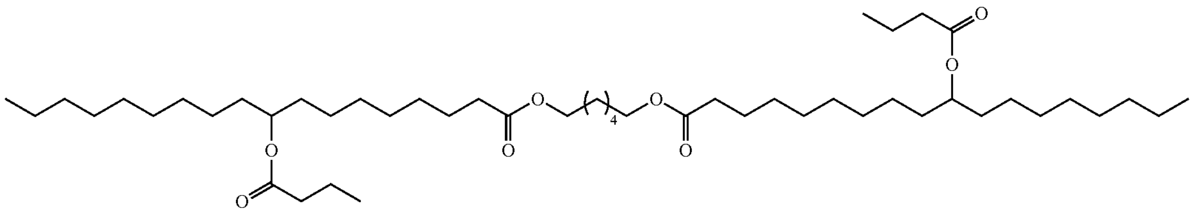
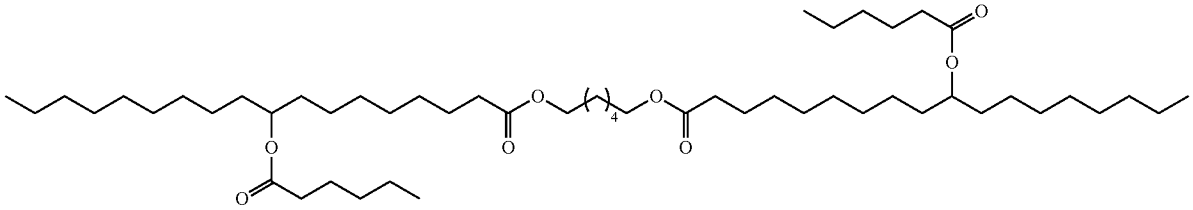
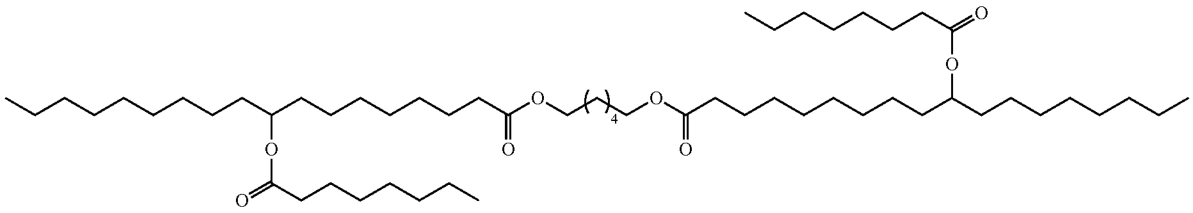
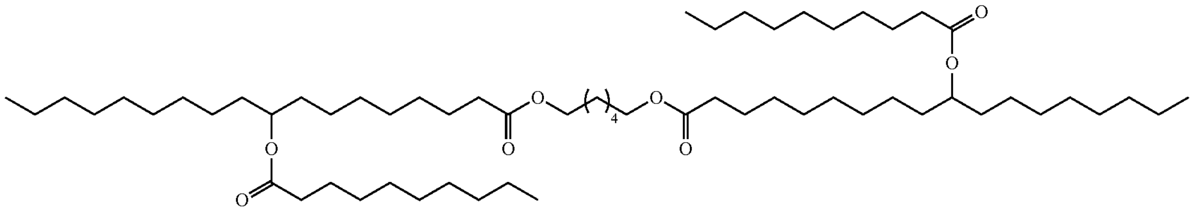
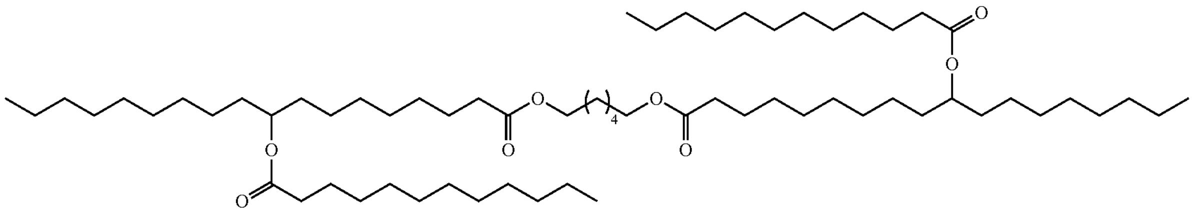
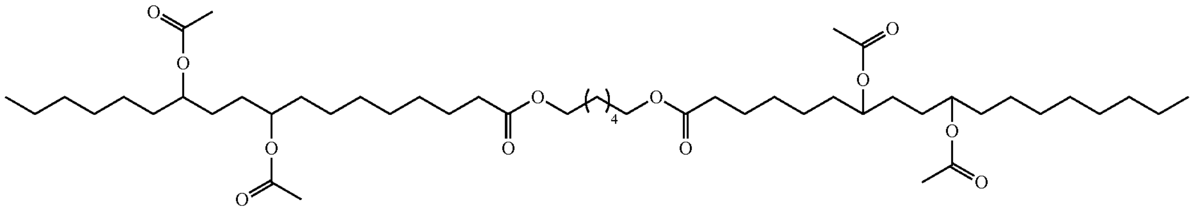
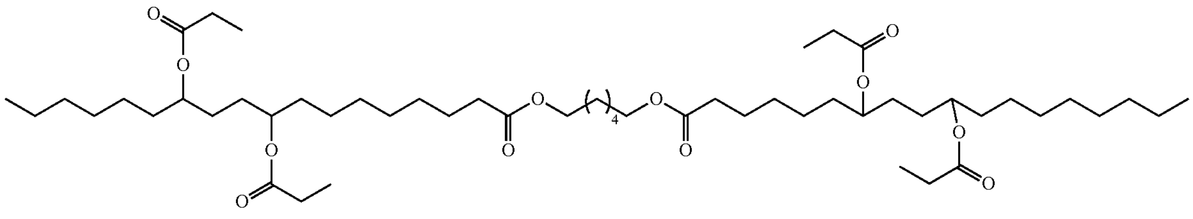
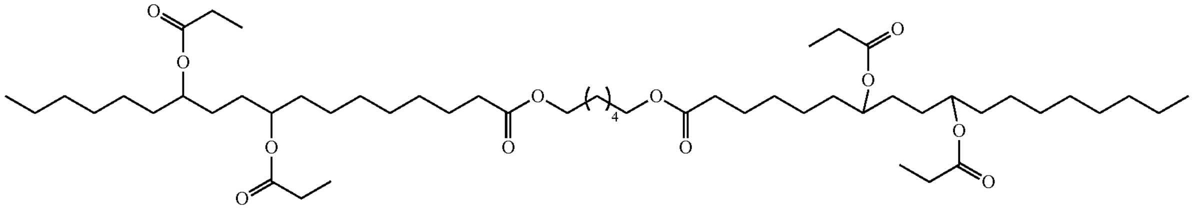

-continued
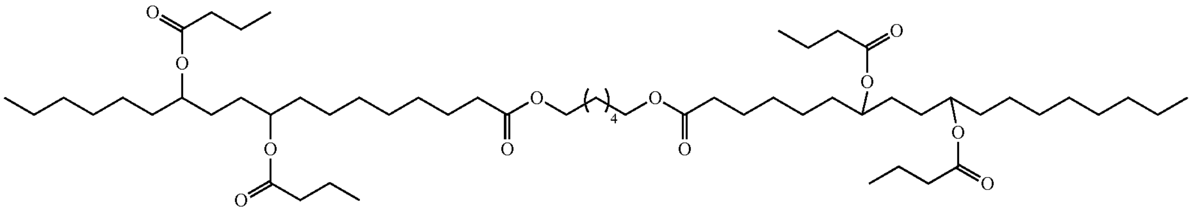
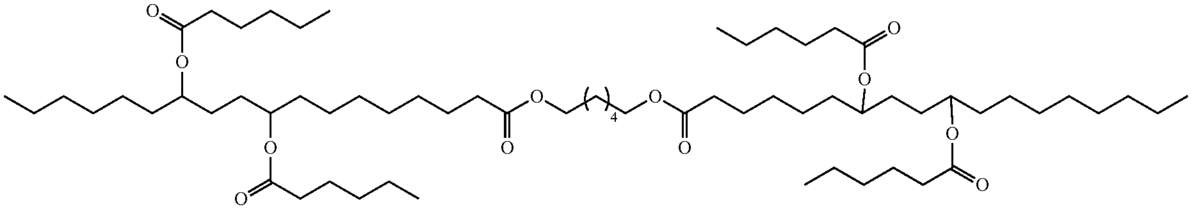
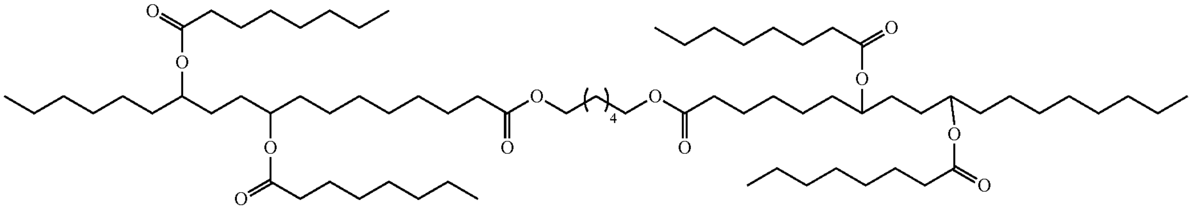
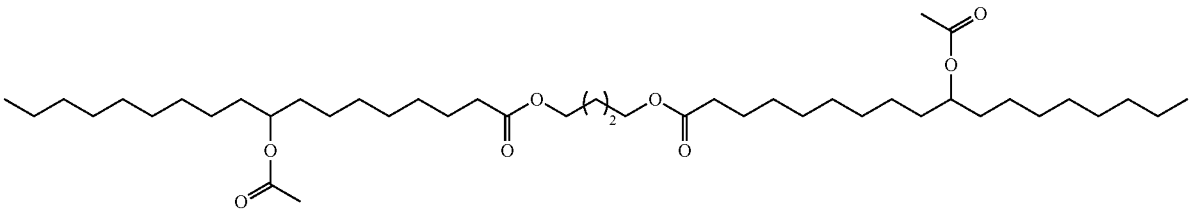
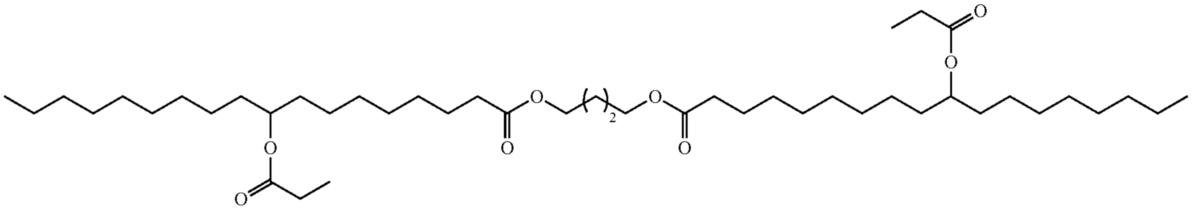
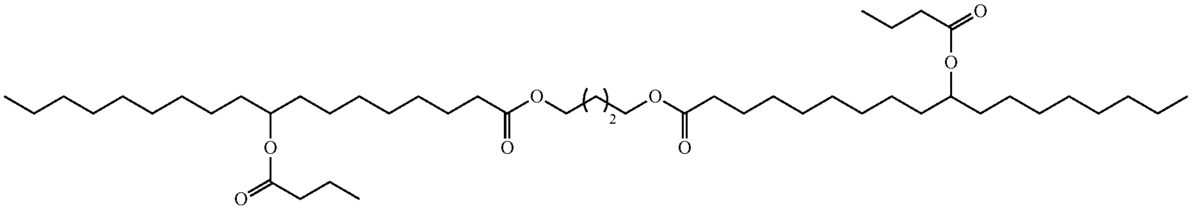
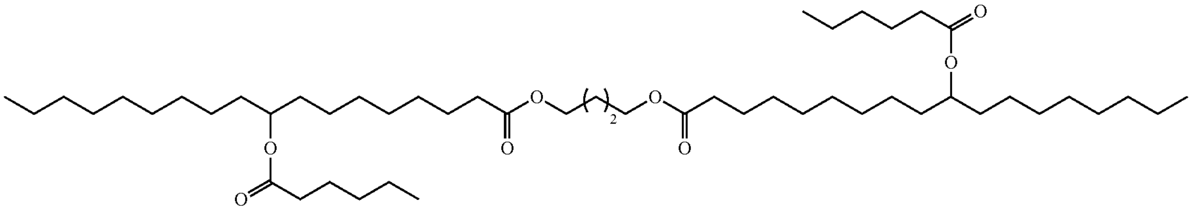
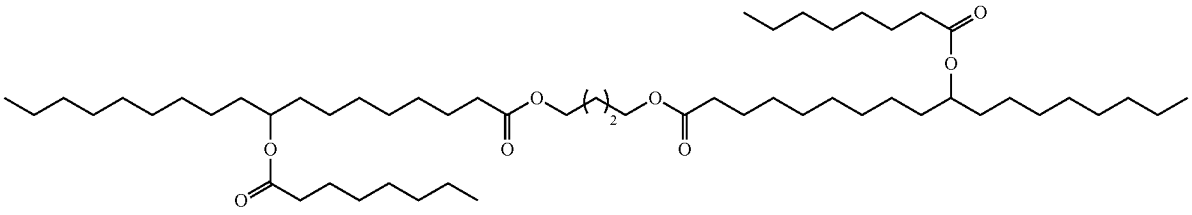

-continued
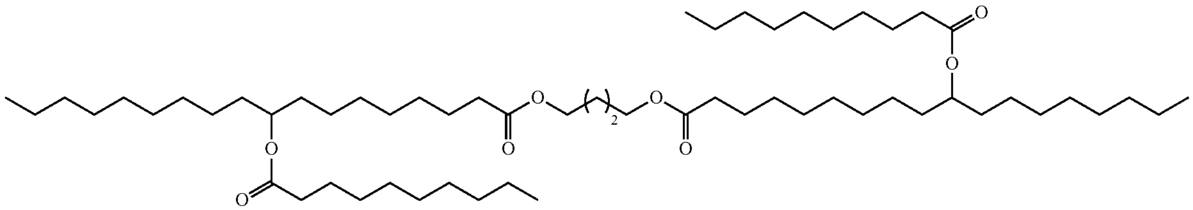
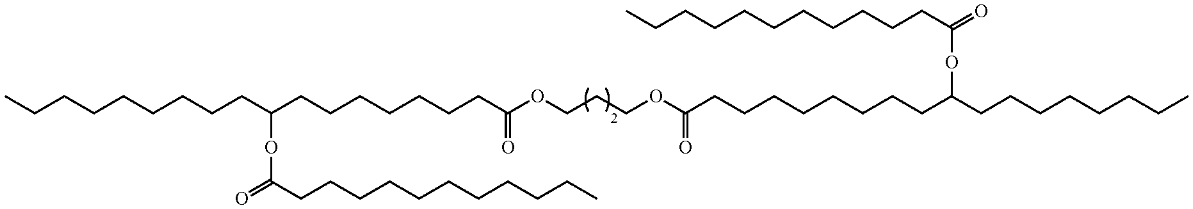
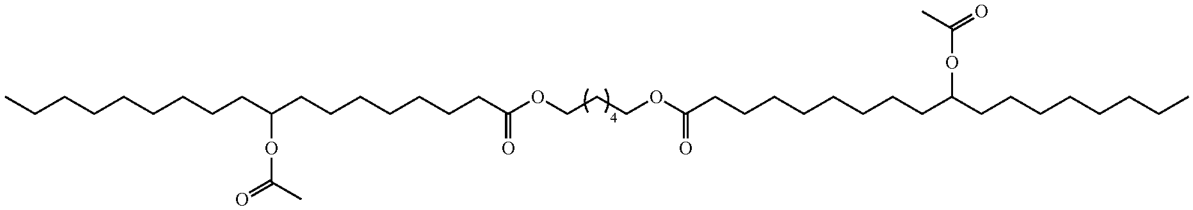
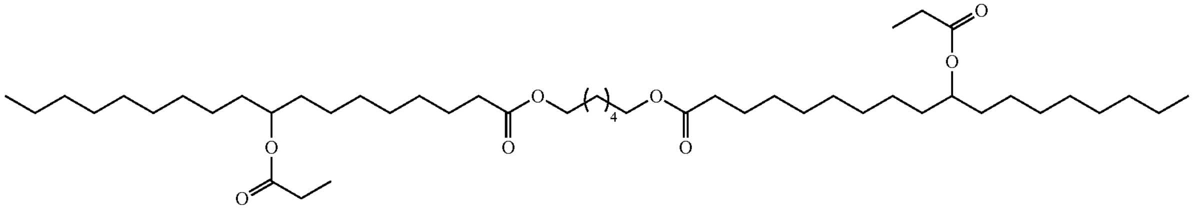
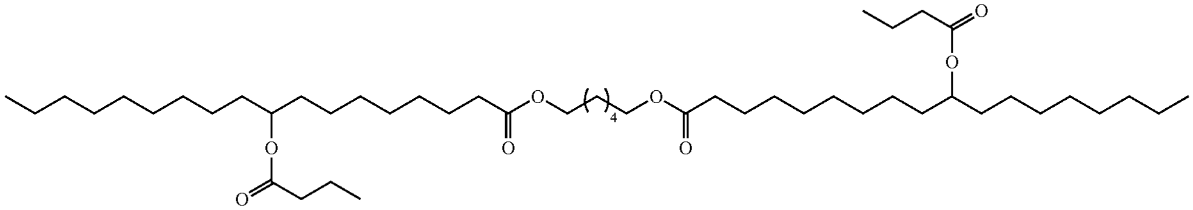
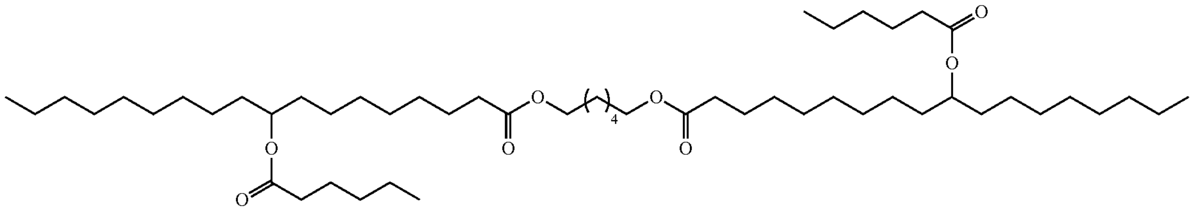
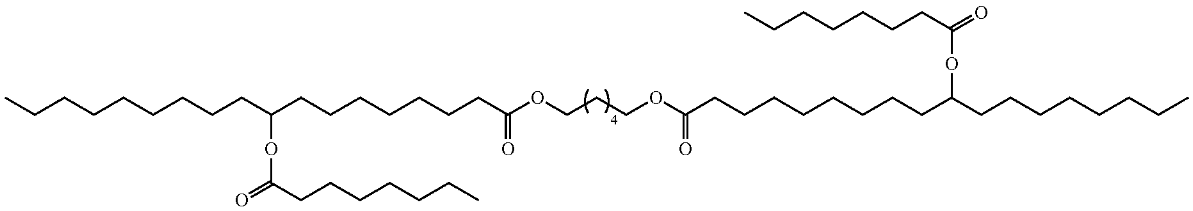
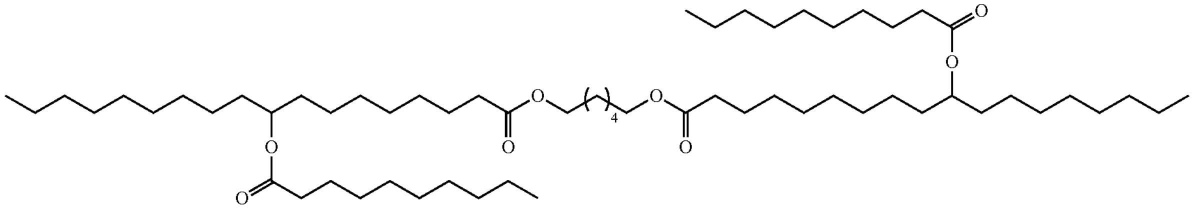

-continued
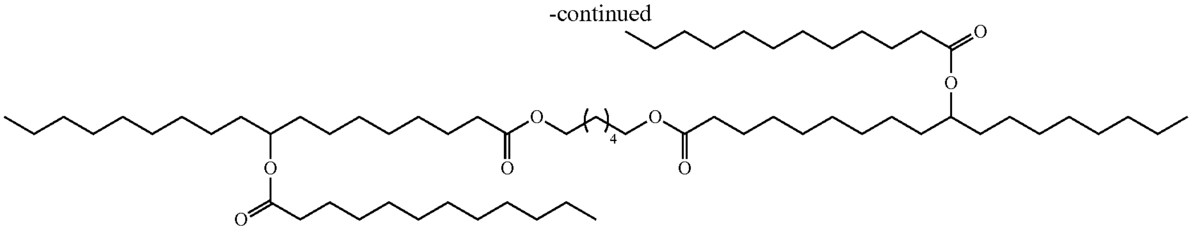
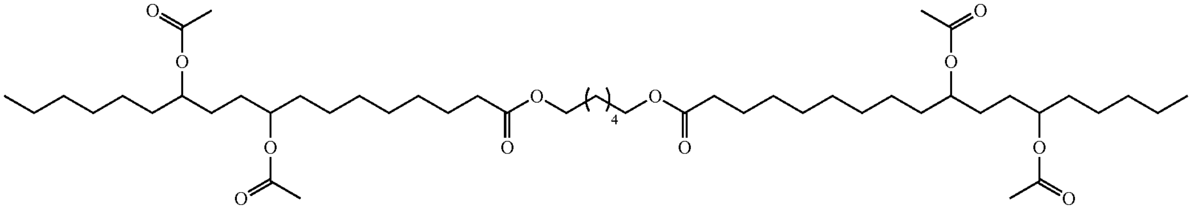
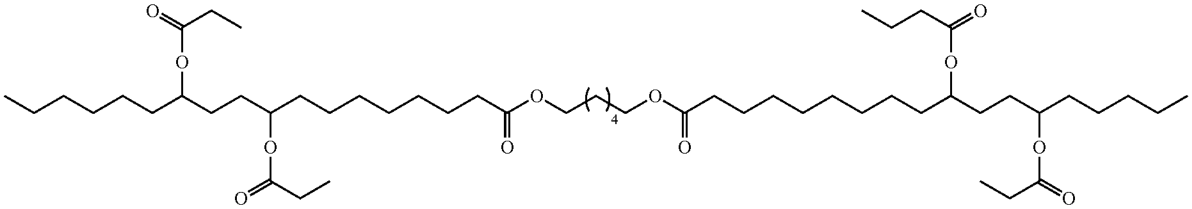
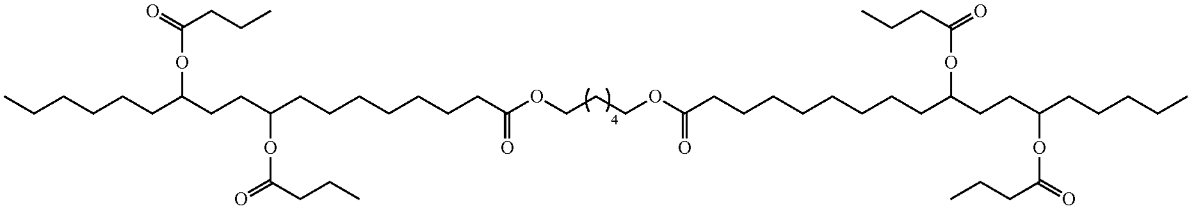
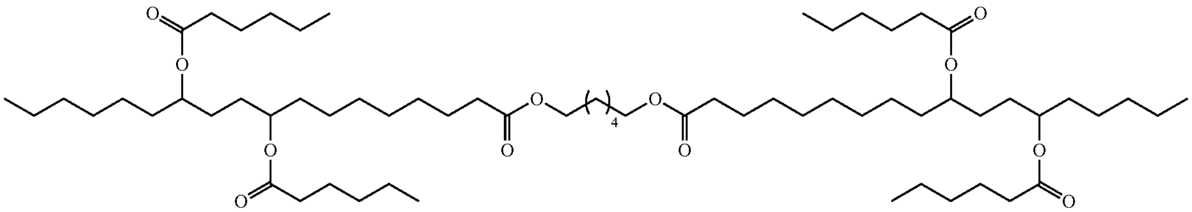
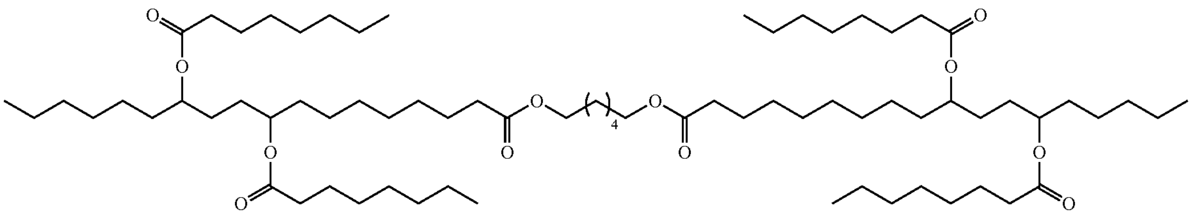
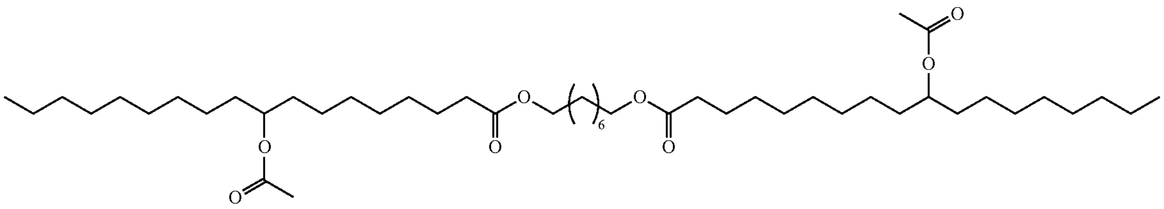

-continued
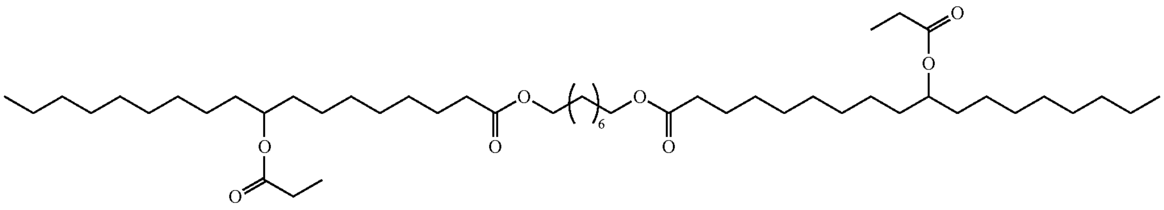
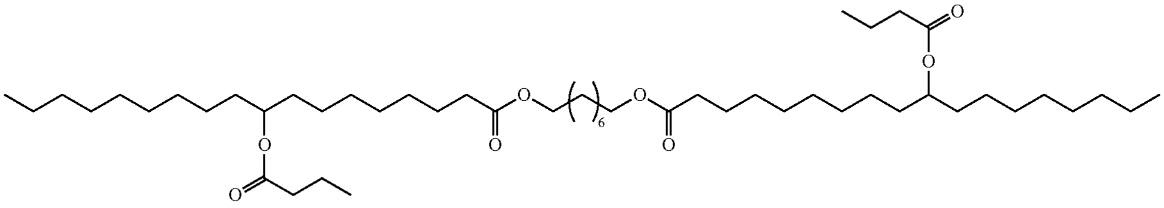
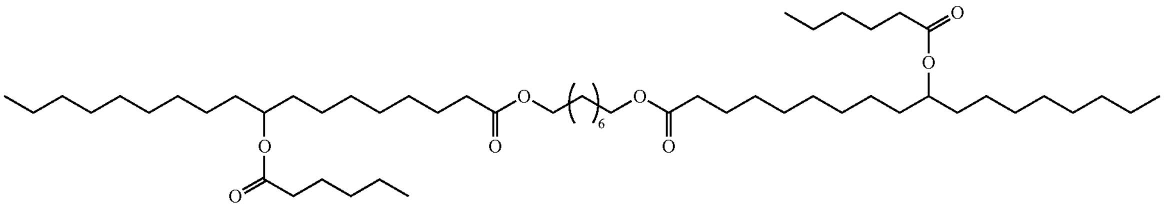
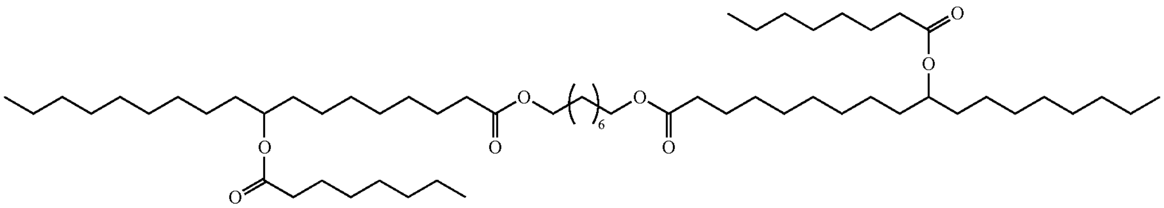
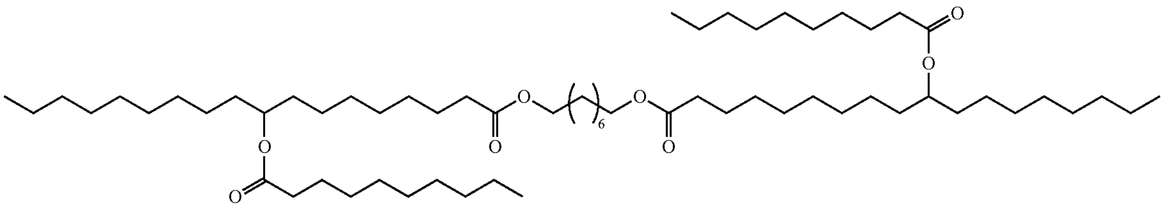
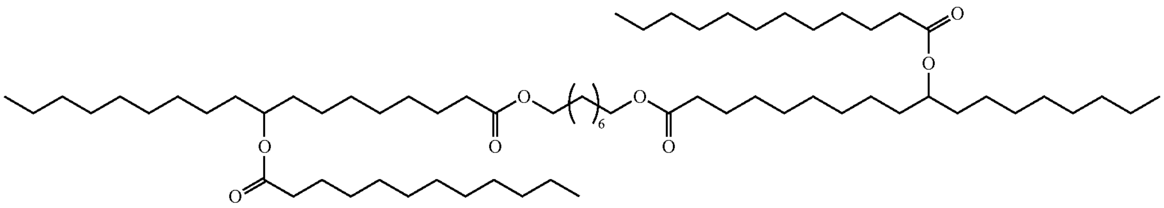
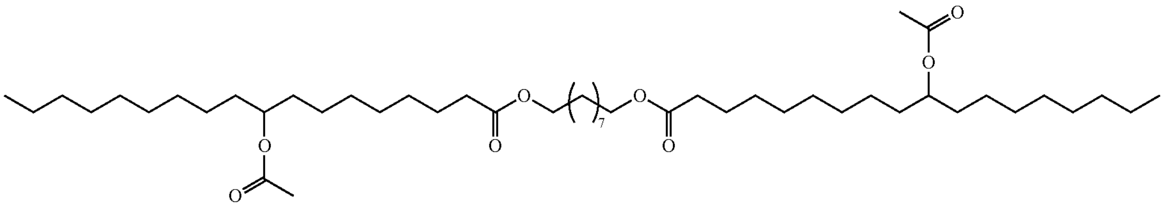
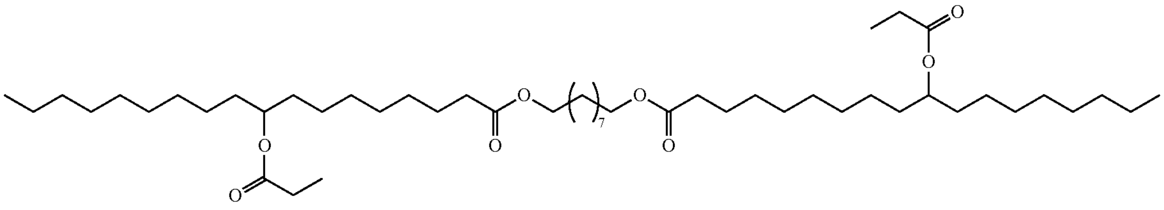

-continued
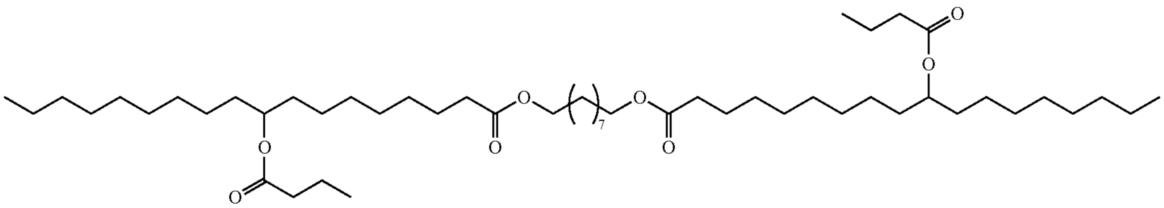
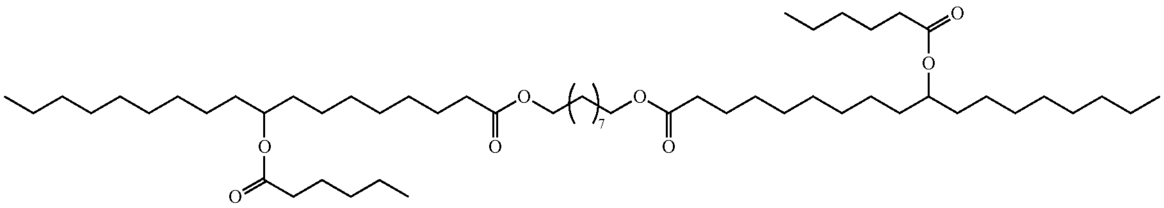
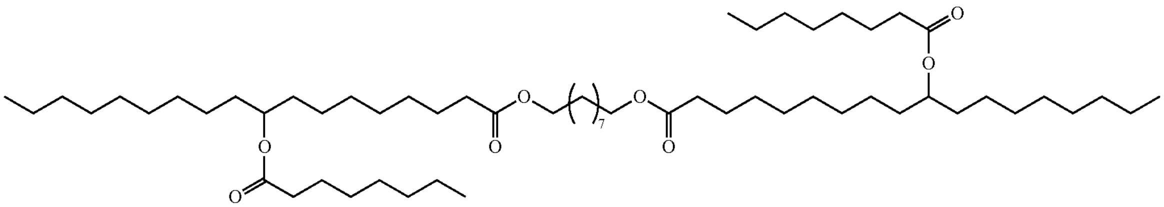
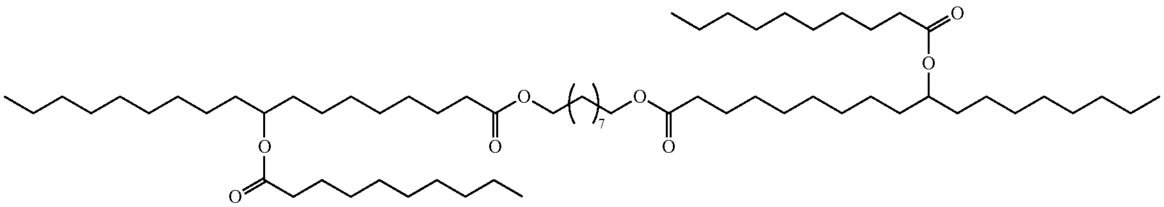
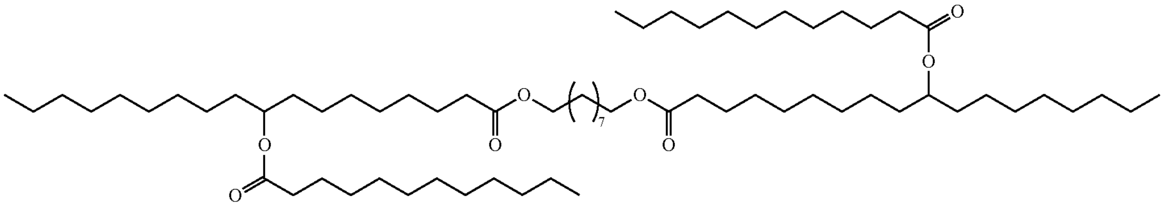
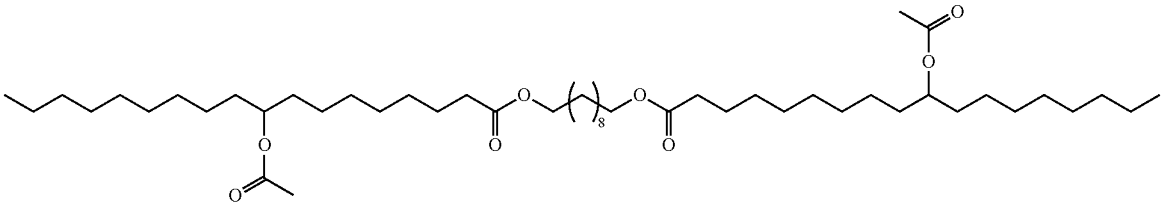
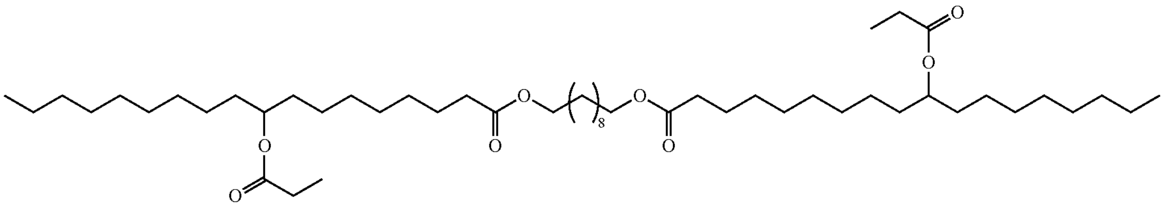
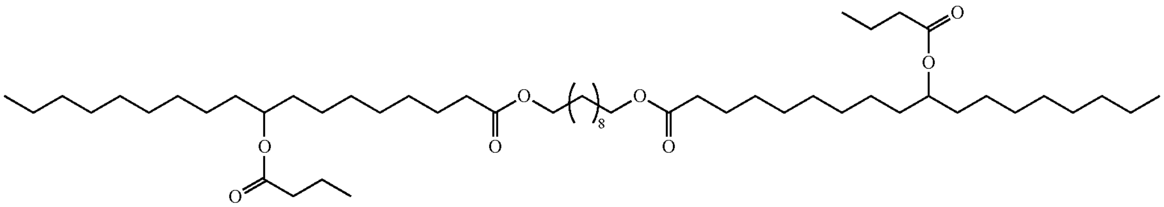

-continued
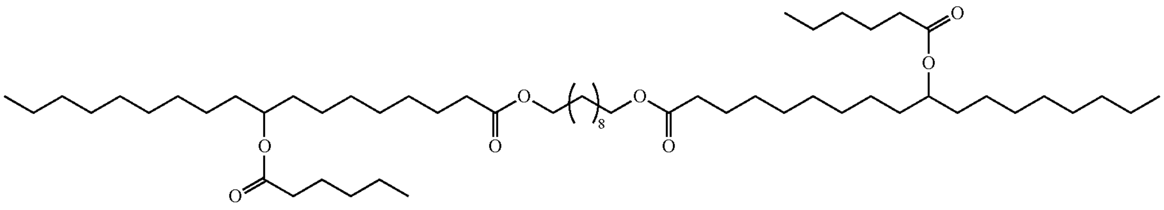
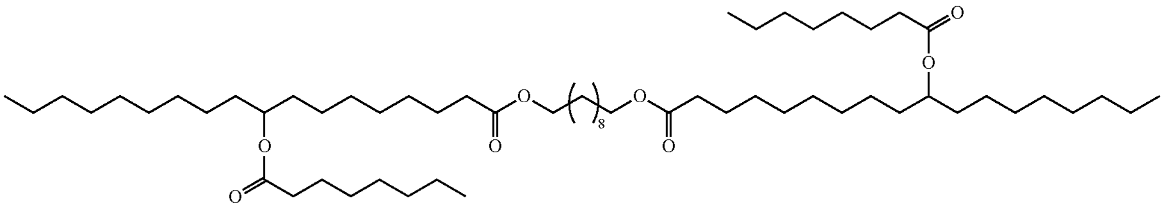
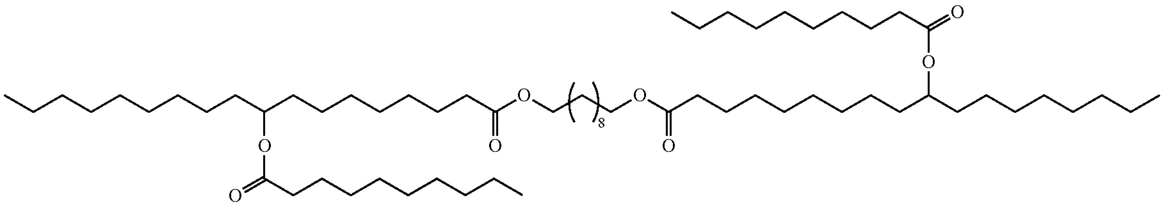
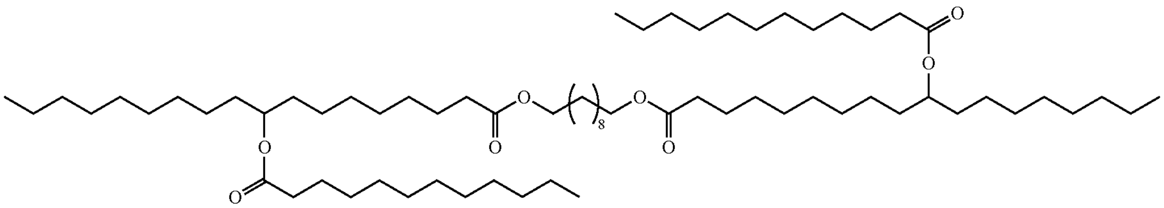
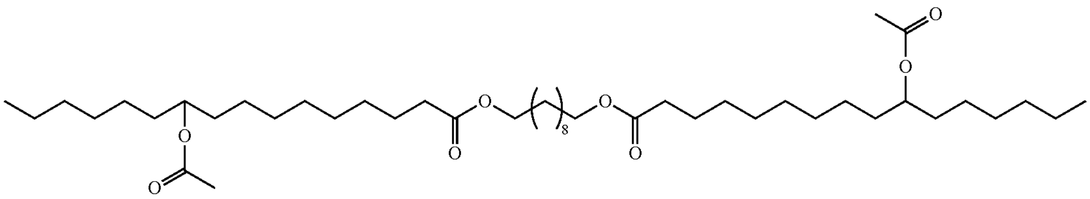
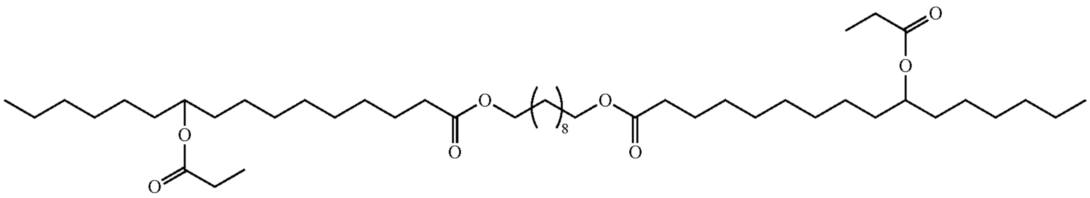
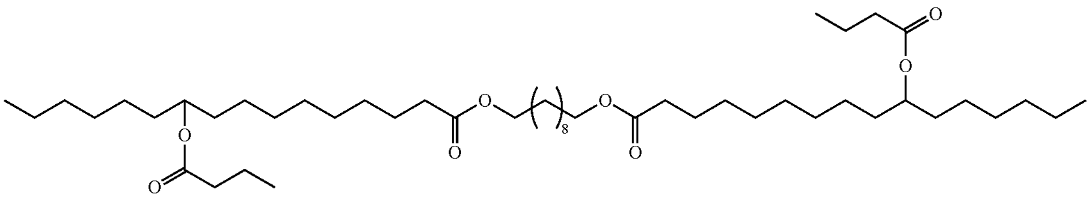
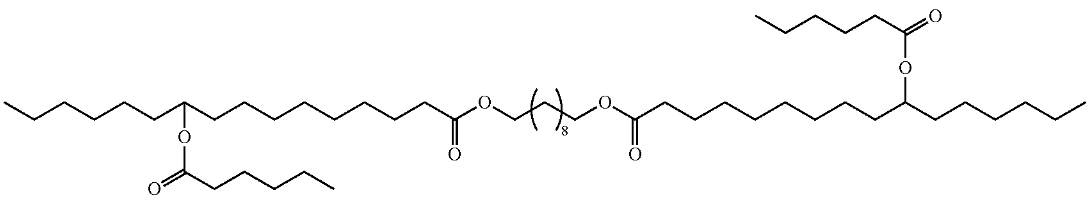

-continued
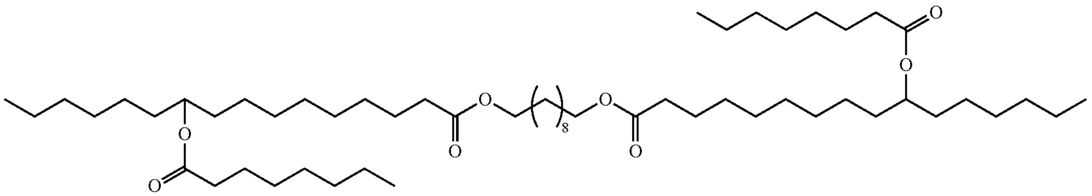
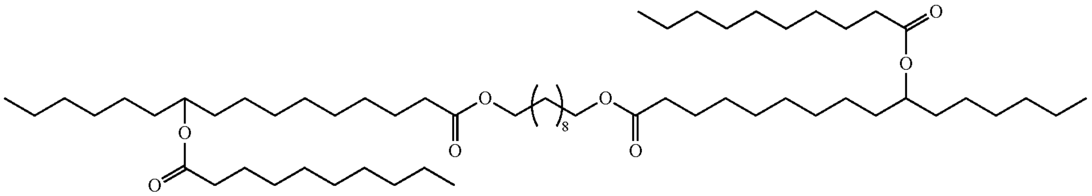
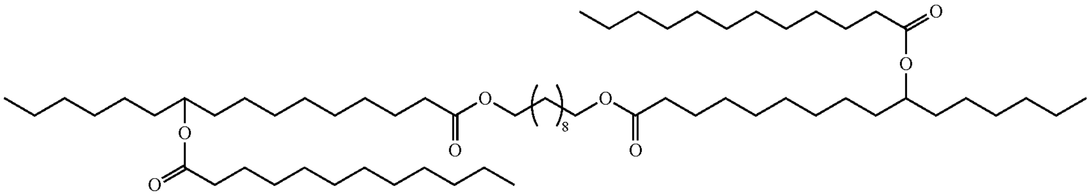
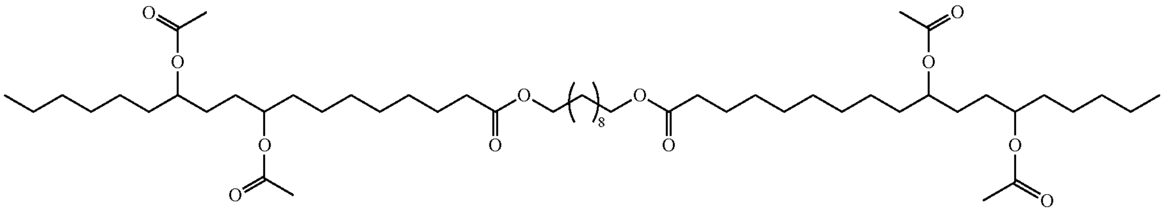
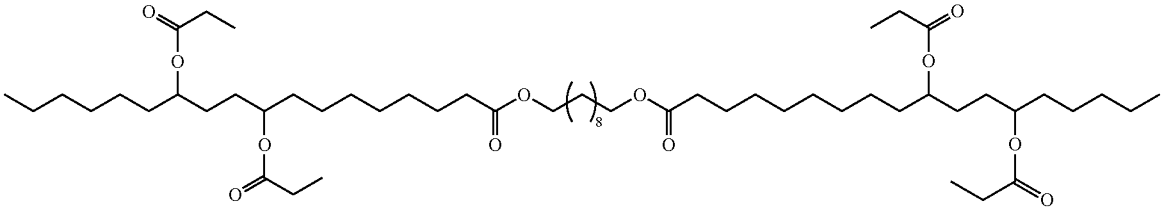
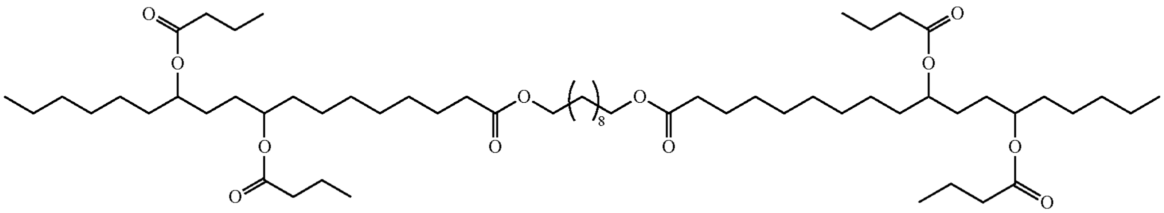
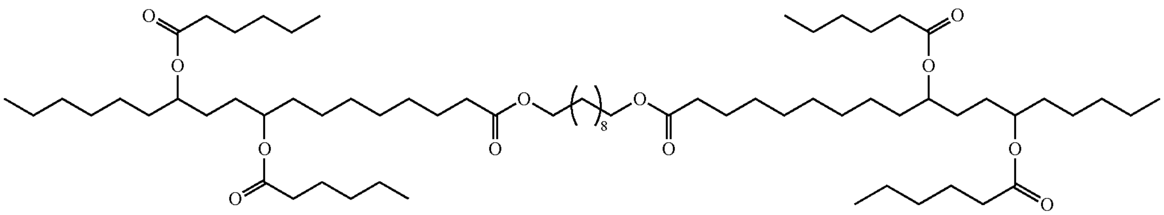
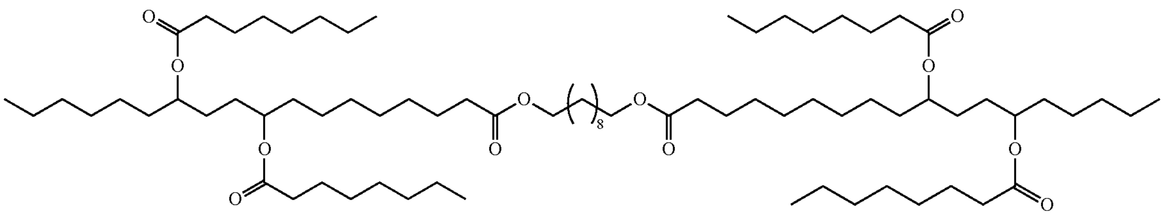

-continued
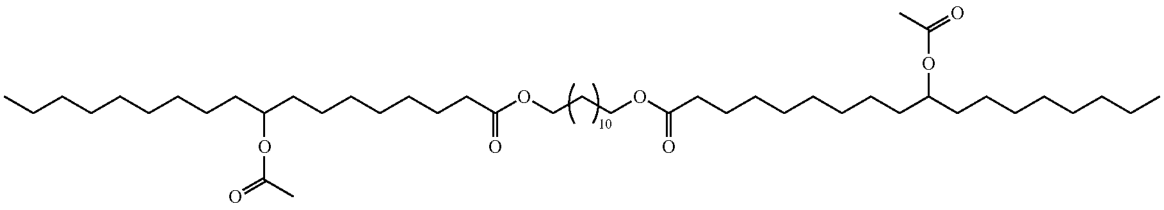
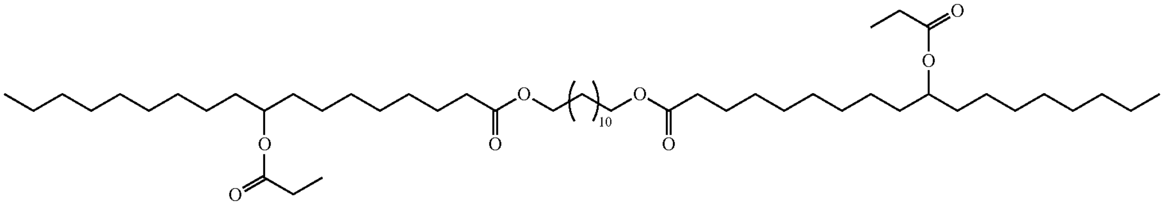
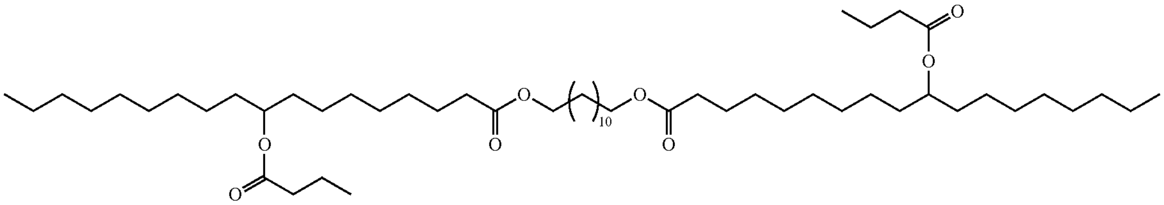
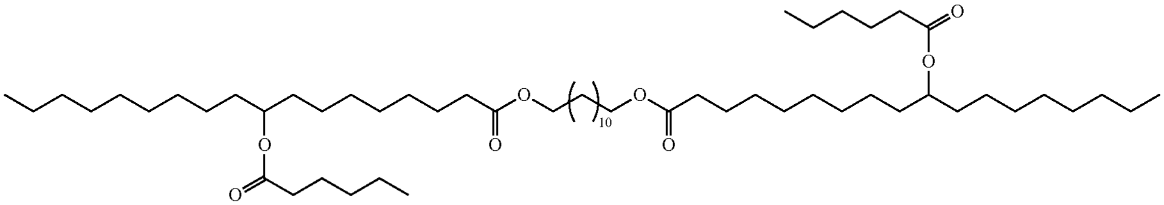
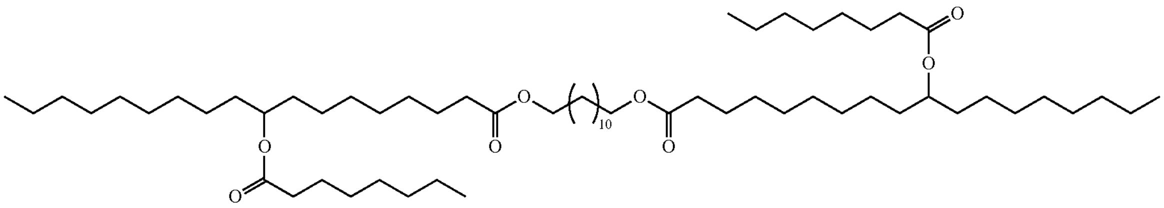
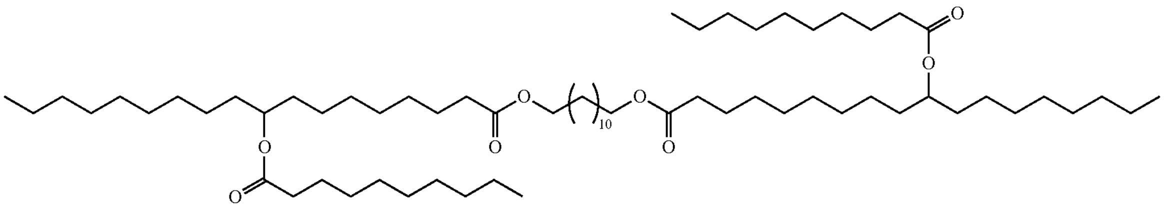
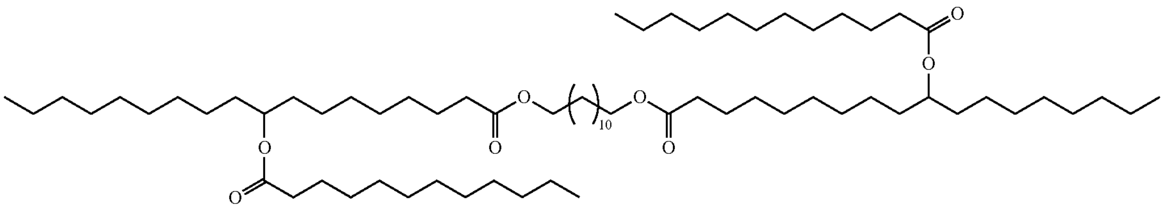
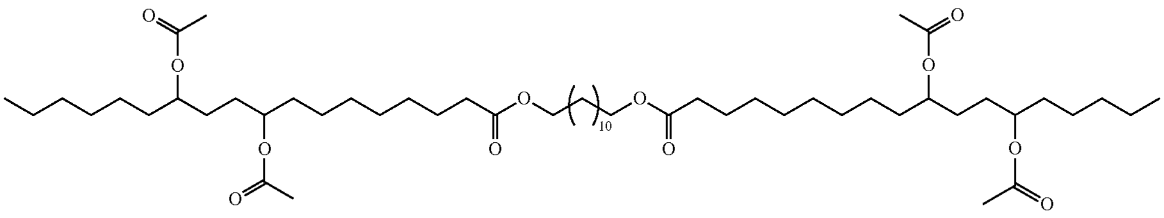

-continued
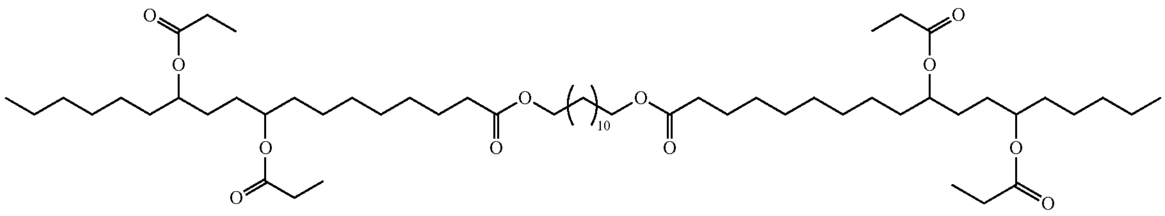
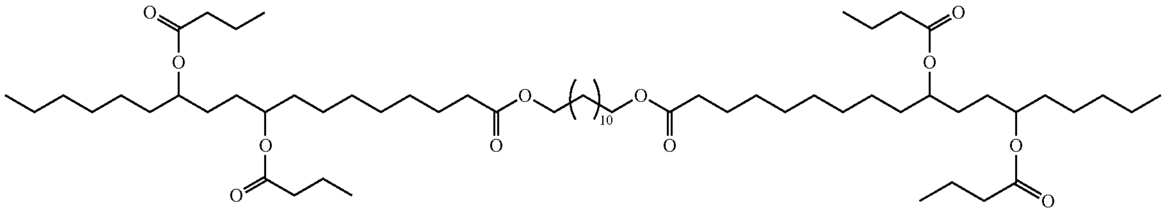
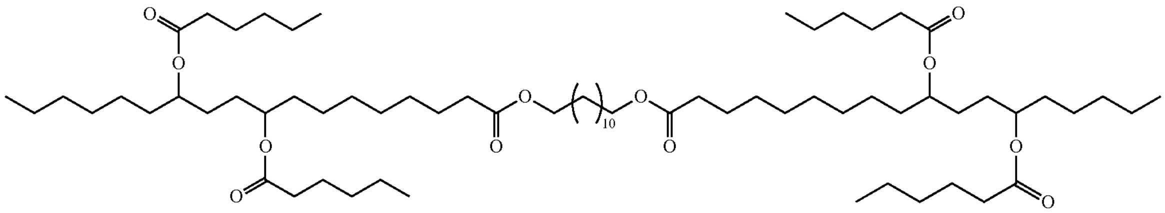
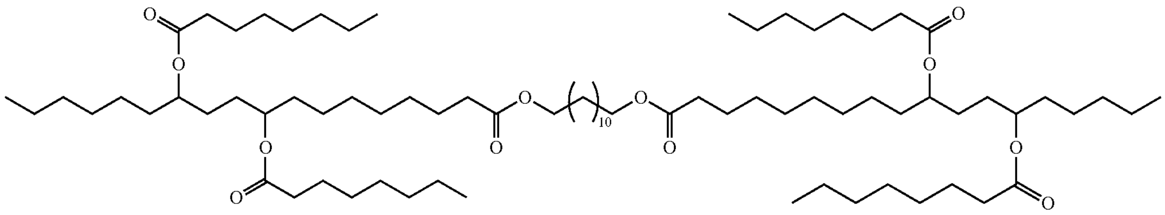
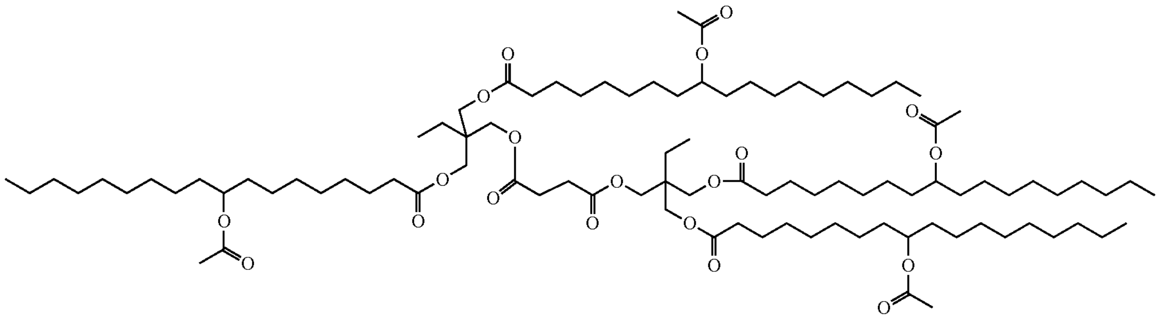
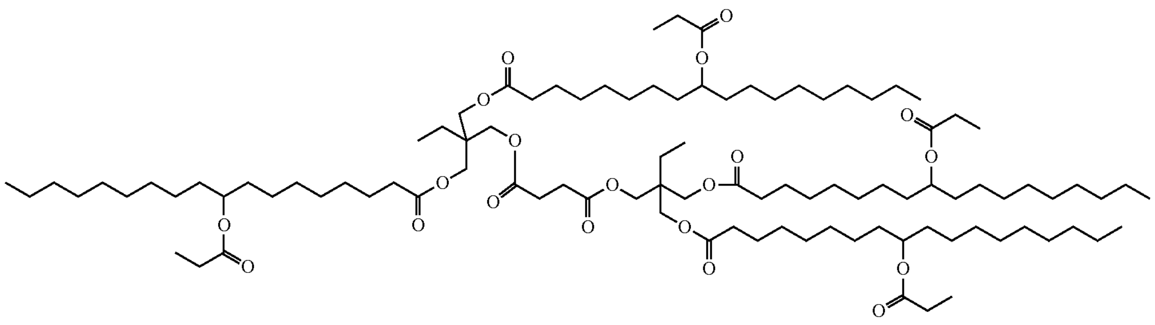

-continued
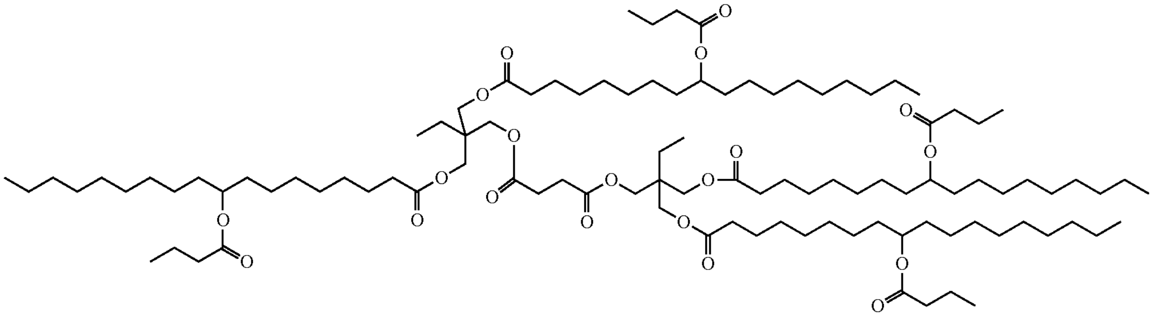
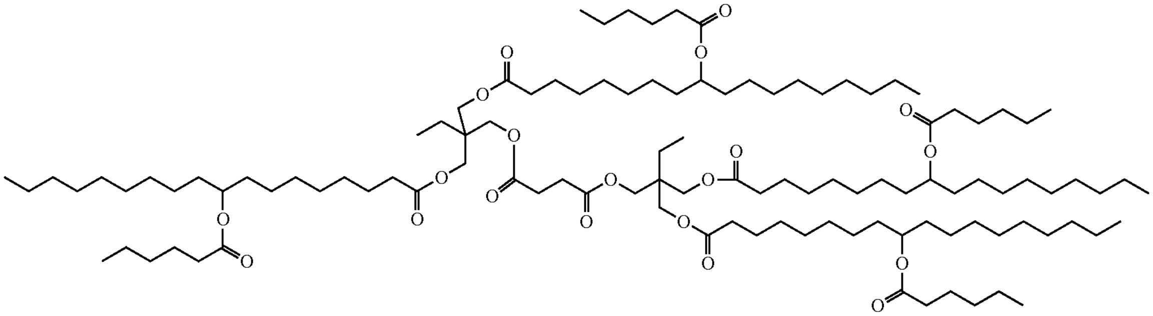
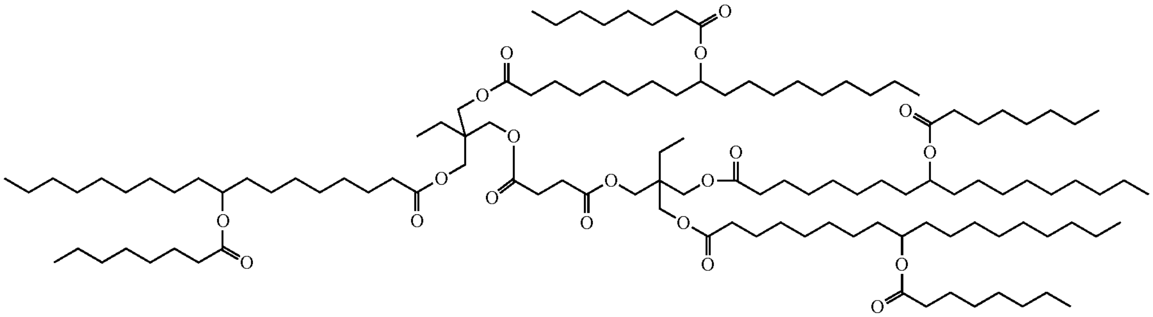
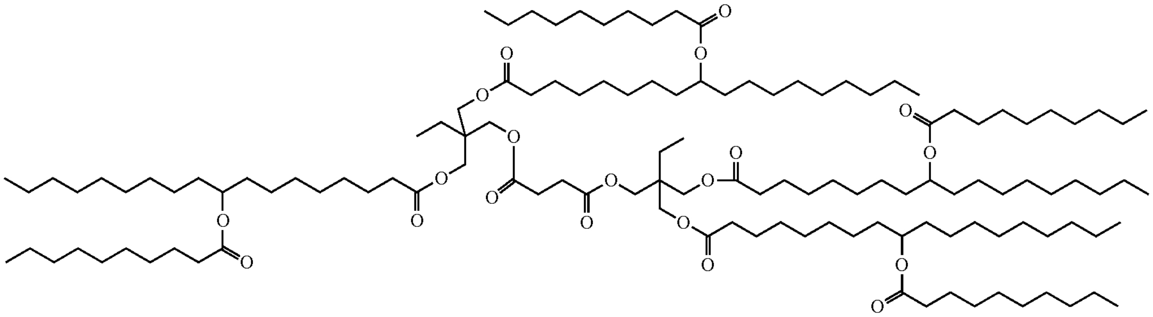
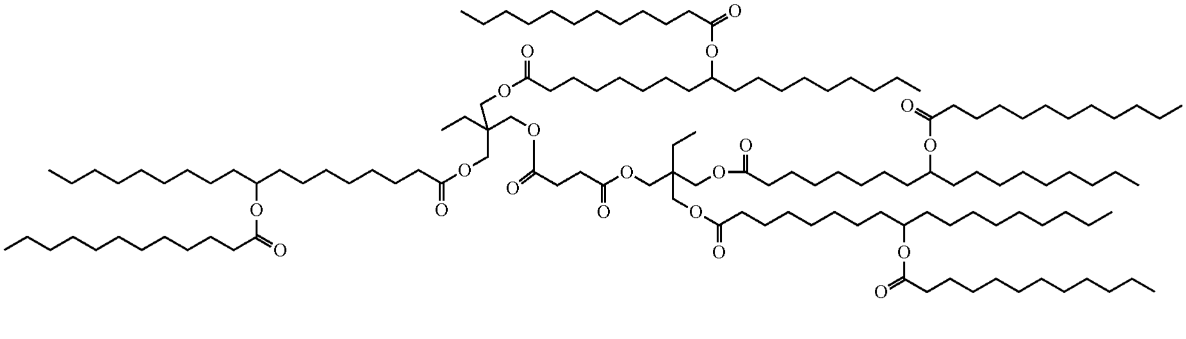

-continued
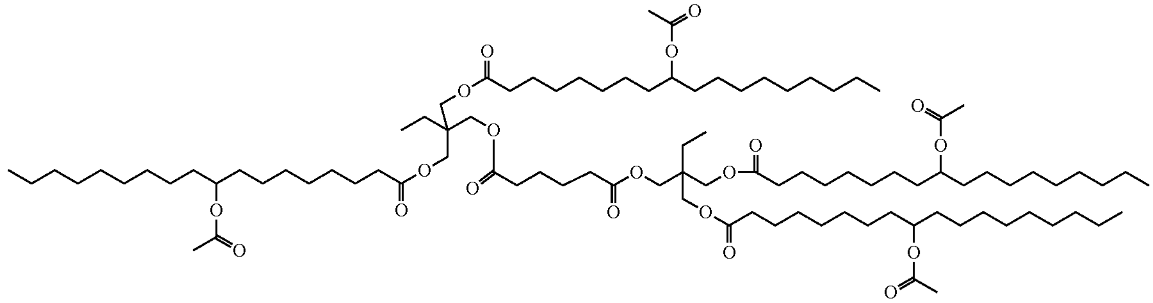
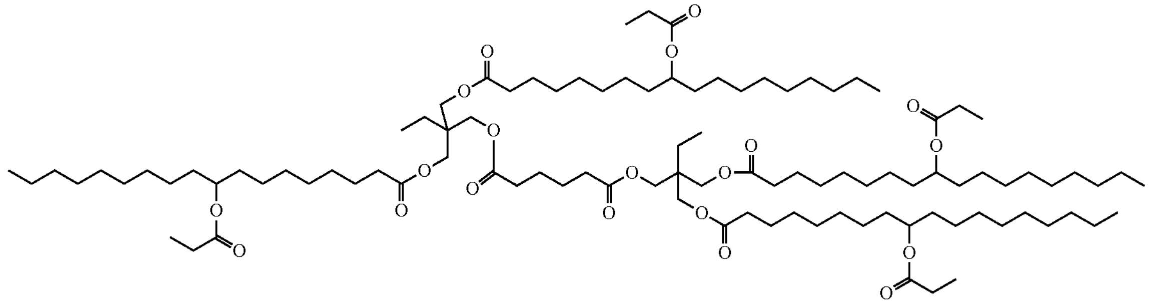
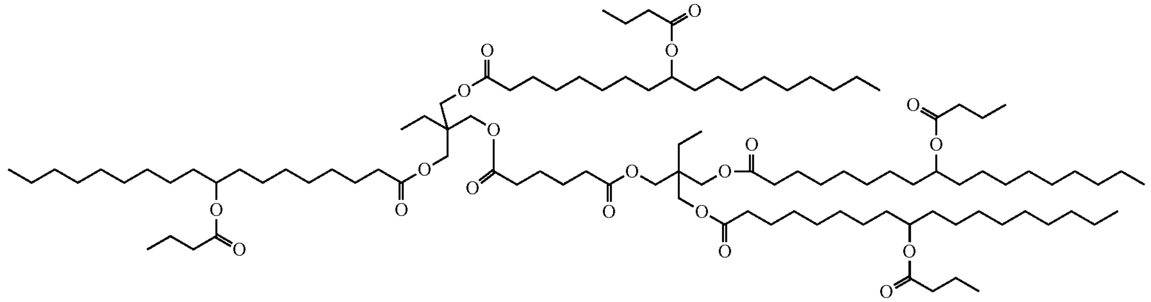
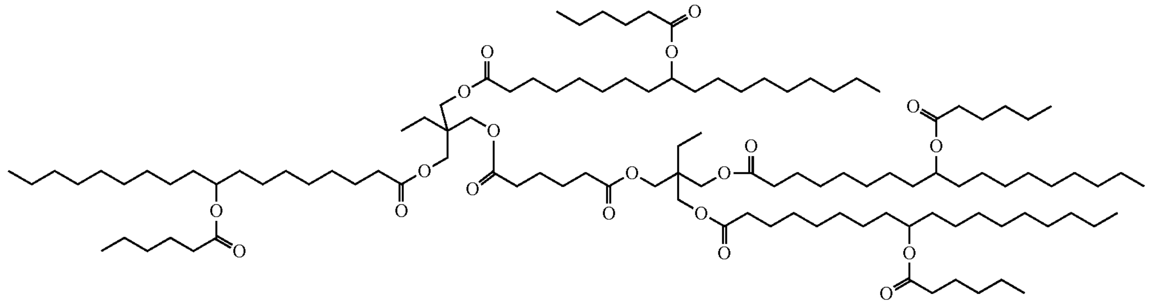
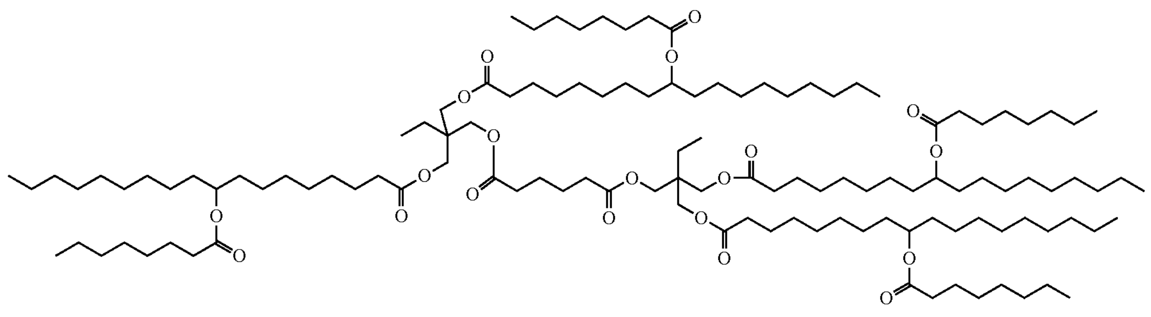

-continued
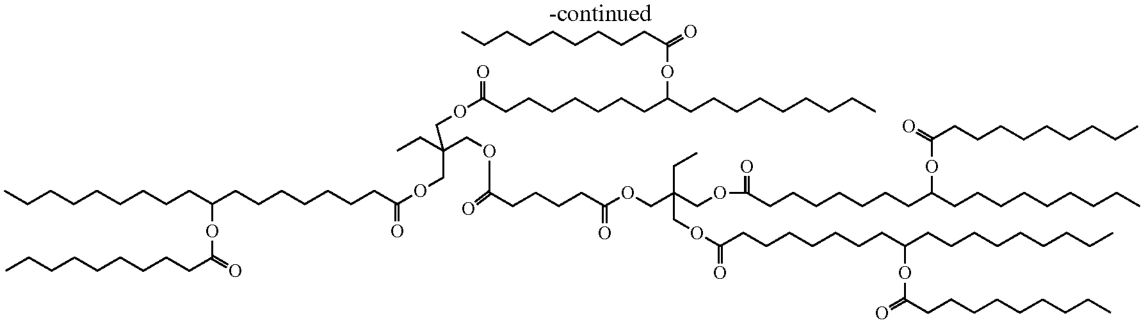
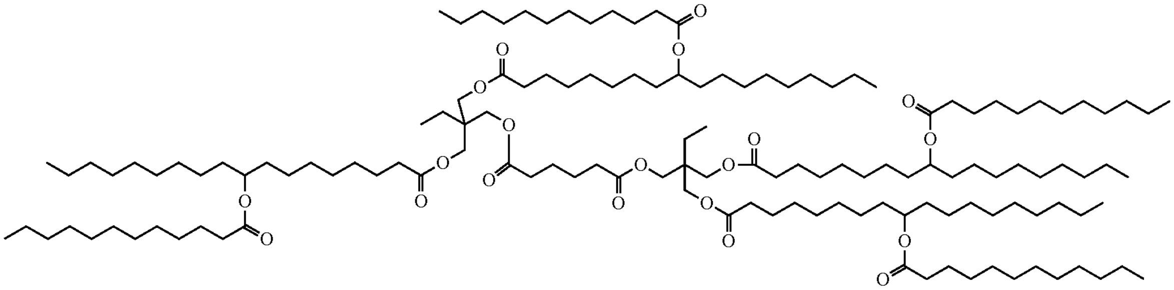
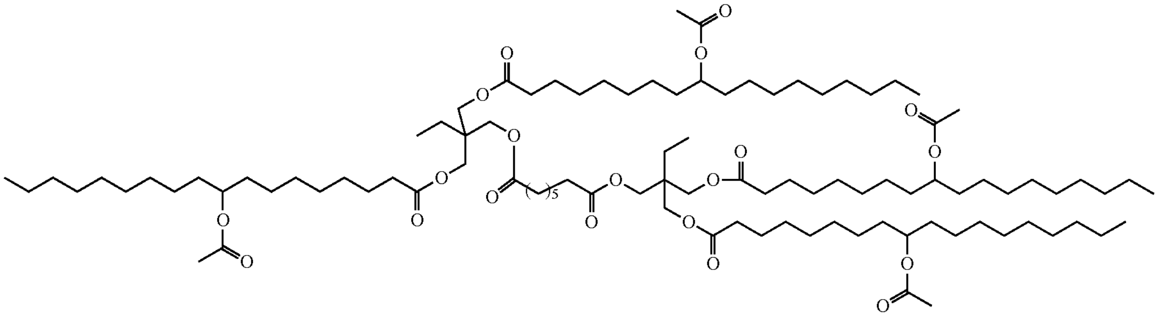
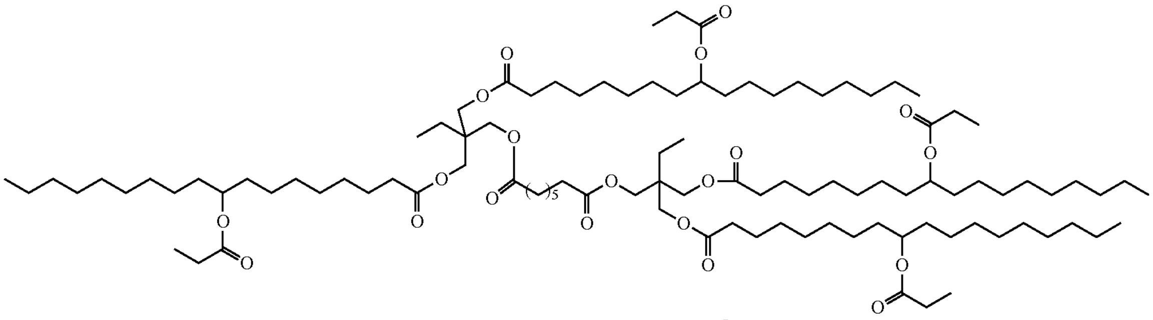
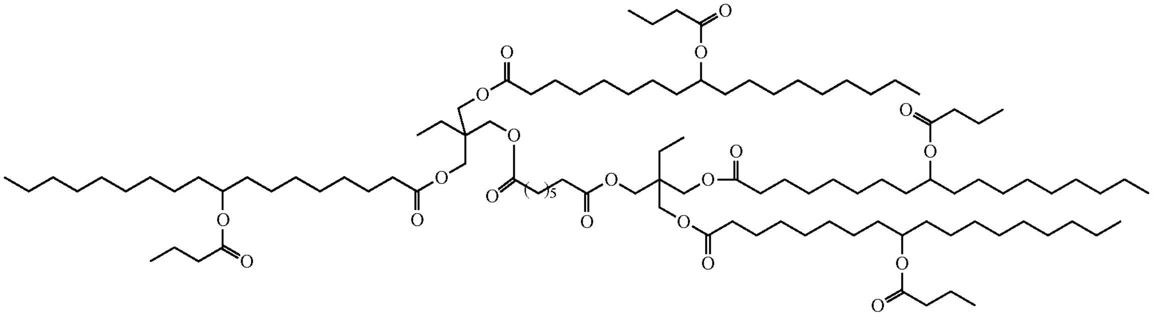

-continued
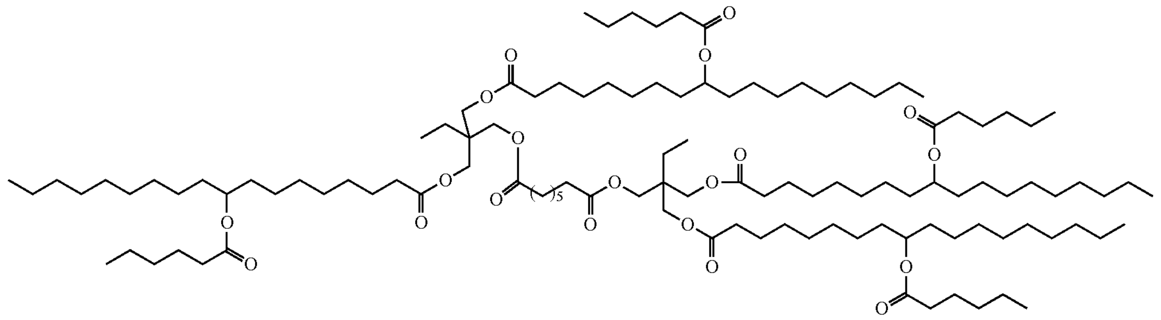
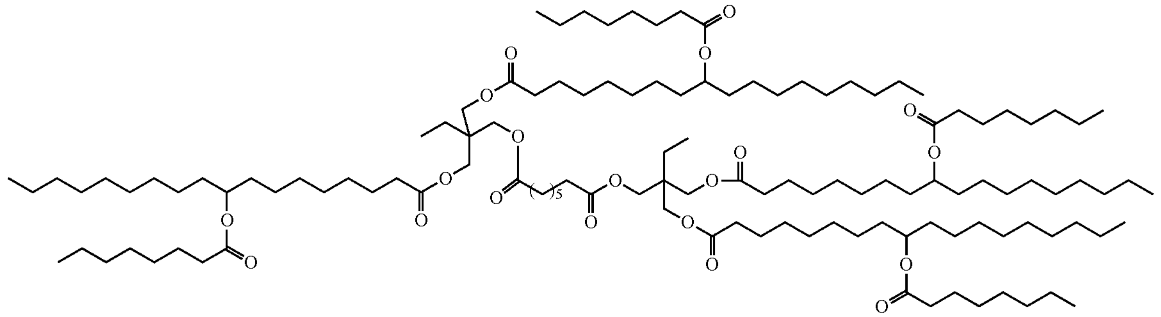
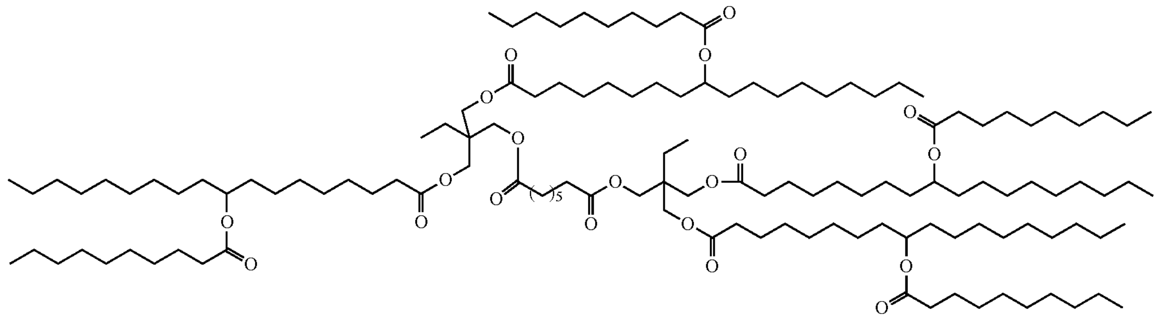
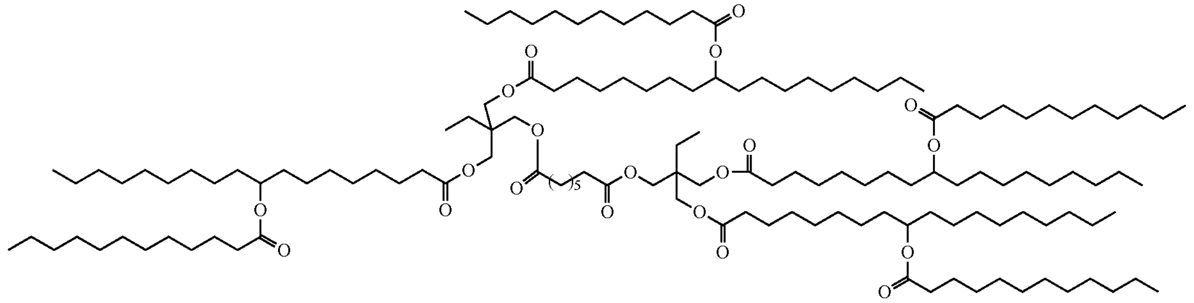
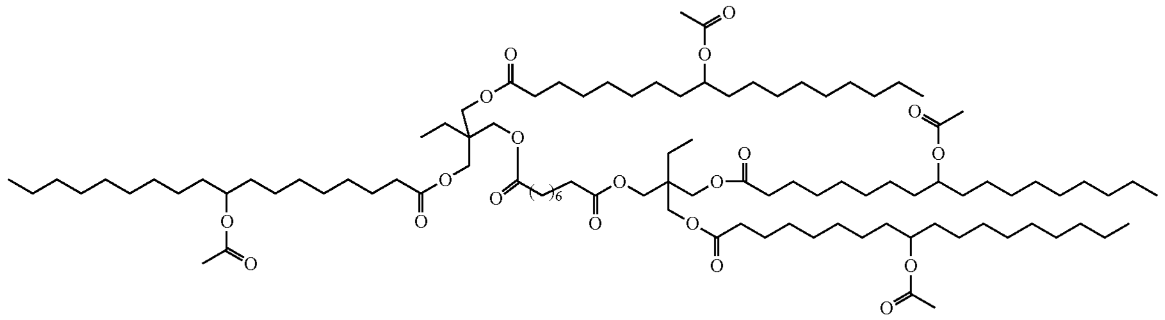

-continued
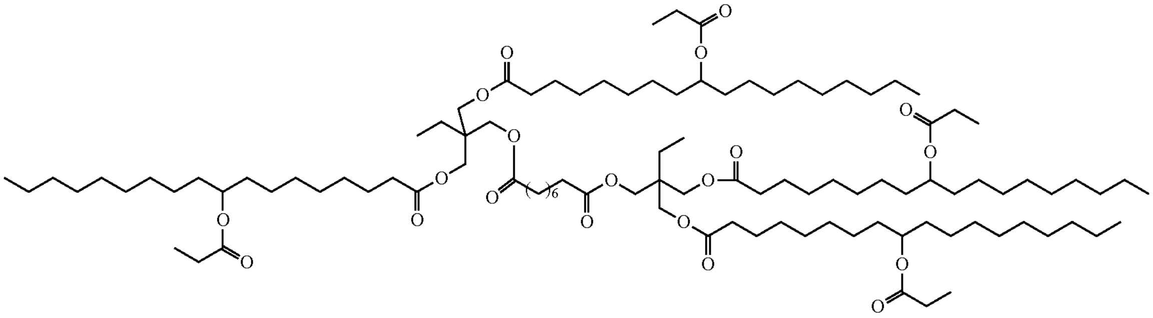
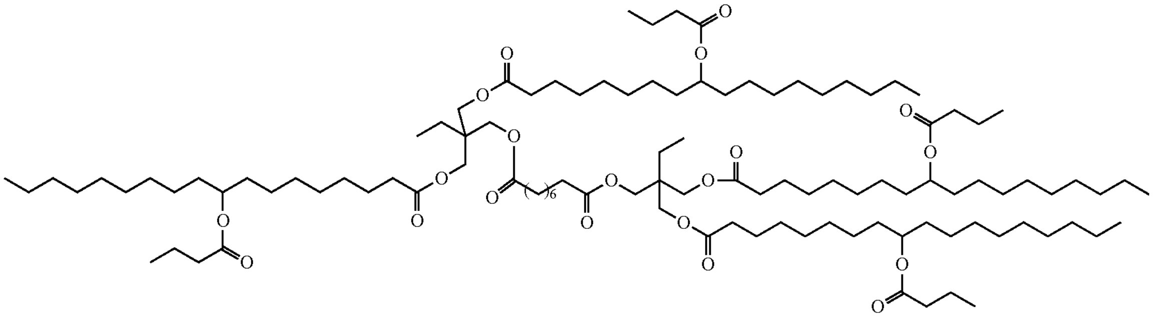
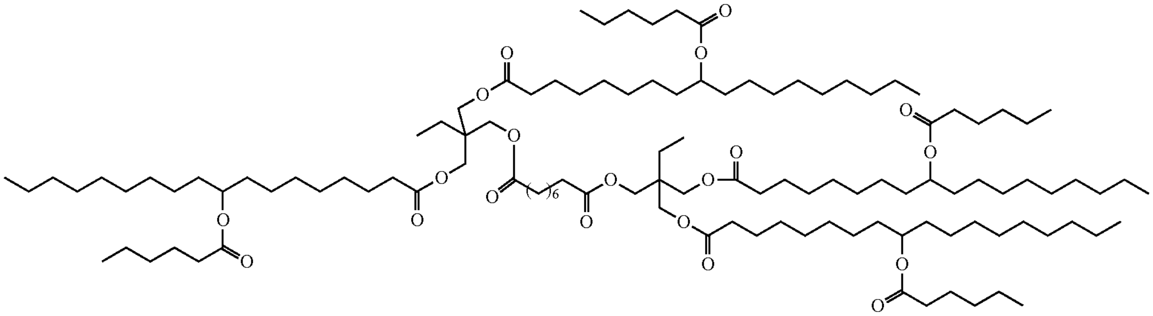
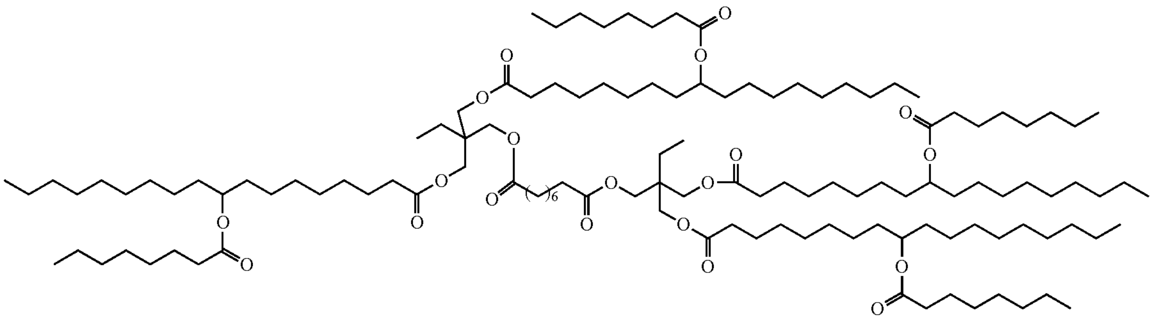
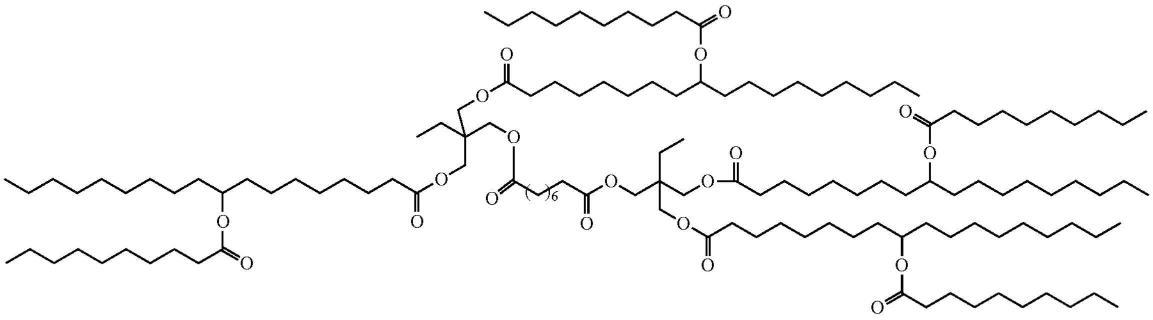

-continued
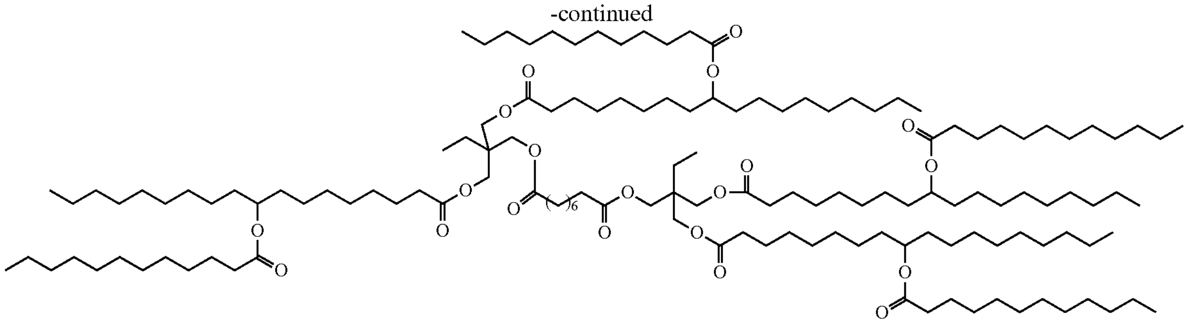

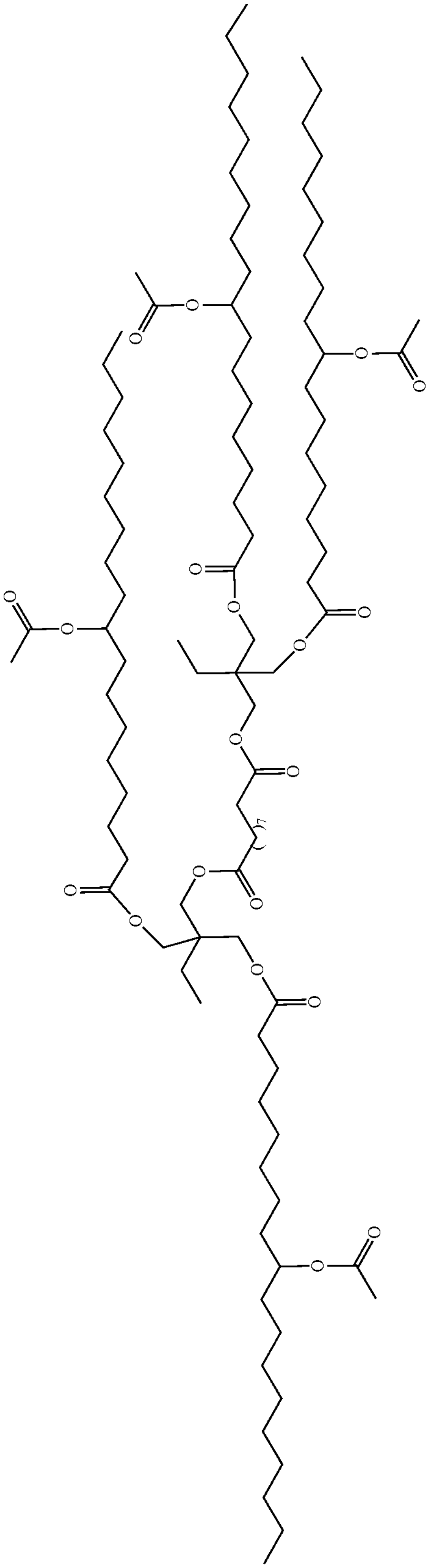
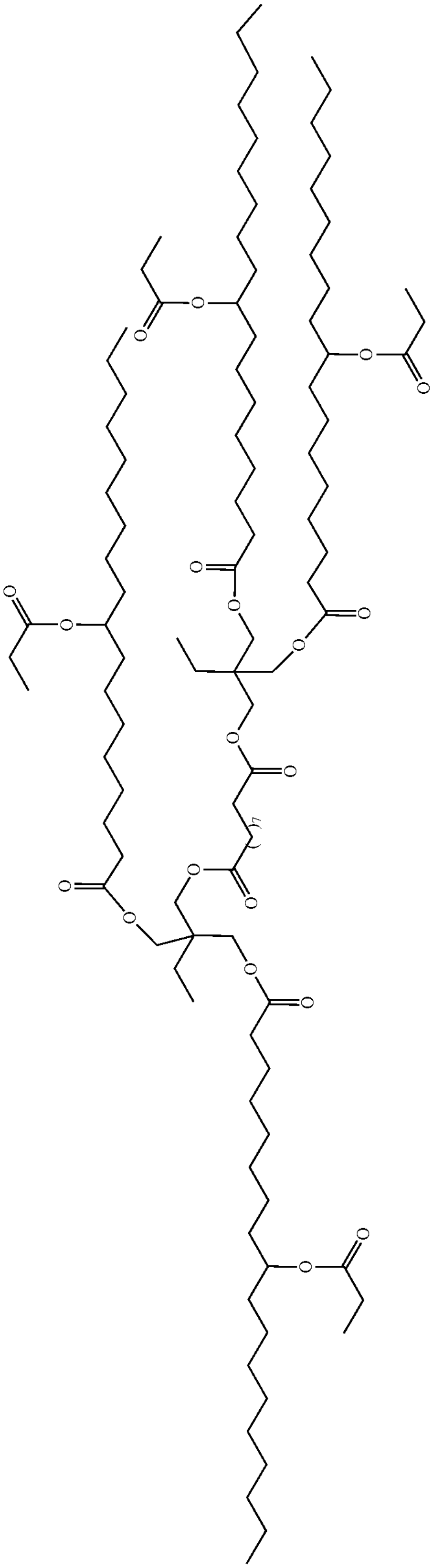

-continued
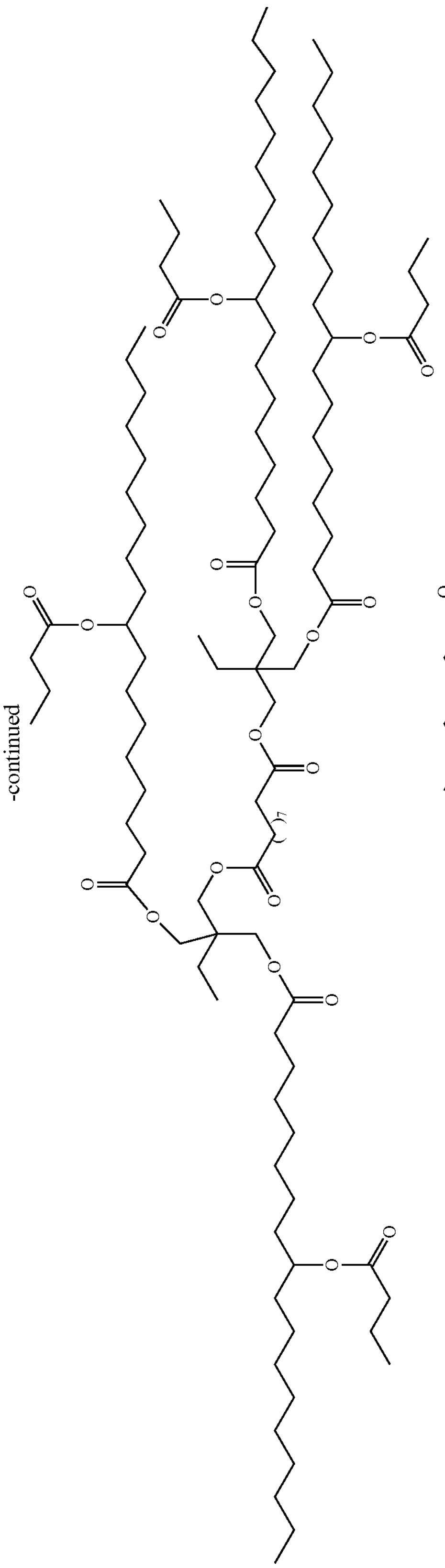
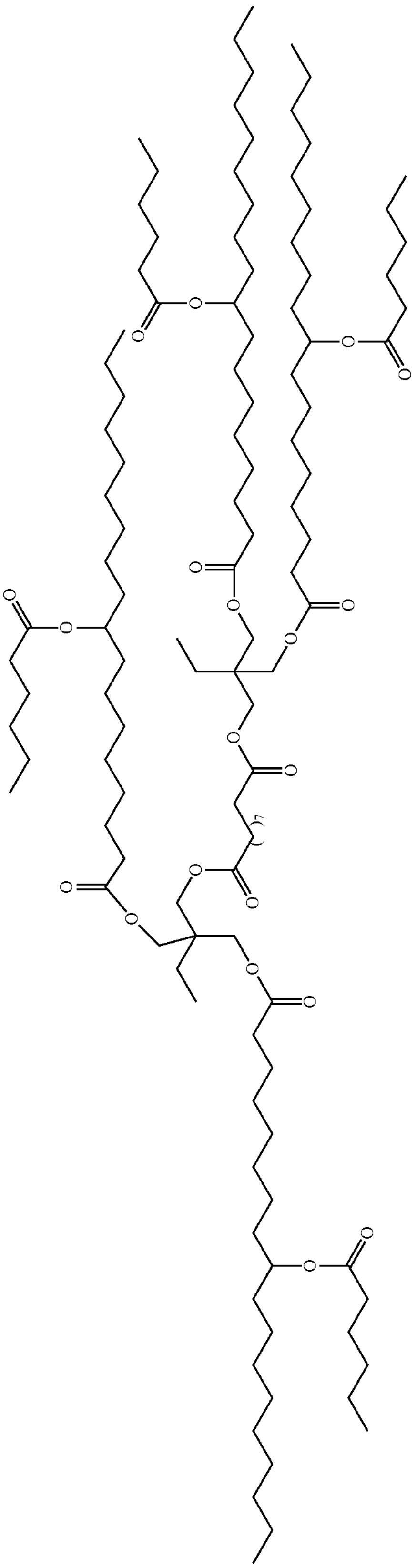

-continued
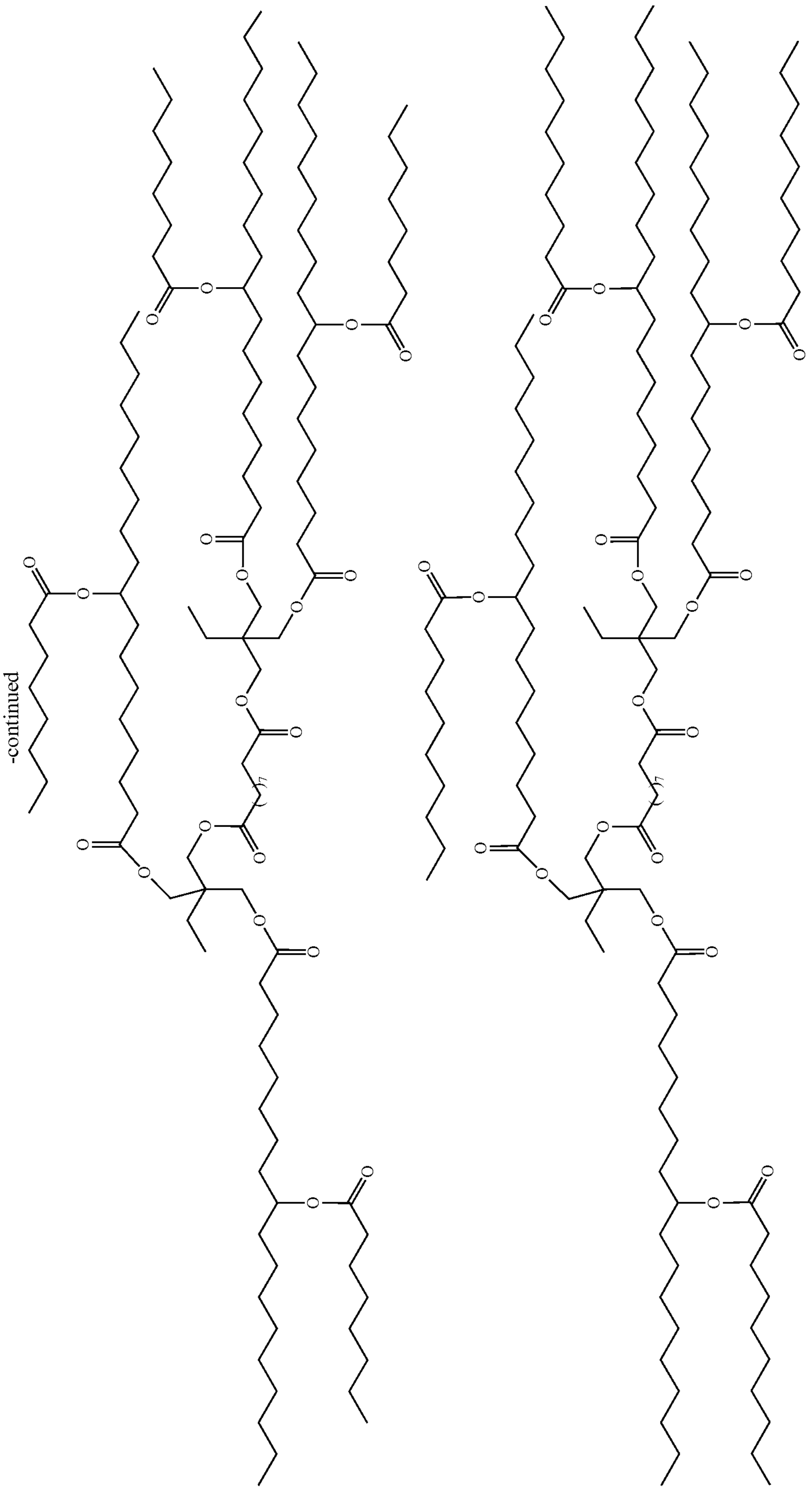

-continued
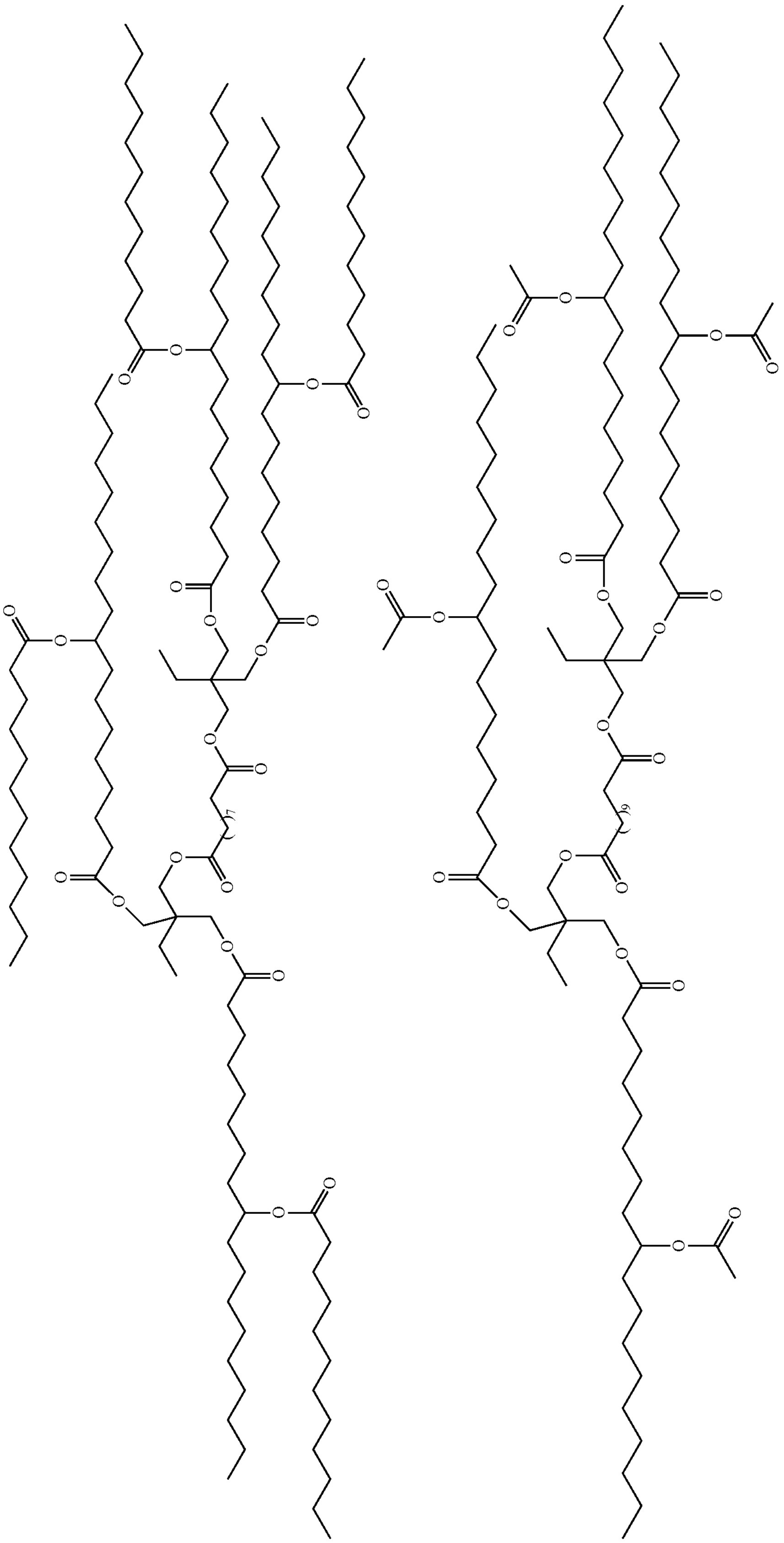

-continued
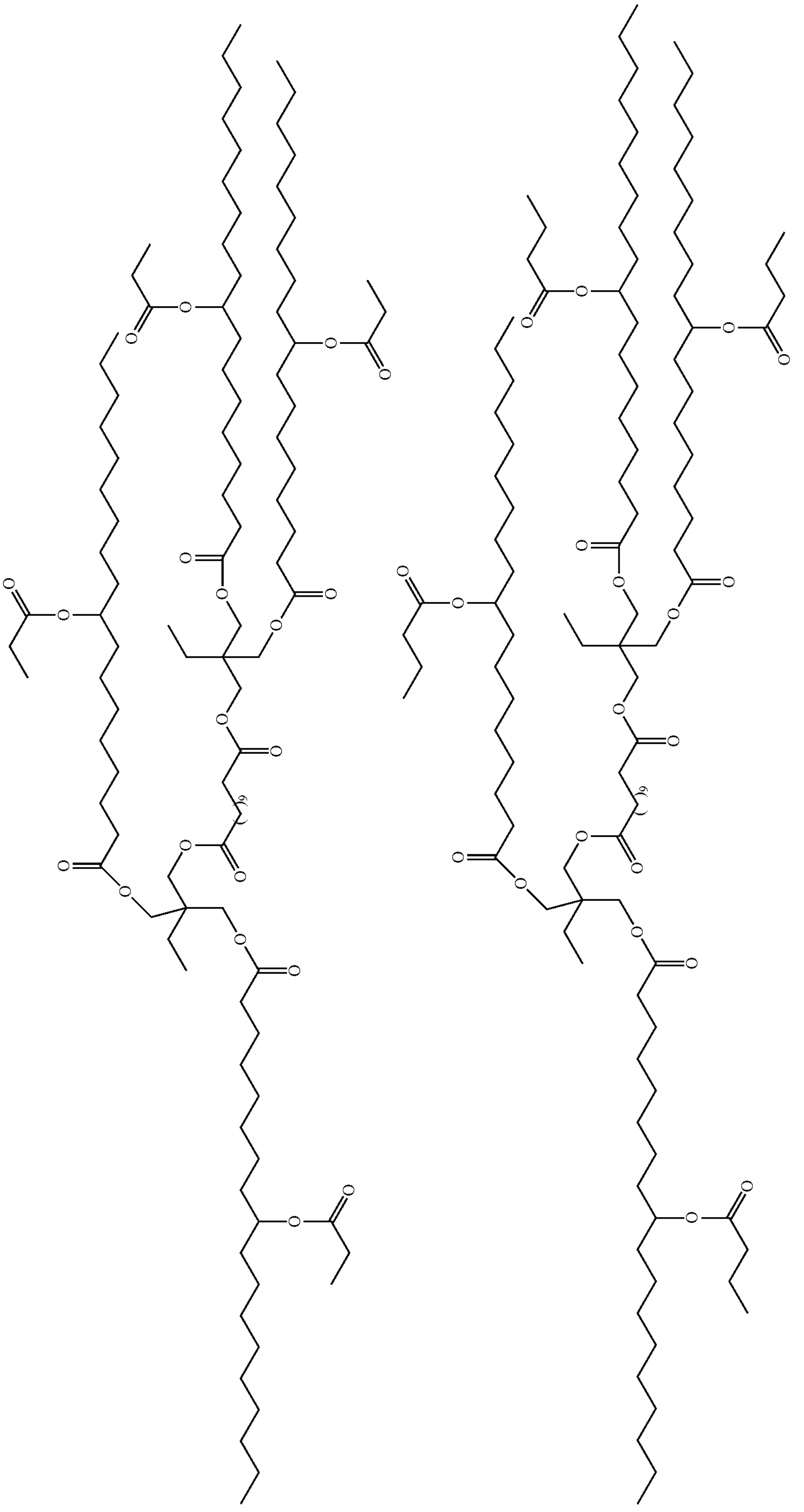

-continued
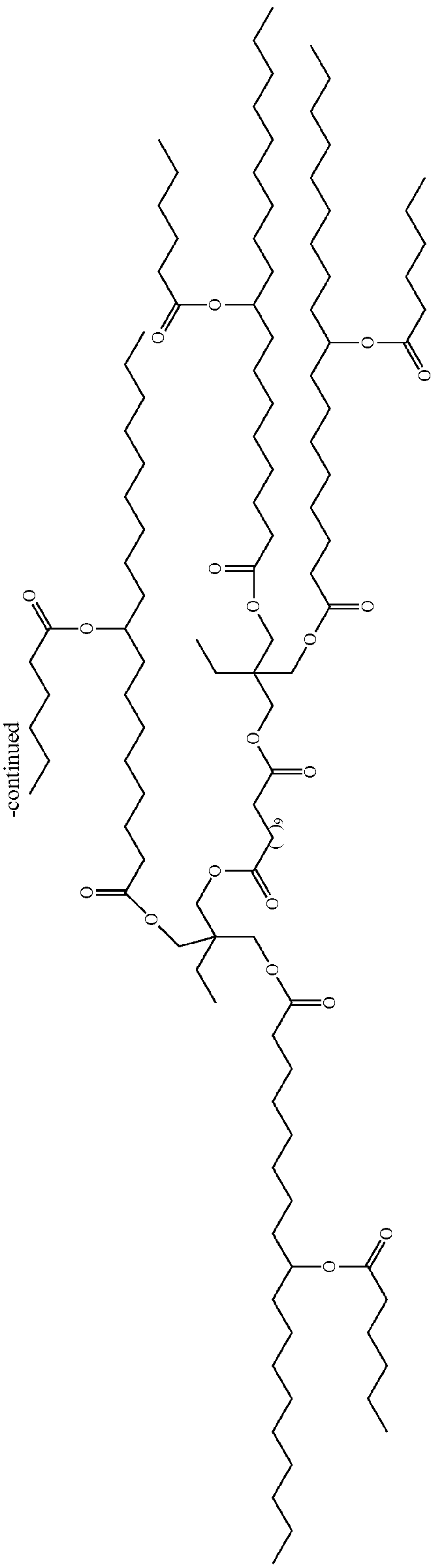
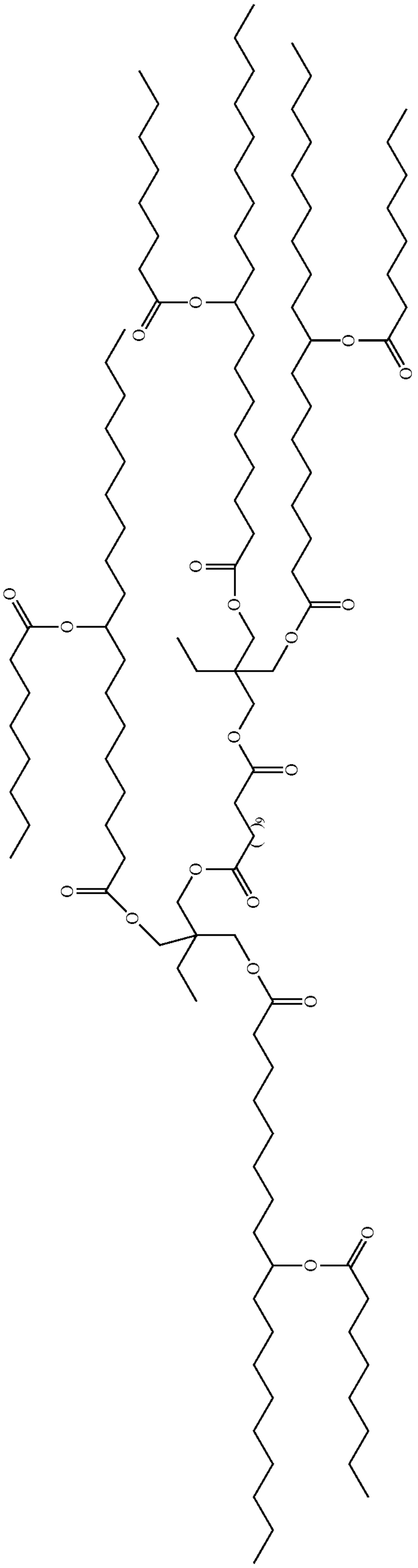

-continued
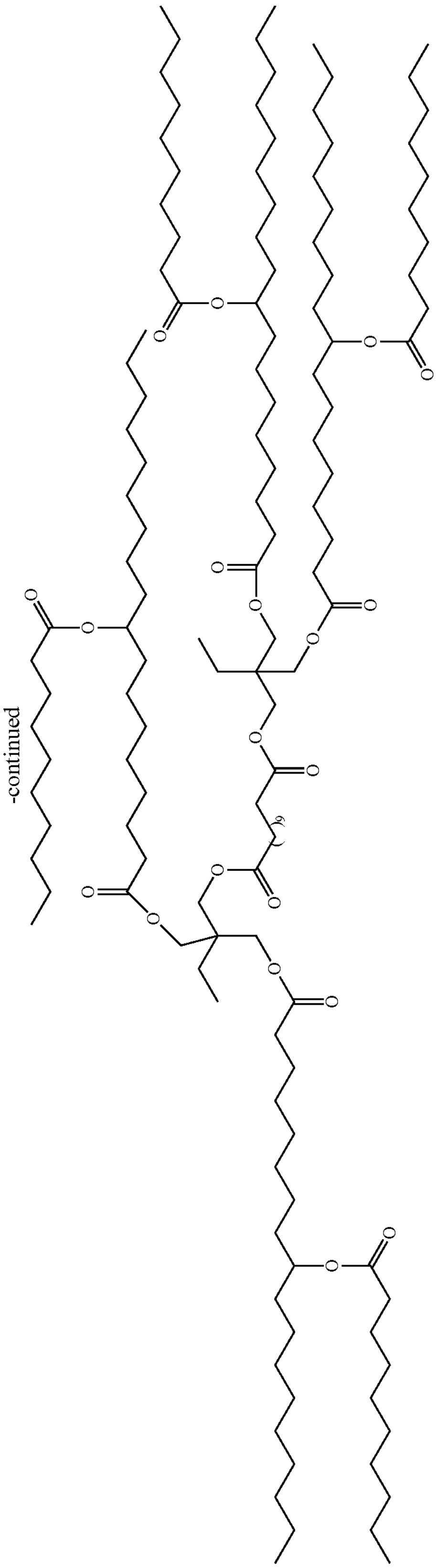
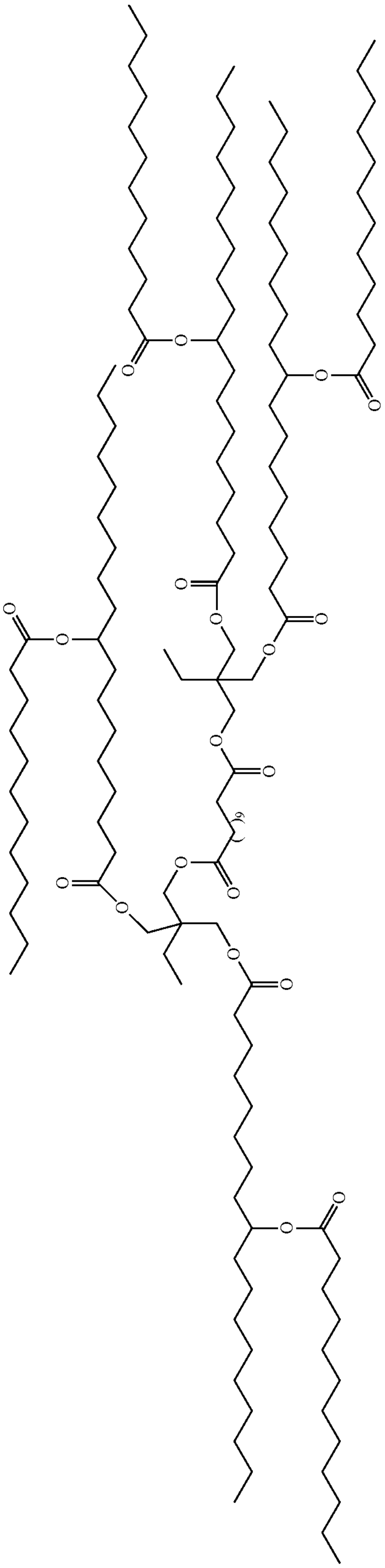

-continued
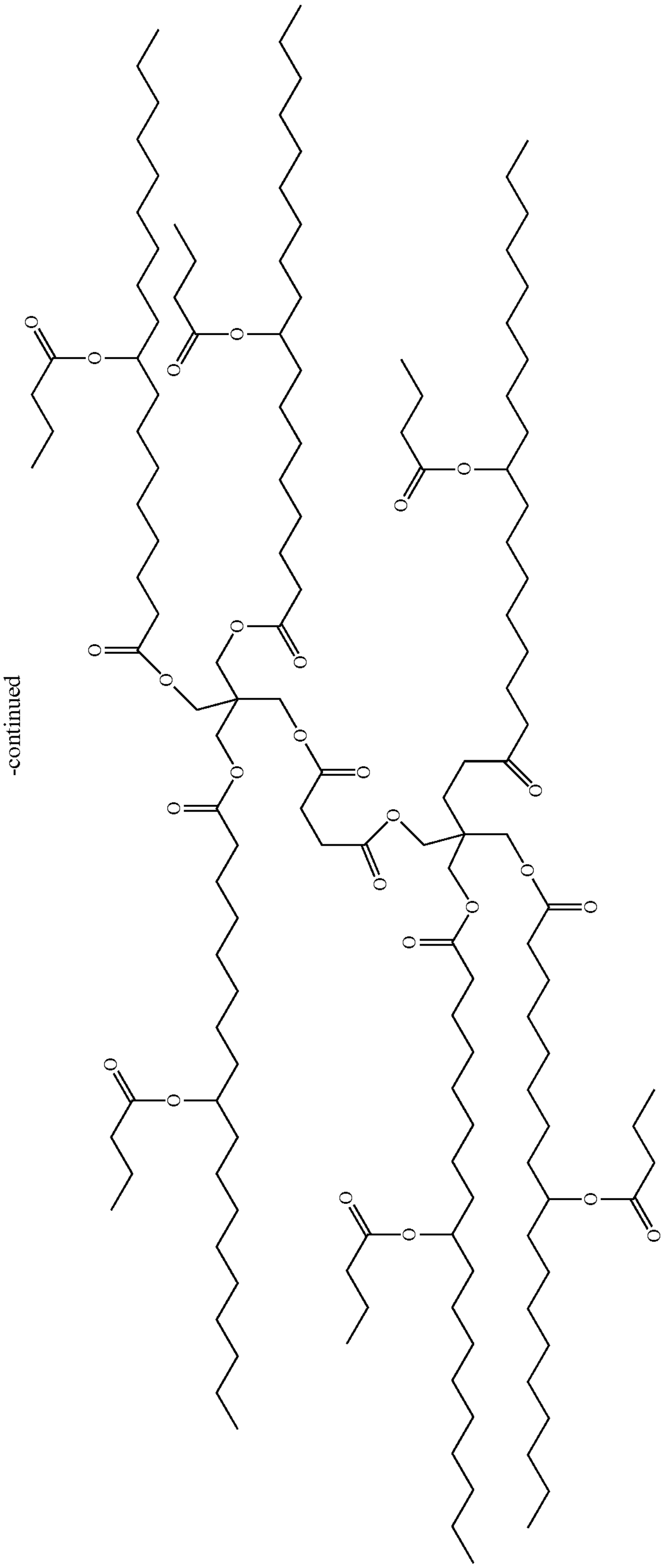

-continued
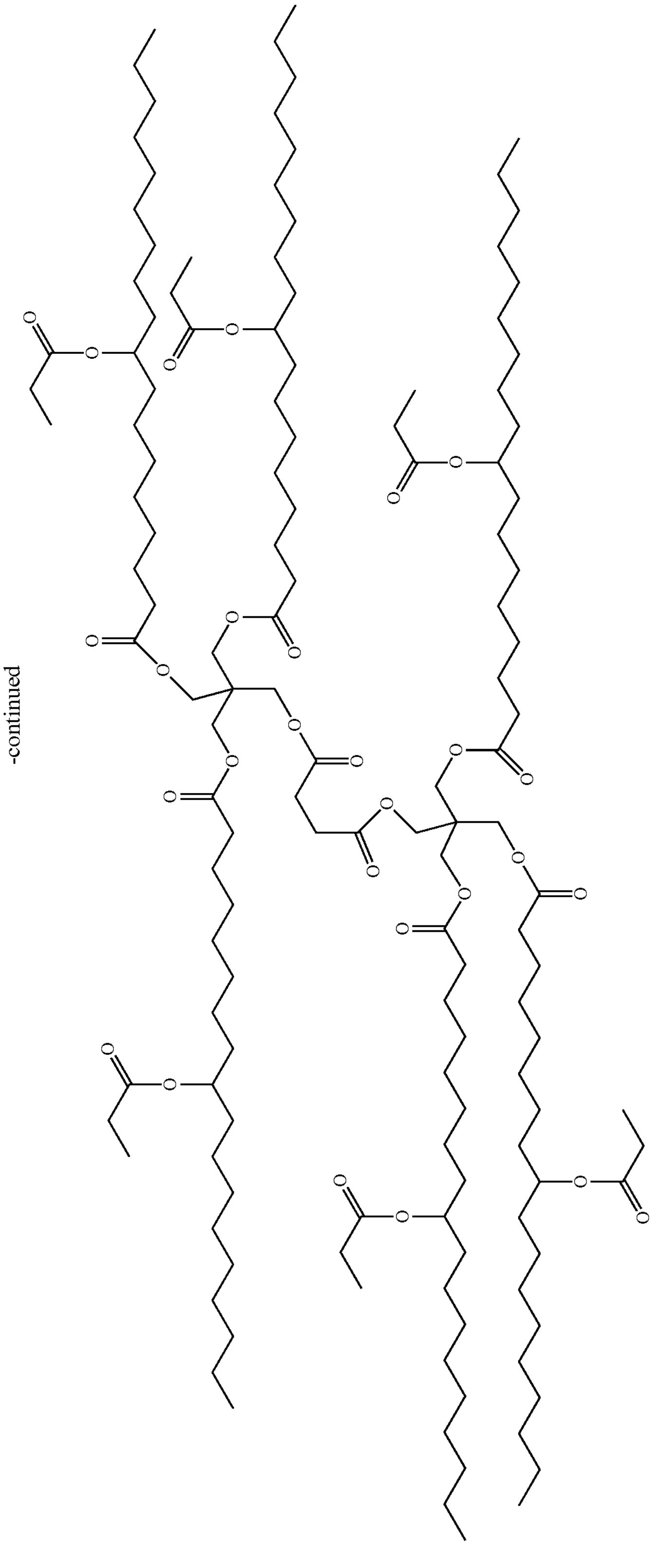

-continued
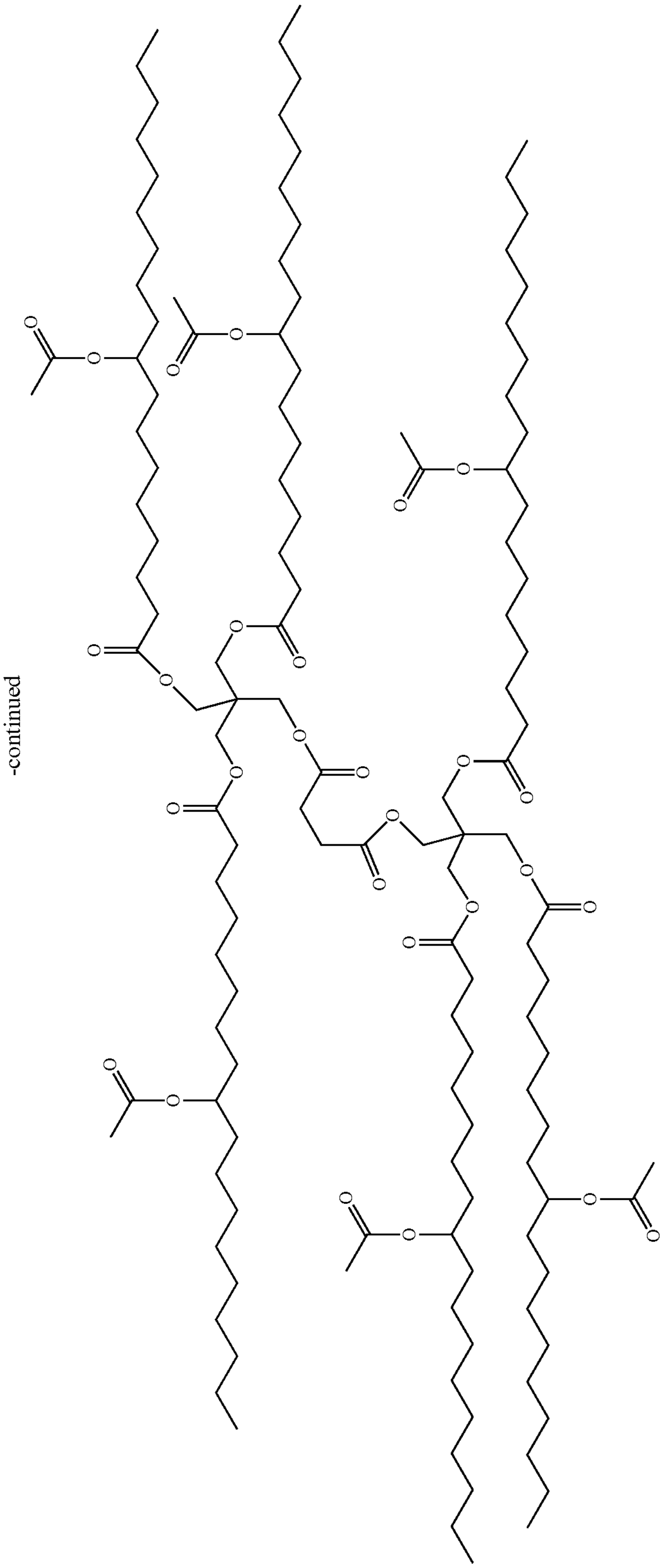

-continued
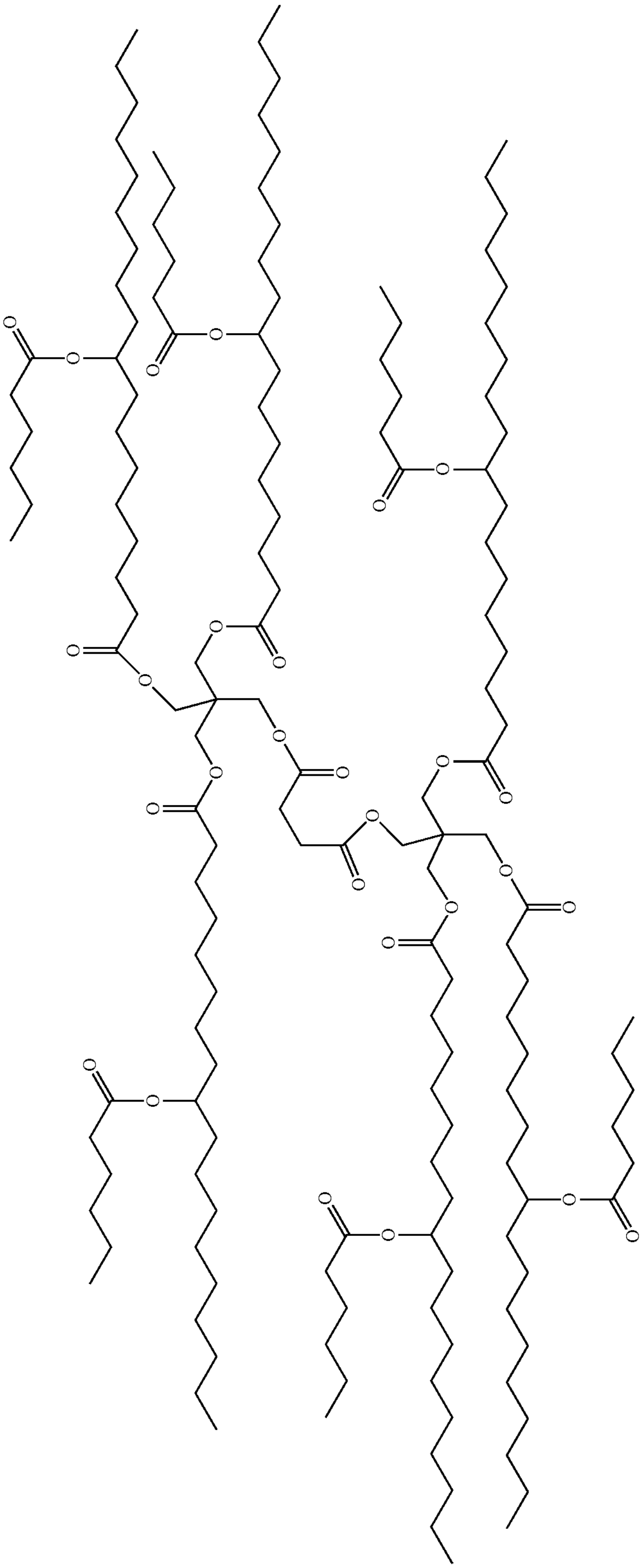

-continued
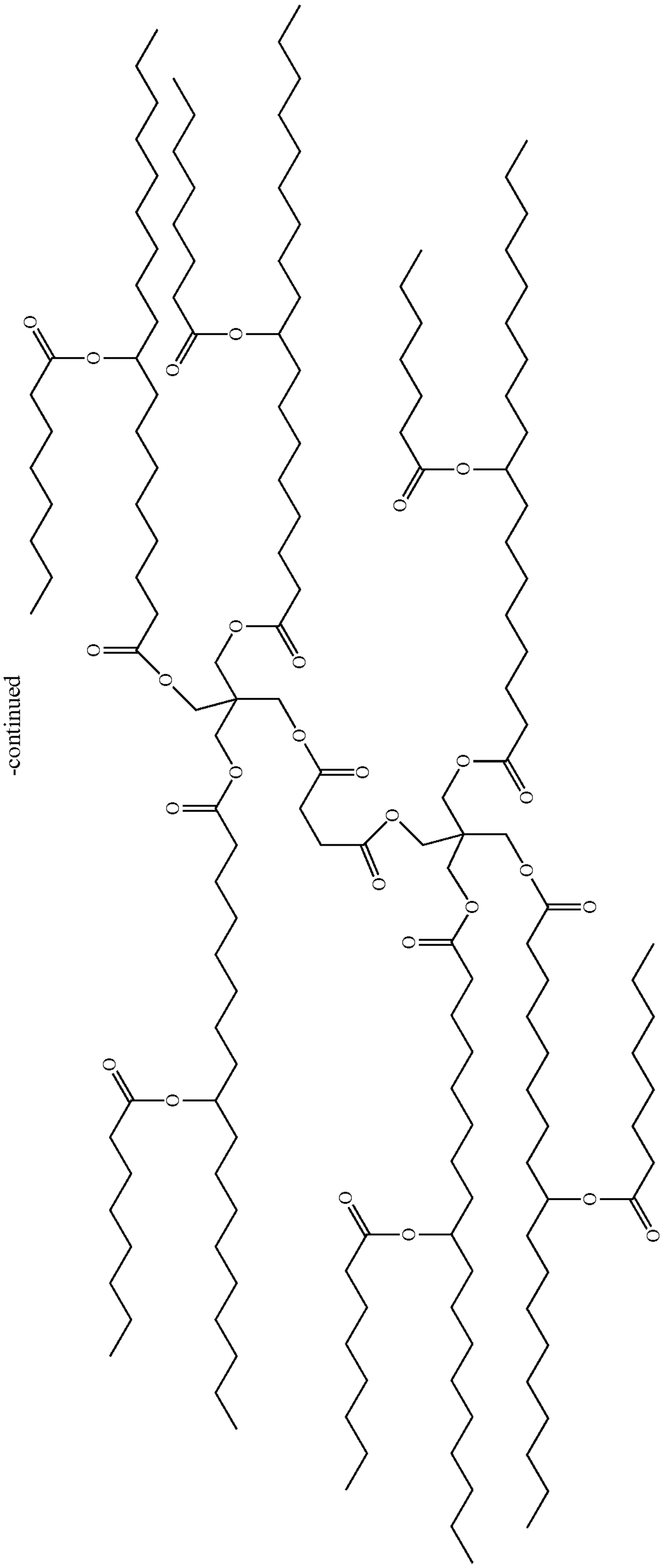

-continued
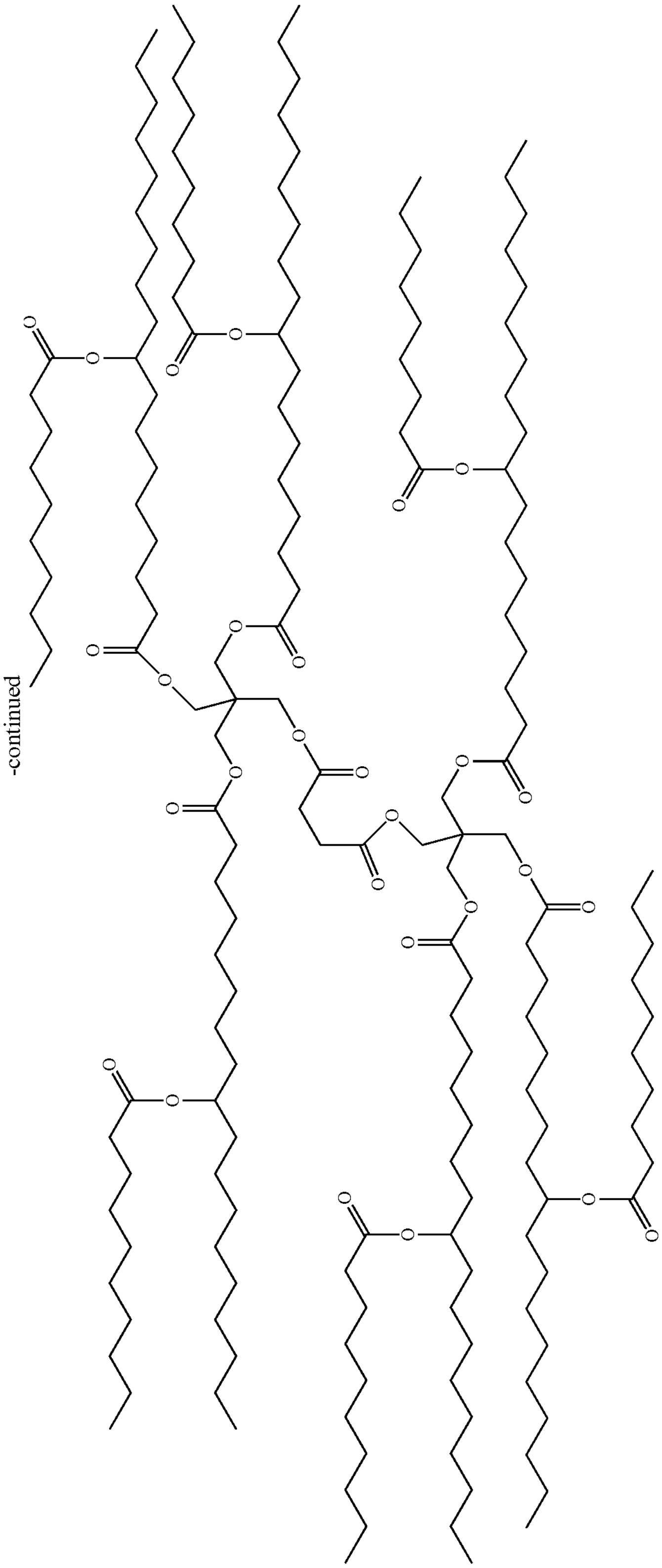

-continued
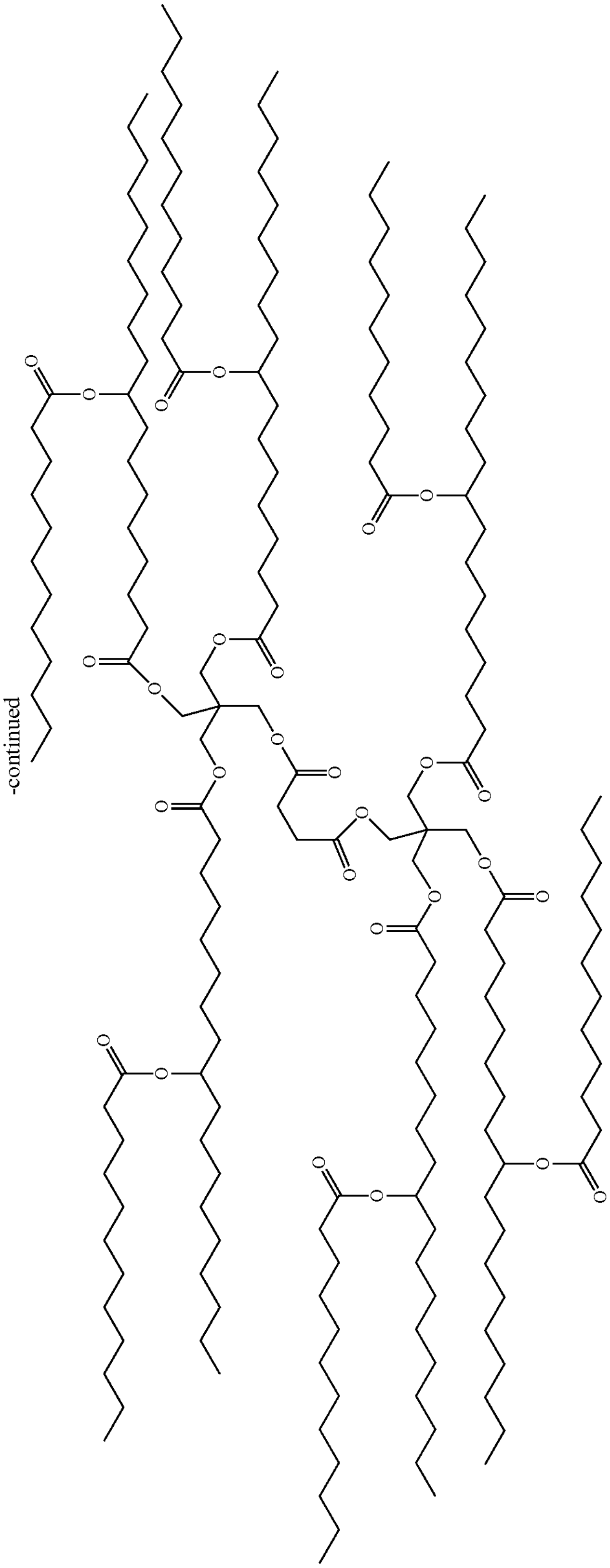

-continued
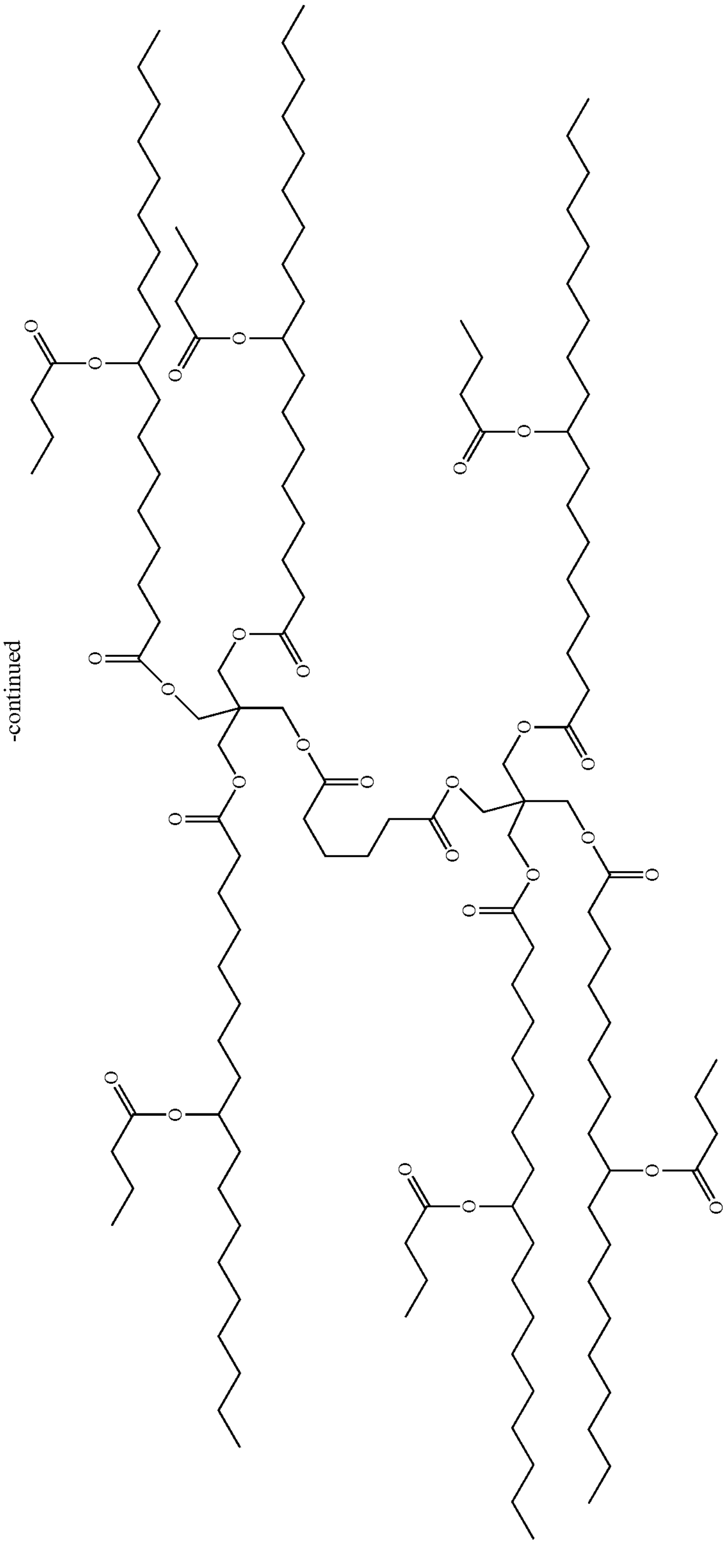

-continued
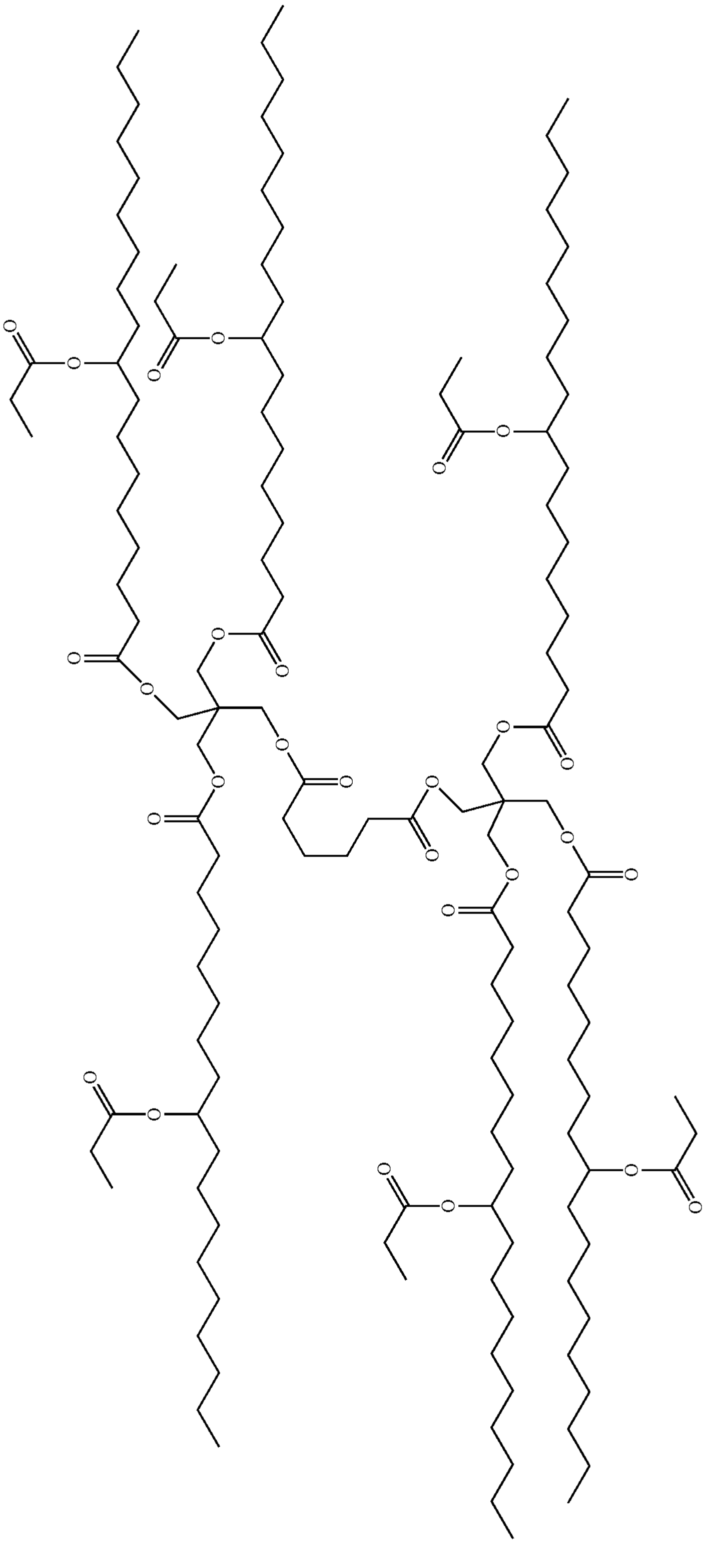

-continued
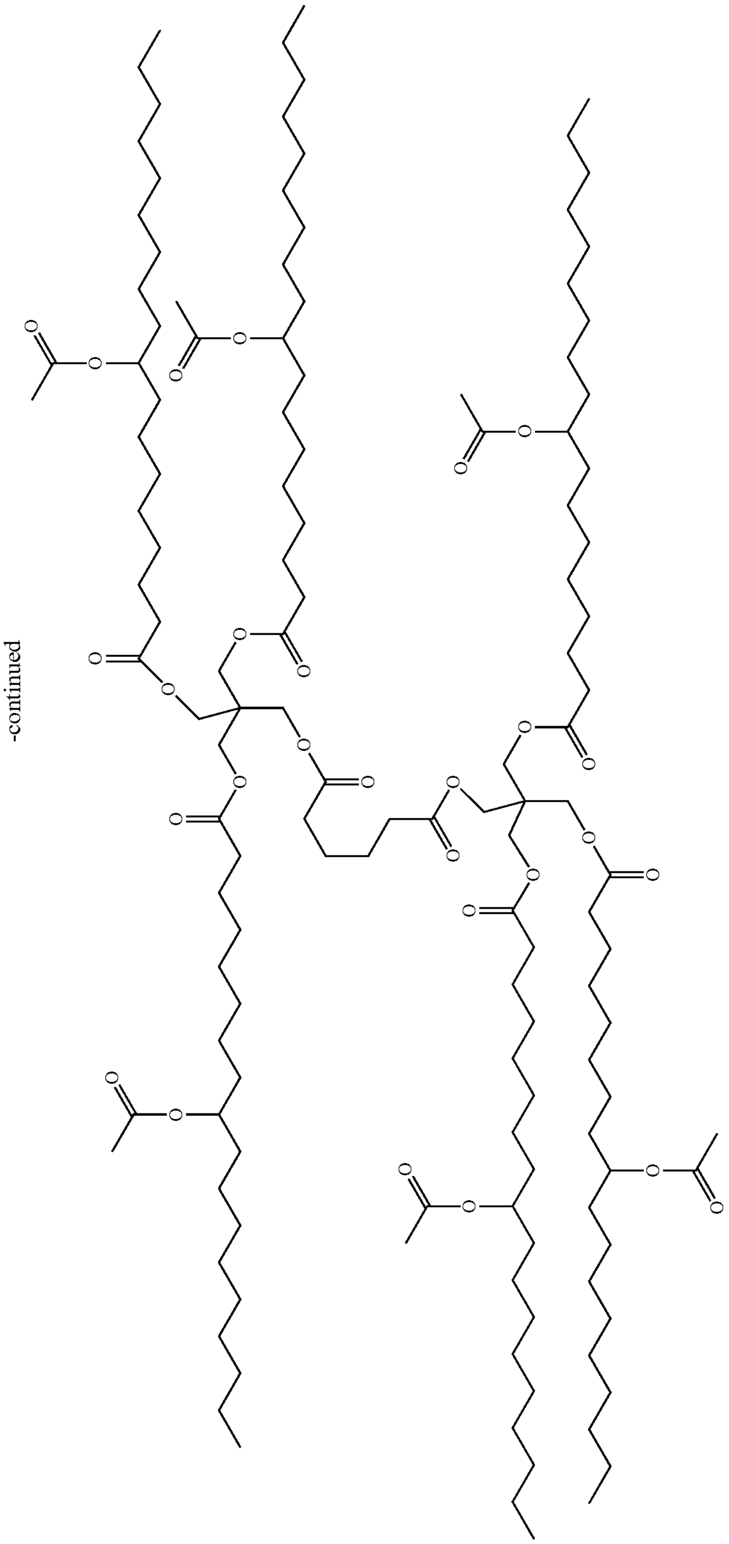

-continued
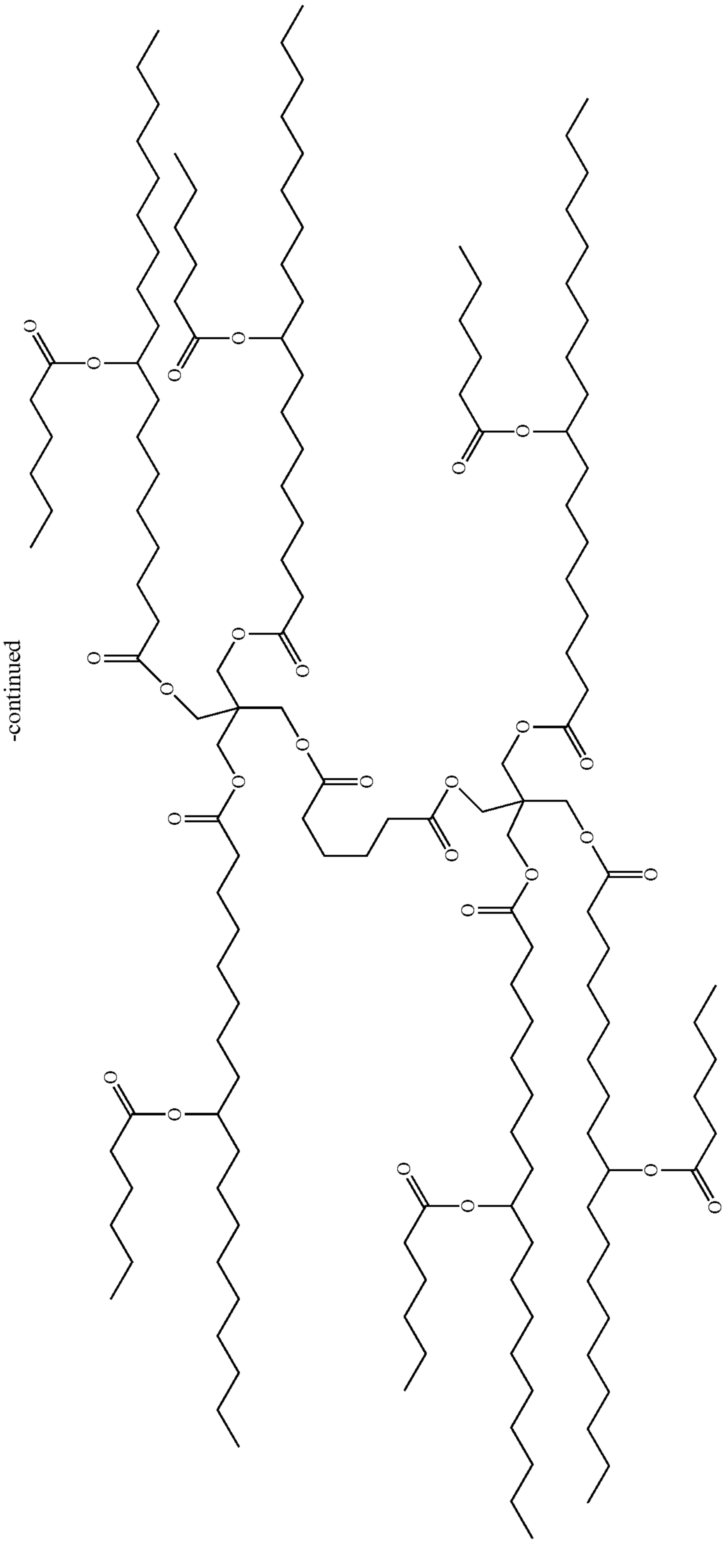

-continued
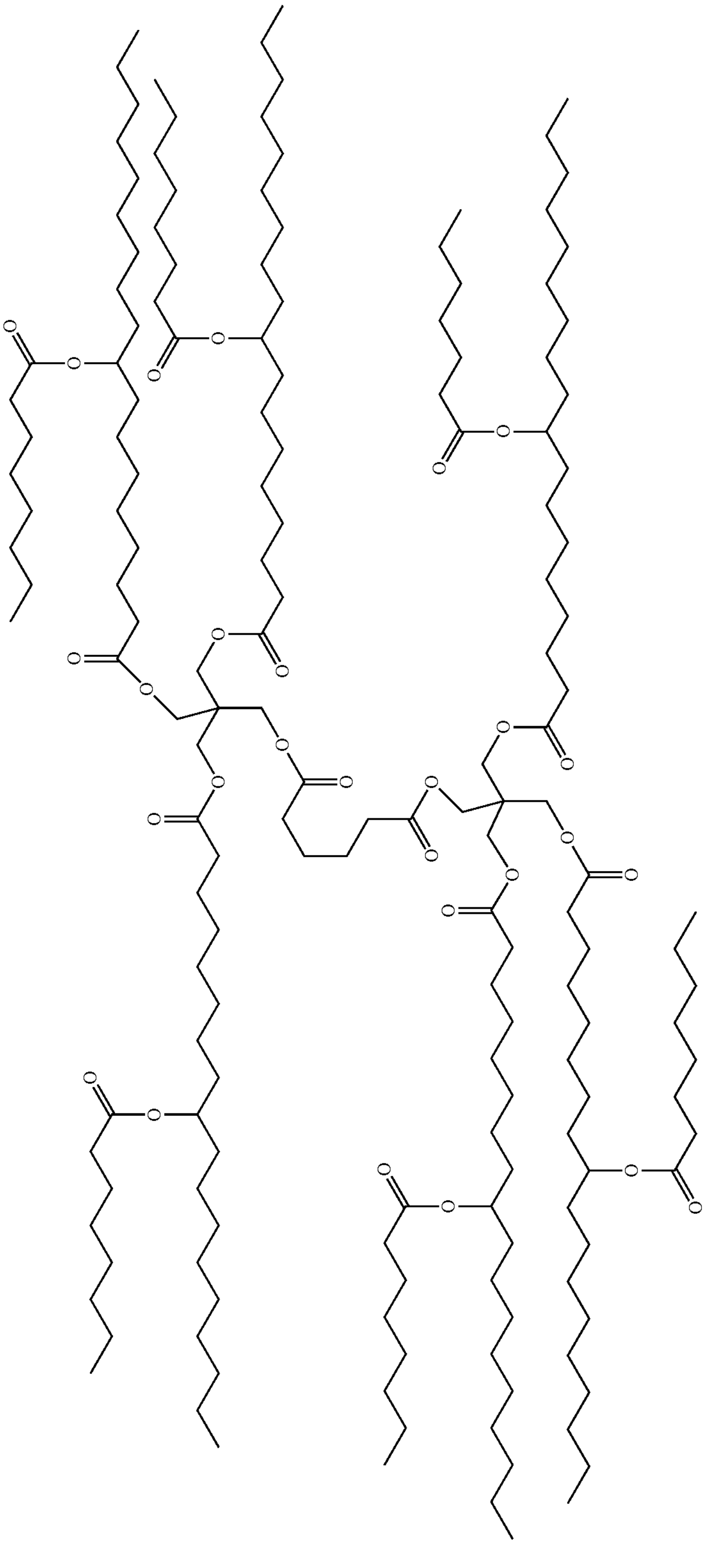

-continued
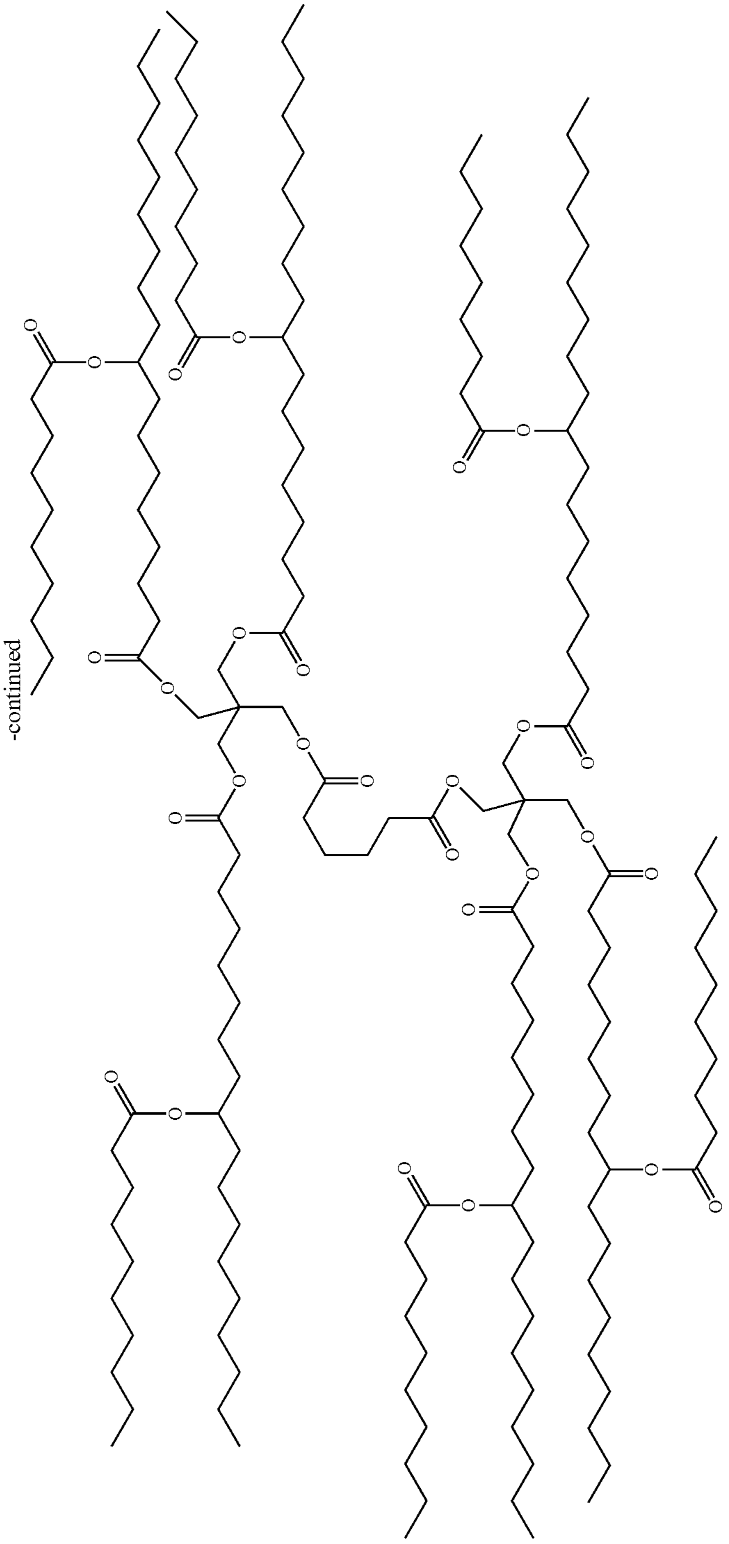

-continued
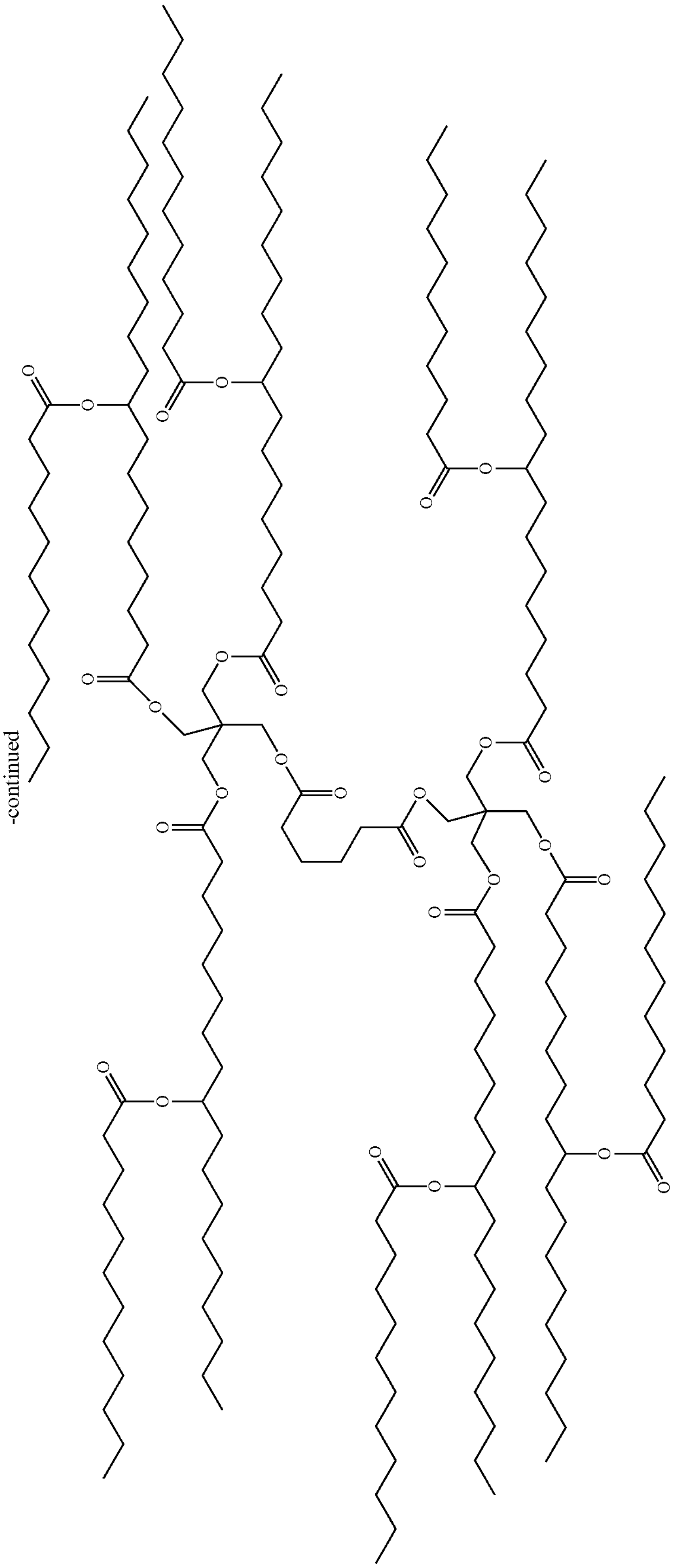

-continued
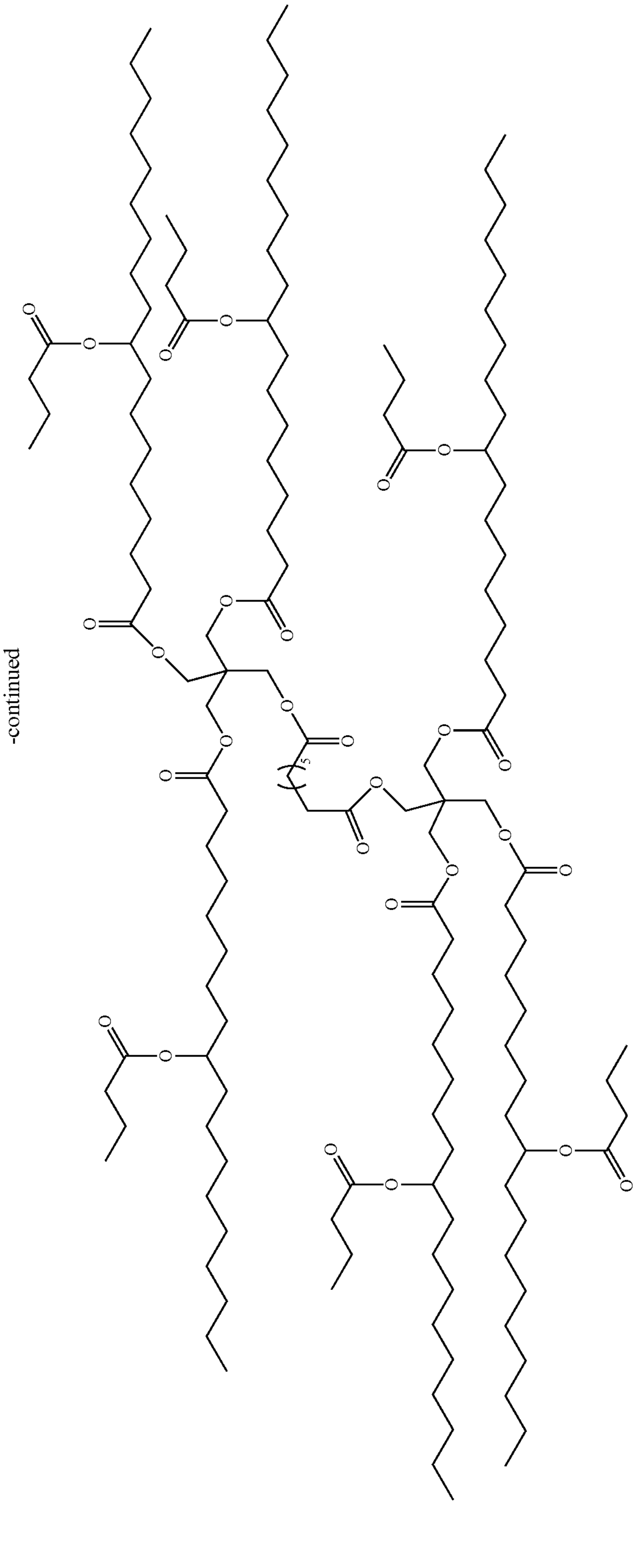

-continued
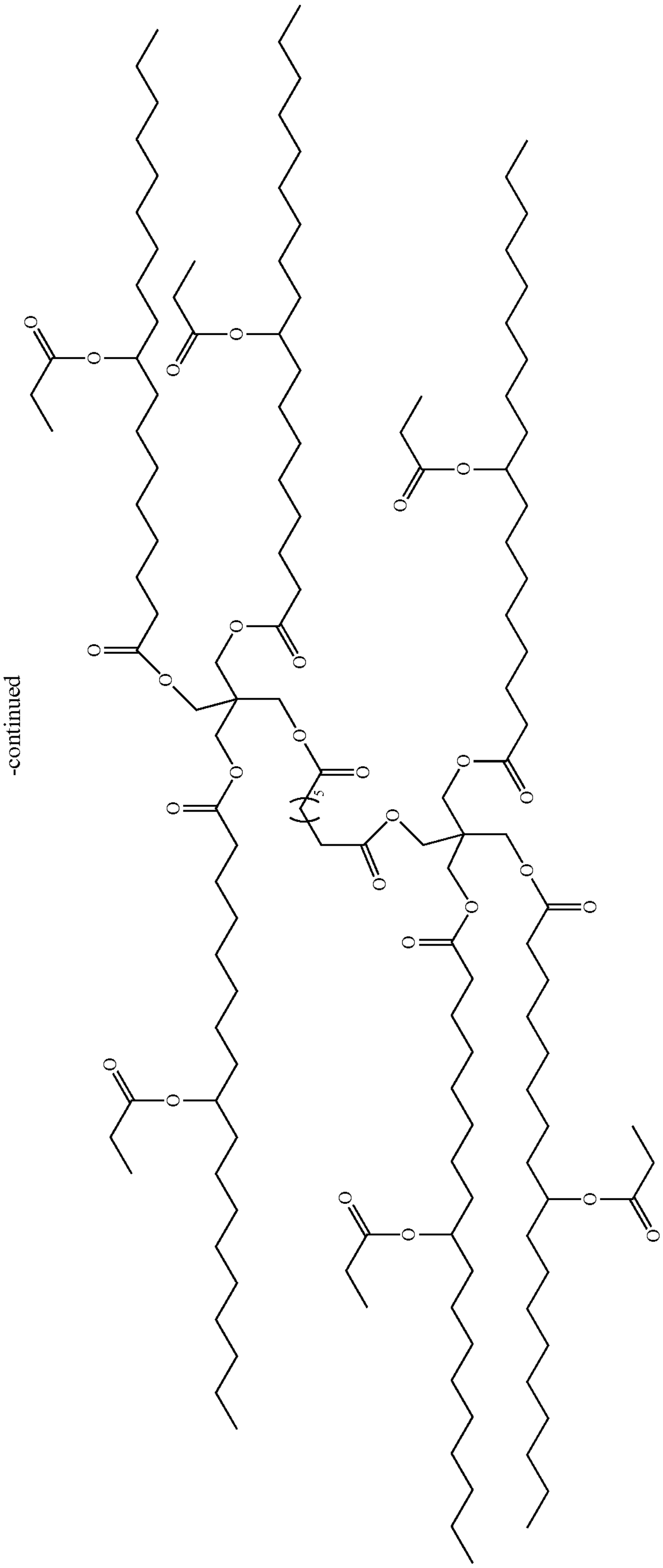

-continued
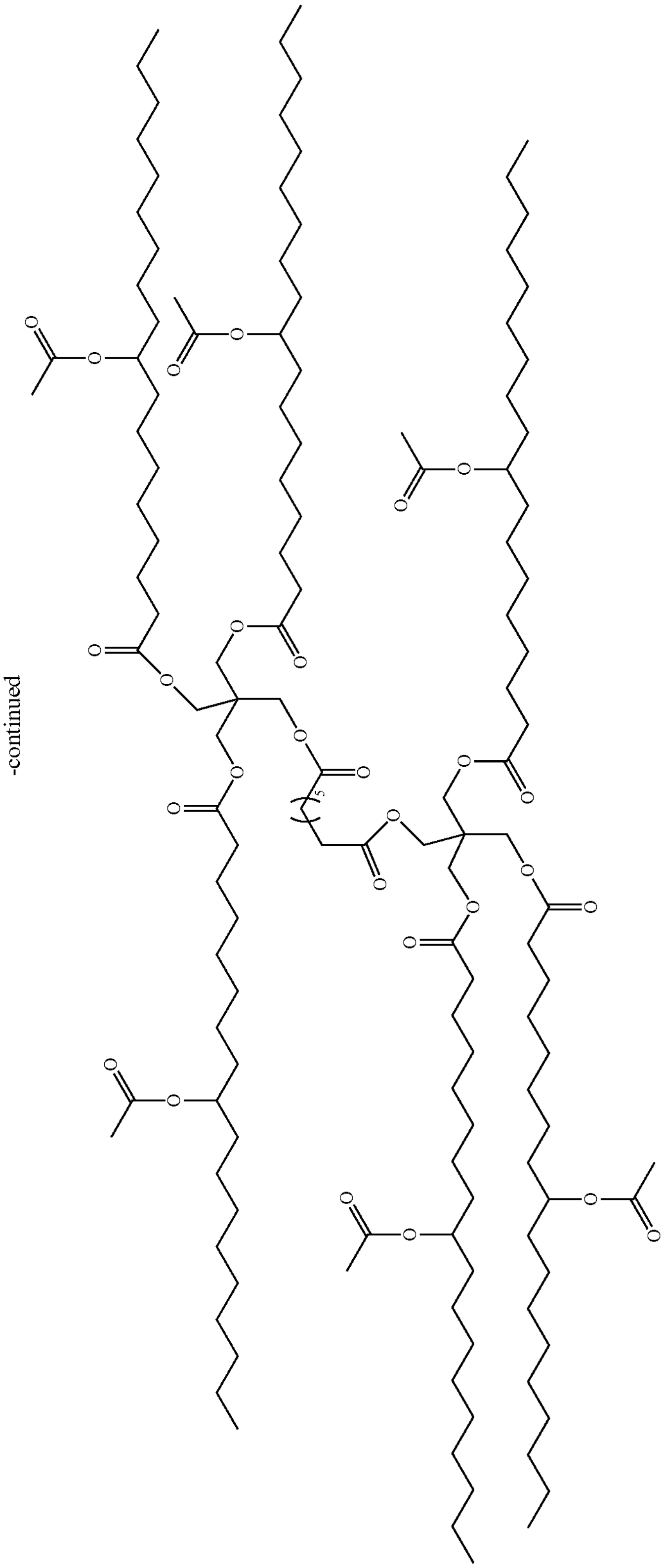

-continued
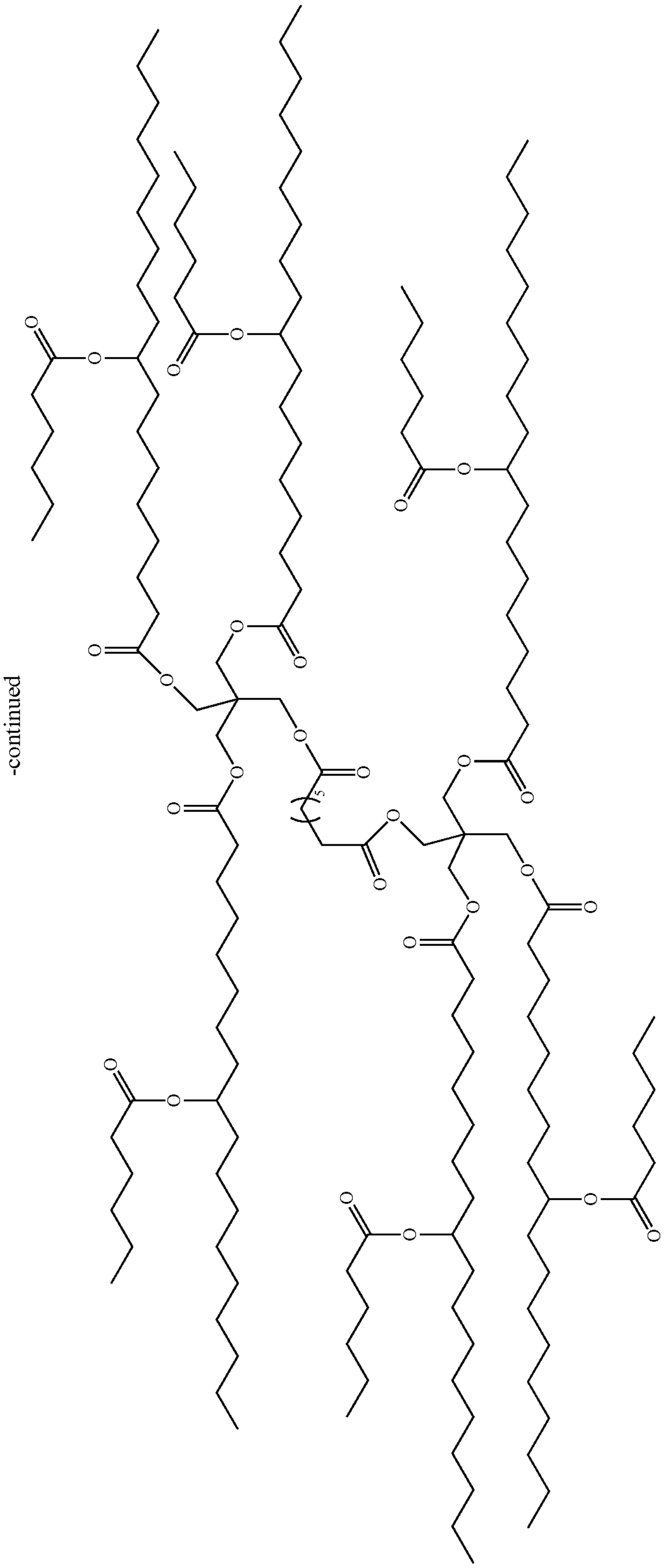

-continued
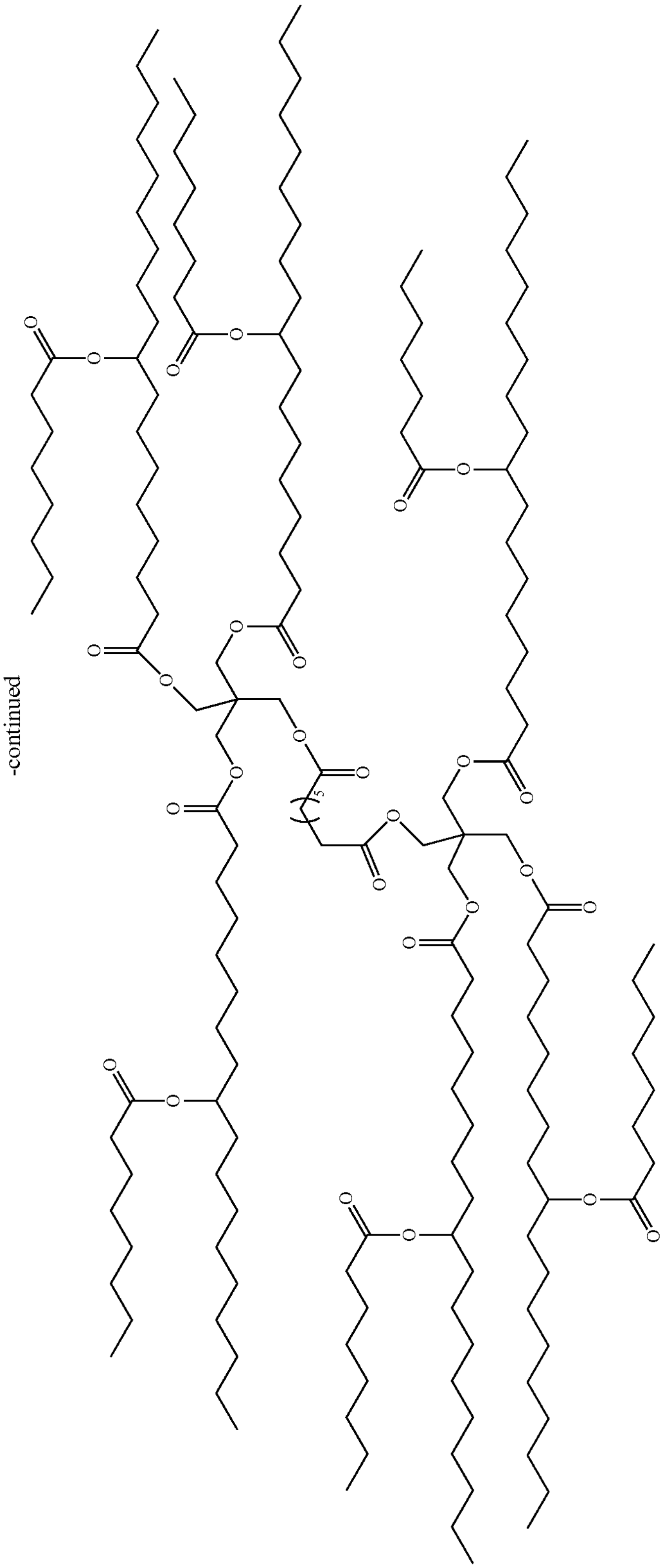

-continued
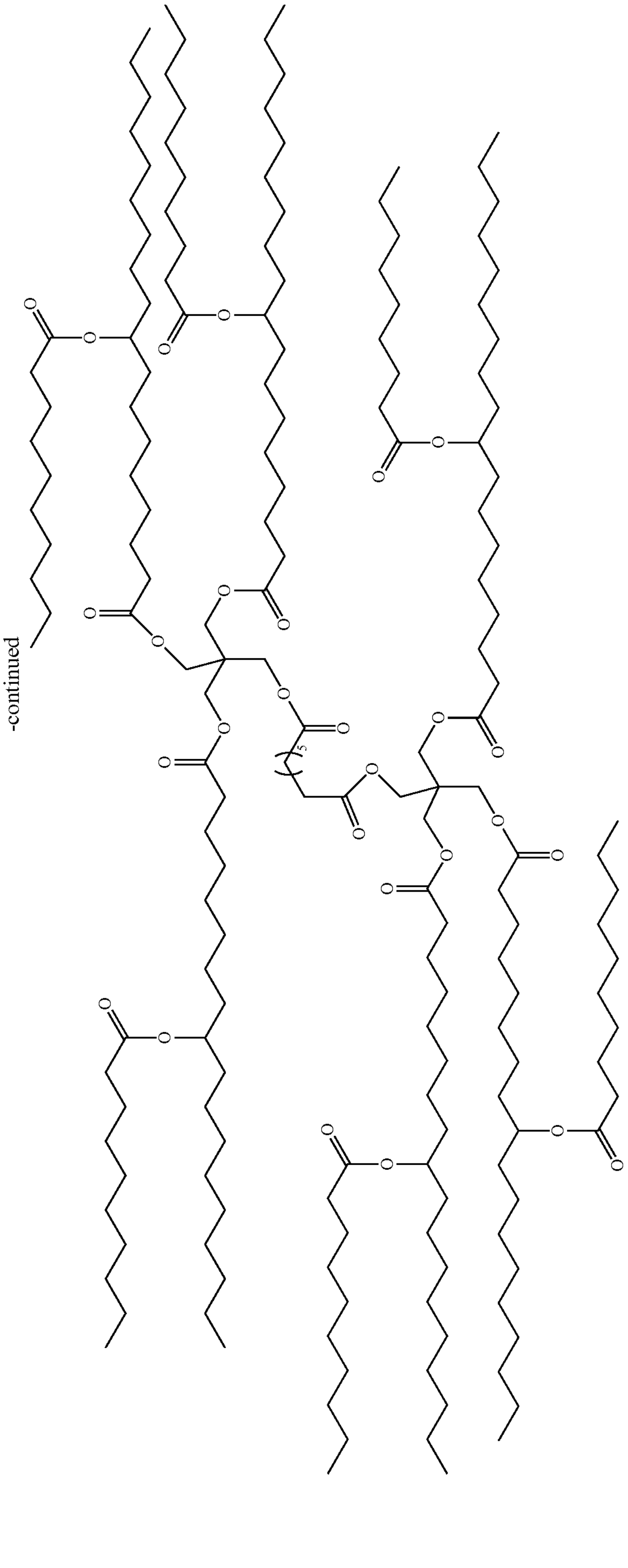

-continued
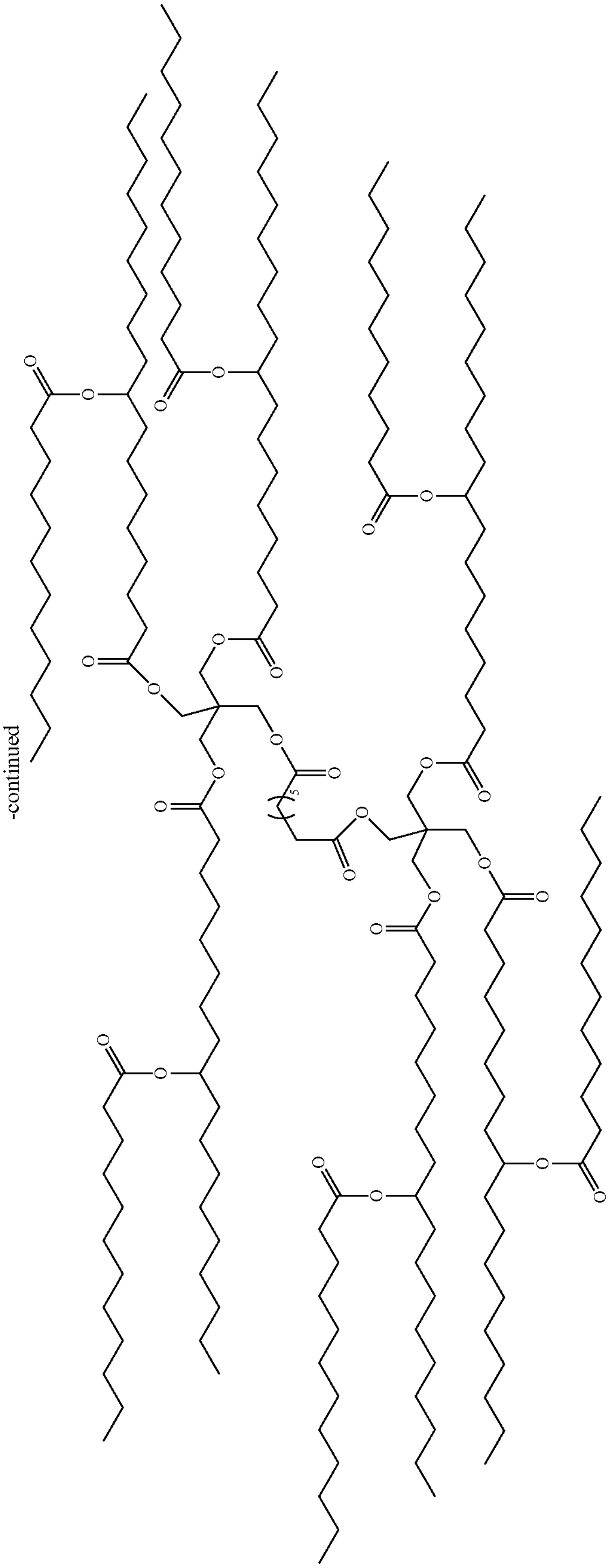

-continued
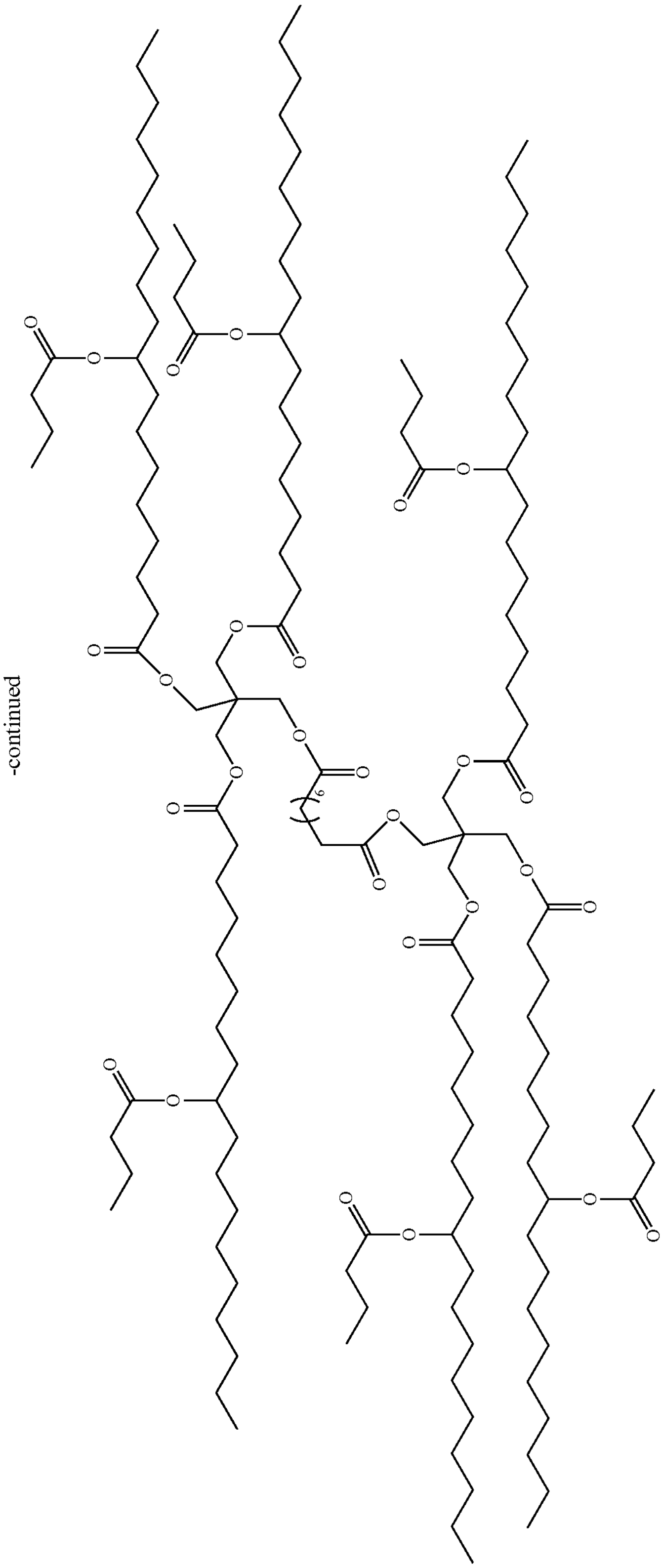

-continued
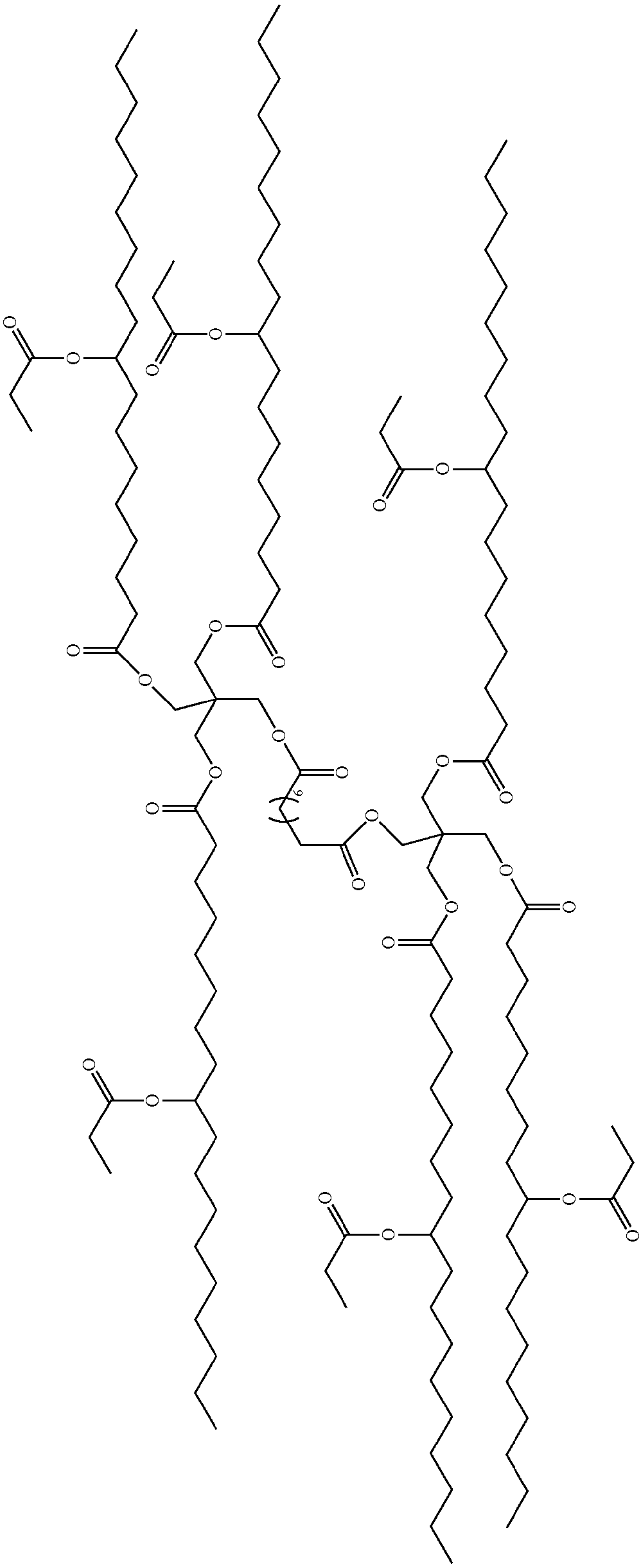

-continued
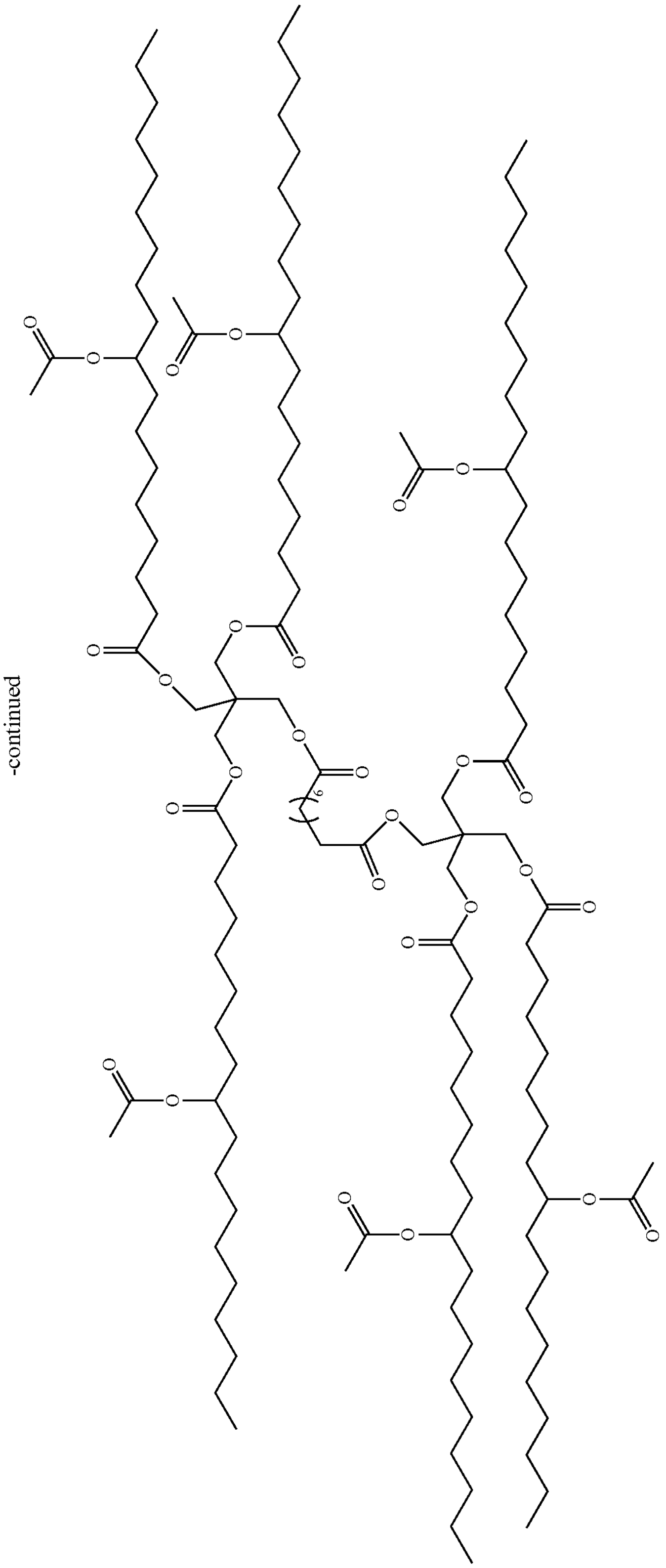

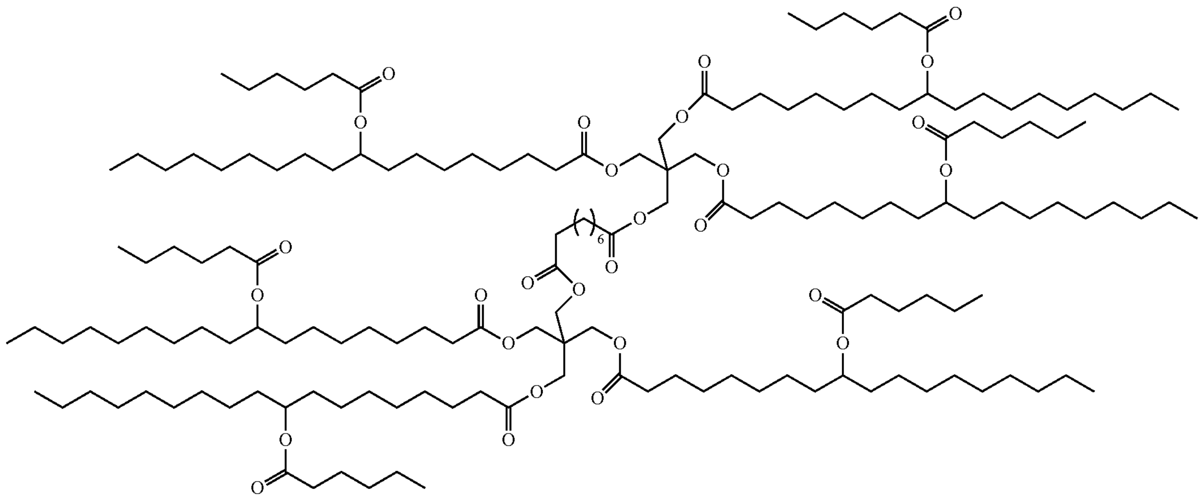
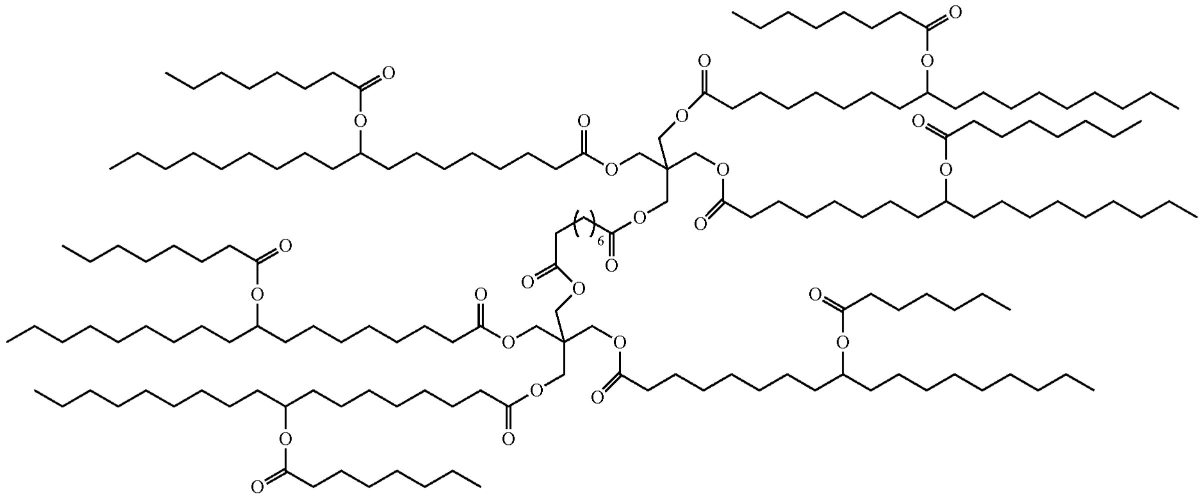
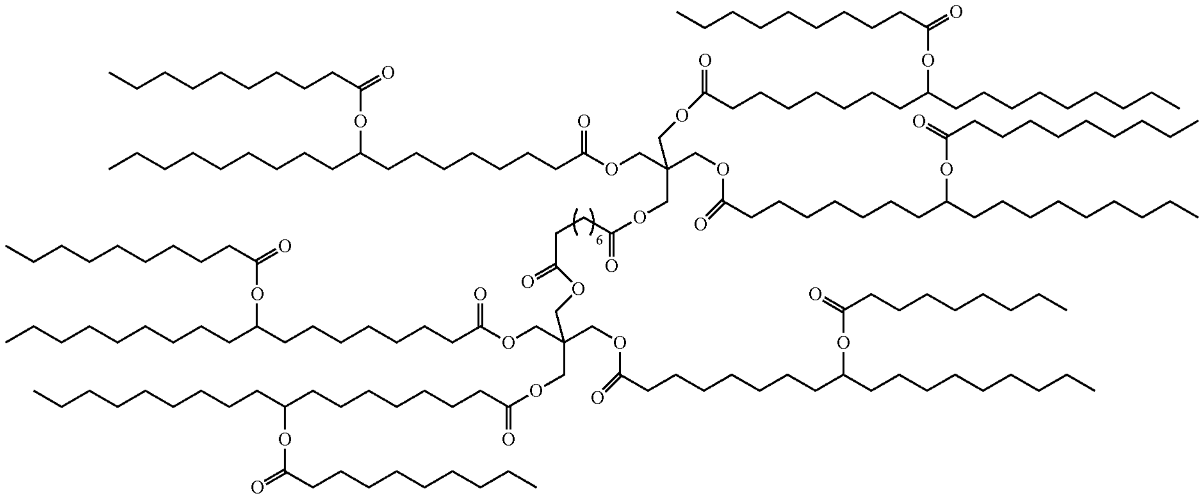

-continued
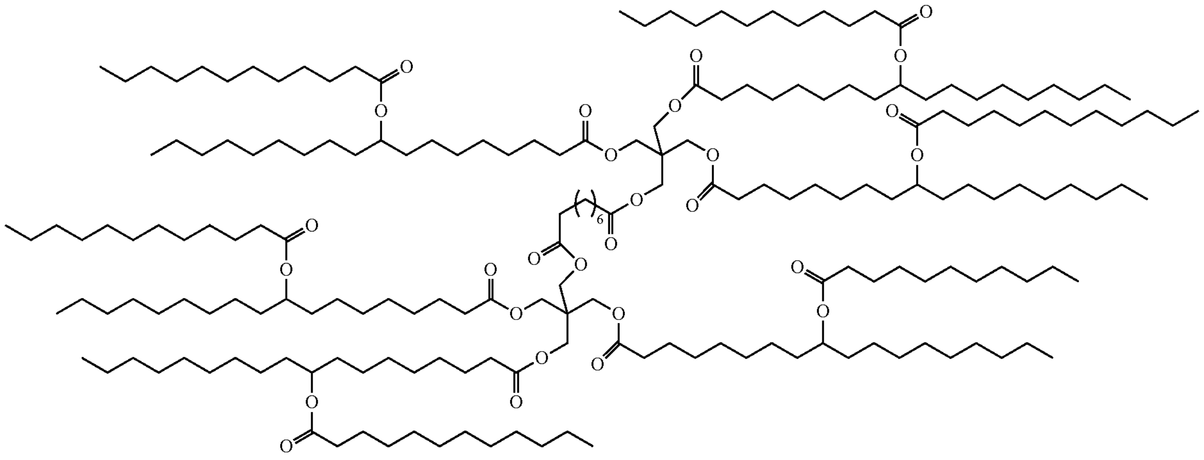 [SMILES: CCCCCCCCCCCC(=O)OC(CCCCCCCCC)CCCCCCCC(=O)OCC(COC(=O)CCCCCCCC(CCCCCCCCC)OC(=O)CCCCCCCCCC)(COC(=O)CCCCCCCC(CCCCCCCCC)OC(=O)CCCCCCCCCCC)COC(=O)CCC(=O)OCC(COC(=O)CCCCCCCC(CCCCCCCCC)OC(=O)CCCCCCCCCCC)(COC(=O)CCCCCCCC(CCCCCCCCC)OC(=O)CCCCCCCCCCC)COC(=O)CCCCCCCC(CCCCCCCCC)OC(=O)CCCCCCCCCCC]
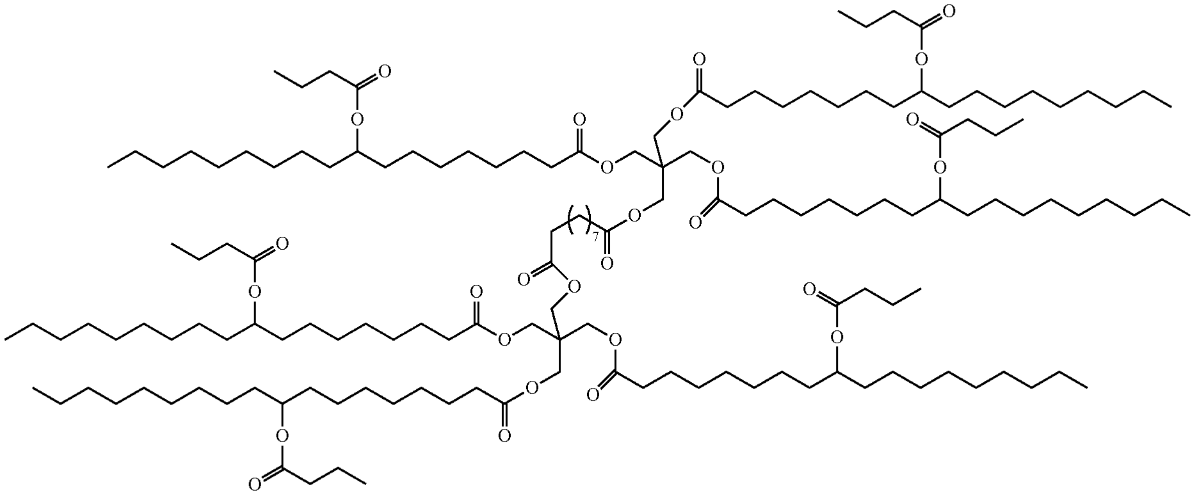
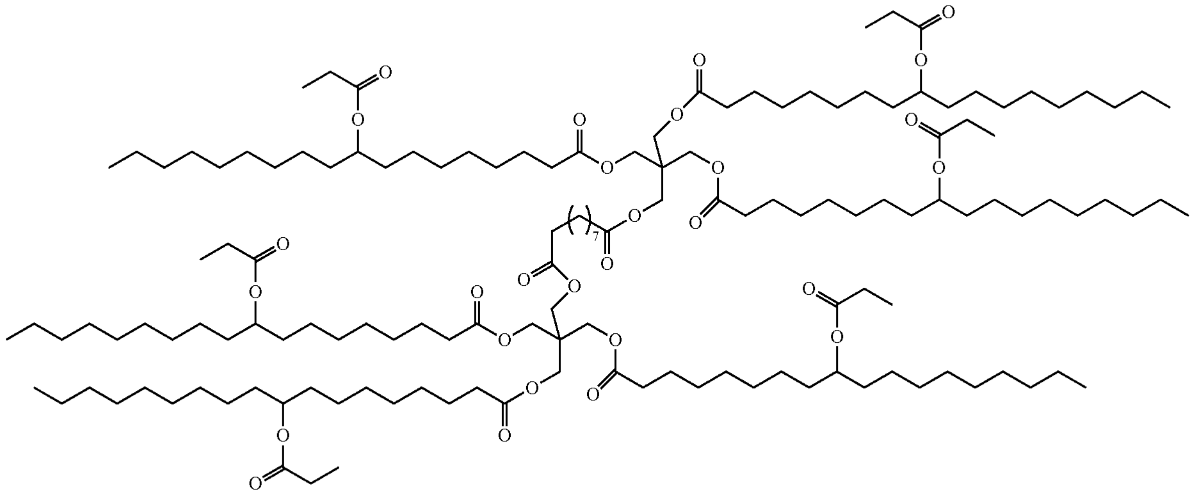

-continued
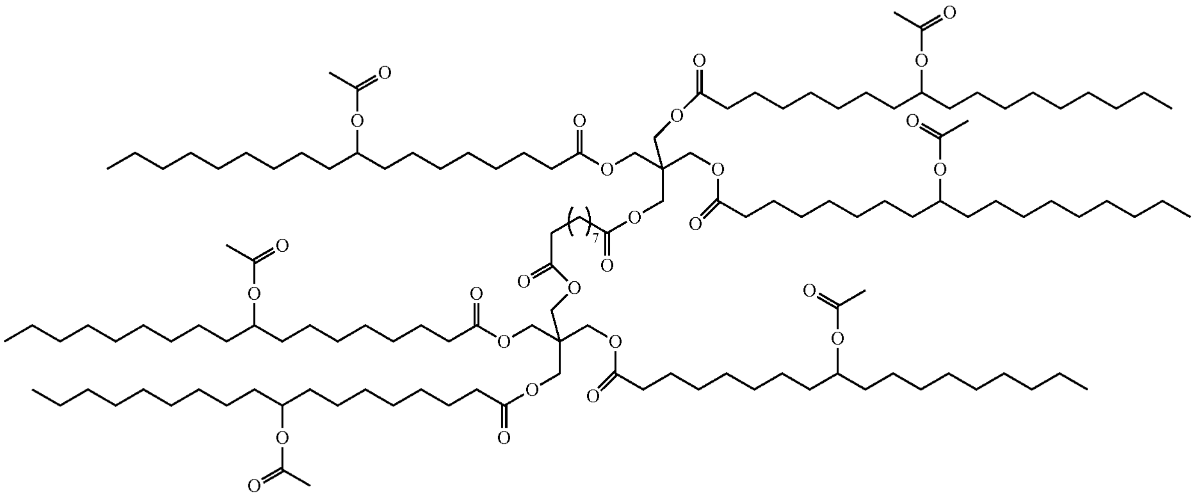
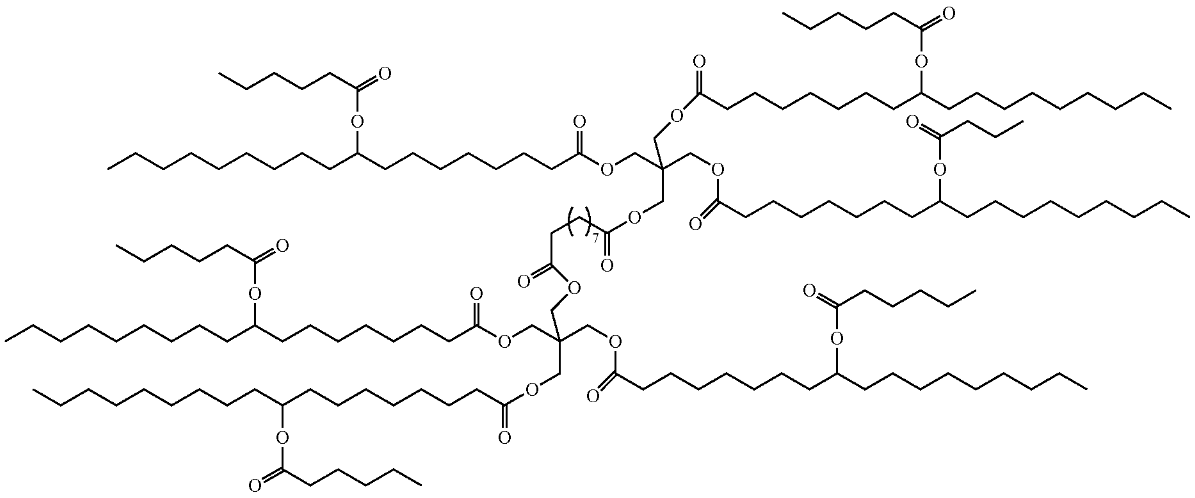
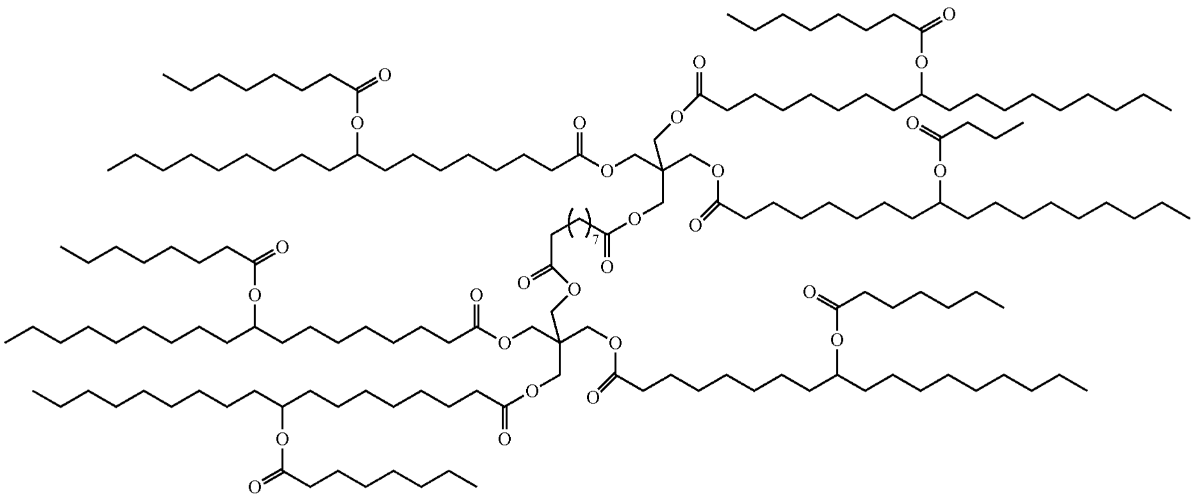

-continued
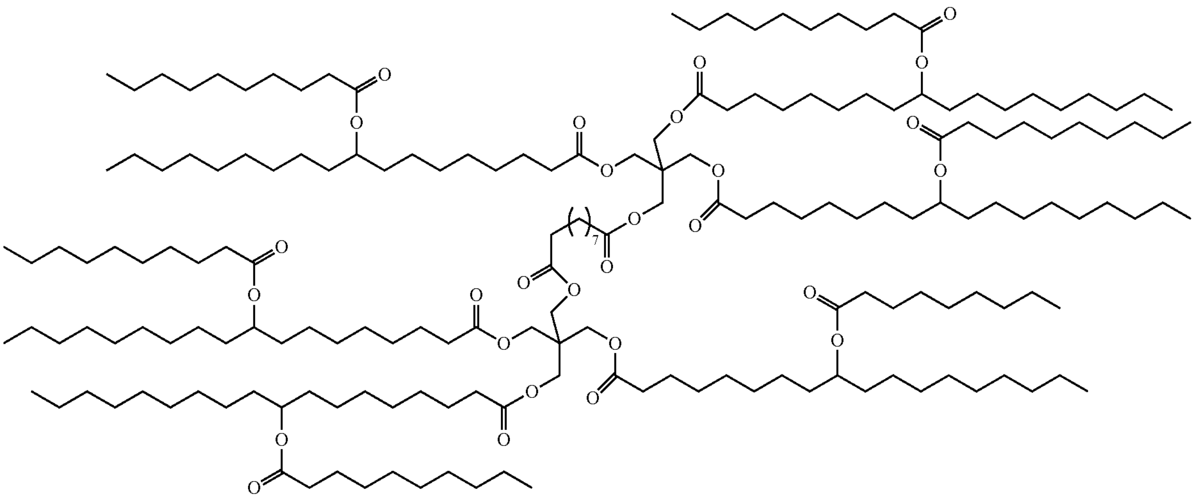
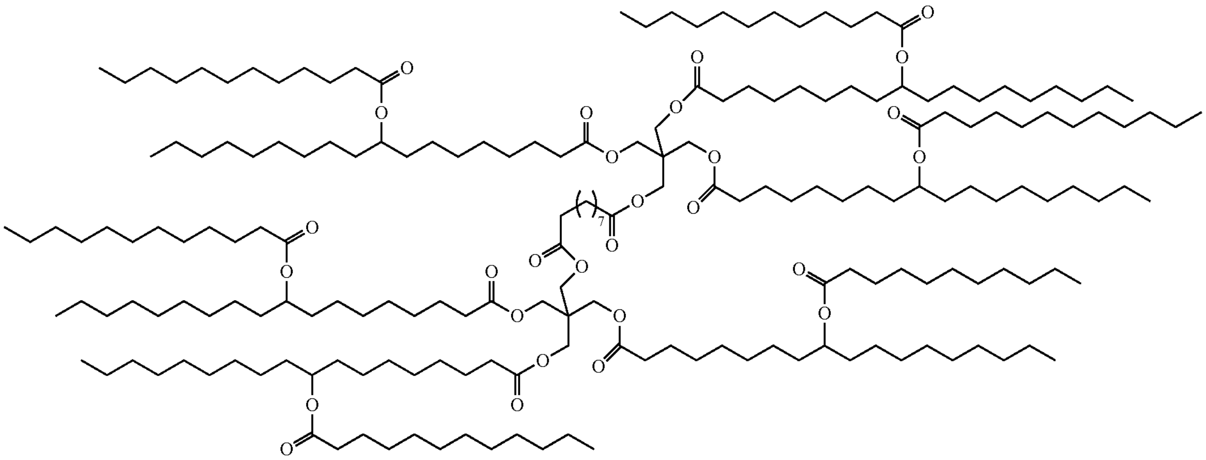
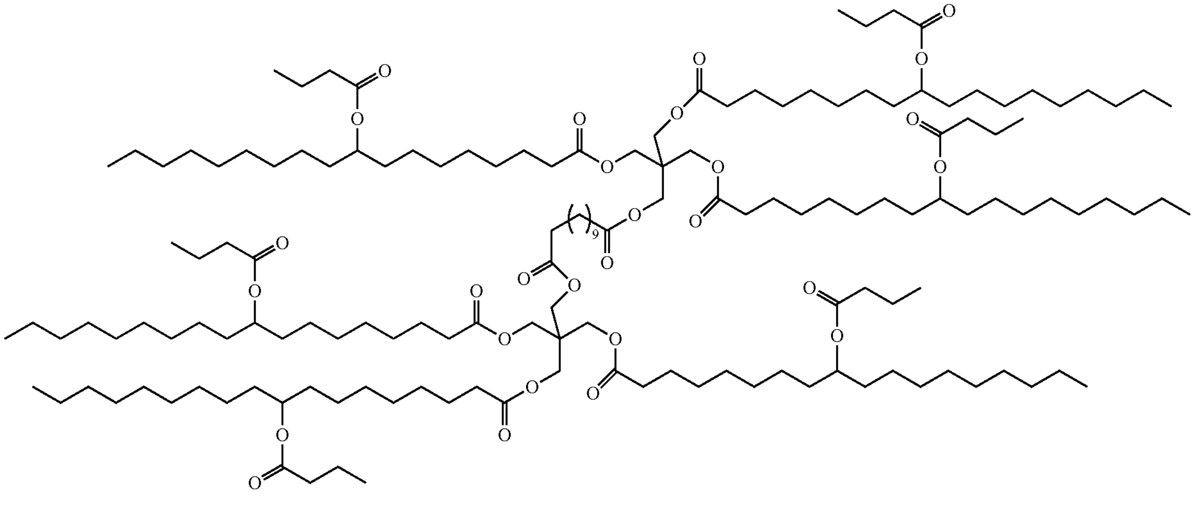

-continued
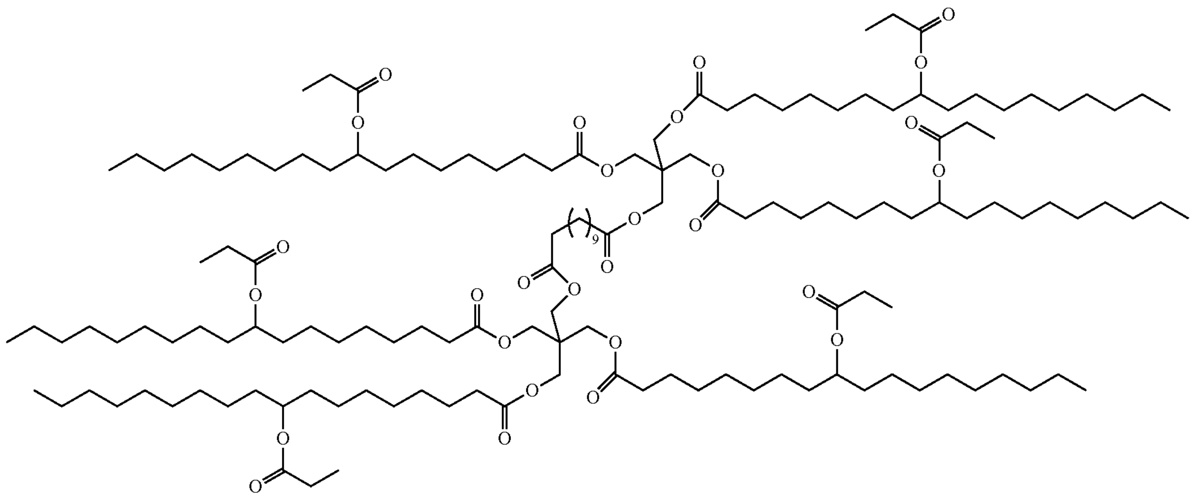
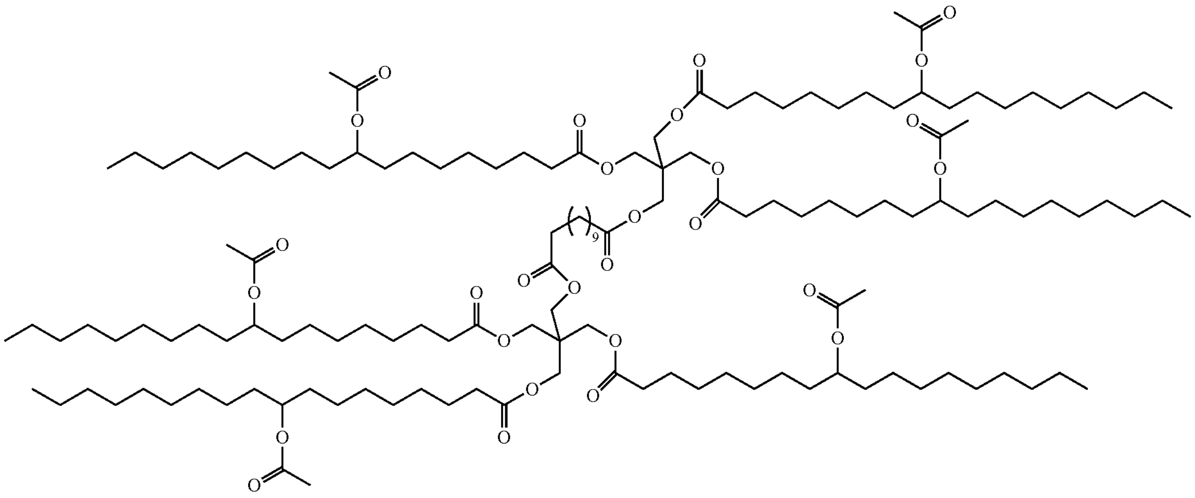
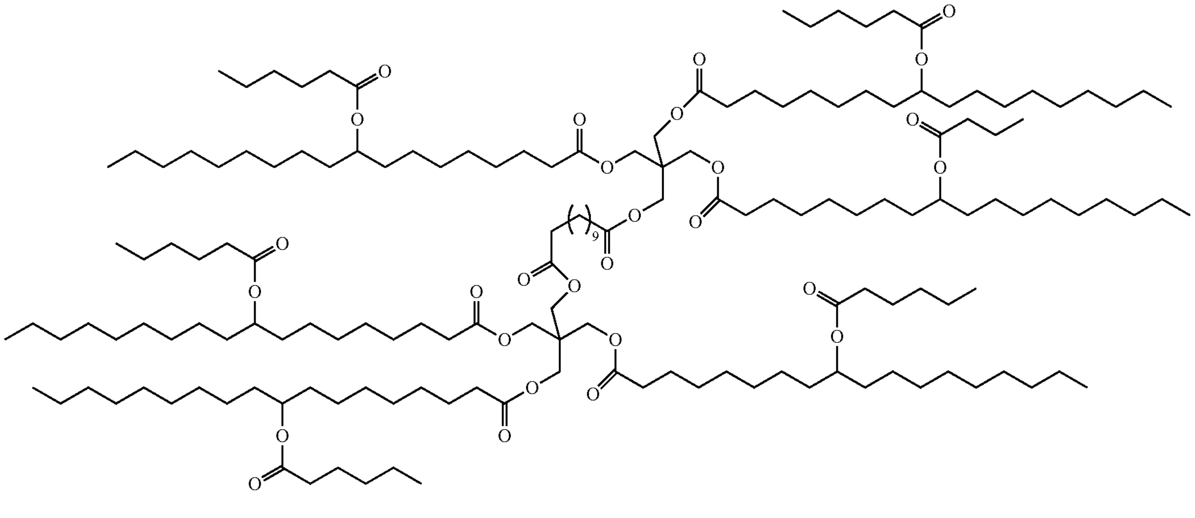

-continued
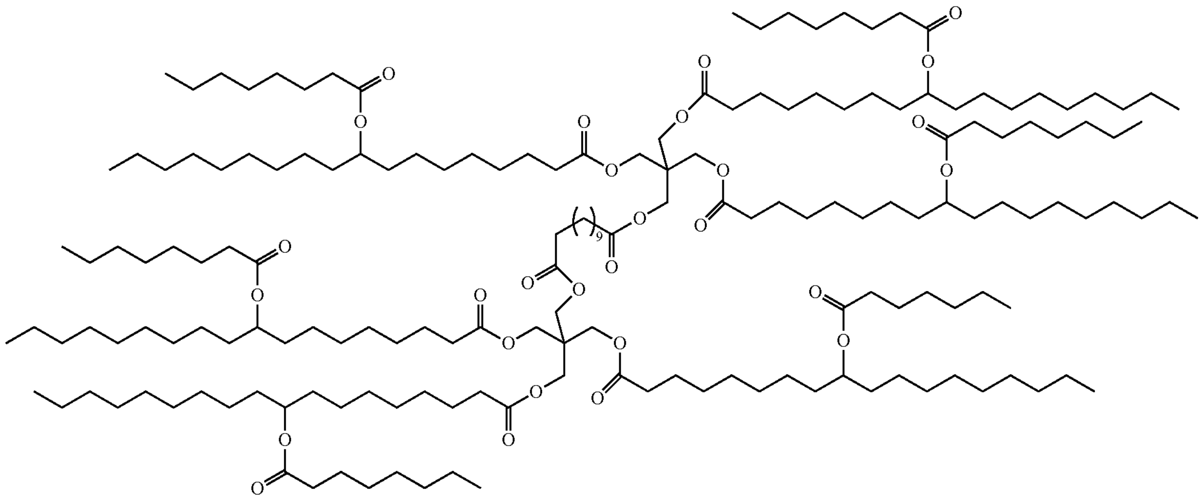
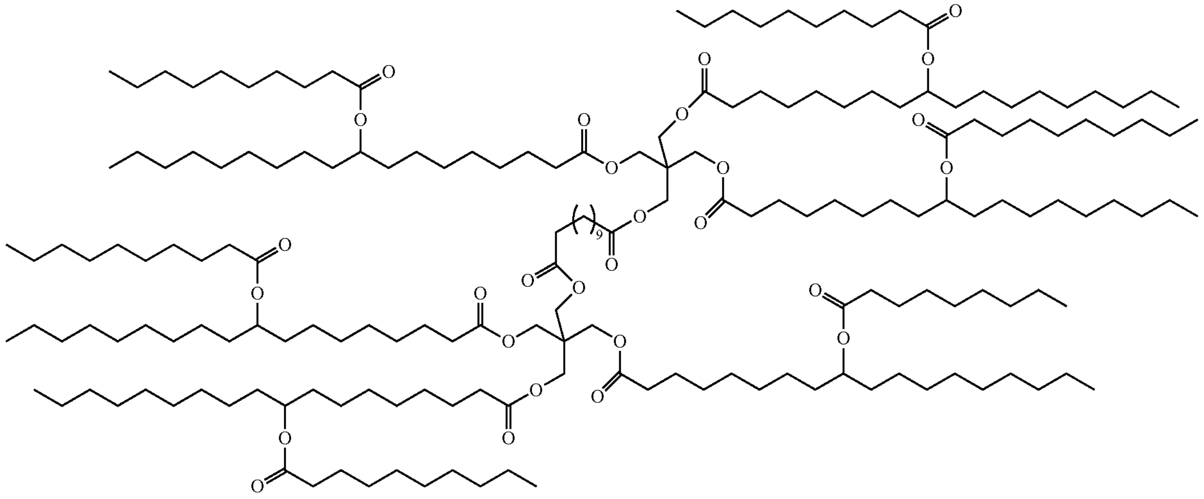
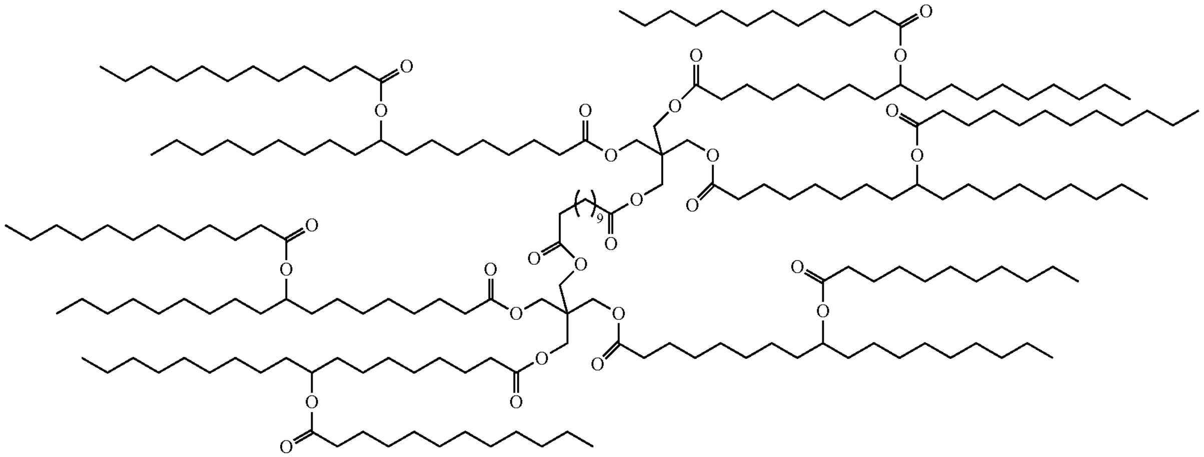

-continued
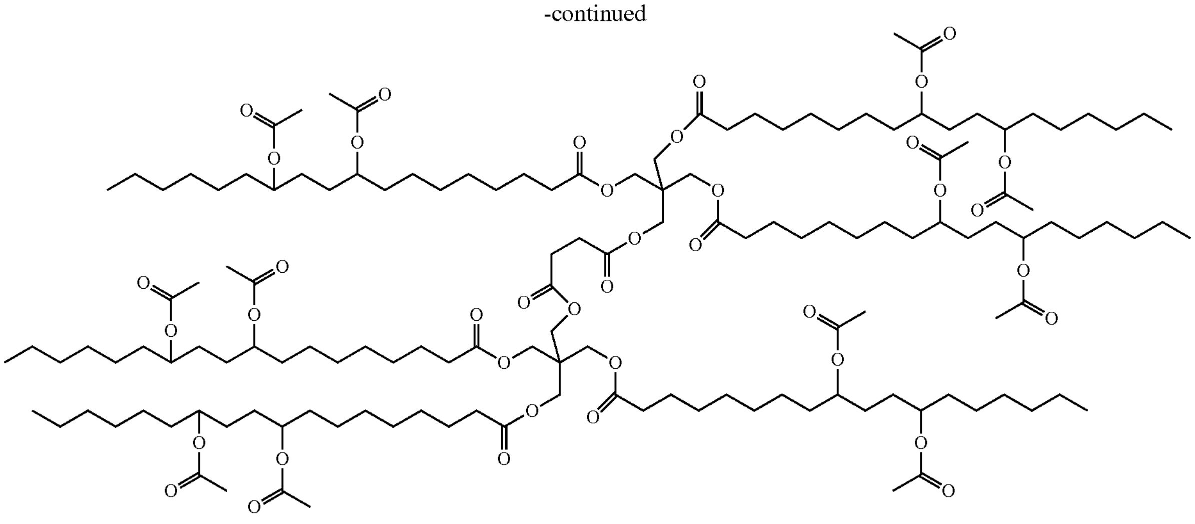
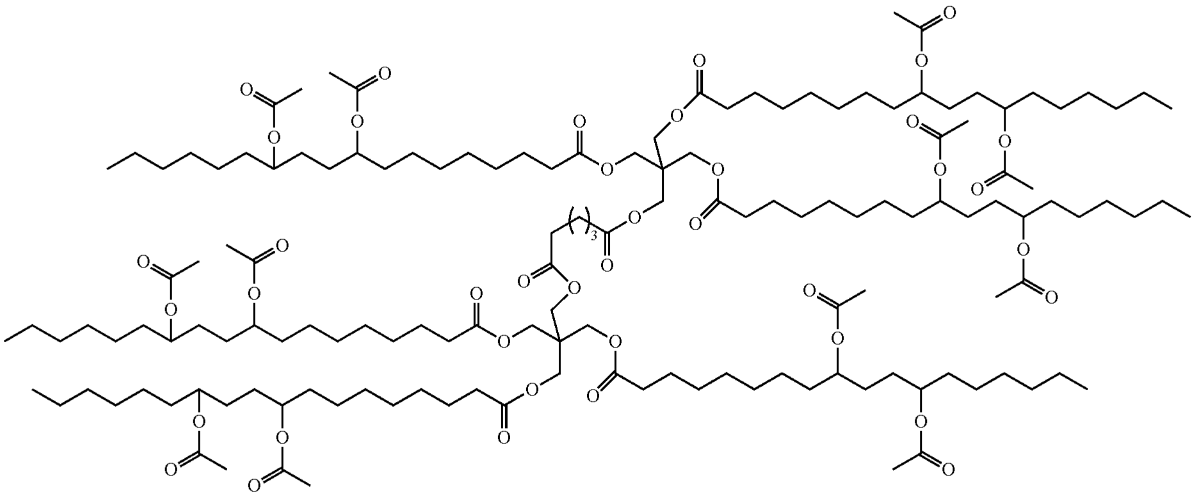
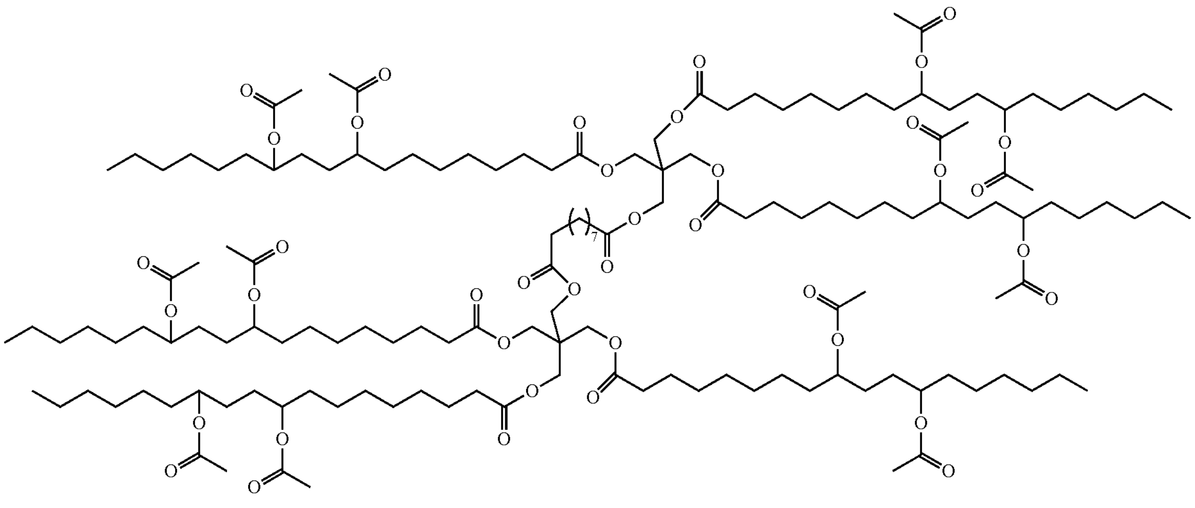

The first invention of the present invention provides a process for preparing an ester compound, which comprises the following steps:

Step (1): a step of reacting a compound represented by formula (α) and a compound represented by formula (β), (α)

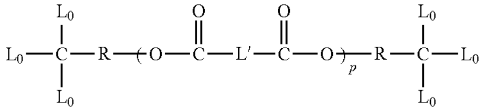

(β)

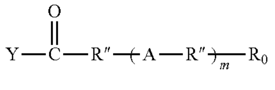

In formula (α), the L' groups, identical to or different from each other, are each independently selected from $C_{1-16}$ linear or branched alkylene (preferably $C_{2-10}$ linear or branched alkylene); the R groups, identical to or different from each other, are each independently selected from a single bond, a $C_{1-50}$ linear or branched alkylene (preferably a $C_{1-20}$ linear or branched alkylene, more preferably a $C_{1-6}$ linear or branched alkylene);

p is an integral number of 0-10 (preferably an integral number of 0-5, more preferably 0, 1, 2, or 3);

the $L_0$ groups, identical to or different from each other, are each independently selected from a hydrogen atom, an optionally substituted $C_{1-10}$ linear or branched alkyl, a group represented by formula (δ) (preferably selected from an optionally substituted $C_{1-6}$ linear or branched alkyl, a group represented by formula (δ)), wherein at least two $L_0$ groups are selected from a group represented by formula (δ),

—R'—OH (δ)

In the formula (δ), the R' group is selected from a single bond, a $C_{1-10}$ linear or branched alkylene (preferably a single bond, a $C_{1-6}$ linear or branched alkylene), and the carbon atoms bonded to the $L_0$ group are at most directly bonded to one oxygen atom, In the formula (β), the R" groups, identical to or different from each other, are each independently selected from a single bond, a $C_{1-10}$ hydrocarbylene (preferably a $C_{1-10}$ linear or branched alkylene, more preferably a $C_{1-8}$ linear or branched alkylene, more preferably a $C_{1-6}$ linear or branched alkylene); the $R_0$ group is selected from H, an optionally substituted $C_{1-10}$ hydrocarbyl (preferably an optionally substituted $C_{1-10}$ linear or branched alkyl, more preferably an optionally substituted $C_{1-6}$ linear or branched alkyl); m is an integral number of 1-10 (preferably an integral number of 1-6, more preferably an integral number of 1-5); m A groups, identical to or different from each other, are each independently selected from a group represented by formula (ε), —C═C—, methylene and ethylene, and at least one A group is selected from a group represented by formula (ε);

(ε)

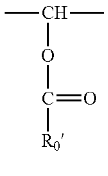

The $R_0$' groups, at each occurrence, are each independently selected from an optionally substituted $C_{1-17}$ hydrocarbyl (preferably an optionally substituted $C_{1-15}$ linear or branched alkyl, more preferably an optionally substituted $C_{1-11}$ linear or branched alkyl);

The Y group is selected from OH, F, Cl, Br, or I (preferably OH, Cl, or Br),

Said substituents that optionally substitute are selected from halogen atoms, hydroxy, amino, $C_{1-6}$ linear or branched alkyl, $C_{6-10}$ aryl, $C_{3-10}$ cycloalkyl.

In one embodiment of the present invention, in case p is not 0, the preparation process further includes a step (2): reacting a compound represented by formula (α-1) with a compound represented by formula (α-2) to produce a compound represented by formula (α), wherein step (2) is carried out before step (1), (α)

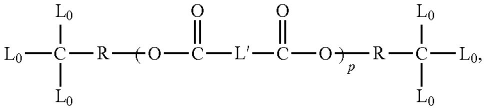

(α-1)

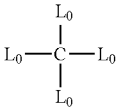

(α-2)

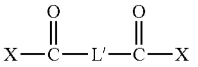

In formula (α-1), the $L_0$ groups, identical to or different from each other, are each independently selected from a hydrogen atom, an optionally substituted $C_{1-10}$ linear or branched alkyl, a group represented by formula (δ) (preferably selected from an optionally substituted $C_{1-6}$ linear or branched alkyl, a group represented by formula (δ)), wherein at least three $L_0$ groups are selected from a group represented by formula (δ), in formula (α-2), the X groups, identical to or different from each other, are each independently selected from OH, F, Cl, Br or I (preferably OH, Cl or Br).

In one embodiment of the present invention, the compound represented by formula (α) is selected from one or more of the following: trimethylolpropane, tri(hydroxyethyl)propane, pentaerythritol, ethylene glycol, propylene glycol, butanediol, pentanediol, hexanediol, heptanediol, octanediol, nonanediol, decanediol, undecanediol, dodecanediol, tridecanediol, tetradecanediol, and pentadecanediol. In one embodiment of the present invention, the compound represented by formula (α-1) is selected from one or more of the following: trimethylolethane, trimethylolpropane, tri(hydroxyethyl)propane, tri(hydroxyethyl)ethane, tri (hydroxylpropyl)propane, and pentaerythritol. In one embodiment of the present invention, the compound represented by formula (α-2) is selected from one or more of the following: ethanedioic acid, propanedioic acid, butanedioic acid, pentanedioic acid, hexanedioic acid, heptanedioic acid, octandioic acid, nonanedioic acid, decanedioic acid, undecanedioic acid, dodecanedioic acid, tridecanedioic acid, tetradecanedioic acid, and pentadecanedioic acid.

In one embodiment of the present invention, the compound represented by formula (β) is obtained by reacting a compound represented by formula (β-1) with a compound represented by formula (β-2),

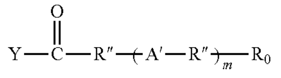

(β-1)

$R_0'$—COOH (β-2)

In the formula (β-1), the m A' groups, identical to or different from each other, are each independently selected from the formula —C═C—, methylene, ethylene, and at least one A' group is —C═C—.

In the formula (β-2), $R_0'$ is an optionally substituted $C_{1-17}$ hydrocarbyl (preferably an optionally substituted $C_{1-15}$ linear or branched alkyl, more preferably an optionally substituted $C_{1-11}$ linear or branched alkyl).

In one embodiment of the present invention, the reaction molar equivalent ratio of the compound represented by formula (β-1) (as —C═C—) to the compound represented by formula (β-2) (as carboxyl) is 0.05-20:1 (preferably is 0.1-10:1); the reaction temperature is 0-200° C. (preferably 50-160° C.); the reaction time is 0.5-72 hours (preferably 3-48 hours).

In one embodiment of the present invention, in the reaction of the compound represented by formula (β-1) and the compound represented by formula (β-2), a catalyst is added (the catalyst can be one or more of inorganic acid, organic acid, solid acid, heteropolyacid, acidic ionic liquid, acidic resin, acidic molecular sieve, metal chloride and metal oxide, for example, can be one or more of sulfuric acid, perchloric acid, $AlCl_3$, tin chloride, n-butyltin oxide, dibutyltin oxide, paratoluenesulfonic acid, acidic resin, phosphotungstic heteropolyacid, acidic ionic liquid, and acidic molecular sieve, preferably one or more of perchloric acid, tin chloride, n-butyltin oxide, paratoluenesulfonic acid, acidic resin and phosphotungstic heteropolyacid). The addition amount of the catalyst is preferably 0.1%-10% by the mass of the compound represented by formula (β-1).

In one embodiment of the present invention, in the reaction of the compound represented by formula (β-1) and the compound represented by formula (β-2), a solvent may or may not be added, preferably a solvent is added. Said solvent is preferably a hydrocarbon solvent, preferably one or more of alkanes, arenes and ethers, more preferably an alkane solvent, for example, can be one or more of hexane, heptane, octane, nonane, decane, cyclohexane, cycloheptane, cyclooctane, cyclononane, cyclodecane, benzene, toluene, xylene, ethylbenzene, propyl benzene, ethyl ether, propyl ether, isopropyl ether and butyl ether. The addition amount of said solvent should be suitable to promote the smooth progress of the reaction, and is not particularly limited.

In one embodiment of the present invention, the compound represented by formula (β-1) is selected from one or more of the following compounds: eicosenoic acid, oleic acid, linoleic acid, linolenic acid, hexadecenoic acid, tetradecenoic acid, dodecenoic acid, undecenoic acid, decenoic acid, and octenoic acid; the compound represented by formula (β-2) is selected from one or more of the following compounds: formic acid, acetic acid, propionic acid, butyric acid, valeric acid, hexanoic acid, octanoic acid, nonanoic acid, decanoic acid, dodecanoic acid, tetradecanoic acid, hexadecanoic acid, octadecanoic acid, eicosanoic acid, eicosenoic acid, oleic acid, linoleic acid, linolenic acid, hexadecenoic acid, tetradecenoic acid, dodecenoic acid, undecenoic acid, decenoic acid, and octenoic acid.

In one embodiment of the present invention, the reaction molar equivalent ratio of the compound represented by formula (α) (as OH) to the compound represented by formula (β) (as Y) is 0.1-10:1 (preferably 0.2-5:1); the reaction temperature is 70-250° C. (preferably 90-200° C.); the reaction time is 0.5-24 hours (preferably 2-15 hours). In one embodiment of the present invention, in the reaction of the compound represented by formula (α) and the compound represented by formula (β), a catalyst is added (the catalyst can be one or more of inorganic acid, organic acid, solid acid, heteropolyacid, acidic ionic liquid, acidic resin, acidic molecular sieve, metal chloride and metal oxide, for example can be one or more of sulfuric acid, perchloric acid, $AlCl_3$, tin chloride, n-butyltin oxide, dibutyltin oxide, paratoluenesulfonic acid, acidic resin, phosphotungstic heteropolyacid, acidic ionic liquid and acidic molecular sieve, preferably one or more of sulfuric acid, tin chloride, n-butyltin oxide, paratoluenesulfonic acid, acidic resin and phosphotungstic heteropolyacid). The addition amount of the catalyst is preferably 0.1%-10% by the mass of the compound represented by formula (β). The catalyst can be removed by a method known in the art (for example, the method of alkali washing and water washing), which is not particularly limited.

In one embodiment of the present invention, in the reaction of the compound represented by formula (α) and the compound represented by formula (β), it is preferable that, the reaction product is washed with a solvent and purified, and the solvent that can be used for washing is preferably a hydrocarbon solvent. The solvent can be removed by conventional technical means such as drying, evaporation and distillation.

In one embodiment of the present invention, the reaction of the compound represented by formula (α) and the compound represented by formula (β) can be performed in a continuous or batch reaction equipment such as a reaction vessel, a fixed bed, a fluid bed, a microchannel reactor and the like.

In one embodiment of the present invention, in the reaction of the compound represented by formula (α) and the compound represented by formula (β), a solvent may or may not be added, preferably a solvent is added. Said solvent is preferably a hydrocarbon solvent, preferably one or more of alkanes, arenes and ethers, more preferably an alkane solvent, for example, can be one or more of hexane, heptane, octane, nonane, decane, cyclohexane, cycloheptane, cyclooctane, cyclononane, cyclodecane, benzene, toluene, xylene, ethylbenzene, propyl benzene, ethyl ether, propyl ether, isopropyl ether and butyl ether. The addition amount of said solvent should be suitable to promote the smooth progress of the reaction, and is not particularly limited. The solvent can also act as a water-carrying agent to promote the smooth progress of the reaction.

In one embodiment of the present invention, when step (1) and step (2) are performed, the reaction molar equivalent ratio of the compound represented by formula (α-2) (as X) to the compound represented by formula (α-1) (as OH) to the compound represented by formula (β) (as Y) is 1:0.8-2:0.5-10 (preferably 1:1-2:1-6); the reaction temperature is 70-250° C. (preferably 90-200° C.). In general, the longer the reaction time is, the better it is, and the reaction time can be 0.5-24 hours, preferably 2-15 hours.

In one embodiment of the present invention, according to the preparation process of the present invention, in the reaction products of the compound represented by formula (α-2), the compound represented by formula (α-1), and the compound represented by formula (β), it is sometimes possible to contain a variety of ester compounds, and these ester compounds can be separated into single-structure compounds by conventional methods, or these ester compounds can also be used directly as products without separating them.

In one embodiment of the present invention, the compound represented by formula (α-2), the compound represented by formula (α-1) and the compound represented by formula (β) are reacted together; or the compound represented by formula (α-2) and the compound represented by formula (α-1) is firstly reacted, and then the resulting product is reacted with the compound represented by formula (β); or the compound represented by formula (α-1) and the compound represented by formula (β) are firstly reacted, and then the resulting product is reacted with the compound represented by formula (α-2).

In one embodiment of the present invention, in the reaction of the compound represented by formula (α-2) with the compound represented by formula (α-1) and the compound represented by formula (β), a solvent may or may not be added, preferably a solvent is added. Said solvent is preferably a hydrocarbon solvent, preferably one or more of alkanes, arenes and ethers, more preferably an alkane solvent, for example, can be one or more of hexane, heptane, octane, nonane, decane, cyclohexane, cycloheptane, cyclooctane, cyclononane, cyclodecane, benzene, toluene, xylene, ethylbenzene, propyl benzene, ethyl ether, propyl ether, isopropyl ether and butyl ether. The addition amount of said solvent should be suitable to promote the smooth progress of the reaction, and is not particularly limited. The solvent can also act as a water-carrying agent to promote the smooth progress of the reaction.

In one embodiment of the present invention, the compound represented by formula (α-2) and the compound represented by formula (α-1) is firstly reacted, and then the resulting product is reacted with the compound represented by formula (β); wherein the reaction temperatures are both 0-300° C. (preferably 50-260° C.); and the reaction times are both 0.5-72 hours (preferably 3-48 hours).

In one embodiment of the present invention, in the reaction of the compound represented by formula (α-2) with the compound represented by formula (α-1) and the compound represented by formula (β), a catalyst may or may not be added. As the catalyst, the catalyst can be one or more of inorganic acid, organic acid, solid acid, heteropolyacid, acidic ionic liquid, acidic resin, acidic molecular sieve, metal chloride and metal oxide, for example, can be one or more of sulfuric acid, perchloric acid, $AlCl_3$, tin chloride, n-butyltin oxide, dibutyltin oxide, paratoluenesulfonic acid, acidic resin, phosphotungstic heteropolyacid, acidic ionic liquid, and acidic molecular sieve, preferably one or more of perchloric acid, tin chloride, n-butyltin oxide, paratoluenesulfonic acid, acidic resin and phosphotungstic heteropolyacid. The addition amount of the catalyst is preferably 0.1%-10% by the mass of the compound represented by formula (β). The catalyst can be removed by a method known in the art (for example, the method of alkali washing, water washing and filtering), which is not particularly limited.

In one embodiment of the present invention, in the reaction of the compound represented by formula (α-2) with the compound represented by formula (α-1) and the compound represented by formula (β), it is preferable that the reaction product is washed with a solvent and purified, and the solvent that can be used for washing is preferably a hydrocarbon solvent. The solvent can be removed by conventional technical means such as drying, evaporation and distillation.

In one embodiment of the present invention, the reaction of the compound represented by formula (α-2) with the compound represented by formula (α-1) and the compound represented by formula (β) can be performed in a continuous or batch reaction equipment such as a reaction vessel, a fixed bed, a fluid bed, a microchannel reactor and the like.

Second Invention

The second invention of the present invention provides an ester compound, which has a structure as shown in the following formula (VI), (VI)

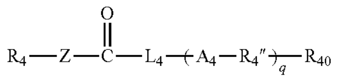

wherein, the $R_4$ group is selected from an optionally substituted $C_{1-10}$ linear or branched alkyl, $-L_4'-(OH)_n$, H (preferably selected from an optionally substituted $C_{1-6}$ linear or branched alkyl, $-L_4'-(OH)_n$, H, more preferably selected from an optionally substituted $C_{1-3}$ linear or branched alkyl, $-L_4'-(OH)_n$, H), wherein n is an integral number of 1-10 (preferably an integral number of 1-6, more preferably 1, 2 or 3), the $L_4'$ group is an (n+1)-valent $C_{1-15}$ linear or branched alkyl (preferably an (n+1)-valent $C_{1-10}$ linear or branched alkyl, more preferably an (n+1)-valent $C_{1-6}$ linear or branched alkyl, further preferably an (n+1)-valent $C_{1-3}$ linear or branched alkyl);

Z represents an oxygen atom or $NR_z$, $R_z$ is selected from H, an optionally substituted $C_{1-6}$ linear or branched alkyl (preferably selected from H, a $C_{1-3}$ linear or branched alkyl);

The $L_4$ group is selected from a single bond, a $C_{1-30}$ linear or branched hydrocarbylene (preferably selected from a $C_{1-20}$ linear or branched alkylene, more preferably selected from a $C_{1-10}$ linear or branched alkylene);

q is an integral number of 1-12 (preferably an integral number of 1-8, more preferably an integral number of 1-5);

the $R_4''$ group(s), identical to or different from each other, are each independently selected from single bond, a $C_{1-10}$ linear or branched hydrocarbylene (preferably a $C_{1-10}$ linear or branched alkylene, more preferably a $C_{1-6}$ linear or branched alkylene, more preferably a $C_{1-3}$ linear or branched alkylene);

the $R_{40}$ group is selected from H, an optionally substituted $C_{1-10}$ hydrocarbyl (preferably an optionally substituted $C_{1-10}$ linear or branched alkyl, more preferably an optionally substituted $C_{1-6}$ linear or branched alkyl, more preferably an optionally substituted $C_{1-3}$ linear or branched alkyl);

The $A_4$ groups, identical to or different from each other, are each independently selected from a group represented by formula (VII), a group represented by formula (VIII), —CH═CH—,

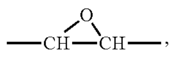, an ethylene group, a propylene group, and at least one A group is selected from a group represented by formula (VII), a group represented by formula (VIII), or at least two A groups are selected from a group represented by formula (IX);

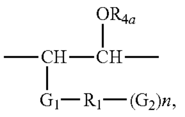

(VII)

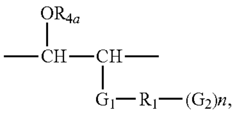

(VIII)

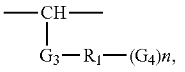

(IX)

In the above Formulae, $R_{4a}$ is independently selected from H, an optionally substituted $C_{1-10}$ hydrocarbyl,

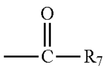

(preferably H, an optionally substituted $C_{1-6}$ linear or branched alkyl,

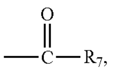

more preferably H, an optionally substituted $C_{1-3}$ linear or branched alkyl,

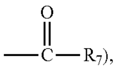

the $R_7$ groups are each independently selected from H, an optionally substituted $C_{1-10}$ linear or branched alkyl (preferably selected from an optionally substituted $C_{1-6}$ linear or branched alkyl, more preferably selected from an optionally substituted $C_{1-3}$ linear or branched alkyl);

the $G_1$ groups are each independently selected from

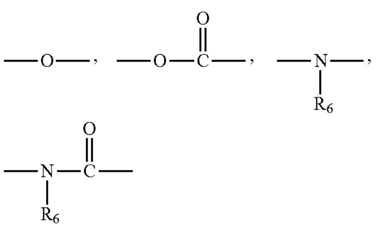

(wherein the carbonyl carbon is attached to the $R_1$ group), the $R_6$ groups are each independently selected from H, an optionally substituted $C_{1-6}$ linear or branched alkyl, optionally substituted $C_{3-10}$ cycloalkyl, an optionally substituted $C_{6-15}$ aryl, an optionally substituted $C_{7-15}$ alkylaryl (preferably selected from H, an optionally substituted $C_{1-3}$ linear or branched alkyl, an optionally substituted $C_{3-6}$ cycloalkyl, an optionally substituted $C_{6-10}$ aryl, an optionally substituted $C_{7-12}$ alkylaryl);

$R_1$ is selected from a single bond, an (n+1)-valent optionally substituted $C_{1-17}$ hydrocarbyl (preferably selected from an (n+1)-valent $C_{1-15}$ linear or branched alkyl, an (n+1)-valent optionally substituted $C_{3-10}$ cycloalkyl, an (n+1)-valent optionally substituted $C_{6-15}$ aryl, an (n+1)-valent optionally substituted $C_{7-15}$ alkylaryl, more preferably selected from an (n+1)-valent optionally substituted $C_{1-11}$ linear or branched alkyl, an (n+1)-valent optionally substituted $C_{3-6}$ cycloalkyl, an (n+1)-valent optionally substituted $C_{6-10}$ aryl, an (n+1)-valent optionally substituted $C_{7-12}$ alkylaryl);

the $G_2$ groups are each independently selected from —$OR_2$,

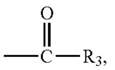

—$N(R_5)_2$, wherein the $R_2$ groups are each independently selected from H, an optionally substituted $C_{1-10}$ linear or branched alkyl (preferably selected from H, an optionally substituted $C_{1-6}$ linear or branched alkyl, more preferably selected from H, an optionally substituted $C_{1-3}$ linear or branched alkyl), the $R_3$ groups are each independently selected from OH, an optionally substituted $C_{1-10}$ linear or branched alkyl, an optionally substituted $C_{1-6}$ linear or branched alkoxyl, an optionally substituted $C_{3-10}$ cycloalkyl, an optionally substituted $C_{6-15}$ aryl, an optionally substituted $C_{7-15}$ alkylaryl (preferably selected from OH, an optionally substituted $C_{1-6}$ linear or branched alkyl, an optionally substituted $C_{1-6}$ linear or branched alkoxyl, an optionally substituted $C_{3-6}$ cycloalkyl, an optionally substituted $C_{6-10}$ aryl, an optionally substituted $C_{7-12}$ alkylaryl); the $R_5$ groups are each independently selected from H, an optionally substituted $C_{1-10}$ linear or branched alkyl (preferably selected from H, an optionally substituted $C_{1-6}$ linear or branched alkyl, more preferably selected from H, an optionally substituted $C_{1-3}$ linear or branched alkyl); n is an integral number of 0-10 (preferably an integral number of 0-6, more preferably 0, 1, 2 or 3);

the $G_3$ group is selected from

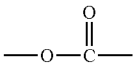

(wherein the carbonyl carbon is attached to the $R_1$ group); the $G_4$ groups are each independently selected from

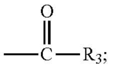

at least one —C(O)—O— group is present in the compound, said substituents that optionally substitute are selected from halogen atoms, hydroxy, amino, $C_{1-6}$ linear or branched alkyl, $C_{6-10}$ aryl, $C_{3-10}$ cycloalkyl.

In one embodiment of the present invention, in the above formula (VI), Z represents an oxygen atom, $R_{4a}$ is independently selected from H, an optionally substituted $C_{1-6}$ linear or branched alkyl (more preferably H, an optionally substituted $C_{1-3}$ linear or branched alkyl); the $G_1$ groups are each independently selected from —O—; $R_1$ is selected from an (n+1)-valent optionally substituted $C_{1-15}$ linear or branched alkyl, an (n+1)-valent optionally substituted $C_{3-10}$ cycloalkyl, an (n+1)-valent optionally substituted $C_{6-15}$ aryl, an (n+1)-valent optionally substituted $C_{7-15}$ alkylaryl, n represents an integral number of 1-6; the $G_2$ groups are each independently selected from —$OR_2$, wherein the $R_2$ groups are each independently selected from H, an optionally substituted $C_{1-10}$ linear or branched alkyl.

In one embodiment of the present invention, in the above formula (VI), Z represents an oxygen atom, $R_{4a}$ is independently selected from H, an optionally substituted $C_{1-6}$ linear or branched alkyl (more preferably H, an optionally substituted $C_{1-3}$ linear or branched alkyl); the $G_1$ groups are each independently selected from

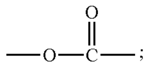

$R_1$ is selected from an (n+1)-valent optionally substituted $C_{1-15}$ linear or branched alkyl, an (n+1)-valent optionally substituted $C_{3-10}$ cycloalkyl, an (n+1)-valent optionally substituted $C_{6-15}$ aryl, an (n+1)-valent optionally substituted $C_{7-15}$ alkylaryl, n represents an integral number of 1-6; the $G_2$ groups are each independently selected from

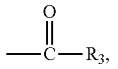

the $R_3$ groups are each independently selected from OH, an optionally substituted $C_{1-6}$ linear or branched alkyl.

In one embodiment of the present invention, in the above formula (VI), $R_{4a}$ is independently selected from H, an optionally substituted $C_{1-6}$ linear or branched alkyl; the $G_1$ groups are each independently selected from

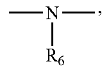

the $R_6$ groups are each independently selected from H, an optionally substituted $C_{1-6}$ linear or branched alkyl, an optionally substituted $C_{3-10}$ cycloalkyl, an optionally substituted $C_{6-15}$ aryl, an optionally substituted $C_{7-15}$ alkylaryl; $R_1$ is selected from an (n+1)-valent optionally substituted $C_{1-15}$ linear or branched alkyl, an (n+1)-valent an optionally substituted $C_{3-10}$ cycloalkyl, an (n+1)-valent $C_{6-15}$ aryl, an (n+1)-valent optionally substituted $C_{7-15}$ alkylaryl, n represents an integral number of 0-6; the $G_2$ groups are each independently selected from —$OR_2$, —$N(R_5)_2$, the $R_2$ groups are each independently selected from H, an optionally substituted $C_{1-10}$ linear or branched alkyl, the $R_5$ groups are each independently selected from H, an optionally substituted $C_{1-10}$ linear or branched alkyl.

In one embodiment of the present invention, in the above formula (VI), $R_{4a}$ is independently selected from H, an optionally substituted $C_{1-6}$ linear or branched alkyl; the $G_1$ groups are each independently selected from

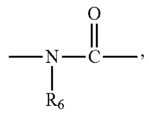

the $R_6$ groups are each independently selected from H, an optionally substituted $C_{1-6}$ linear or branched alkyl, an optionally substituted $C_{3-10}$ cycloalkyl, an optionally substituted $C_{6-15}$ aryl, an optionally substituted $C_{7-15}$ alkylaryl; $R_1$ is selected from an (n+1)-valent optionally substituted $C_{1-15}$ linear or branched alkyl, an (n+1)-valent optionally substituted $C_{3-10}$ cycloalkyl, an (n+1)-valent optionally substituted $C_{6-15}$ aryl, an (n+1)-valent optionally substituted $C_{7-15}$ alkylaryl, n represents 0.

In one embodiment of the present invention, said ester compound is selected from one or more of the following compounds:

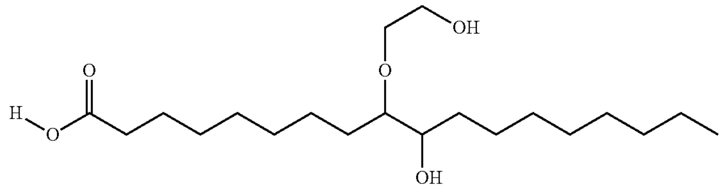

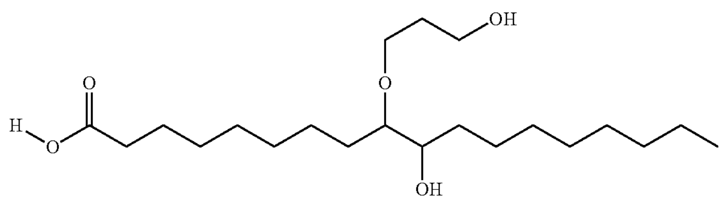

-continued
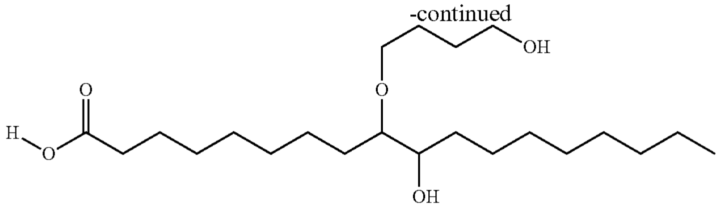
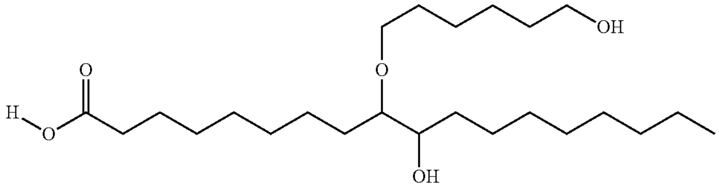
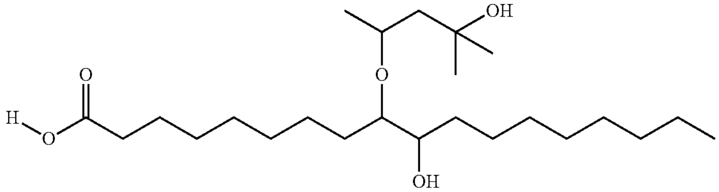
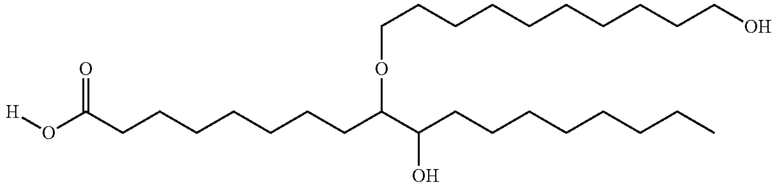
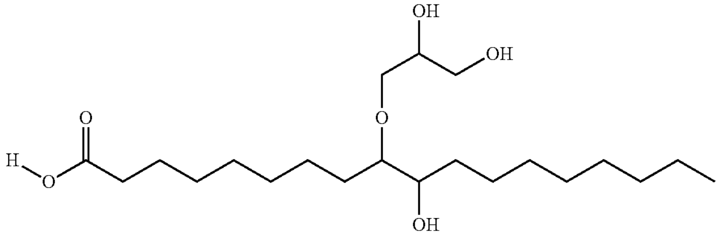
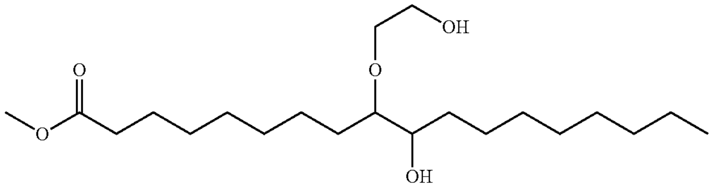
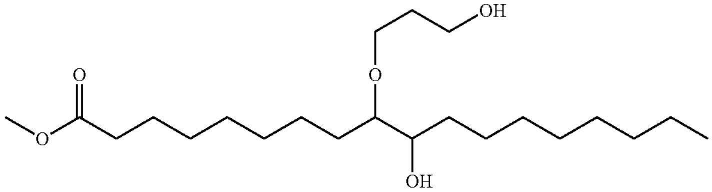
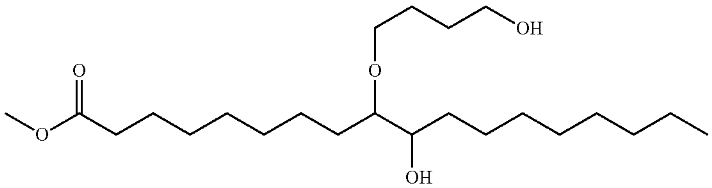
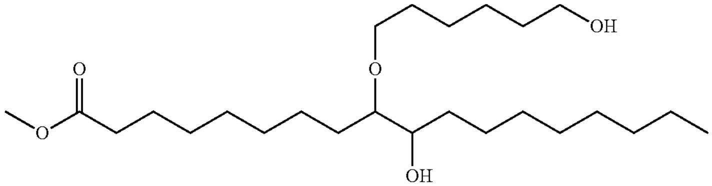

-continued
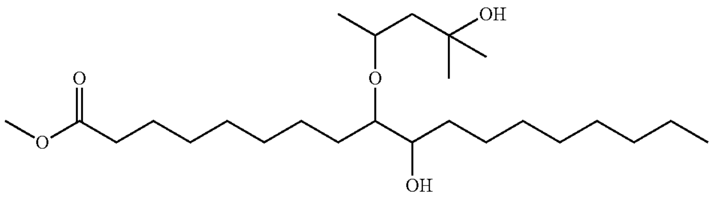
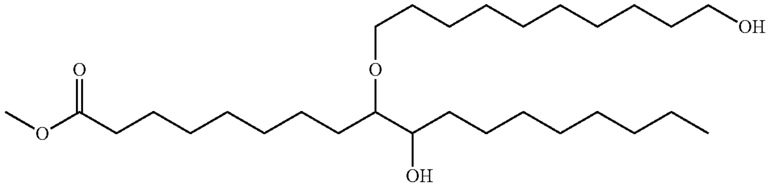
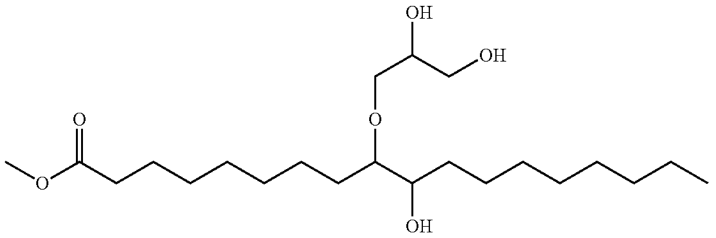
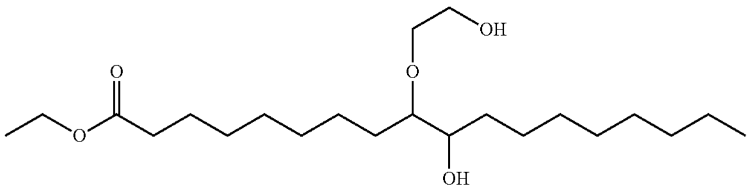
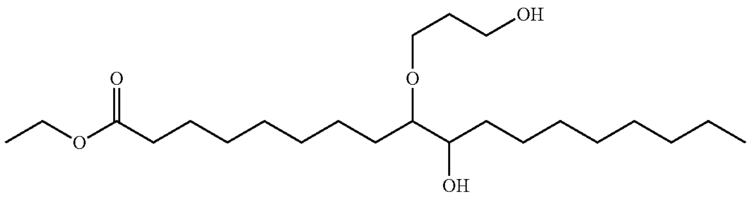
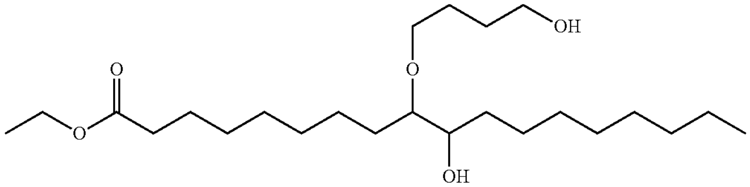
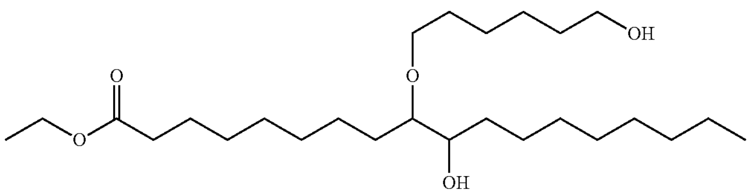
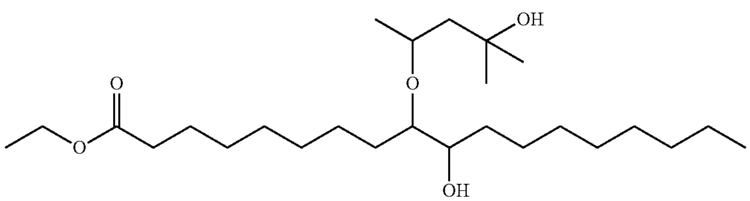

-continued
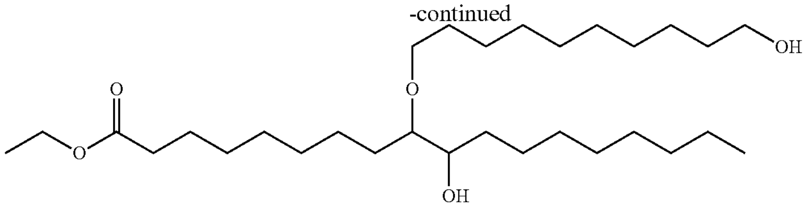
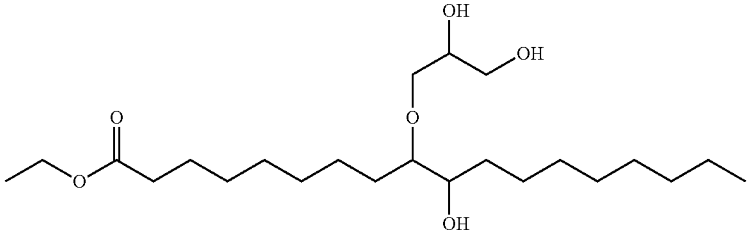
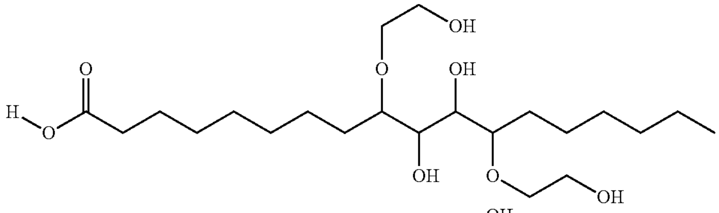
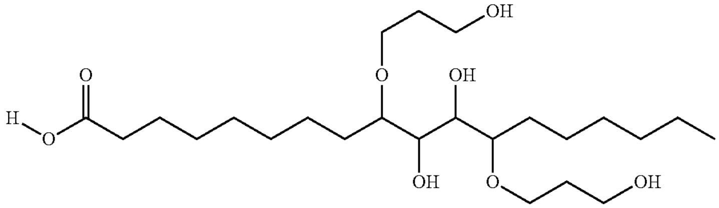
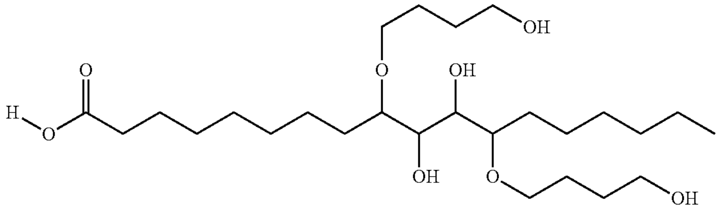
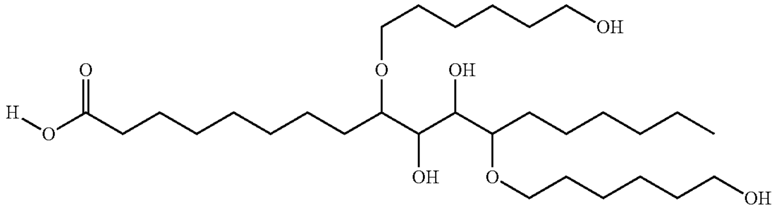
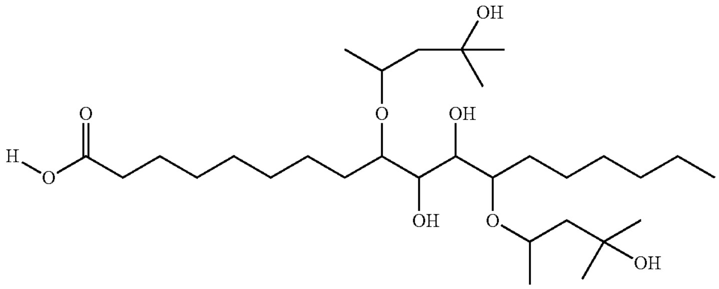

-continued
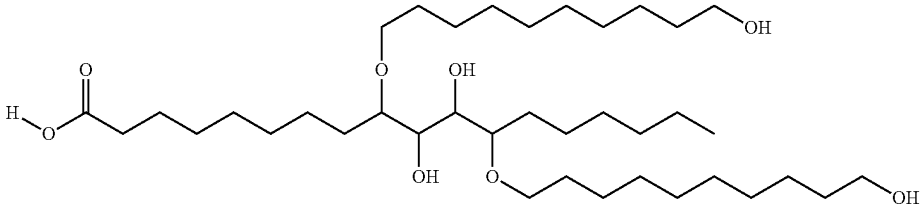
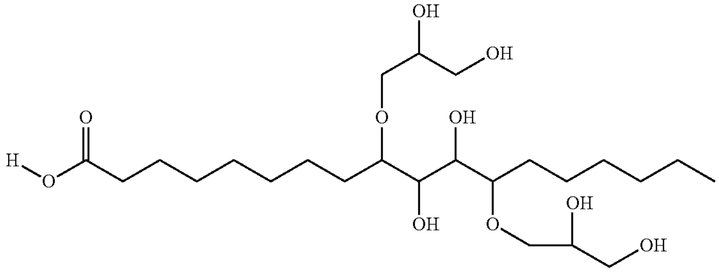
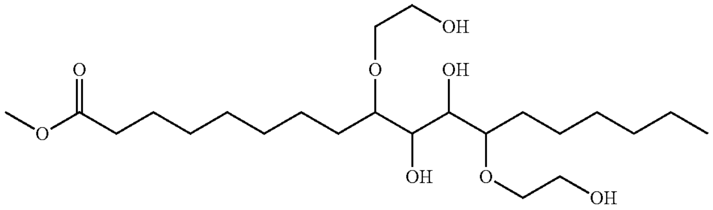
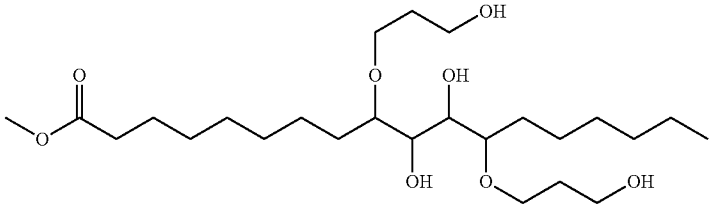
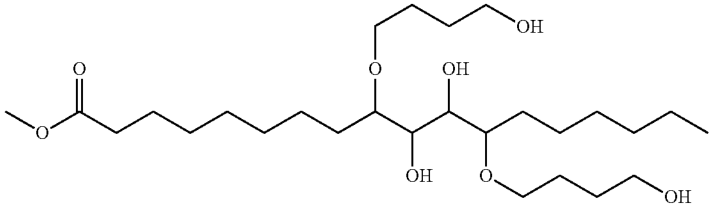
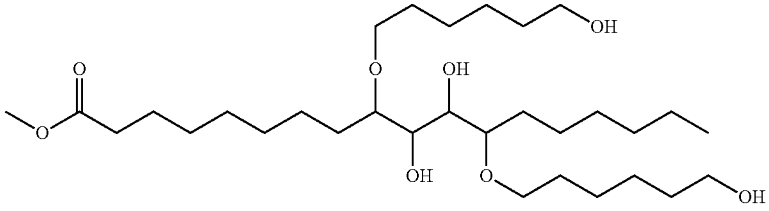
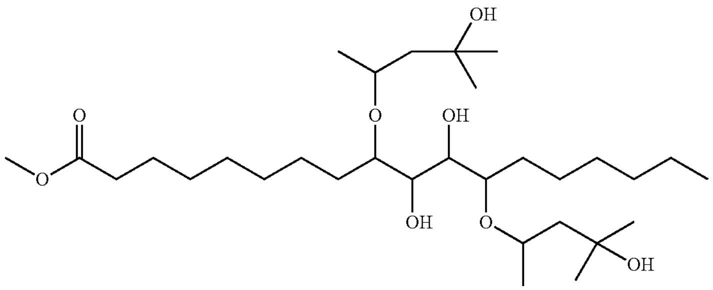

-continued
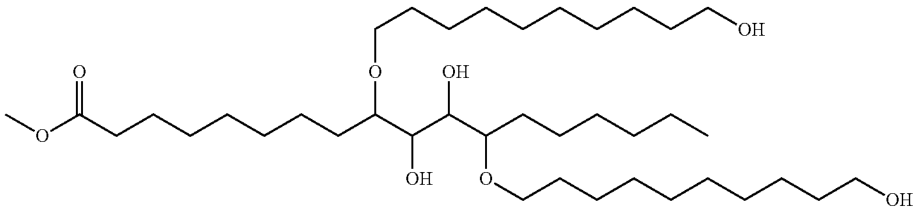
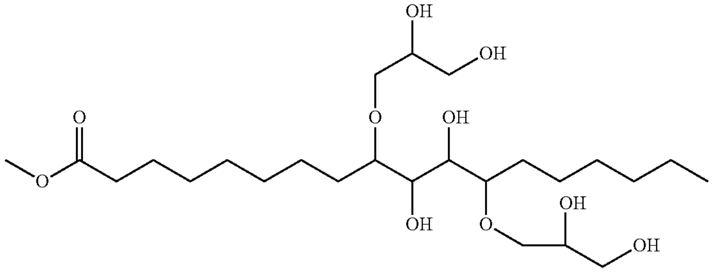
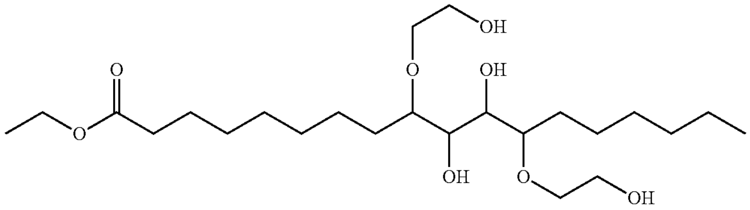
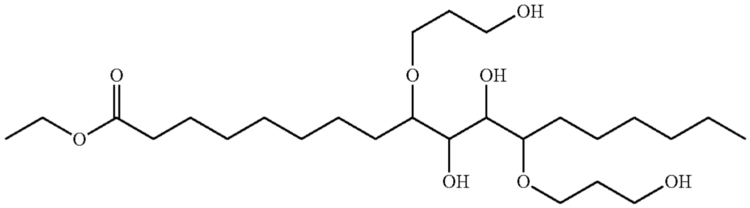
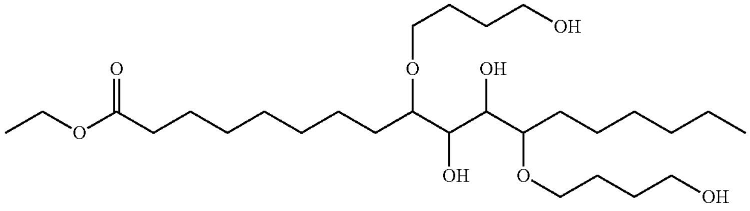
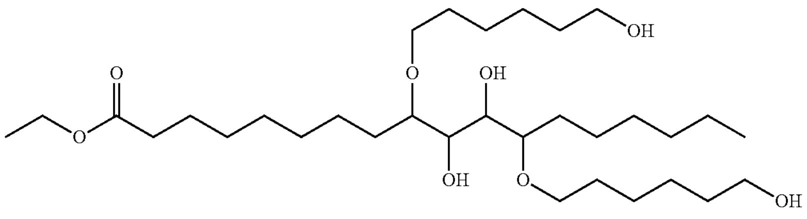
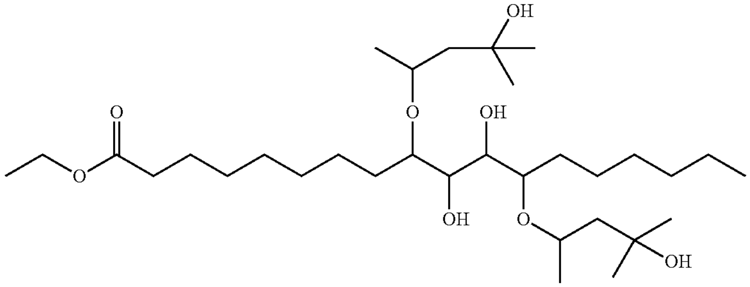

-continued
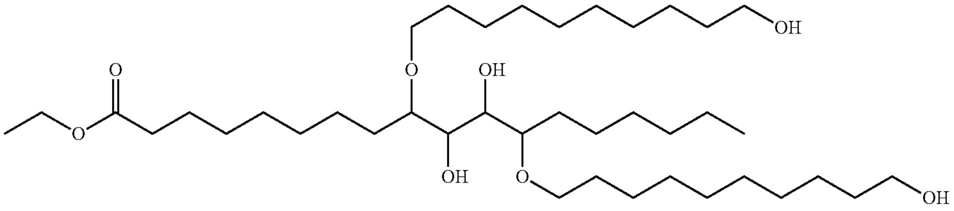
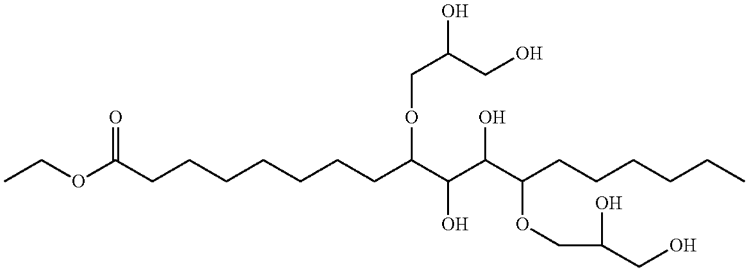
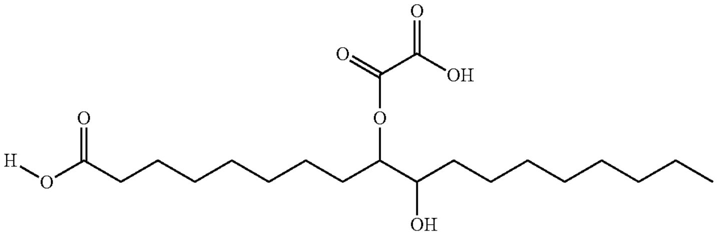
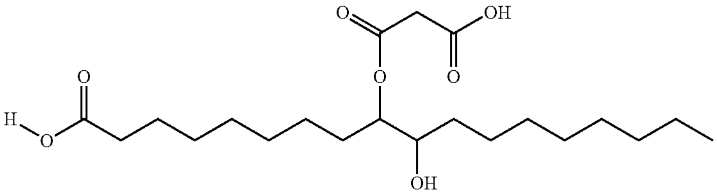
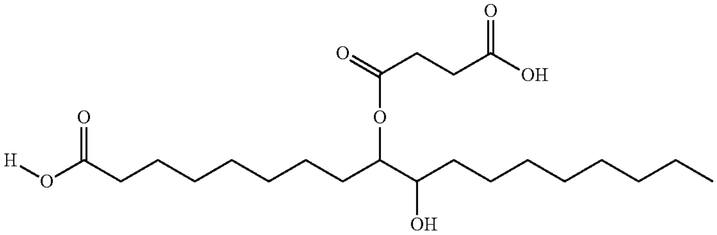
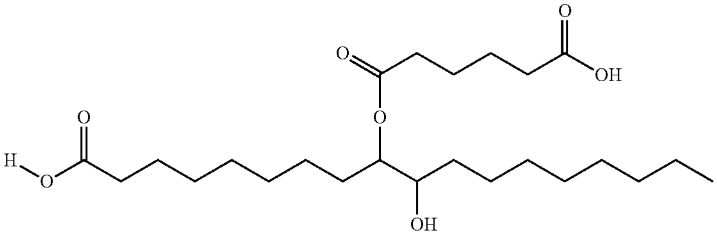
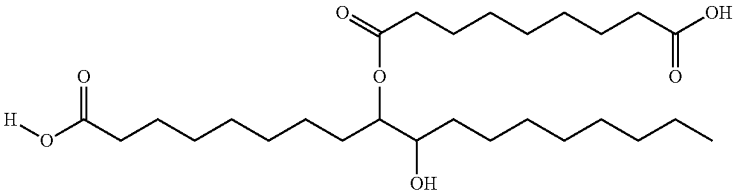

-continued
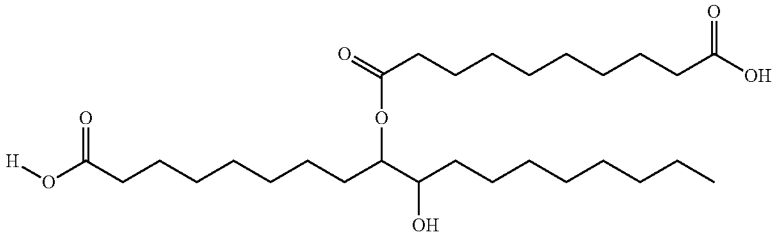
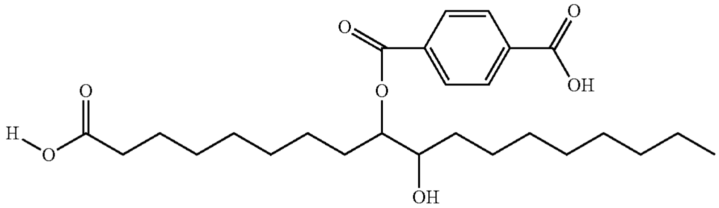
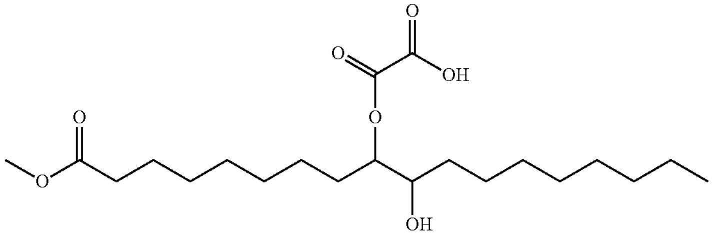
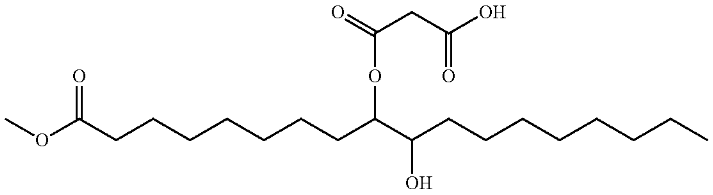
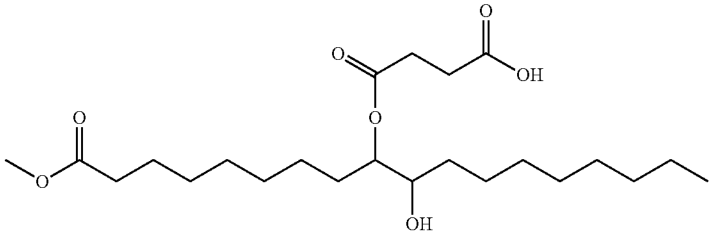
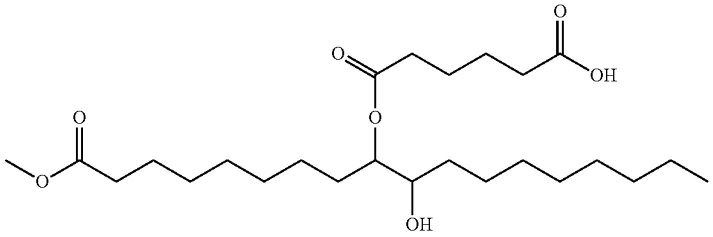
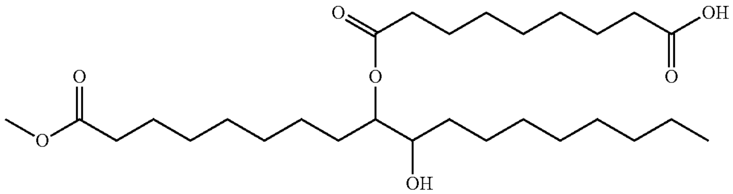

-continued
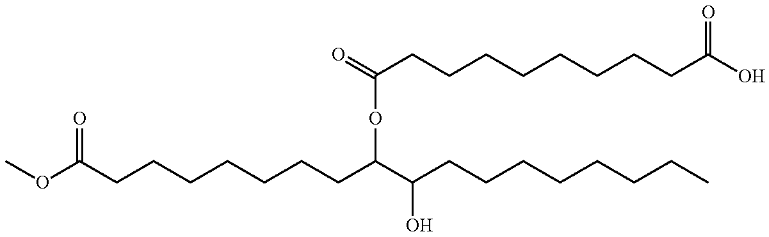
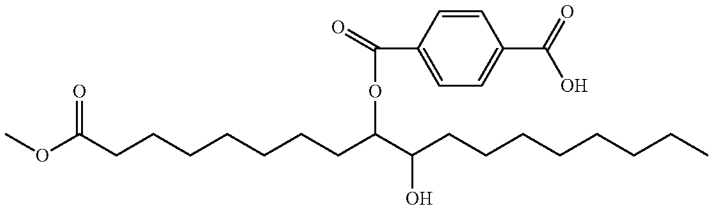
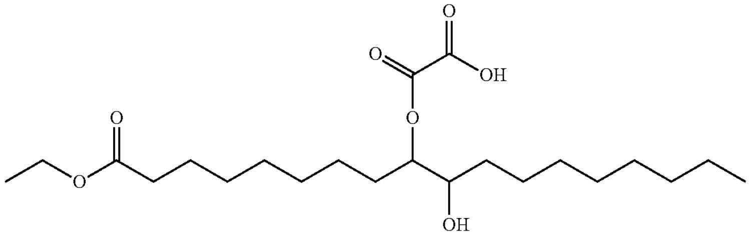
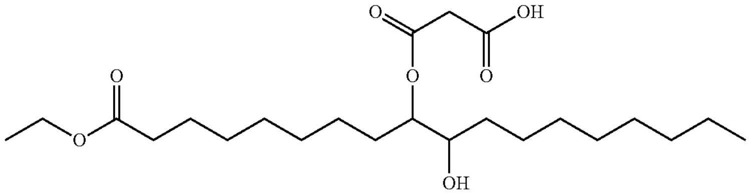
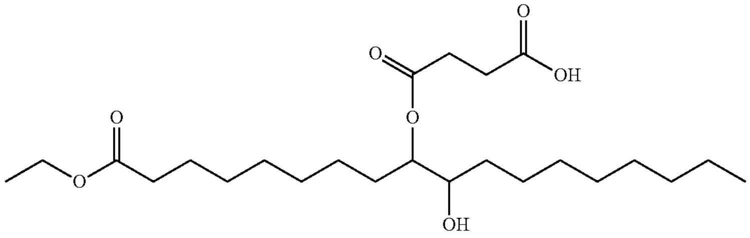
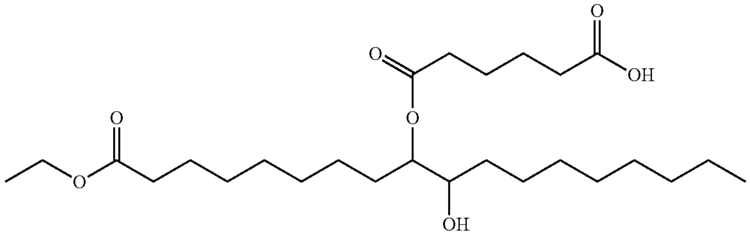
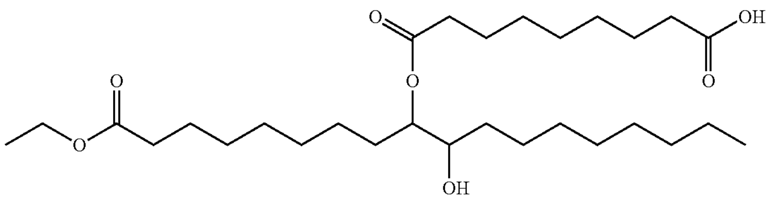

-continued
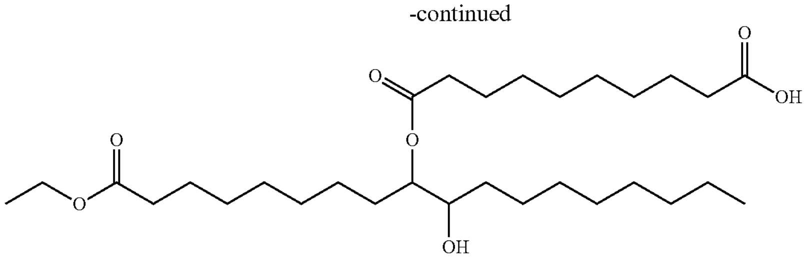
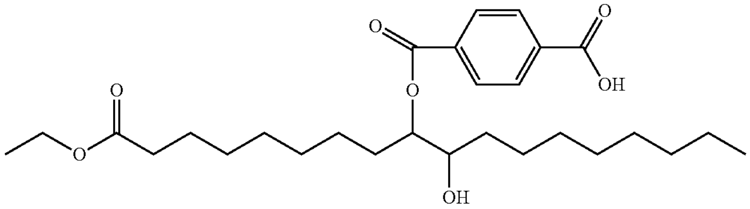
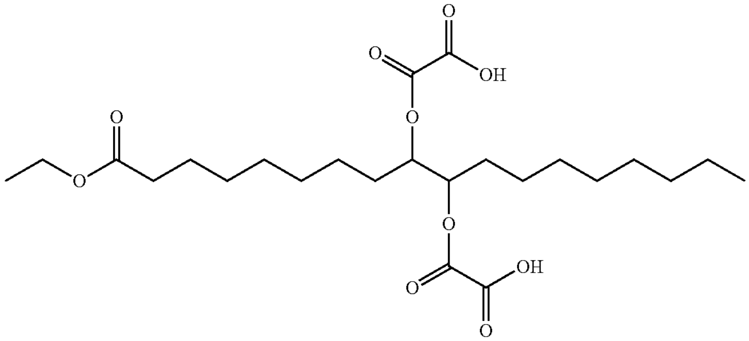
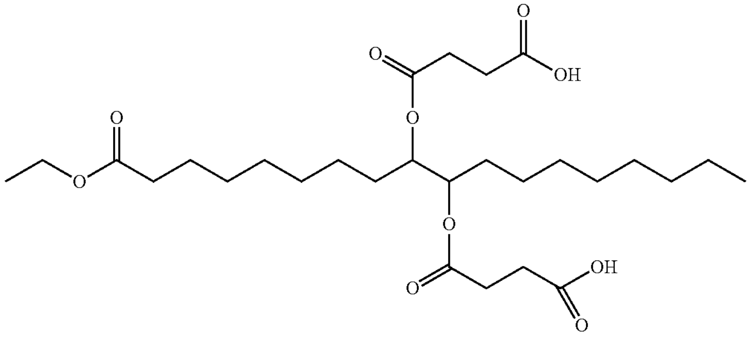
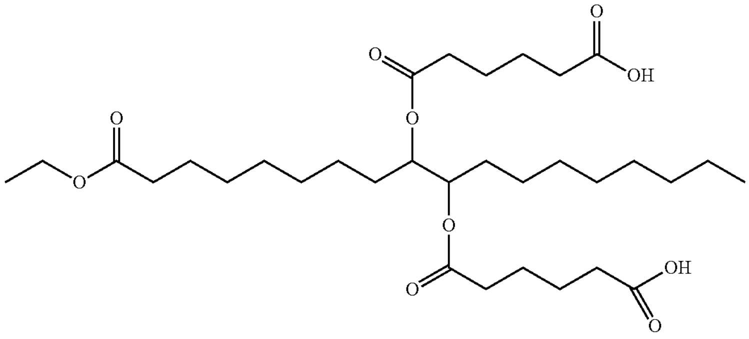

-continued
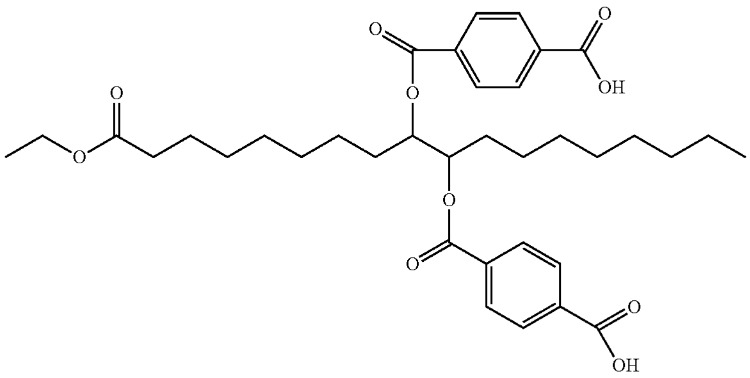
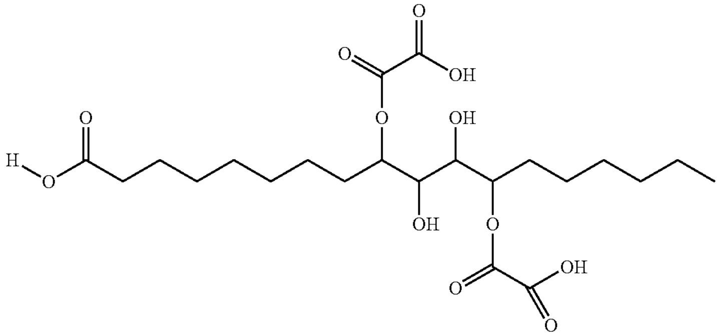
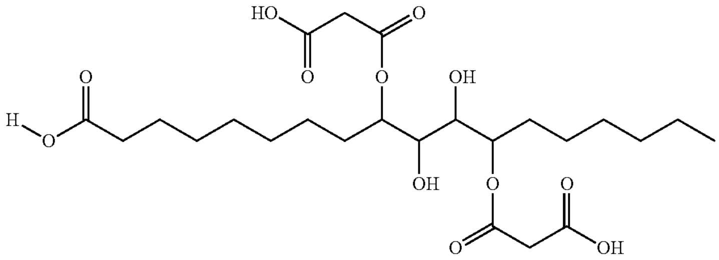
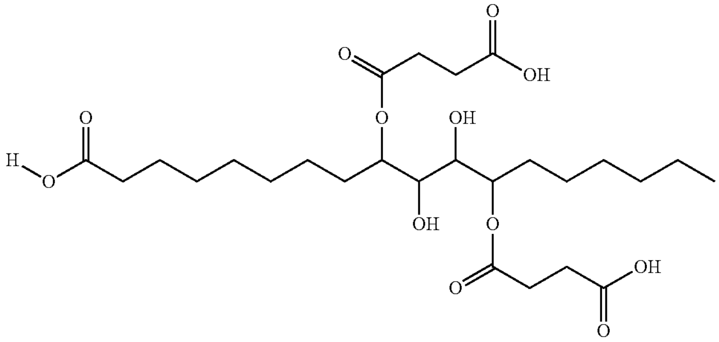
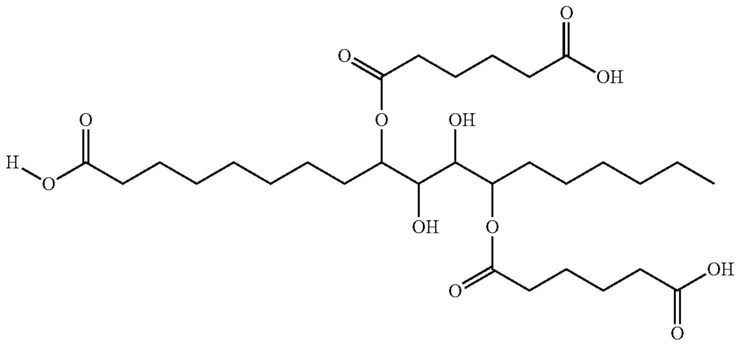

-continued
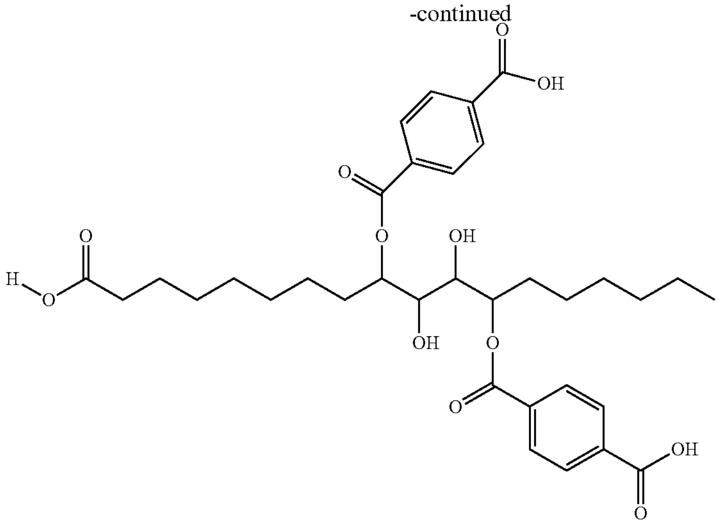
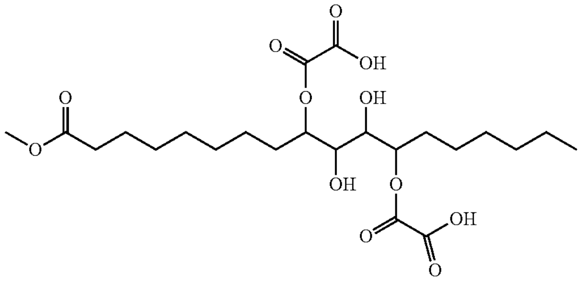
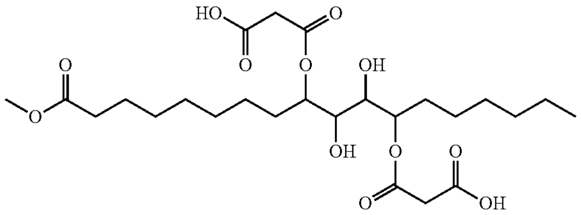
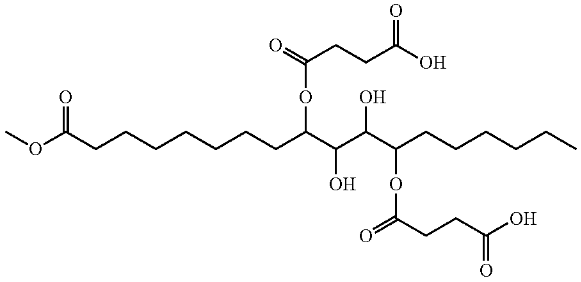
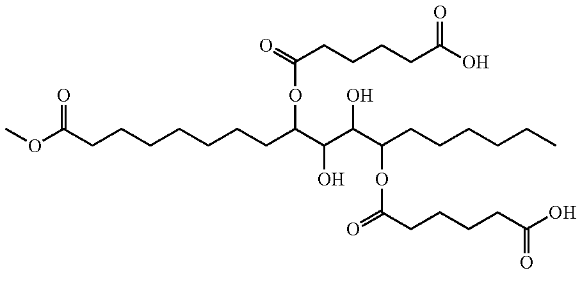

-continued
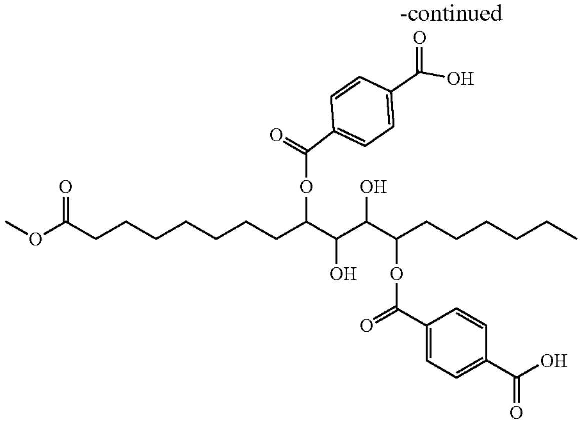
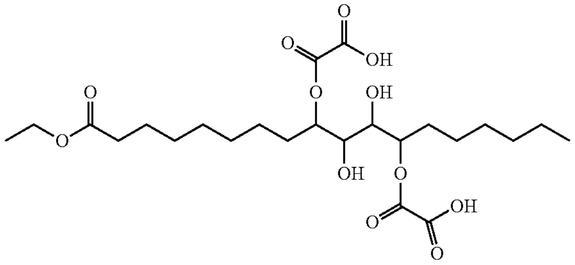
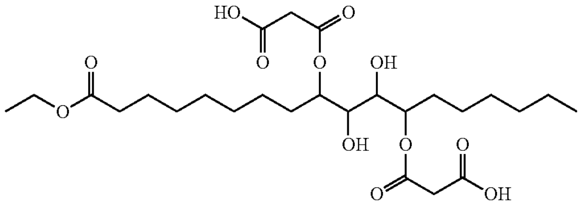
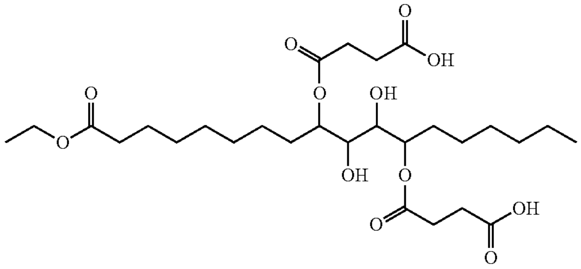
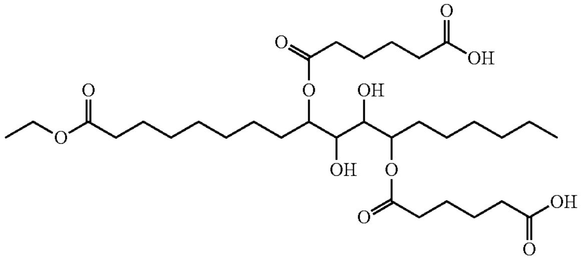

-continued
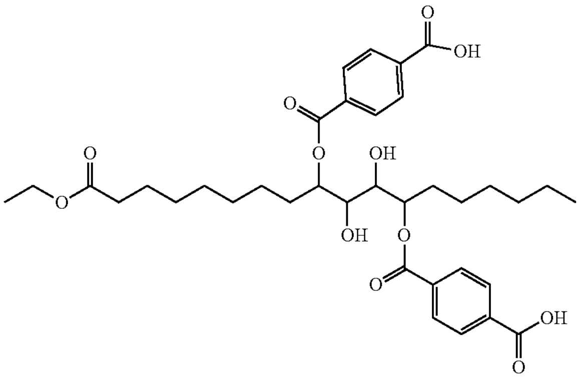
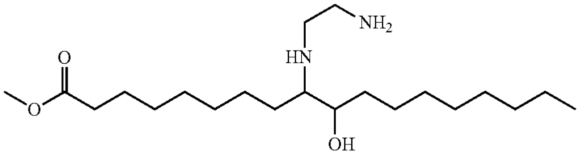
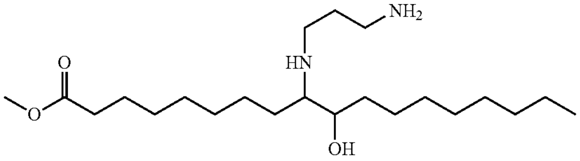
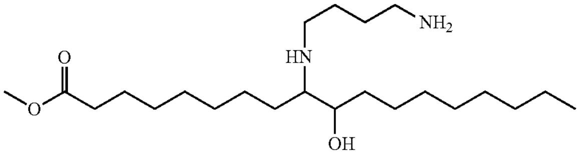
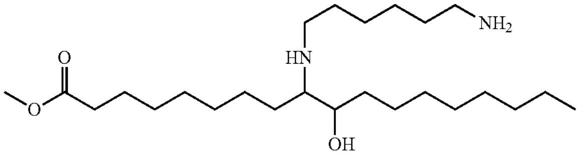
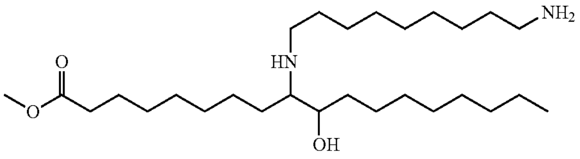
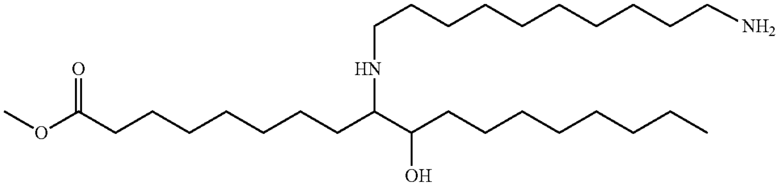
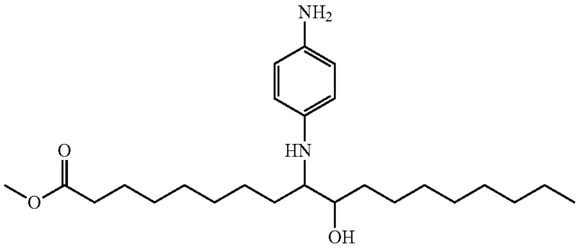

-continued
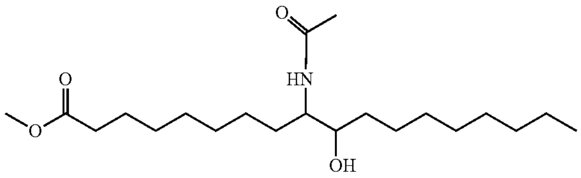
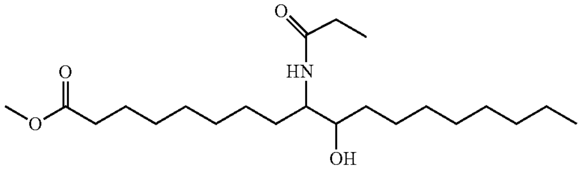
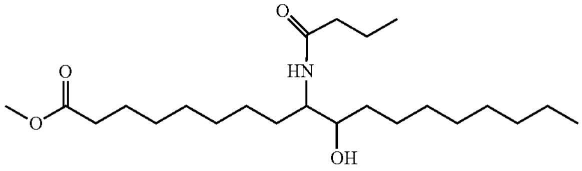
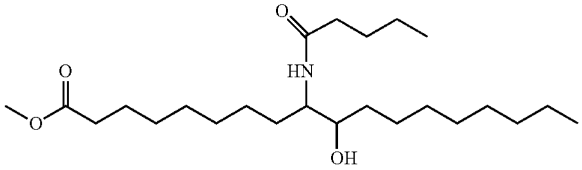
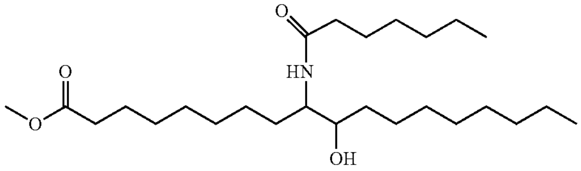
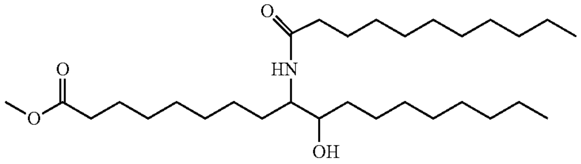
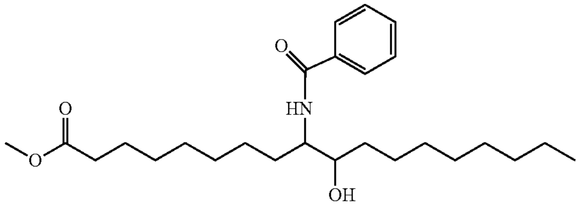
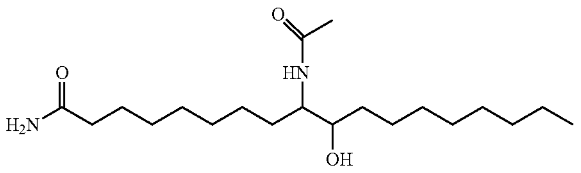
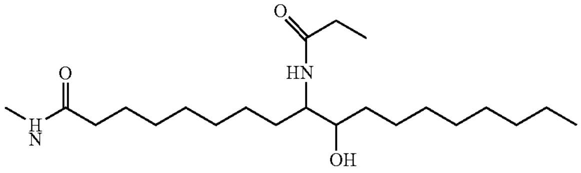
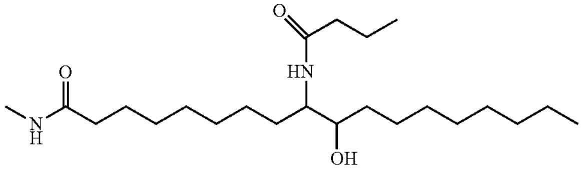

-continued
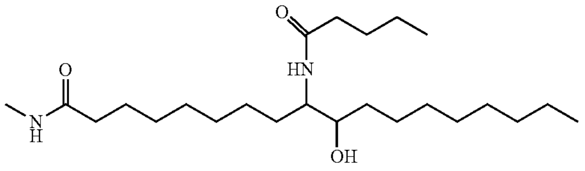
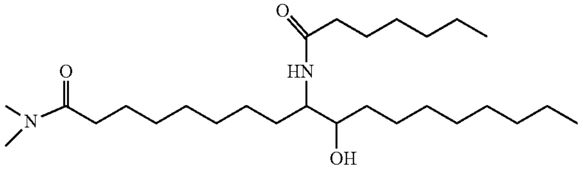
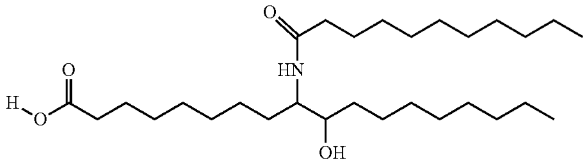
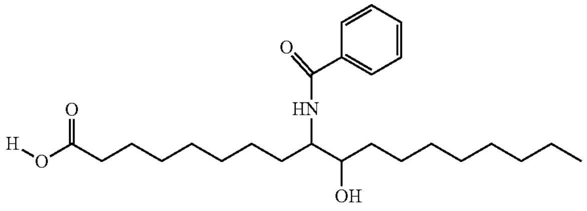
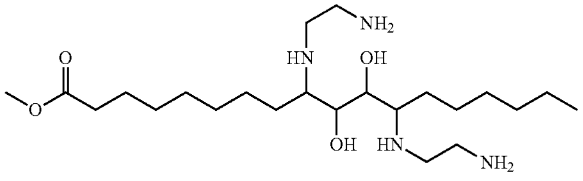
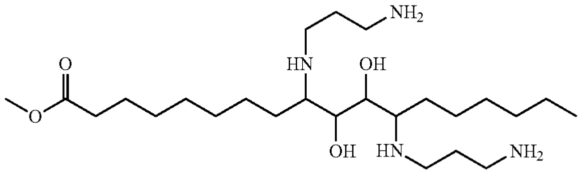
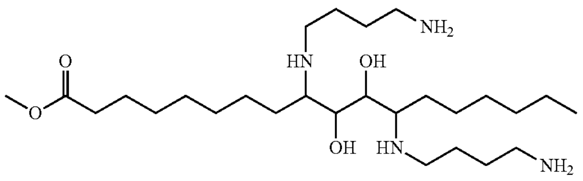
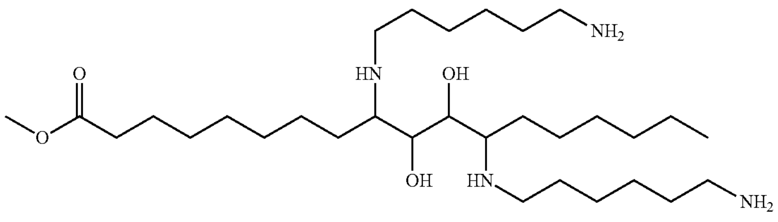
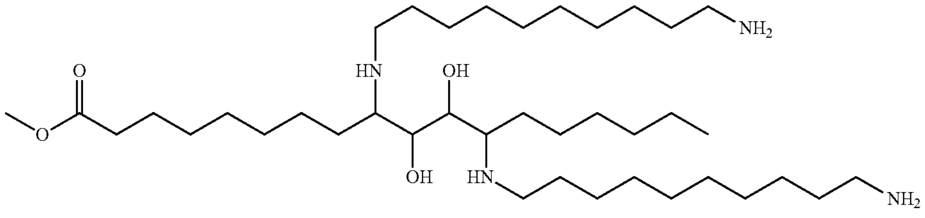

-continued
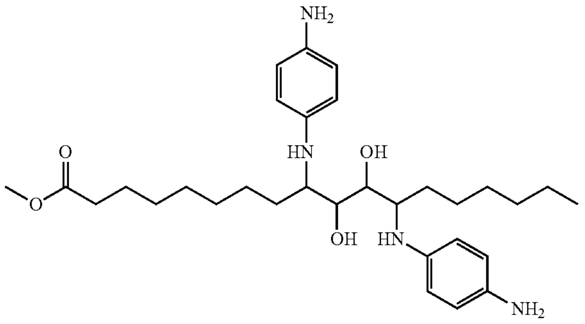
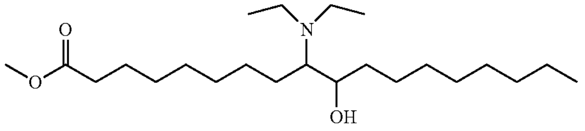
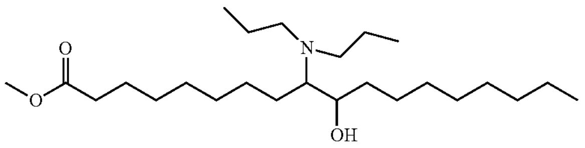
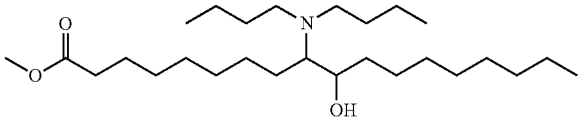
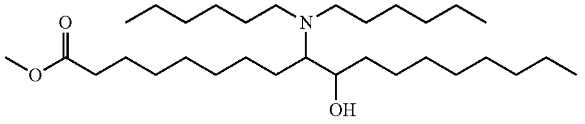
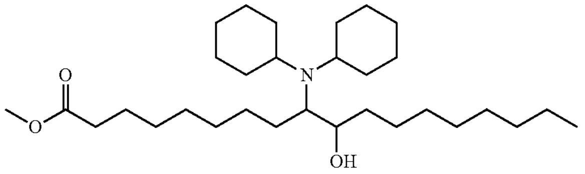
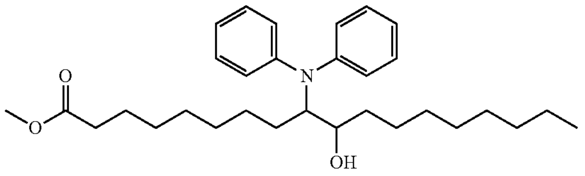
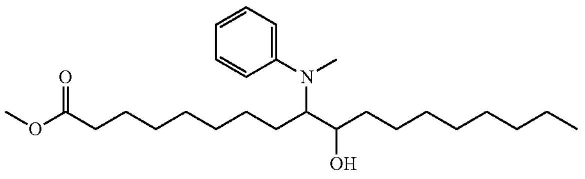
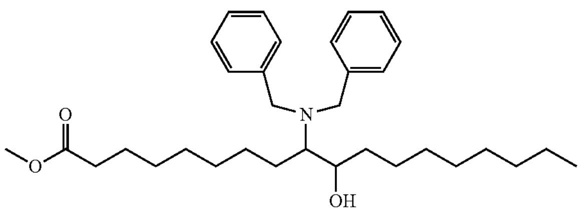

-continued
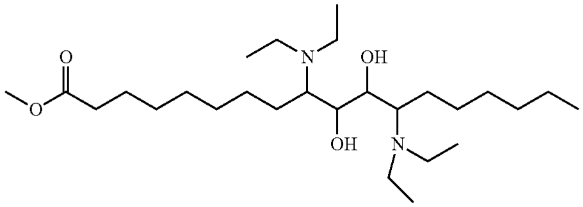
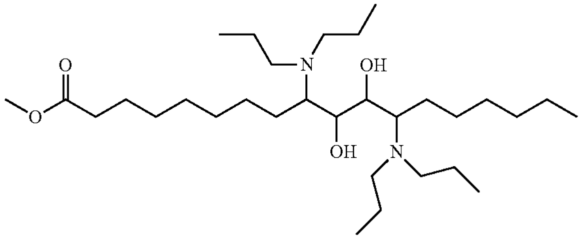
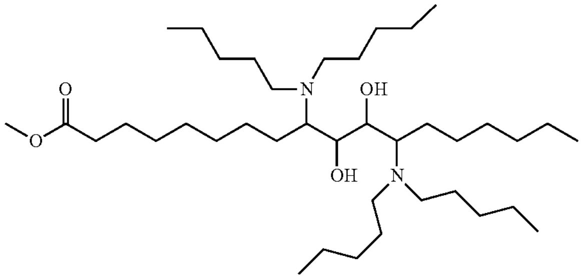
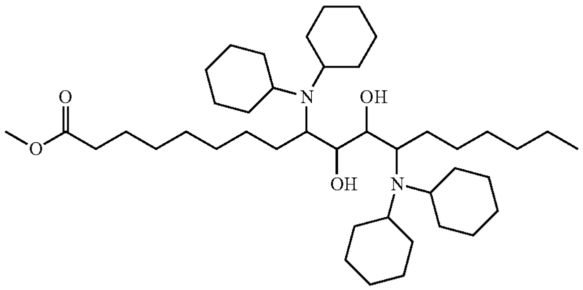
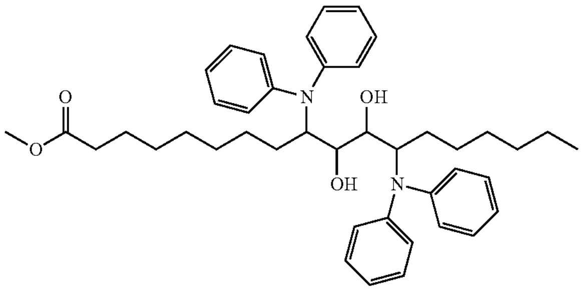
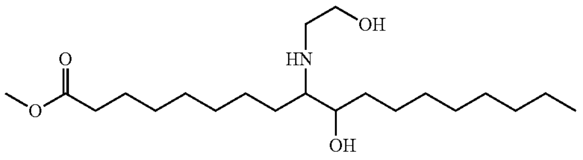
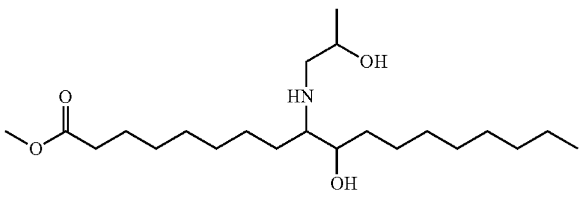

-continued
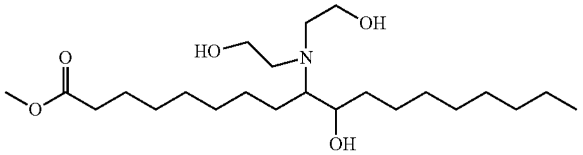
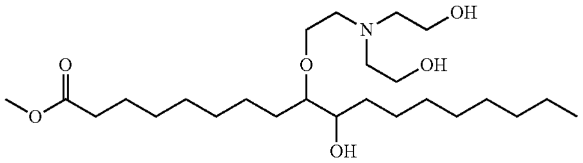
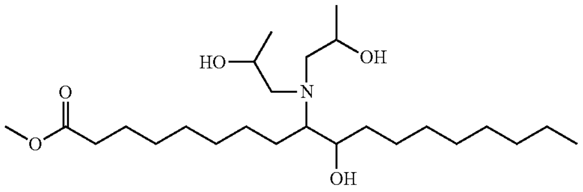
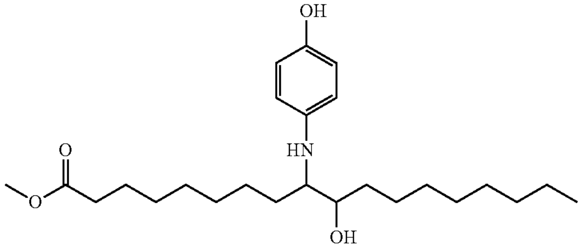
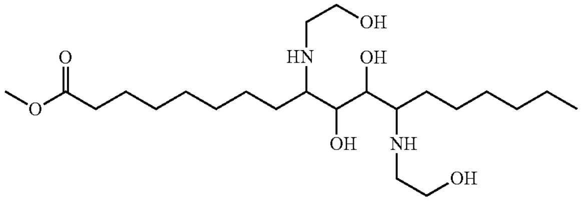
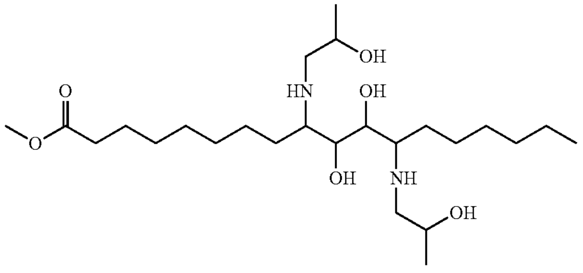
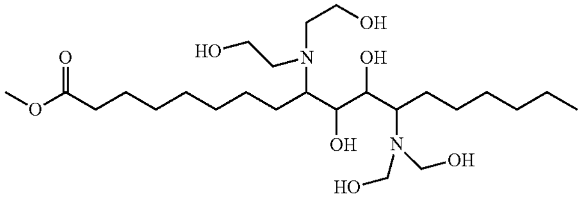
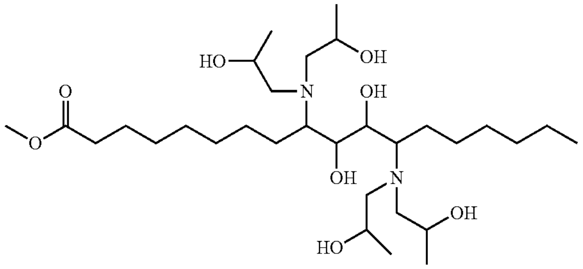

-continued

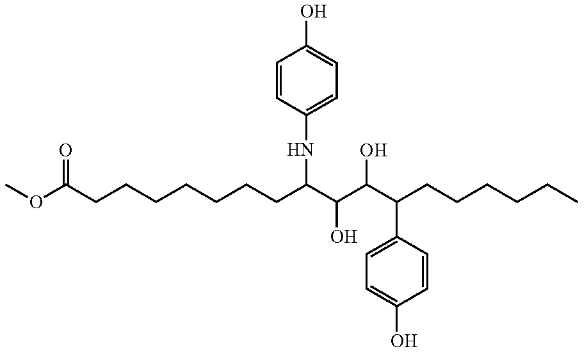

The second invention of the present invention provides a process for preparing an ester compound, comprising:

(1) epoxidizing at least one olefinic bond in a compound represented by formula (XII), and (2) reacting the product of step (1) with a compound represented by formula (XIII);

(XII)

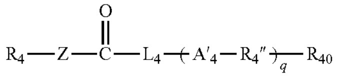

(XIII)

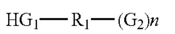

the $R_4$ group is selected from an optionally substituted $C_{1-10}$ linear or branched alkyl, $-L_4'-(OH)_n$, H (preferably selected from an optionally substituted $C_{1-6}$ linear or branched alkyl, $-L_4'-(OH)_n$, H, more preferably selected from an optionally substituted $C_{1-3}$ linear or branched alkyl, $-L_4'-(OH)_n$, H), wherein n is an integral number of 1-10 (preferably an integral number of 1-6, more preferably 1, 2 or 3), the $L_4'$ group is an (n+1)-valent $C_{1-15}$ linear or branched alkyl (preferably an (n+1)-valent $C_{1-10}$ linear or branched alkyl, more preferably an (n+1)-valent $C_{1-6}$ linear or branched alkyl, further preferably an (n+1)-valent $C_{1-3}$ linear or branched alkyl); Z represents an oxygen atom or $NR_z$, $R_z$ is selected from H, an optionally substituted $C_{1-6}$ linear or branched alkyl (preferably selected from H, an optionally substituted $C_{1-3}$ linear or branched alkyl);

The $L_4$ group is selected from a single bond, a $C_{1-30}$ linear or branched hydrocarbylene (preferably selected from a $C_{1-20}$ linear or branched alkylene, more preferably selected from a $C_{1-10}$ linear or branched alkylene);

q is an integral number of 1-12 (preferably an integral number of 1-8, more preferably an integral number of 1-5);

the $R_4''$ group(s), identical to or different from each other, are each independently selected from single bond, a $C_{1-10}$ linear or branched hydrocarbylene (preferably a $C_{1-10}$ linear or branched alkylene, more preferably a $C_{1-6}$ linear or branched alkylene, more preferably a $C_{1-3}$ linear or branched alkylene);

the $R_{40}$ group is selected from H, an optionally substituted $C_{1-10}$ hydrocarbyl (preferably an optionally substituted $C_{1-10}$ linear or branched alkyl, more preferably an optionally substituted $C_{1-6}$ linear or branched alkyl, more preferably an optionally substituted $C_{1-3}$ linear or branched alkyl);

the $A'_4$ groups, identical to or different from each other, are each independently selected from —CH═CH—,

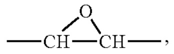

an ethylene group, a propylene group, and at least one $A'_4$ group is selected from —CH═CH—;

the $G_1$ group is selected from —O—,

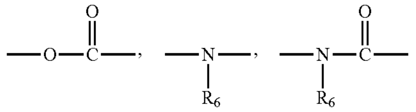

(wherein the carbonyl carbon is attached to the $R_1$ group), the $R_6$ group is selected from H, an optionally substituted $C_{1-6}$ linear or branched alkyl, optionally substituted $C_{3-10}$ cycloalkyl, an optionally substituted $C_{6-15}$ aryl, an optionally substituted $C_{7-15}$ alkylaryl (preferably selected from H, an optionally substituted $C_{1-3}$ linear or branched alkyl, an optionally substituted $C_{3-6}$ cycloalkyl, an optionally substituted $C_{6-10}$ aryl, an optionally substituted $C_{7-12}$ alkylaryl):

$R_1$ is selected from a single bond, an (n+1)-valent optionally substituted $C_{1-17}$ hydrocarbyl (preferably selected from an (n+1)-valent optionally substituted $C_{1-15}$ linear or branched alkyl, an (n+1)-valent optionally substituted $C_{3-10}$ cycloalkyl, an (n+1)-valent optionally substituted $C_{6-15}$ aryl, an (n+1)-valent optionally substituted $C_{7-15}$ alkylaryl, more preferably selected from an (n+1)-valent optionally substituted $C_{1-11}$ linear or branched alkyl, an (n+1)-valent optionally substituted $C_{3-6}$ cycloalkyl, an (n+1)-valent optionally substituted $C_{6-10}$ aryl, an (n+1)-valent optionally substituted $C_{7-12}$ alkylaryl);

the $G_2$ group is selected from $—OR_2$,

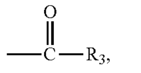

$—N(R_5)_2$, wherein $R_2$ is selected from H, an optionally substituted $C_{1-10}$ linear or branched alkyl (preferably selected from H, an optionally substituted $C_{1-6}$ linear or branched alkyl, more preferably selected from H, an optionally substituted $C_{1-3}$ linear or branched alkyl), the $R_3$ group is selected from OH, an optionally substituted $C_{1-10}$ linear or branched alkyl, an optionally substituted $C_{1-6}$ linear or branched alkoxyl, an optionally substituted $C_{3-10}$ cycloalkyl, an optionally substituted $C_{6-15}$ aryl, an optionally substituted $C_{7-15}$ alkylaryl (preferably selected from OH, an optionally substituted $C_{1-6}$ linear or branched alkyl, an optionally substituted $C_{1-6}$ linear or branched alkoxyl, an optionally substituted $C_{3-6}$ cycloalkyl, an optionally substituted $C_{6-10}$ aryl, an optionally substituted $C_{7-12}$ alkylaryl); the $R_5$ groups are each independently selected from H, an optionally substituted $C_{1-10}$ linear or branched alkyl (preferably selected from H, an optionally substituted $C_{1-6}$ linear or branched alkyl, more preferably selected from H, an optionally substituted $C_{1-3}$ linear or branched alkyl);

n is an integral number of 0-10 (preferably an integral number of 0-6, more preferably 0, 1, 2 or 3);

Optionally, step (1') is carried out between step (1) and step (2), wherein $R'_{4n}$—OH is reacted with the product of step (1), and in step (2), the product of step (1') is reacted with the compound represented by formula (XIII);

$R'_{4a}$ is selected from an optionally substituted $C_{1-10}$ hydrocarbyl,

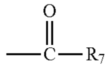

(preferably an optionally substituted $C_{1-6}$ linear or branched alkyl,

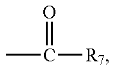

more preferably an optionally substituted $C_{1-3}$ linear or branched alkyl,

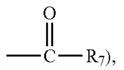

the $R_7$ groups are each independently selected from H, an optionally substituted $C_{1-10}$ linear or branched alkyl (preferably selected from an optionally substituted $C_{1-6}$ linear or branched alkyl, more preferably selected from an optionally substituted $C_{1-3}$ linear or branched alkyl), said substituents that optionally substitute are selected from halogen atoms, hydroxy, amino, $C_{1-6}$ linear or branched alkyl, $C_{6-10}$ aryl, $C_{3-10}$ cycloalkyl.

In one embodiment of the present invention, the compound represented by formula (XII) is selected from one or more of the following compounds: eicosenoic acid, oleic acid, linoleic acid, linolenic acid, hexadecenoic acid, tetradecenoic acid, dodecenoic acid, undecenoic acid, decenoic acid, octenoic acid, eicosenoic acid methyl ester, oleic acid methyl ester, linoleic acid methyl ester, linolenic acid methyl ester, hexadecenoic acid methyl ester, tetradecenoic acid methyl ester, dodecenoic acid methyl ester, undecenoic acid methyl ester, decenoic acid methyl ester, octenoic acid methyl ester, eicosenoic acid amide, oleic acid amide, linoleic acid amide, linolenic acid amide, hexadecenoic acid amide, tetradecenoic acid amide, dodecenoic acid amide, undecenoic acid amide, decenoic acid amide, octenoic acid amide; or the condensation products of these compounds themselves or each other.

In one embodiment of the present invention, the compound represented by formula (XIII) is selected from one or more of the following compounds: ethylene glycol, propylene glycol, butanediol, pentanediol, hexanediol, nonanediol, decanediol, undecanediol, dodecanediol, tridecanediol, tetradecanediol, pentadecanediol, phenol, methylphenol, benzenediol, tert-butylbenzenediol, benzenetriol, naphthalene diol, glycerol, trimethylolpropane, tri(hydroxyethyl)propane, pentaerythritol, ethanedioic acid, propanedioic acid, butanedioic acid, pentanedioic acid, hexanedioic acid, nonanedioic acid, decanedioic acid, undecanedioic acid, dodecanedioic acid, tridecanedioic acid, tetradecanedioic acid, pentadecanedioic acid, phthalic acid, terephthalic acid, ethylene diamine, propylene diamine, butylene diamine, pentamethylene diamine, hexamethylene diamine, phenylene diamine, nonamethylene diamine, decamethylene diamine, dimethylamine, diethylamine, dipropylamine, diisopropylamine, dibutylamine, diisobutylamine, diamylamine, dihexylamine, dioctylamine, diisooctylamine, ethanolamine, diethanolamine, n-propanolamine, isopropanolamine, diisopropanolamine, 2-amino-1-butanol, 6-amino-1-hexanol, 8-amino-1-octanol; or the condensation products of these compounds themselves or each other.

In one embodiment of the present invention, the compound represented by formula (XII) is subjected to an epoxidation reaction with an oxidizing agent. The oxidizing agent is capable of epoxidizing at least one olefinic bond in the compound represented by formula (XII) (the conversion of the alkenyl group into an epoxy group). The oxidizing agent includes an organic peroxide and/or an inorganic peroxide, and can be one or more of the following compounds: hydrogen peroxide, tert-butyl hydroperoxide, ethylphenyl hydroperoxide, cumenyl hydroperoxide. The reaction equivalent ratio of the compound represented by formula (XII) (as —C═C—) to the oxidizing agent is preferably 1:1-5, more preferably 1:1-3; the reaction temperature is preferably 0-200° C., more preferably 30-100° C. The epoxidation reaction time should be suitable for the epoxidation reaction to proceed smoothly. In general, the longer the reaction time is, the better it is, and the reaction time is preferably 0.5-24 hours, more preferably 1-10 hours. The epoxidation reaction of the compound represented by formula (XII) can adopt a conventional phase-transfer reaction, such as performing an in-situ reaction of hydrogen peroxide and formic acid to produce a peroxyacid, and then completing the oxygen atom transfer reaction with the olefinic bond. A catalyst can be added to the epoxidation reaction of the compound represented by formula (XII). The catalyst can be a catalyst containing one or more metals of titanium, tungsten, molybdenum, rhenium and aluminum and/or an acid catalyst, and specifically can be one or more of titanium-silicate materials, tungsten heteropolyacid salts, molybdenum-containing complexes, methylrhenium trioxide, aluminium sulfate, sulfuric acid, hydrochloric acid, nitric acid or phosphoric acid. The amount of the catalyst is preferably 0.01%-10% by the mass of the compound represented by formula (XII).

In one embodiment of the present invention, the compound represented by formula (XII) is subjected to an epoxidation reaction with an oxidizing agent (the oxidizing agent preferably comprises an organic peroxide and/or an inorganic peroxide). The reaction equivalent ratio of the compound represented by formula (XII) (as —C═C—) to the oxidizing agent is 1:1-5 (preferably 1:1-3); and the reaction temperature is 0-200° C. (preferably 30-100° C.).

In one embodiment of the present invention, at least one olefinic bond in the compound represented by formula (XII) undergoes an epoxidation reaction to generate an epoxidation product of the compound represented by formula (XII). The epoxidation product of the compound represented by formula (XII) may be purified and then subjected to the next reaction, or may be directly subjected to the next reaction without purification. The epoxidation product of the compound represented by formula (XII) is then reacted with the compound represented by formula (XIII) to produce the ester compound of the present invention. The ester compound may be a compound of a single structure, or may be a mixture containing compounds of different structures. For the mixture containing compounds of different structures, it is sometimes possible to separate the mixture into single-structure compounds, or sometimes the mixture containing compounds of different structures can also be directly used without the need of separating the mixture into single-structure compounds.

In one embodiment of the present invention, the reaction molar equivalent ratio of the epoxidation product of the compound represented by formula (XII) (as the epoxy group) to the compound represented by formula (XIII) (as the $G_1H$ moiety) is allowed to be 1:0.1-100 (preferably 1:0.2-10); and the reaction temperature is 20-200° C. (preferably 40-150° C.). The reaction time should be suitable for the reaction to proceed smoothly. In general, the longer the reaction time is, the better it is, and the reaction time is preferably 0.5-24 hours, more preferably 2-16 hours.

In one embodiment of the present invention, in the reaction of the epoxidation product of the compound represented by formula (XII) with the compound represented by formula (XIII), a catalyst may or may not be added, preferably the catalyst is added. The catalyst can be one or more of inorganic acid, organic acid, solid acid, heteropolyacid, acidic ionic liquid, acidic resin, acidic molecular sieve, metal chloride and metal oxide, and for example can be one or more of sulfuric acid, perchloric acid, $AlCl_3$, tin chloride, n-butyltin oxide, dibutyltin oxide, paratoluenesulfonic acid, acidic resin, phosphotungstic heteropolyacid, acidic ionic liquid and acidic molecular sieve, preferably one or more of sulfuric acid, tin chloride, n-butyltin oxide, paratoluenesulfonic acid, acidic resin and phosphotungstic heteropolyacid. The addition amount of the catalyst is preferably 0.1%-10% by the mass of the compound represented by formula (XII).

In one embodiment of the present invention, in the epoxidation reaction of the compound represented by formula (XII), in the reaction of the epoxidation product of the compound represented by formula (XIII) with the compound represented by formula (XIII), a solvent may or may not be added, preferably the solvent is added. Said solvent is preferably a hydrocarbon solvent, preferably one or more of alkanes, arenes and ethers, more preferably an alkane solvent, for example, can be one or more of hexane, heptane, octane, nonane, decane, cyclohexane, cycloheptane, cyclooctane, cyclononane, cyclodecane, benzene, toluene, xylene, ethylbenzene, propyl benzene, ethyl ether, propyl ether, isopropyl ether and butyl ether. The addition amount of said solvent should be suitable to promote the smooth progress of the reaction, and is not particularly limited. The solvent can be removed by a known method, such as distillation, rectification, and the like, which is not particularly limited.

In one embodiment of the present invention, in the epoxidation reaction of the compound represented by formula (XII), and in the reaction of the epoxidation product of the compound represented by formula (XII) with the compound represented by formula (XIII), it is preferable that the reaction product is washed with a solvent and purified, and the solvent that can be used for washing is preferably a hydrocarbon solvent. The solvent can be removed by conventional technical means such as drying, evaporation and distillation.

In one embodiment of the present invention, the epoxidation reaction of the compound represented by formula (XII) and the reaction of the epoxidation product of the compound represented by formula (XII) with the compound represented by formula (XIII) can be performed in a continuous or batch reaction equipment such as a reaction vessel, a fixed bed, a fluid bed, a microchannel reactor and the like.

Third Invention

The third invention of the present invention provides an ester compound, which has a structure as shown in the following formula (X), (X)

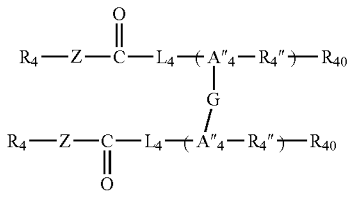

wherein, the G group represent

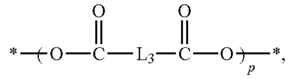

the $L_3$ group is selected from a single bond, a $C_{1-30}$ linear or branched hydrocarbylene (preferably a single bond, a $C_{1-20}$ linear or branched alkylene, a $C_{3-20}$ cycloalkylene, a $C_{6-20}$ arylene, a $C_{7-15}$ alkylarylene; more preferably a single bond, a $C_{1-10}$ linear or branched alkylene, a $C_{5-10}$ cycloalkylene, a $C_{6-10}$ arylene, a $C_{7-12}$ alkylarylene), p is an integral number of 1-10 (preferably an integral number of 1-5, more preferably 1, 2 or 3);

the $R_4$ group is independently selected from an optionally substituted $C_{1-10}$ linear or branched alkyl, $-L_4'-(OH)_n$, H (preferably selected from an optionally substituted $C_{1-6}$ linear or branched alkyl, $-L_4'-(OH)_n$, H, more preferably selected from an optionally substituted $C_{1-3}$ linear or branched alkyl, $-L_4'-(OH)_n$, H), wherein n is an integral number of 1-10 (preferably an integral number of 1-6, more preferably 1, 2 or 3), the $L_4'$ group is an (n+1)-valent $C_{1-15}$ linear or branched alkyl (preferably an (n+1)-valent $C_{1-10}$ linear or branched alkyl, more preferably an (n+1)-valent $C_{1-6}$ linear or branched alkyl, further preferably an (n+1)-valent $C_{1-3}$ linear or branched alkyl);

Z independently represents an oxygen atom or $NR_z$, $R_z$ is selected from H, an optionally substituted $C_{1-6}$ linear or branched alkyl (preferably selected from H, an optionally substituted $C_{1-3}$ linear or branched alkyl);

The $L_4$ group is independently selected from a single bond, a $C_{1-30}$ linear or branched hydrocarbylene (preferably selected from a $C_{1-20}$ linear or branched alkylene, more preferably selected from a $C_{1-10}$ linear or branched alkylene);

$R_4''$ is independently selected from a single bond, a $C_{1-10}$ linear or branched hydrocarbylene (preferably a $C_{1-10}$ linear or branched alkylene, more preferably a $C_{1-6}$ linear or branched alkylene, more preferably a $C_{1-3}$ linear or branched alkylene);

the $R_{40}$ group is selected from H, an optionally substituted $C_{1-10}$ hydrocarbyl (preferably an optionally substituted $C_{1-10}$ linear or branched alkyl, more preferably an optionally substituted $C_{1-6}$ linear or branched alkyl, more preferably an optionally substituted $C_{1-3}$ linear or branched alkyl); The $A''_4$ group is independently selected from a group represented by formula (XI);

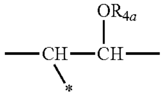

(XI)

$R_{4a}$ is independently selected from H, an optionally substituted $C_{1-10}$ hydrocarbyl,

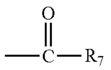

(preferably H, an optionally substituted $C_{1-6}$ linear or branched alkyl,

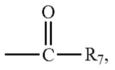

more preferably H, an optionally substituted $C_{1-3}$ linear or branched alkyl,

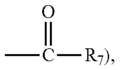

the $R_7$ groups are each independently selected from H, an optionally substituted $C_{1-10}$ linear or branched alkyl (preferably selected from an optionally substituted $C_{1-6}$ linear or branched alkyl, more preferably selected from an optionally substituted $C_{1-3}$ linear or branched alkyl);

is the bonding site between the G group and the $A''_4$ group, said substituents that optionally substitute are selected from halogen atoms, hydroxy, amino, $C_{1-6}$ linear or branched alkyl. $C_{6-10}$ aryl, $C_{3-10}$ cycloalkyl.

In one embodiment of the present invention, in the above formula (X), p is 1, the $R_4$ group is an optionally substituted $C_{1-6}$ linear or branched alkyl, Z represents independently selected from H, an optionally substituted $C_{1-6}$ linear or branched alkyl,

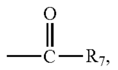

the $R_7$ groups are each independently selected from an optionally substituted $C_{1-6}$ linear or branched alkyl.

In one embodiment of the present invention, the ester compound is selected from one or more of the following compounds:

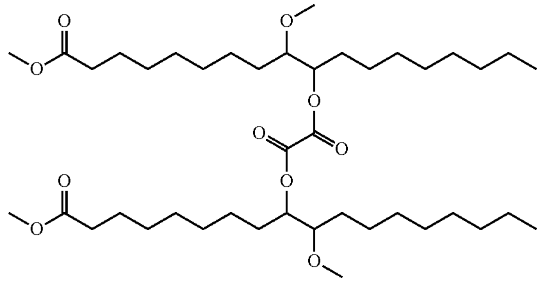

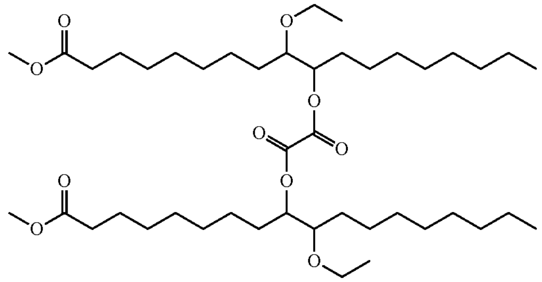

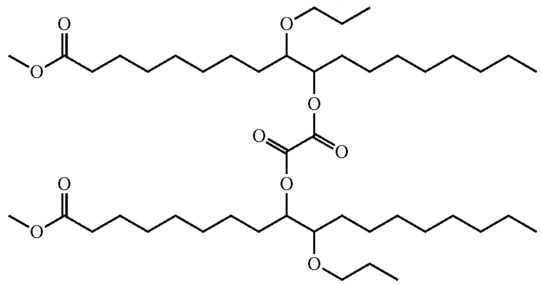

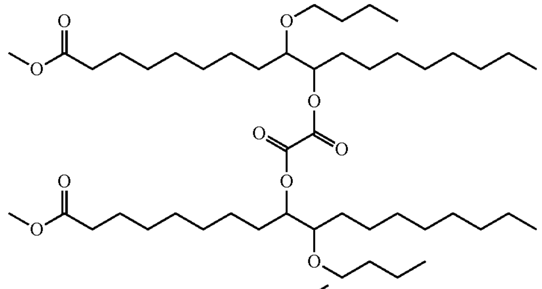

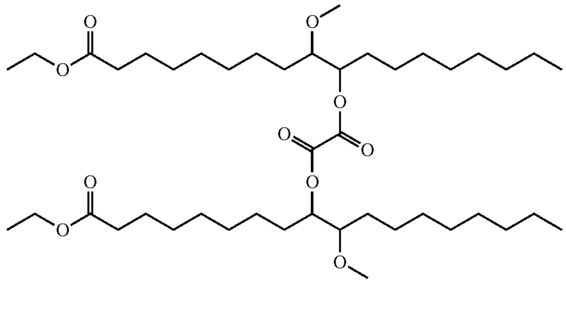

-continued
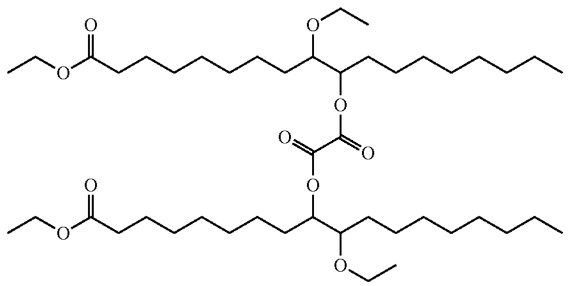
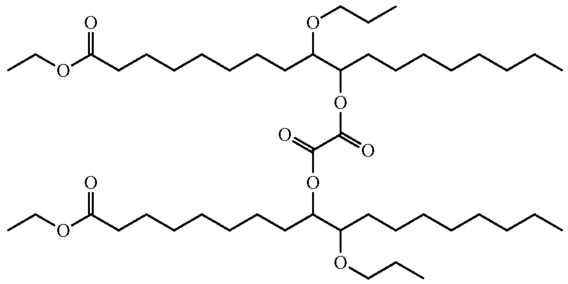
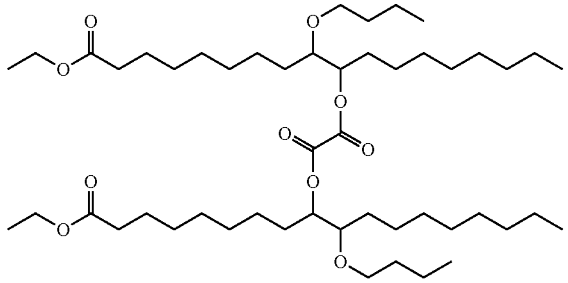
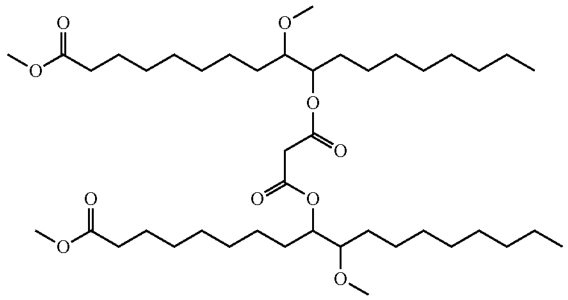
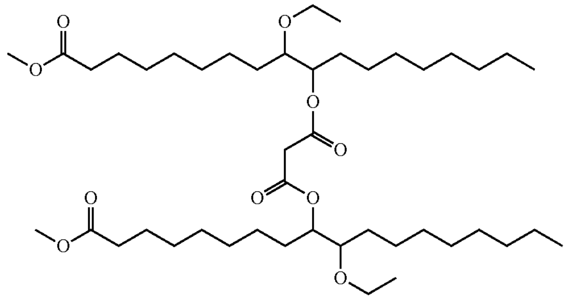
-continued
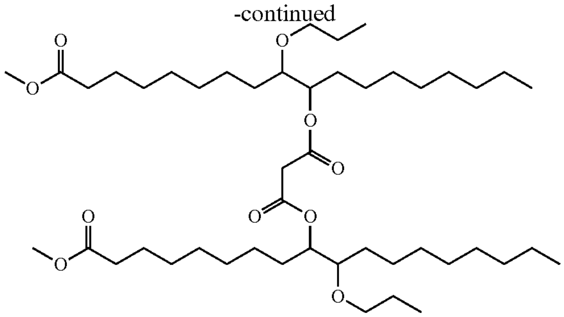
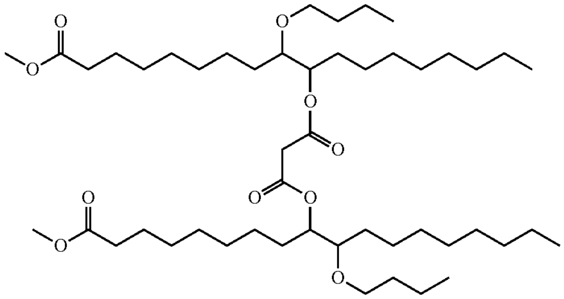
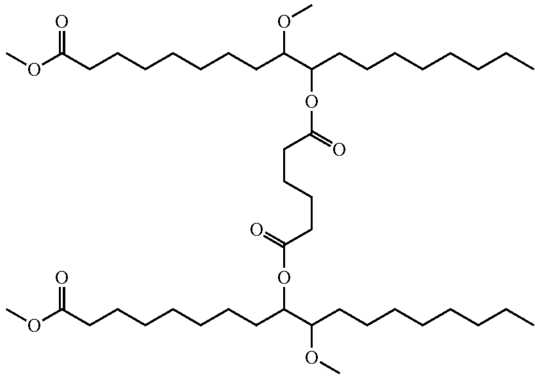
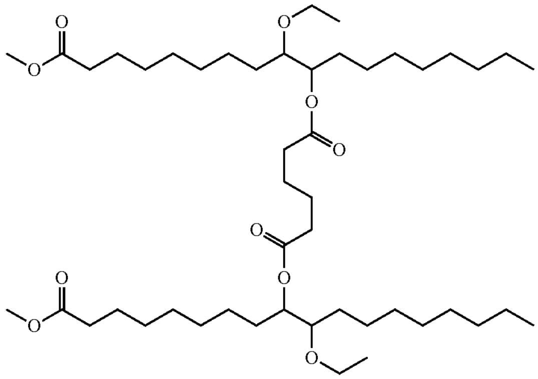
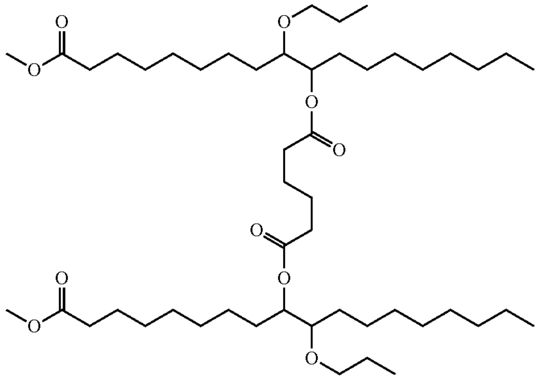

-continued
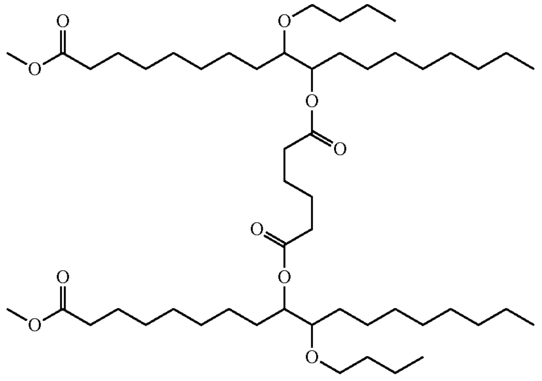
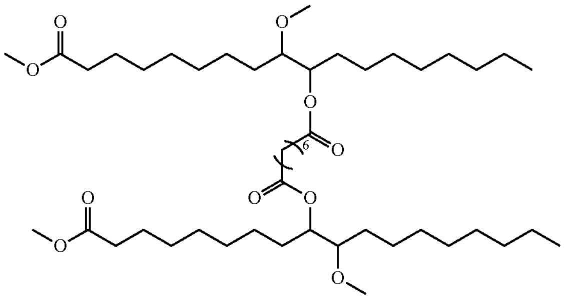
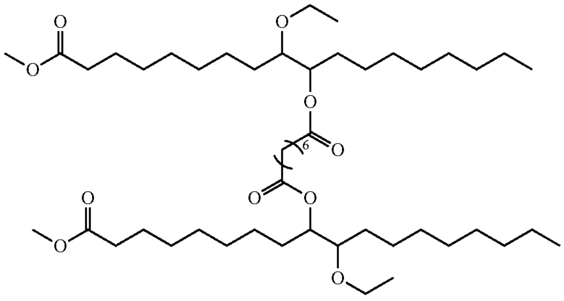
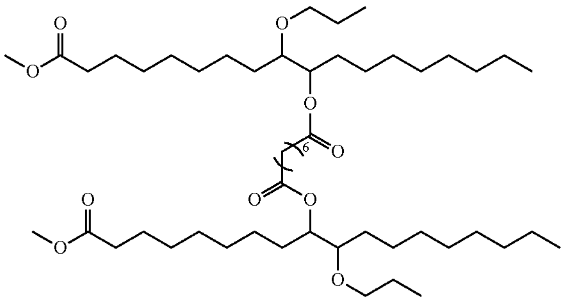
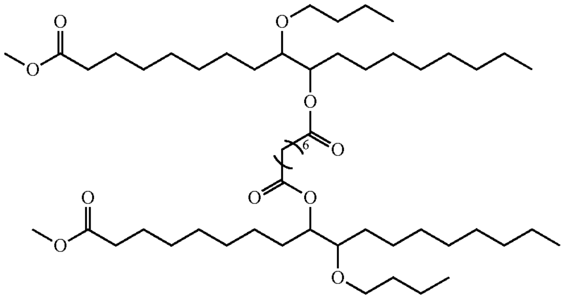
-continued
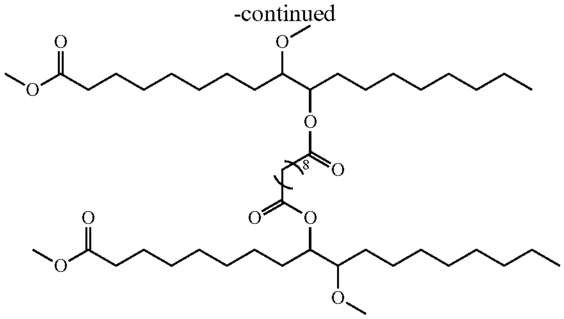
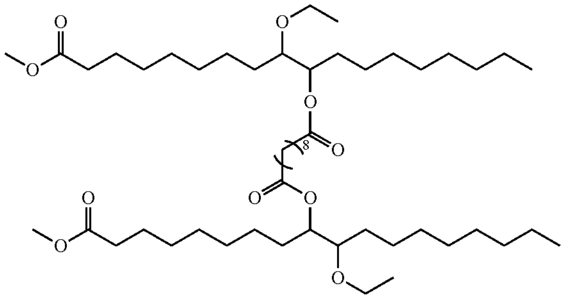
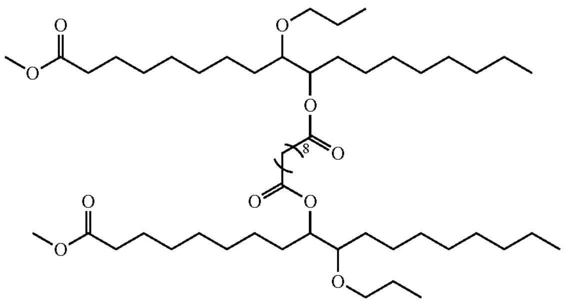
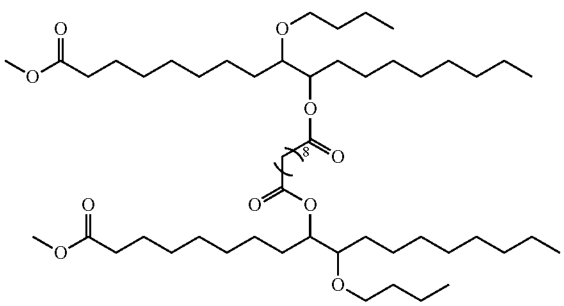

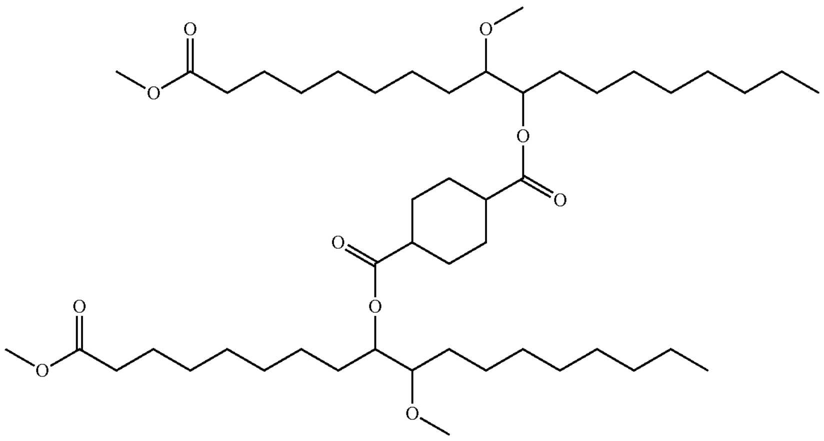
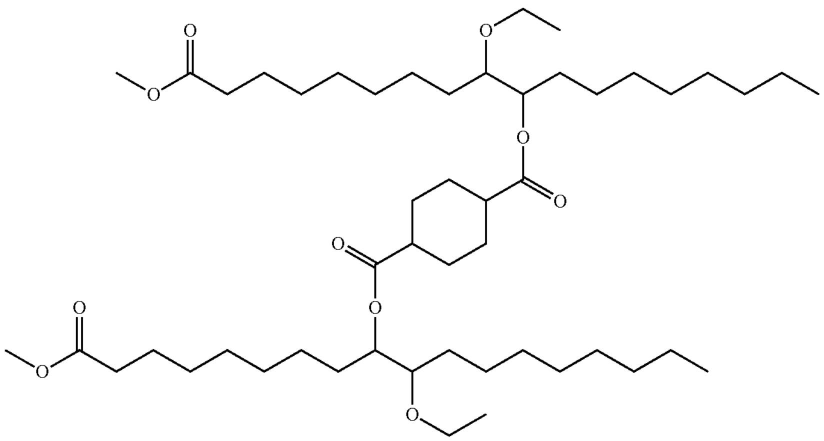
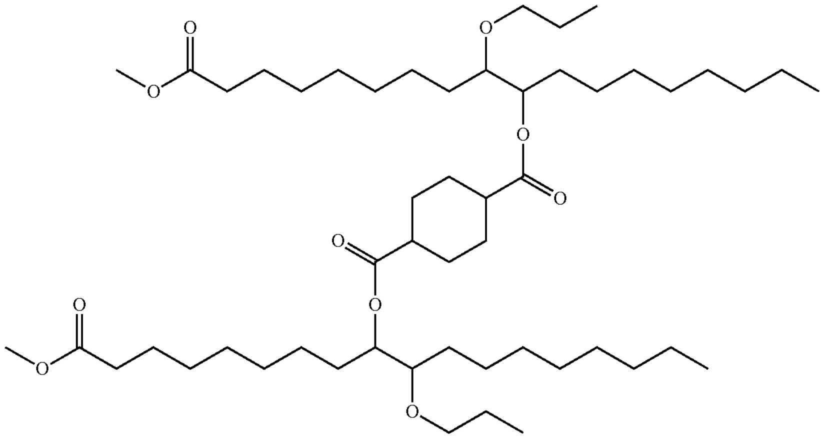

-continued
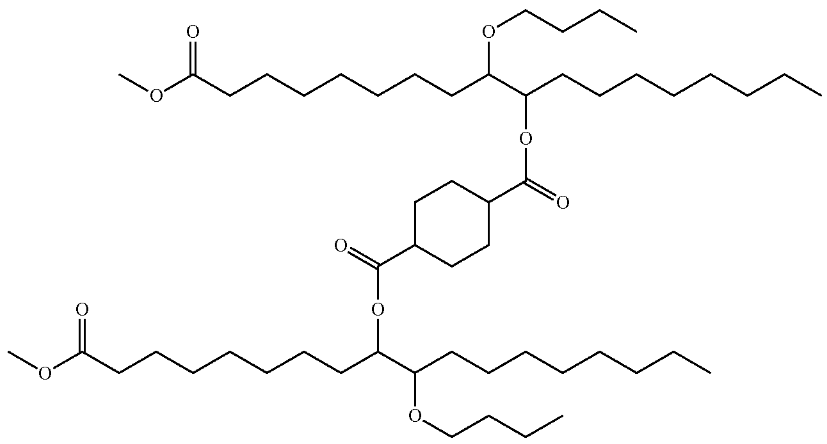
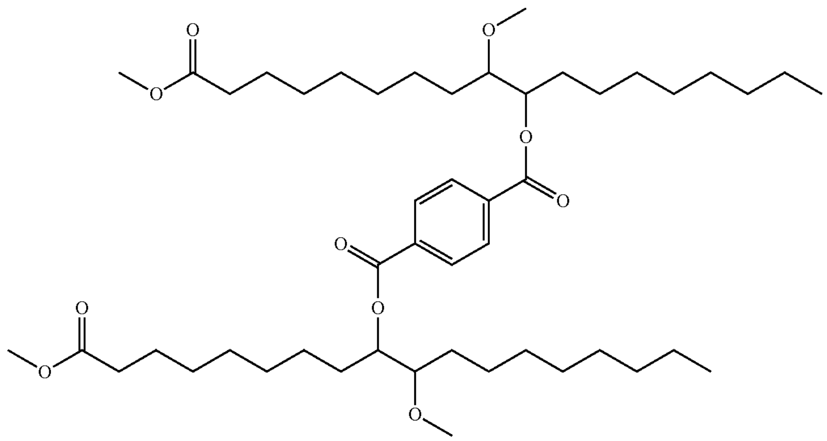
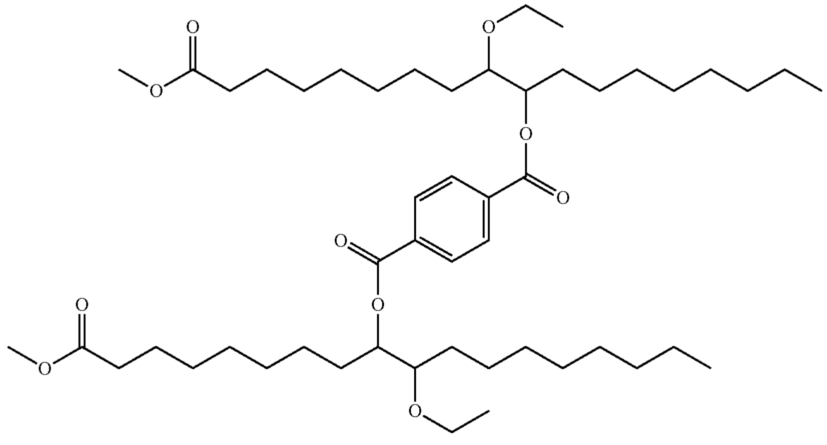

-continued
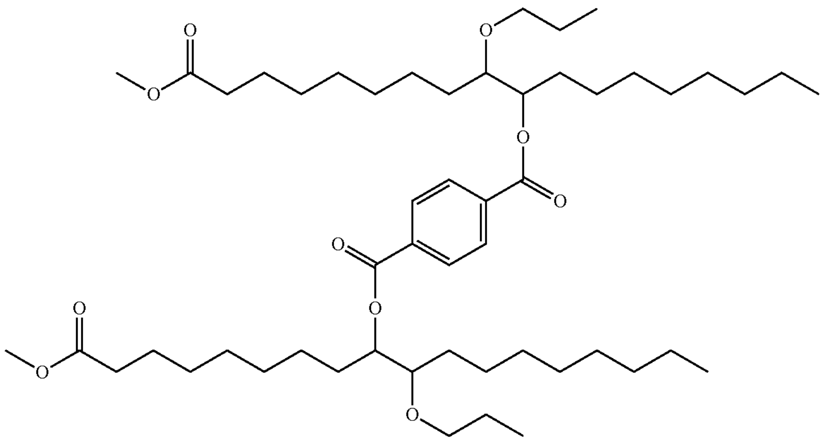
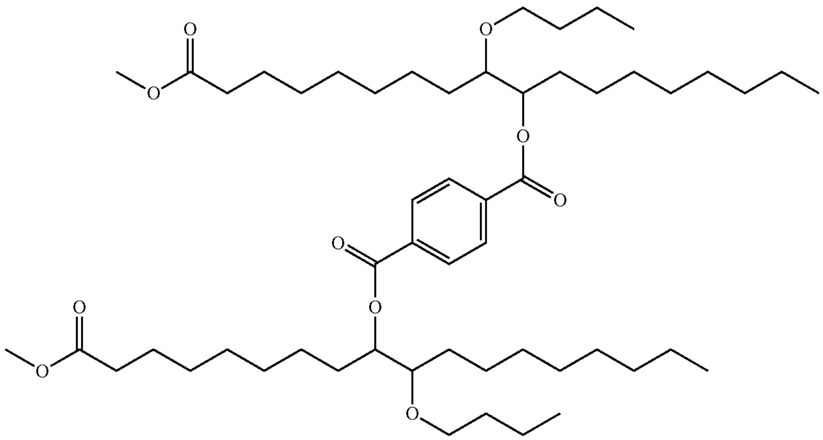
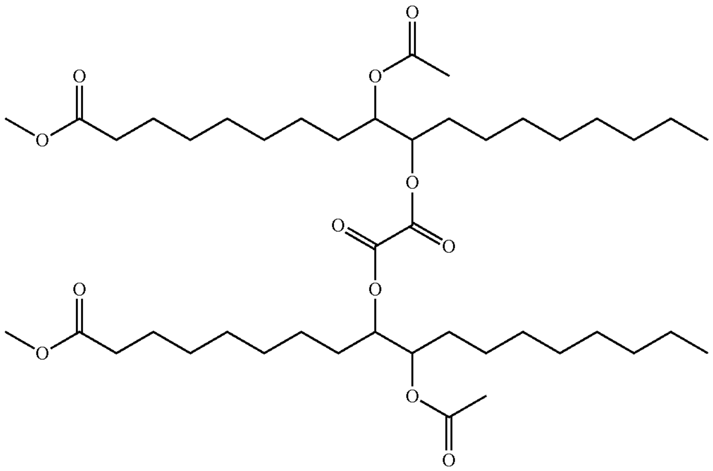

-continued
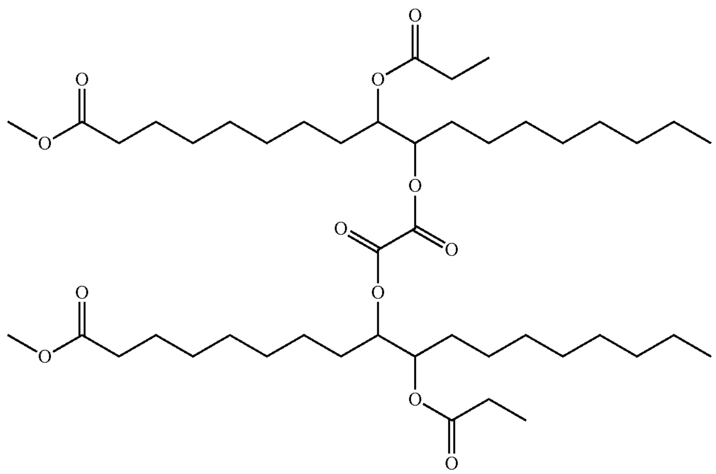
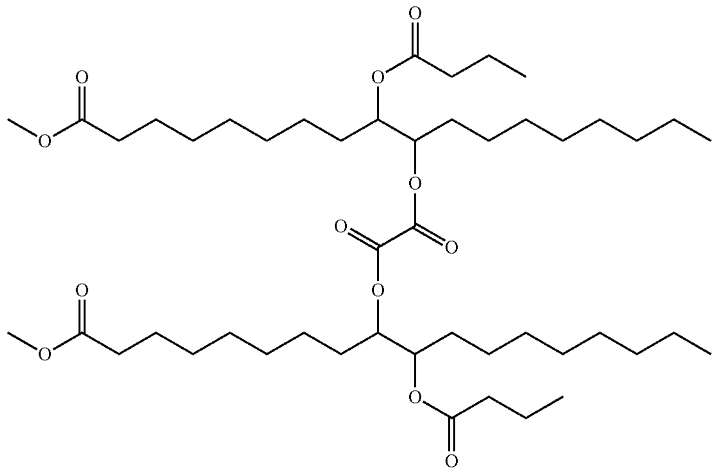
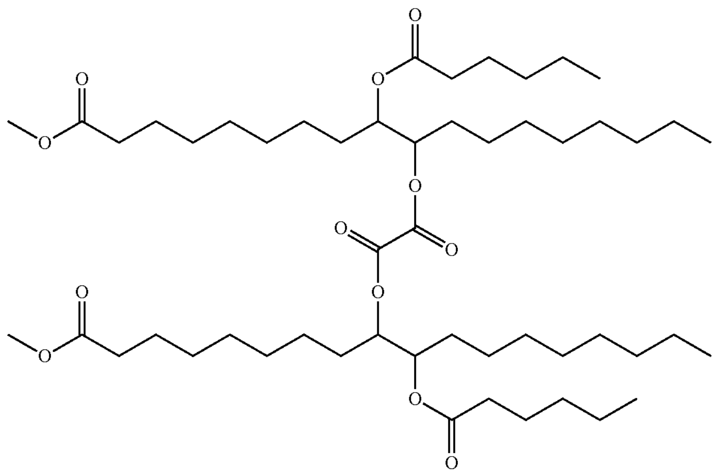

-continued
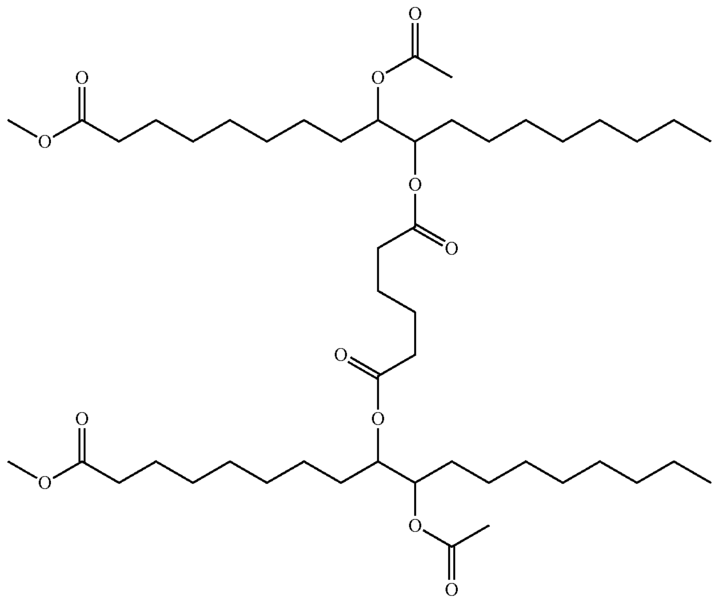
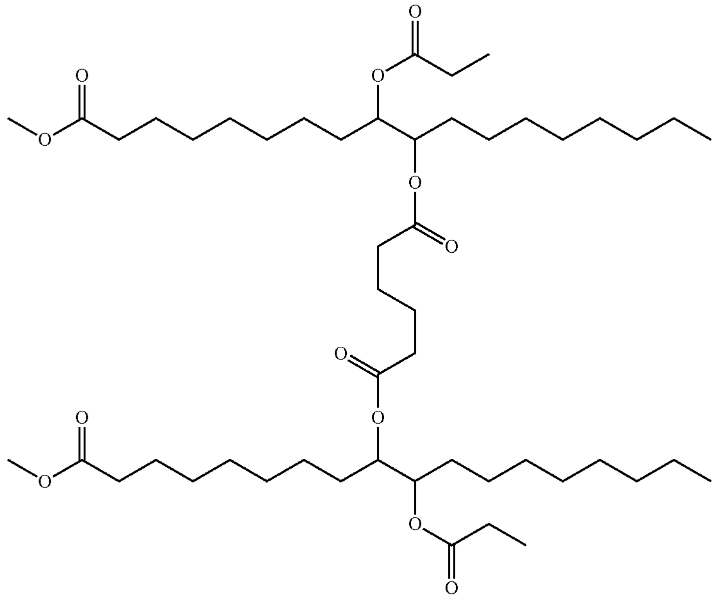

-continued
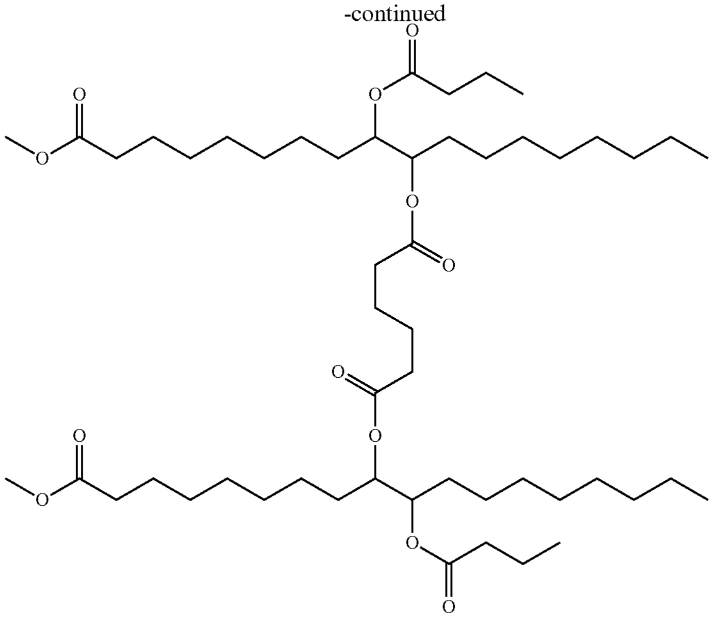
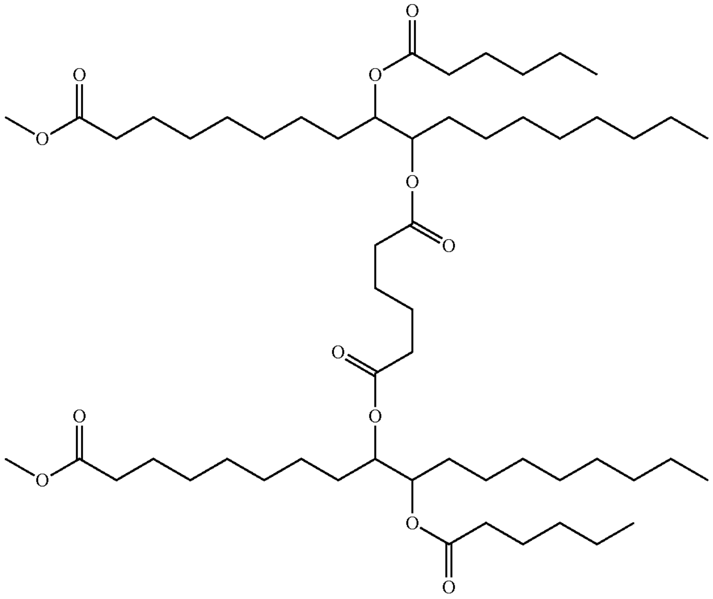
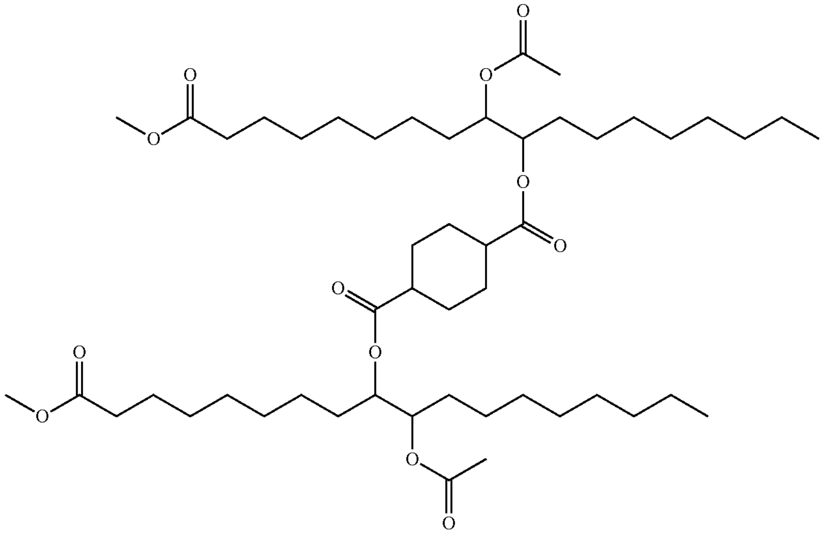

-continued
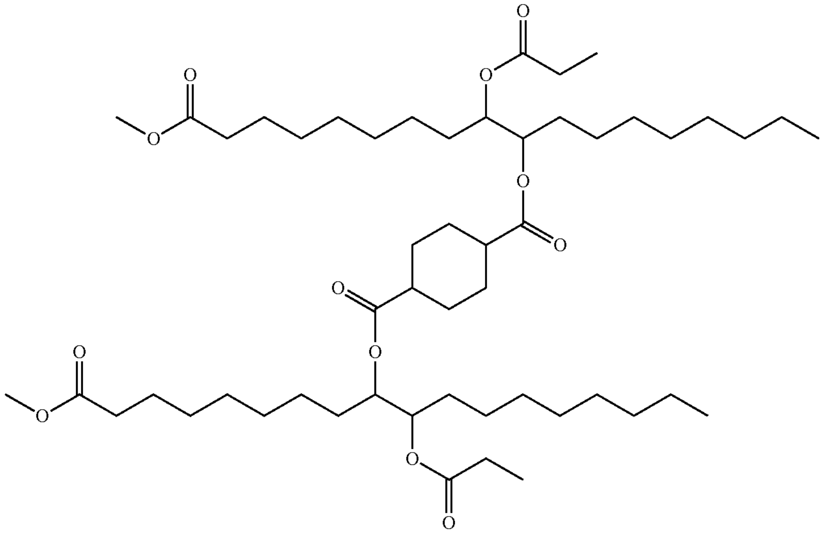
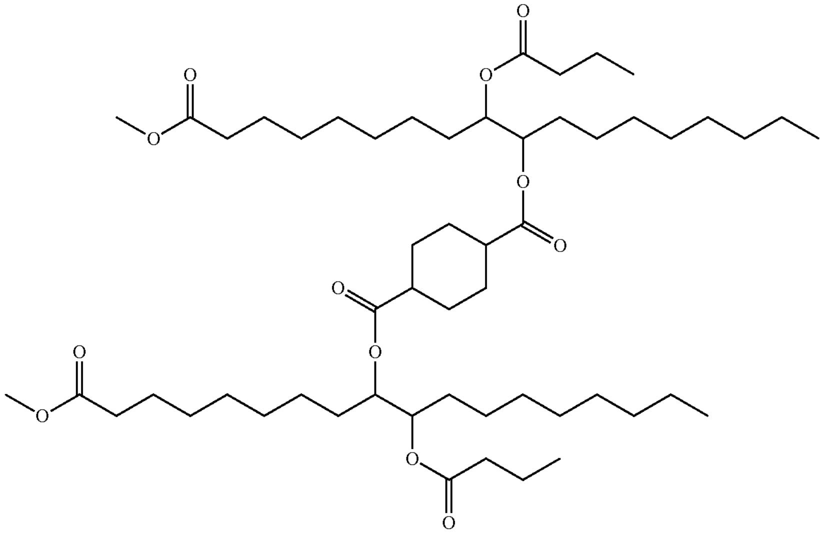
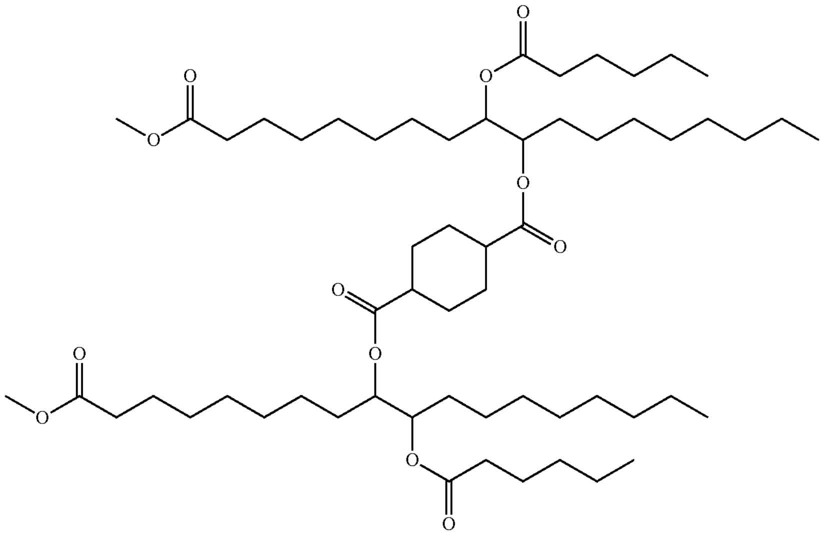

-continued
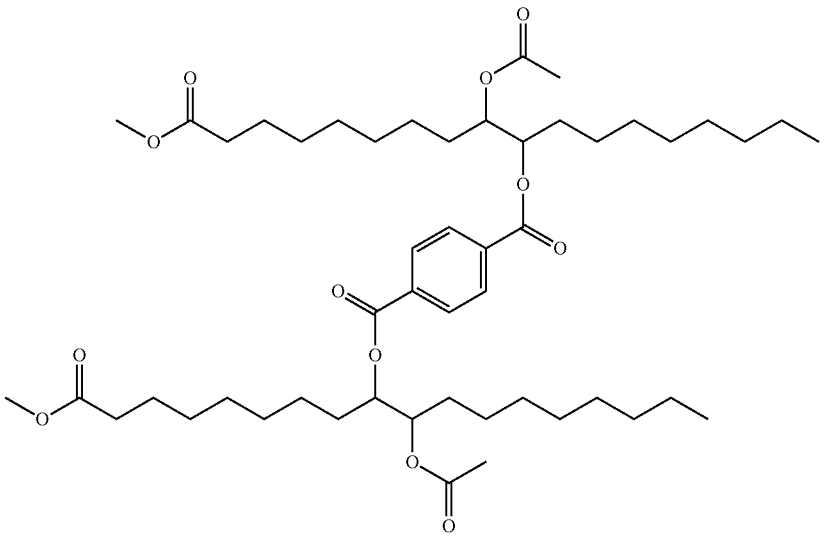
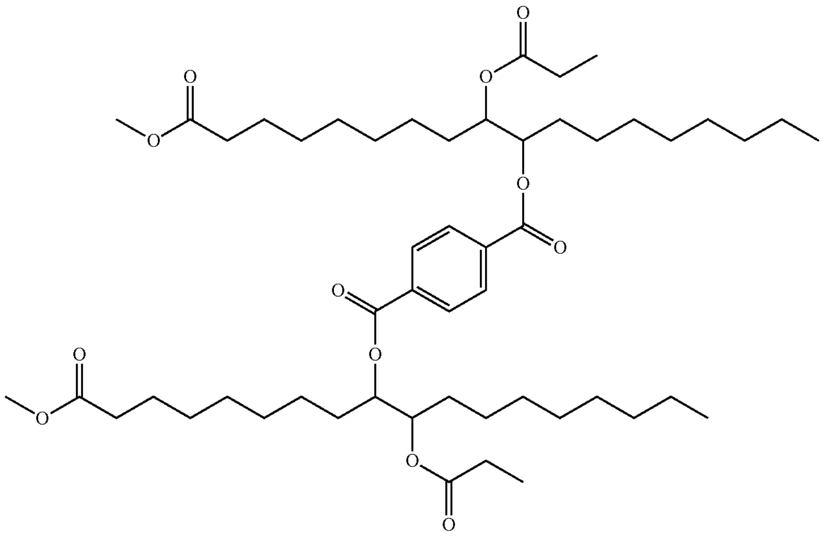
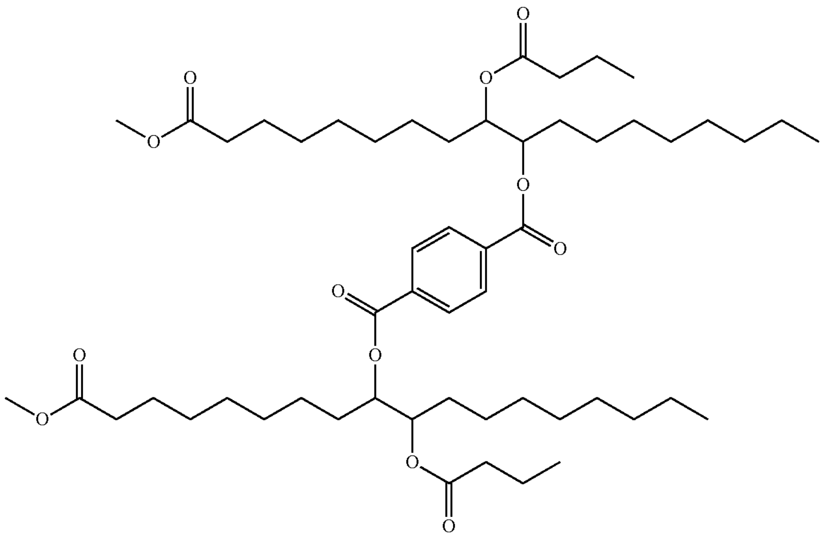

-continued

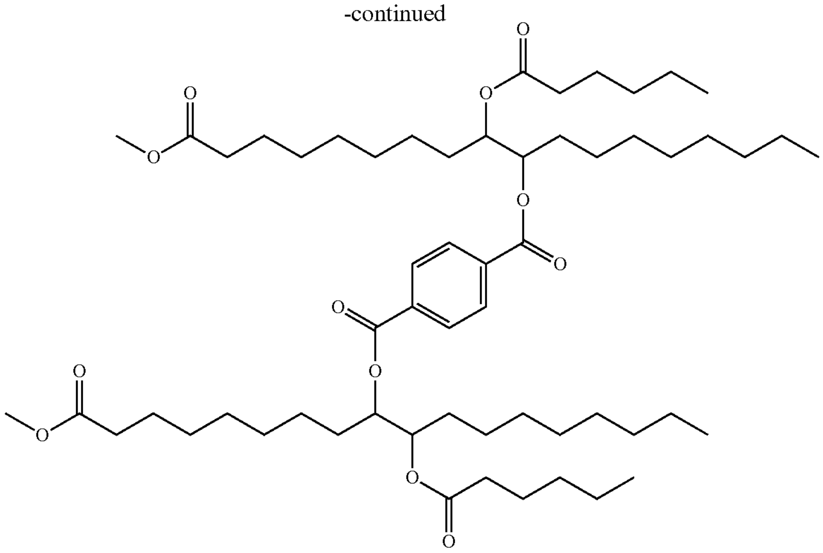

The third invention of the present invention provides a process for preparing an ester compound, which comprises the following steps, (1) epoxidizing at least one olefinic bond in a compound represented by formula (XIV), (1') reacting $R'_{4a}$—OH with the product of step (1), (2) reacting the product of step (1') with a compound represented by formula (XV);

(XIV)

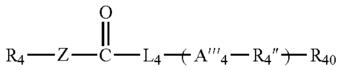

(XV)

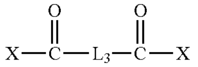

the $R_4$ group is selected from an optionally substituted $C_{1-10}$ linear or branched alkyl, -$L_4$'-$(OH)_n$, H (preferably selected from an optionally substituted $C_{1-6}$ linear or branched alkyl, -$L_4$'-$(OH)_n$, H, more preferably selected from an optionally substituted $C_{1-3}$ linear or branched alkyl, -$L_4$'-$(OH)_n$, H), wherein n is an integral number of 1-10 (preferably an integral number of 1-6, more preferably 1, 2 or 3), the $L_4$' group is an (n+1)-valent $C_{1-15}$ linear or branched alkyl (preferably an (n+1)-valent $C_{1-10}$ linear or branched alkyl, more preferably an (n+1)-valent $C_{1-6}$ linear or branched alkyl, further preferably an (n+1)-valent $C_{1-3}$ linear or branched alkyl);

Z represents an oxygen atom or $NR_z$, $R_z$ is selected from H, an optionally substituted $C_{1-6}$ linear or branched alkyl (preferably selected from H, an optionally substituted $C_{1-3}$ linear or branched alkyl);

the $L_4$ group is selected from a single bond, a $C_{1-30}$ linear or branched hydrocarbylene (preferably selected from a $C_{1-20}$ linear or branched alkylene, more preferably selected from a $C_{1-10}$ linear or branched alkylene);

the $R_4$" group(s), identical to or different from each other, are each independently selected from single bond, a $C_{1-10}$ linear or branched hydrocarbylene (preferably a $C_{1-10}$ linear or branched alkylene, more preferably a $C_{1-6}$ linear or branched alkylene, more preferably a $C_{1-3}$ linear or branched alkylene);

the $R_{40}$ group is selected from H, a $C_{1-10}$ hydrocarbyl (preferably an optionally substituted $C_{1-10}$ linear or branched alkyl, more preferably a $C_{1-6}$ linear or branched alkyl, more preferably a $C_{1-3}$ linear or branched alkyl);

the A'''$_4$ groups, identical to or different from each other, are each independently selected from —CH═CH—,

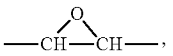

an ethylene group, a propylene group, and at least one A'''$_4$ group is selected from —CH═CH—;

$R'_{4a}$ is selected from an optionally substituted $C_{1-10}$ hydrocarbyl,

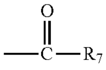

(preferably an optionally substituted $C_{1-6}$ linear or branched alkyl,

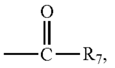

more preferably $C_{1-3}$ linear or branched alkyl,

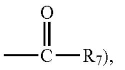

the $R_7$ groups are each independently selected from H, an optionally substituted $C_{1-10}$ linear or branched alkyl (preferably selected from an optionally substituted $C_{1-6}$ linear or branched alkyl, more preferably selected from an optionally substituted $C_{1-3}$ linear or branched alkyl), The $L_3$ group is selected from a single bond, a $C_{1-30}$ linear or branched hydrocarbylene (preferably a single bond, a $C_{1-20}$ linear or branched alkylene, a $C_{3-20}$ cycloalkylene, a $C_{6-20}$ arylene, a $C_{7-15}$ alkylarylene; more preferably a single bond, a $C_{1-10}$ linear or branched alkylene, a $C_{5-10}$ cycloalkylene, a $C_{6-10}$ arylene, a $C_{7-12}$ alkylarylene), The X group is selected from OH, F, Cl, Br or I (preferably OH, Cl or Br), said substituents that optionally substitute are selected from halogen atoms, hydroxy, amino, $C_{1-6}$ linear or branched alkyl, $C_{6-10}$ aryl, $C_{3-10}$ cycloalkyl.

In one embodiment of the present invention, the compound represented by formula (XIV) is selected from one or more of the following compounds: eicosenoic acid, oleic acid, linoleic acid, linolenic acid, hexadecenoic acid, tetradecenoic acid, dodecenoic acid, undecenoic acid, decenoic acid, octenoic acid, eicosenoic acid methyl ester, oleic acid methyl ester, linoleic acid methyl ester, linolenic acid methyl ester, hexadecenoic acid methyl ester, tetradecenoic acid methyl ester, dodecenoic acid methyl ester, undecenoic acid methyl ester, decenoic acid methyl ester, octenoic acid methyl ester.

In one embodiment of the present invention, the compound represented by $R'_{4a}$—OH is selected from one or more of the following compounds: methanol, ethanol, propanol, isopropanol, n-butanol, tert-butanol, iso-butanol, pentanol, hexanol, cyclohexanol, heptanol, octanol, isooctanol, nonanol, decanol, dodecanol, tetradecanol, hexadecanol, octadecanol, formic acid, acetic acid, propionic acid, isopropionic acid, n-butyric acid, tert-butyric acid, isobutyric acid, pentanoic acid, hexanoic acid, heptanoic acid, methylcyclohexanoic acid, octanoic acid, isooctanoic acid, benzoic acid, nonanoic acid, decanoic acid, dodecanoic acid, tetradecanoic acid, hexadecanoic acid, octadecanoic acid.

In one embodiment of the present invention, the compound represented by formula (XV) is selected from one or more of the following compounds: ethanedioic acid, propanedioic acid, butanedioic acid, pentanedioic acid, hexanedioic acid, heptanedioic acid, octanedioic acid, cyclohexanedicarboxylic acid, nonanedioic acid, decanedioic acid, undecanedioic acid, dodecanedioic acid, tridecanedioic acid, tetradecanedioic acid, pentadecanedioic acid, phthalic acid, terephthalic acid.

According to the preparation process of the present invention, optionally the compound represented by formula (XIV) is subjected to an epoxidation reaction with an oxidizing agent. The oxidizing agent can convert —C═C— in the compound represented by formula (XIV) to

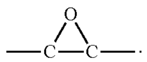

The oxidizing agent includes an organic peroxide and an inorganic peroxide, and specifically can be one or more of the following compounds: hydrogen peroxide, tert-butyl hydroperoxide, ethylphenyl hydroperoxide, cumenyl hydroperoxide. The reaction equivalent ratio of the compound represented by formula (XIV) (as —C═C—) to the oxidizing agent is preferably 1:1-5, more preferably 1:1-3; the reaction temperature is preferably 0-200° C., more preferably 30-100° C. The epoxidation reaction time should be suitable for the epoxidation reaction to proceed smoothly. In general, the longer the reaction time is, the better it is, and the reaction time is preferably 0.5-24 hours, more preferably 1-10 hours. The epoxidation reaction of the compound represented by formula (XIV) can adopt a conventional phase-transfer reaction, such as performing an in-situ reaction of hydrogen peroxide and formic acid to produce a peroxyacid, and then completing the oxygen atom transfer reaction with the olefinic bond. A catalyst can be added to the epoxidation reaction of the compound represented by formula (XIV). The catalyst can be a catalyst containing one or more metals of titanium, tungsten, molybdenum, rhenium and aluminum and/or an acid catalyst, and specifically can be one or more of titanium-silicate materials, tungsten heteropolyacid salts, molybdenum-containing complexes, methylrhenium trioxide, aluminium sulfate, sulfuric acid, hydrochloric acid, nitric acid or phosphoric acid. The amount of the catalyst is preferably 0.01%-10% by the mass of the compound represented by formula (XIV).

In one embodiment of the present invention, the olefinic bond in the compound represented by formula (XIV) undergoes an epoxidation reaction to generate an epoxidation product of the compound represented by formula (XIV). The epoxidation product of the compound represented by formula (XIV) may be purified and then subjected to the next reaction, or may be directly subjected to the next reaction without purification.

In one embodiment of the present invention, the reaction molar equivalent ratio of the epoxidation product of the compound represented by formula (XIV)

(as 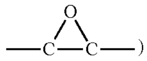 )

to the compound represented by $R'_{4a}$—OH (as-OH) is allowed to be 1:0.5-100 (preferably 1:1-10); the reaction temperature is 0-200° C. (preferably 40-150° C.). The reaction time should be suitable for the reaction to proceed smoothly. In general, the longer the reaction time is, the better it is, and the reaction time is preferably 1-24 hours, more preferably 2-10 hours.

In one embodiment of the present invention, in the reaction of the epoxidation product of the compound represented by formula (XIV) with the compound represented by $R'_{4a}$—OH, a catalyst may or may not be added, preferably the catalyst is added. The catalyst can be one or more of inorganic acid, organic acid, solid acid, heteropolyacid, acidic ionic liquid, acidic resin, acidic molecular sieve, metal chloride and metal oxide, for example, can be one or more of sulfuric acid, perchloric acid, $AlCl_3$, tin chloride, n-butyltin oxide, dibutyltin oxide, paratoluenesulfonic acid, acidic resin, phosphotungstic heteropolyacid, acidic ionic liquid, and acidic molecular sieve, preferably one or more of perchloric acid, tin chloride, n-butyltin oxide, paratoluenesulfonic acid, acidic resin and phosphotungstic heteropolyacid. The addition amount of the catalyst is preferably 0.1%-10% by the mass of the compound represented by formula (XIV). The addition amount of the catalyst is preferably 0.1%-10% by the mass of the compound represented by formula (XIV).

In one embodiment of the present invention, the reaction product of the epoxidation product of the compound represented by formula (XIV) and the compound represented by $R'_{4a}$—OH may be purified and then subjected to the next reaction, or may be directly subjected to the next reaction without purification.

In one embodiment of the present invention, the molar ratio of the compound represented by formula (XV) to the reaction product of step (1') is 1:1-10 (preferably 1:1-6); the reaction temperature is 50-300° C. (preferably 70-280° C.), a catalyst is added in the reaction of the compound represented by formula (XV) and the reaction product of step (1') (the catalyst is preferably selected from one or more of sulfuric acid, perchloric acid, $AlCl_3$, tin chloride, n-butyltin oxide, dibutyltin oxide, sodium hydrogen sulfate, paratoluenesulfonic acid, acidic resin, phosphotungstic heteropolyacid, acidic ionic liquid and acidic molecular sieve, more preferably one or more of sulfuric acid, sodium hydrogen sulfate, tin chloride, n-butyltin oxide, paratoluenesulfonic acid, acidic resin and phosphotungstic heteropolyacid).

In one embodiment of the present invention, in each of the reactions, a solvent may or may not be added, preferably a solvent is added. Said solvent is preferably a hydrocarbon solvent, preferably one or more of alkanes, arenes and ethers, more preferably an alkane solvent, for example, can be one or more of hexane, heptane, octane, nonane, decane, cyclohexane, cycloheptane, cyclooctane, cyclononane, cyclodecane, benzene, toluene, xylene, ethylbenzene, propyl benzene, ethyl ether, propyl ether, isopropyl ether and butyl ether. The addition amount of said solvent should be suitable to promote the smooth progress of the reaction, and is not particularly limited. The solvent can be removed by a known method, such as distillation, rectification, and the like, which is not particularly limited.

In one embodiment of the present invention, the reaction product is washed with a solvent and purified, and the solvent that can be used for washing is preferably a hydrocarbon solvent. The solvent can be removed by conventional technical means such as drying, evaporation and distillation.

In one embodiment of the present invention, each of the reactions can be performed in a continuous or batch reaction equipment such as a reaction vessel, a fixed bed, a fluid bed, a microchannel reactor and the like.

Fourth Invention

The fourth aspect of the present invention provides a lubricating oil composition, comprising the above-mentioned ester compound of the present invention or the ester compound prepared by the process of the present invention, and a base oil of lubricating oil. Said ester compound comprises 0.001%-100%, preferably 0.005%-90%, more preferably 0.01%-50%, further optionally 0.05%-30%, further optionally 0.1%-25%, further optionally 0.5%-20% by mass of said lubricating oil composition.

According to the present invention, the lubricating oil composition may also contain other components. As the other components, for example, various additives that are allowed to be added to lubricating oil compositions in the art can be mentioned. For example, phenolic, amine or sulfur-phosphorus type antioxidants; carboxylate, sulfonate or alkylphenate salt-type detergents; succinimide type ashless dispersants; polyester, polyolefin or alkylnaphthalene type pour point depressants; methacrylate copolymer, ethylene-propylene copolymer, polyisobutylene, hydrogenated styrene/butadiene copolymer type viscosity index improvers; sulfur/phosphorus type friction modifier; sulfur/phosphorus, boric acid-containing type extreme pressure agent; or silicon type, or non-silicon type antifoaming agents, and the like can be specifically enumerated. The types and amounts of these additives are well known to those skilled in the art and will not be repeated here. These additives can be used alone, or some of these can be used in combination in any ratio.

The fourth invention of the present invention provides use of the above-mentioned ester compounds of the present invention or the ester compounds prepared by the process of the present invention as one or more of the base oil of the lubricating oil, the viscosity index improver, the antiwear agent and/or the anti-friction agent, and the friction property improver.

The ester compounds of the present invention are excellent in various properties such as viscosity-temperature property, low-temperature property, anti-oxidation property, and anti-friction property.

The ester compounds of the present invention have excellent viscosity-temperature properties and low-temperature properties as base oil, have excellent viscosity-temperature properties and low-temperature properties as viscosity index improver, can significantly reduce the wear scar diameter of the base oil as anti-wear agent, and can significantly reduce the friction coefficient of the base oil as friction modifier. In addition, the ester compounds of the present invention is excellent in the oxidation resistance.

It should be noted that the ester compounds obtained by the preparation process of the present invention may be a compound of a single structure, or may be a mixture comprising compounds of different structures. For the mixture containing compounds of different structures, it is sometimes possible to separate the mixture into single-structure compounds, or sometimes the mixture containing compounds of different structures can also be directly used without the need of separating the mixture into single-structure compounds.

EXAMPLES

In order to better understand the present invention, the content of the present invention is further described below in conjunction with the examples, but the content of the present invention is not limited to the following examples.

Example I-1: Preparation of Isomeric Acid I-A

The reaction was carried out in a high-pressure reaction vessel equipped with a gas vent, a stirrer and a thermocouple. 565 g of oleic acid was gradually pumped into a reaction vessel containing 1200 g of acetic acid and 10 g of perchloric acid having a concentration of 70%. The reaction was carried out at 70° C. for 24 hours, and then the heating was stopped to finish the reaction. The residual acetic acid was removed by distillation. The resulting reaction product was cooled to room temperature, washed with a base, and washed with water. The resulting organic phase was treated, for example, washed three times with potassium dihydrogen phosphate at pH=3.7, dried over anhydrous sodium sulfate, and filtered. The unreacted oleic acid was removed by molecular distillation to obtain an addition product of acetic acid-oleic acid, an isomeric acid I-A, which was confirmed by $^1$H-NMR to have the following structure.

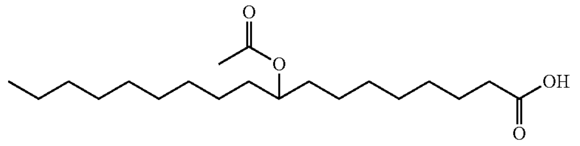 [SMILES: CCCCCCCCCC(CCCCCCCC(=O)O)OC(C)=O]

Example I-2: Preparation of Ester Compound I-A-1

171 g of isomeric acid I-A, 22 g of trimethylolpropane, 1.8 g of p-toluenesulfonic acid (catalyst) and a water-carrying agent (90-120° C. petroleum ether) were added to a 500 mL three-neck glass flask. The reaction mixture was heated to reflux temperature. $H_2O$ produced in the reaction process was collected with a water separator, and the reaction was stopped when the actual water output was identical to the theoretical value. The crude product was washed with a base to remove the catalyst and washed with water until neutral, and then the reaction solvent was removed to obtain an ester compound I-A-1. It was confirmed by $^1$H-NMR to have the following structure.

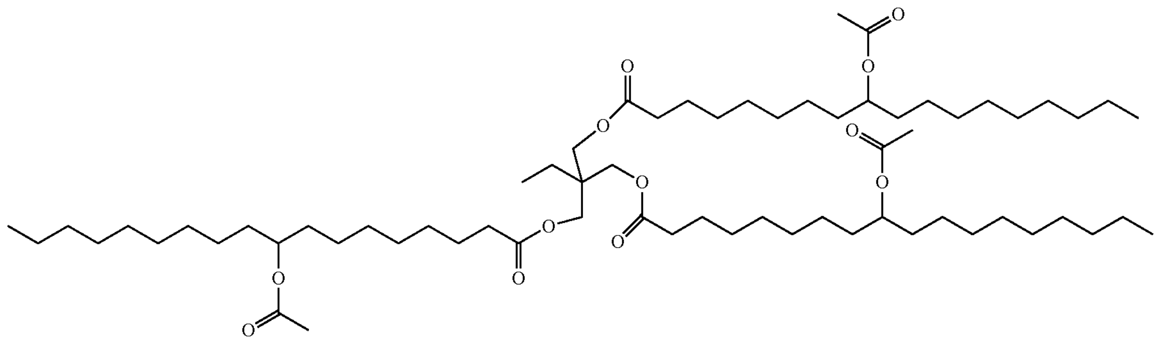 [SMILES: CCCCCCCCCC(CCCCCCCC(=O)OCC(CC)(COC(=O)CCCCCCCC(CCCCCCCCC)OC(C)=O)COC(=O)CCCCCCCC(CCCCCCCCC)OC(C)=O)OC(C)=O]

Example I-3: Preparation of Ester Compound I-A-2

171 g of isomeric acid I-A, 17 g of pentaerythritol, 1.8 g of p-toluenesulfonic acid (catalyst) and a water-carrying agent (90-120° C. petroleum ether) were added to a 500 mL three-neck glass flask. The reaction mixture was heated to reflux temperature. $H_2O$ produced in the reaction process was collected with a water separator, and the reaction was stopped when the actual water output was identical to the theoretical value. The crude product was washed with a base to remove the catalyst and washed with water until neutral, and then the reaction solvent was removed to obtain an ester compound I-A-2. It was confirmed by $^1$H-NMR to have the following structure.

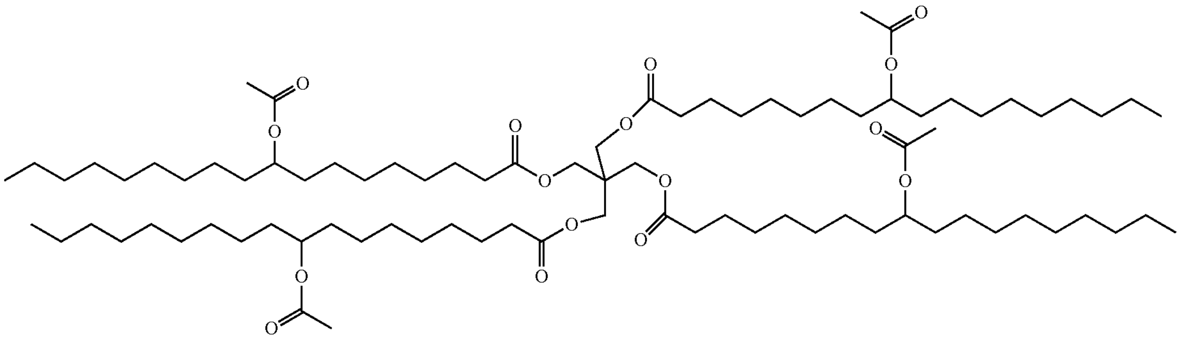 [SMILES: CCCCCCCCCC(CCCCCCCC(=O)OCC(COC(=O)CCCCCCCC(CCCCCCCCC)OC(C)=O)(COC(=O)CCCCCCCC(CCCCCCCCC)OC(C)=O)COC(=O)CCCCCCCC(CCCCCCCCC)OC(C)=O)OC(C)=O]

Example I-4: Preparation of Ester Compound I-A-3

67 g of trimethylolpropane, 0.5 g of p-toluenesulfonic acid (catalyst), and a water-carrying agent (toluene) were added to a 500 mL three-necked glass flask. The reaction mixture was heated to reflux temperature. 85 g of isomeric acid I-A was gradually added dropwise to the three-necked flask over 3 hours. $H_2O$ produced in the reaction process was collected with a water separator, and the reaction was stopped when the actual water output was identical to the theoretical value. The excess trimethylolpropane was removed by distillation. The crude product was washed with a base to remove the catalyst and washed with water until neutral, and then the reaction solvent was removed to obtain an ester compound I-A-3. It was confirmed by $^1$H-NMR to have the following structure.

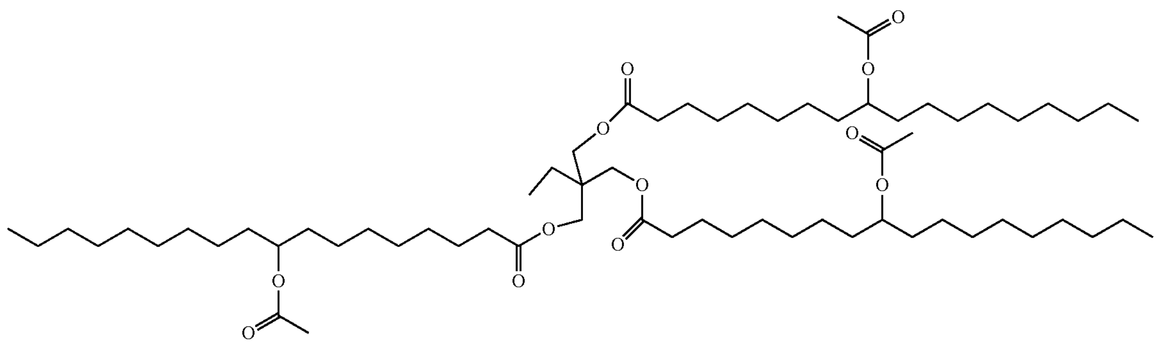 [SMILES: CCCCCCCCCC(CCCCCCCC(=O)OCC(CC)(COC(=O)CCCCCCCC(CCCCCCCCC)OC(C)=O)COC(=O)CCCCCCCC(CCCCCCCCC)OC(C)=O)OC(C)=O]

Comparative Example I-1: Preparation of Ester Compound I-D-1

The preparation process of I-D-1 was identical to that of Example I-2 except that the isomeric acid A was replaced with equimolar oleic acid. It was confirmed by $^1$H-NMR to have the following structure.

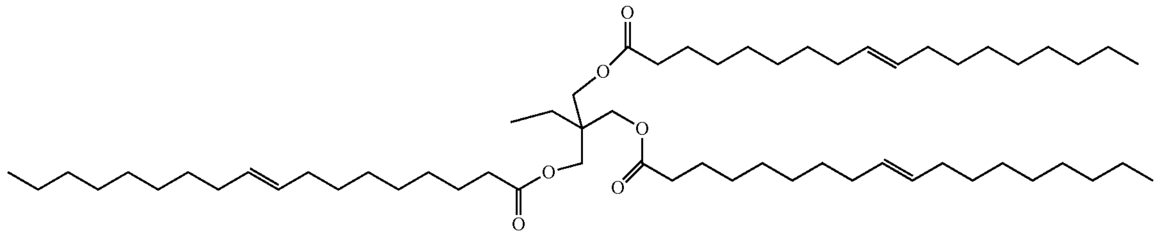 [SMILES: CCCCCCCC/C=C/CCCCCCCC(=O)OCC(CC)(COC(=O)CCCCCCC/C=C/CCCCCCCC)COC(=O)CCCCCCC/C=C/CCCCCCCC]

Comparative Example I-2: Preparation of Ester Compound I-D-2

The preparation process of I-D-2 was identical to that of Example I-2 except that trimethylolpropane was replaced with equimolar glycerol. It was confirmed by $^1$H-NMR to have the following structure.

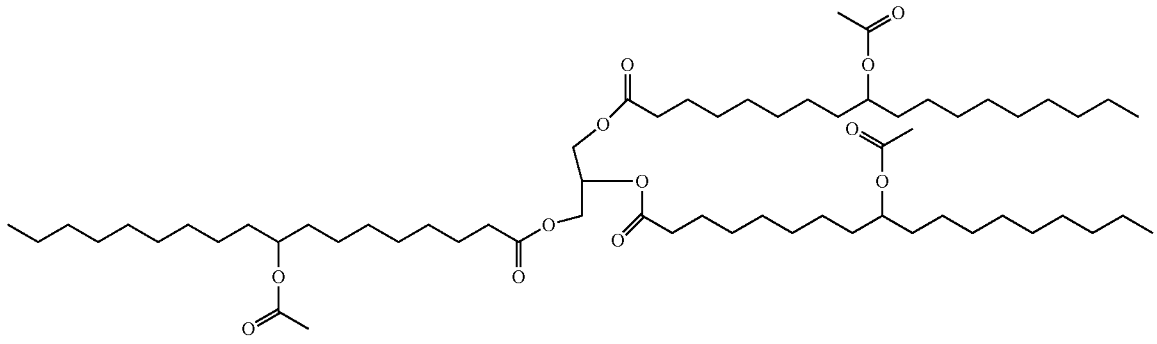 [SMILES: CCCCCCCCCC(CCCCCCCC(=O)OCC(COC(=O)CCCCCCCC(CCCCCCCCC)OC(C)=O)OC(=O)CCCCCCCC(CCCCCCCCC)OC(C)=O)OC(C)=O]

Example I-5: Preparation of Isomeric Acid I-B

The reaction was carried out in a high-pressure reaction vessel equipped with a gas vent, a stirrer and a thermocouple. 560 g of linoleic acid was gradually pumped into a reaction vessel containing 1800 g of acetic acid and 10 g of perchloric acid having a concentration of 70%. The reaction was carried out at 70° C. for 18 hours, and then the heating was stopped to finish the reaction. The residual acetic acid was removed by distillation. The resulting reaction product was cooled to room temperature, washed with a base, and washed with water. The resulting organic phase was washed three times with potassium dihydrogen phosphate at pH=3.7, dried over anhydrous sodium sulfate, and filtered. The unreacted linoleic acid was removed by molecular distillation to obtain an addition product of acetic acid-linoleic acid, an isomeric acid I-B, which was confirmed by $^1$H-NMR to have the following structure.

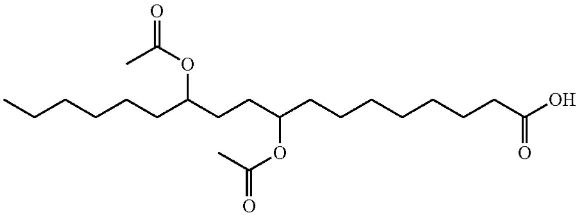 [SMILES: CCCCCCC(CCC(CCCCCCCC(=O)O)OC(C)=O)OC(C)=O]

Example I-6: Preparation of Ester Compound I-B-1

201 g of isomeric acid I-B, 22 g of trimethylolpropane, 3.2 g of p-toluenesulfonic acid (catalyst) and a water-carrying agent (90-120° C. petroleum ether) were added to a 500 mL three-neck glass flask. The reaction mixture was heated to reflux temperature. $H_2O$ produced in the reaction process was collected with a water separator, and the reaction was stopped when the actual water output was identical to the theoretical value. The crude product was washed with a base to remove the catalyst and washed with water until neutral, and then the reaction solvent was removed to obtain an ester compound I-B-1. It was confirmed by $^1$H-NMR to have the following structure.

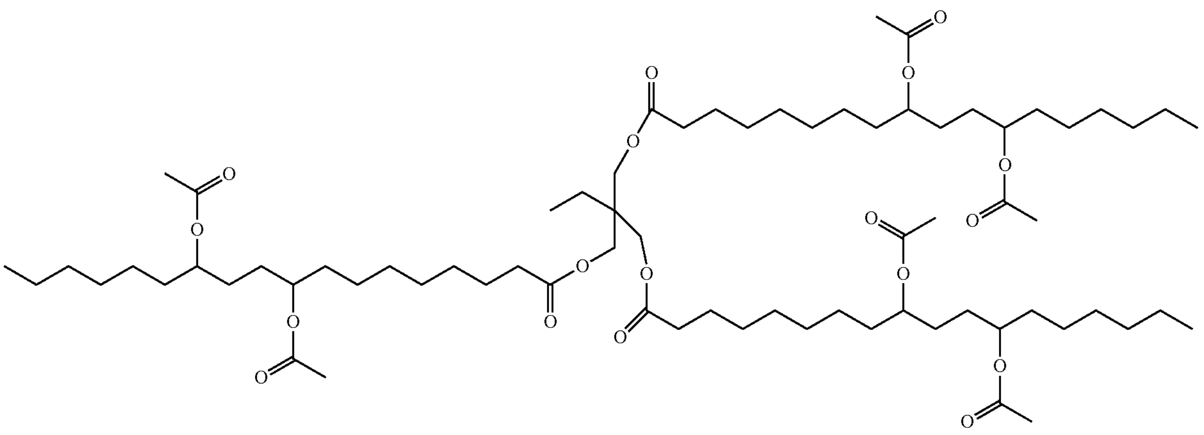 [SMILES: CCCCCCC(CCC(CCCCCCCC(=O)OCC(CC)(COC(=O)CCCCCCCC(CCC(CCCCCC)OC(C)=O)OC(C)=O)COC(=O)CCCCCCCC(CCC(CCCCCC)OC(C)=O)OC(C)=O)OC(C)=O)OC(C)=O]

Example I-7: Preparation of Ester Compound I-B-2

121 g of isomeric acid I-B, 10 g of pentaerythritol, 2.5 g of p-toluenesulfonic acid (catalyst) and a water-carrying agent (90-120° C. petroleum ether) were added to a 250 mL three-neck glass flask. The reaction mixture was heated to reflux temperature. $H_2O$ produced in the reaction process was collected with a water separator, and the reaction was stopped when the actual water output was identical to the theoretical value. The crude product was washed with a base to remove the catalyst and washed with water until neutral, and then the reaction solvent was removed to obtain an ester compound I-B-2. It was confirmed by $^1$H-NMR to have the following structure.

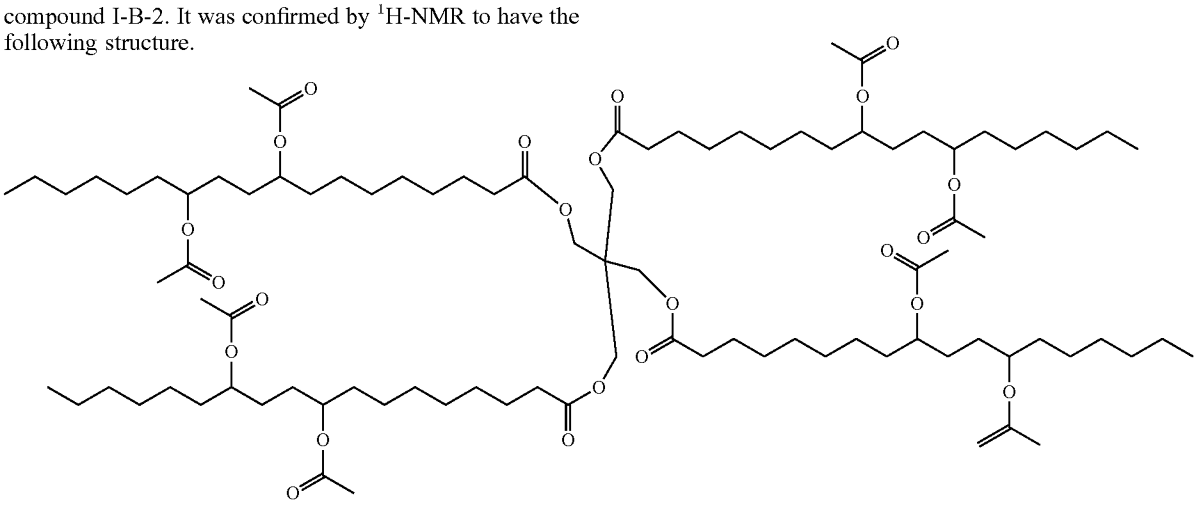

Example I-8: Preparation of Ester Compound I-B-3

134 g of trimethylolpropane, 2 g of p-toluenesulfonic acid (catalyst) and a water-carrying agent (toluene) were added to a 500 mL three-necked glass flask. The reaction mixture was heated to reflux temperature. 201 g of isomeric acid I-B was gradually added dropwise to the three-necked flask over 5 hours. $H_2O$ produced in the reaction process was collected with a water separator, and the reaction was stopped when the actual water output was identical to the theoretical value. The excess trimethylolpropane was removed by distillation. The crude product was washed with a base to remove the catalyst and washed with water until neutral, and then the reaction solvent was removed obtain an ester compound I-B-3. It was confirmed by $^1$H-NMR to have the following structure.

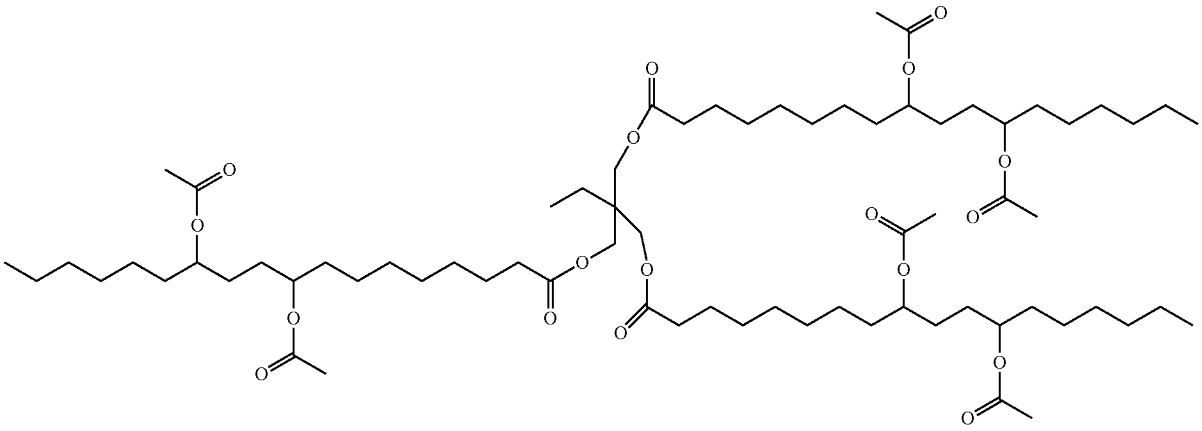 [SMILES: CCCCCCC(CCC(CCCCCCCC(=O)OCC(CC)(COC(=O)CCCCCCCC(CCC(CCCCCC)OC(C)=O)OC(C)=O)COC(=O)CCCCCCCC(CCC(CCCCCC)OC(C)=O)OC(C)=O)OC(C)=O)OC(C)=O]

Comparative Example I-3: Preparation of Ester Compound I-DM-1

The preparation process of I-DM-1 was identical to that of Example I-6 except that trimethylolpropane was replaced with equimolar ethanol, to produce the ester compound I-DM-1. It was confirmed by $^{1}$H-NMR to have the following structure.

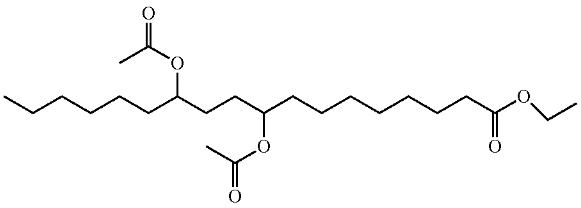 [SMILES: CCCCCCC(CCC(CCCCCCCC(=O)OCC)OC(C)=O)OC(C)=O]

The physical and chemical properties of ester compounds I-A-1 to I-A-3, I-B-1 to I-B-2, I-D-1, and I-D-2 were investigated, and the measurement methods were GB/T265 Petroleum products-determination of kinematic viscosity and calculation of dynamic viscosity, GB/T1995 Petroleum products-Calculation of viscosity index, GB/T3535 Petroleum products-Determination of pour point, and SH/T0074 Test method for oxidation stability of gasoline engine oils by thin-film oxygen uptake. The measurement results were shown in Table I-1.

TABLE I-1

| | Kinematic viscosity/(mm$^2$/ s) | | Viscosity | Pour | Oxidation induction |
|---|---|---|---|---|---|
| Sample | 40° C. | 100° C. | index | point/° C. | period/min |
| I-A-1 | 59 | 11.2 | 189 | −48 | 220 |
| I-A-2 | 78 | 13.7 | 183 | −36 | 215 |
| I-A-3 | 33 | 6.3 | 150 | −51 | 203 |
| I-D-1 | 50 | 9.5 | 177 | −30 | 140 |
| I-D-2 | 49 | 9.8 | 191 | −27 | 176 |
| I-B-1 | 79 | 13.5 | 175 | −42 | 198 |
| I-B-2 | 90 | 15.1 | 179 | −39 | 203 |

The anti-wear properties of ester compounds I-A-3, I-B-3 and I-DM-1 were investigated, and the measurement method was SH/T0762 the test method for determination of the coefficient of friction of lubricants using the four-ball wear test machine. The measurement results were shown in Table I-2.

TABLE I-2

| Sample | Steel ball wear scar diameter/um |
|---|---|
| I-A-3 | 331 |
| I-B-3 | 285 |
| I-DM-1 | 585 |

Example II-1: Preparation of Isomeric Acid

The reaction was carried out in a high-pressure reaction vessel equipped with a gas vent, a stirrer and a thermocouple. 565 g of oleic acid was gradually pumped into a reaction vessel containing 1000 g of acetic acid and 10 g of perchloric acid having a concentration of 70%. The reaction was carried out at 70° C. for 24 hours, and then the heating was stopped to finish the reaction. The residual acetic acid was removed by distillation. The resulting reaction product was cooled to room temperature, washed with a base, and washed with water. The resulting organic phase was treated, for example, washed three times with potassium dihydrogen phosphate at pH=3.7, dried over anhydrous sodium sulfate, and filtered. The unreacted oleic acid was removed by molecular distillation to obtain an addition product of acetic acid-oleic acid, an isomeric acid II-A, which was confirmed by $^{1}$H-NMR to have the following structure.

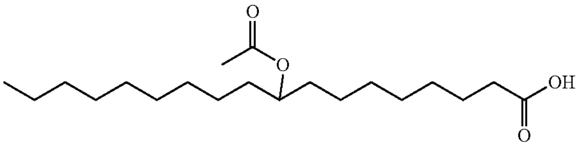 [SMILES: CCCCCCCCCC(CCCCCCCC(=O)O)OC(C)=O]

Example II-2: Preparation of Ester Compound II-A-1

171 g of isomeric acid II-A, 15.5 g of ethylene glycol, 1.3 g of a concentrated sulfuric acid (catalyst) and a water-carrying agent (90-120° C. petroleum ether) were added to a 500 mL three-neck glass flask. The reaction mixture was heated to reflux temperature. $H_2O$ produced in the reaction process was collected with a water separator, and the reaction was stopped when the actual water output was identical to the theoretical value. The crude product was washed with a base to remove the catalyst and washed with water until neutral, and then the reaction solvent was removed to obtain an ester compound II-A-1. It was confirmed by $^{1}$H-NMR to have the following structure.

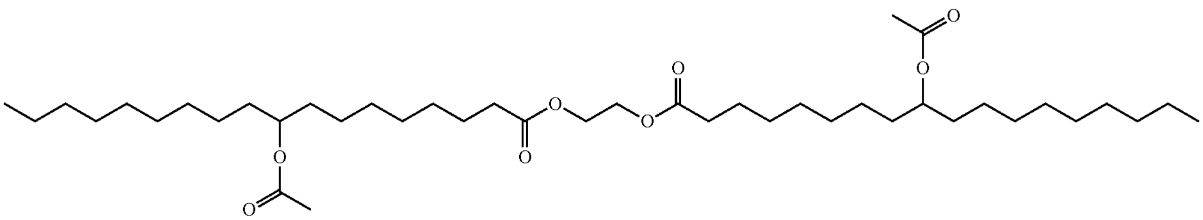 [SMILES: CCCCCCCCCC(CCCCCCCC(=O)OCCOC(=O)CCCCCCCC(CCCCCCCCC)OC(C)=O)OC(C)=O]

Example II-3: Preparation of Ester Compound II-A-2

171 g of isomeric acid II-A, 30 g of hexanediol, 2 g of a concentrated sulfuric acid (catalyst) and a water-carrying agent (90-120° C. petroleum ether) were added to a 500 mL three-neck glass flask. The reaction mixture was heated to reflux temperature. $H_2O$ produced in the reaction process was collected with a water separator, and the reaction was stopped when the actual water output was identical to the theoretical value. The crude product was washed with a base to remove the catalyst and washed with water until neutral, and then the reaction solvent was removed to obtain an ester compound II-A-2. It was confirmed by $^1$H-NMR to have the following structure.

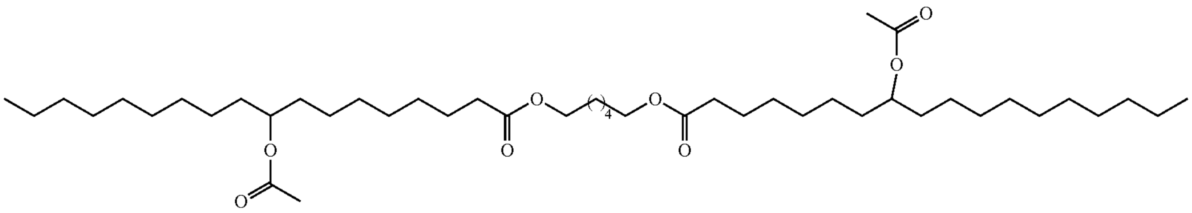 [SMILES: CCCCCCCCCCC(CCCCCCC(=O)OCCCOC(=O)CCCCCCCC(CCCCCCCCC)OC(C)=O)OC(C)=O]

Comparative Example II-1: Preparation of Ester Compound II-D-1

The preparation process of II-D-1 was identical to that of Example II-2 except that the isomeric acid II-A was replaced with equimolar oleic acid to produce the ester compound II-D-1. It was confirmed by $^1$H-NMR to have the following structure.

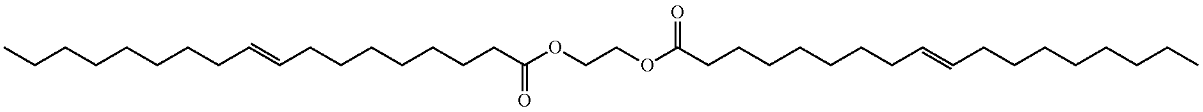 [SMILES: CCCCCCCC/C=C/CCCCCCCC(=O)OCCOC(=O)CCCCCCC/C=C/CCCCCCCC]

Comparative Example II-2: Preparation of Ester Compound II-D-2

The preparation process of II-D-2 was identical to that of Example II-2 except that ethylene glycol was replaced with equimolar glycerol to produce the ester compound II-D-2. It was confirmed by $^1$H-NMR to have the following structure.

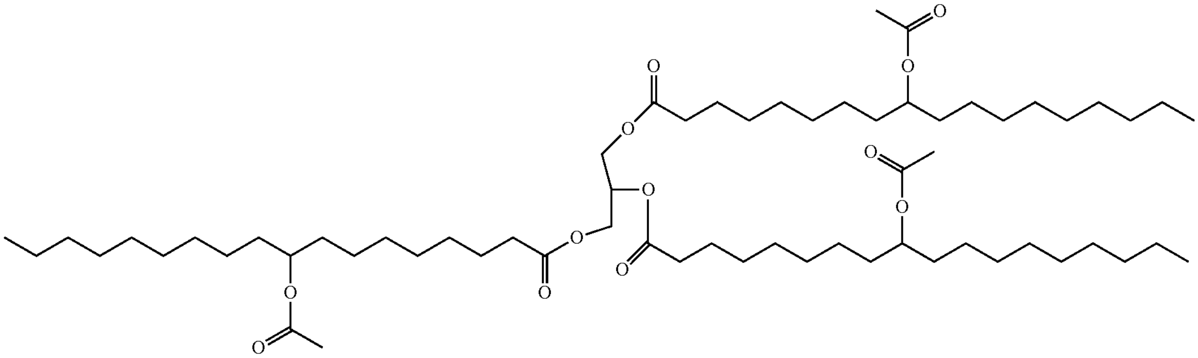 [SMILES: CCCCCCCCCC(CCCCCCCC(=O)OCC(COC(=O)CCCCCCCC(CCCCCCCCC)OC(C)=O)OC(=O)CCCCCCCC(CCCCCCCCC)OC(C)=O)OC(C)=O]

Example II-4: Preparation of Isomeric Acid II-B 10 g of a strong acid ion exchange resin treated by washing with HCl was installed in a fixed bed reactor. The temperature of the reactor was controlled at 60° C. The weighed hexadecylenic acid and hexanoic acid (molar ratio 1.20) were preheated to the same temperature, and pumped into the reactor. The reaction was performed at a space velocity of 0.4 $h^{-1}$. The discharged product was collected. The residual hexanoic acid was removed by preliminary distillation, and the unreacted hexadecylenic acid was further removed by molecular distillation to produce an addition product of hexanoic acid-hexadecylenic acid, an isomeric acid II-B, which was confirmed by $^1$H-NMR to have the following structure.

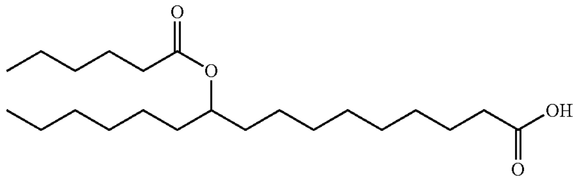 [SMILES: CCCCCCC(CCCCCCCCC(=O)O)OC(=O)CCCCC]

Example II-5: Preparation of Ester Compound II-B-1

370 g of isomeric acid II-B, 90 g of decanediol, 3 g of a concentrated sulfuric acid (catalyst) and a water-carrying agent (90-120° C. petroleum ether) were added to a 1000 mL three-neck glass flask. The reaction mixture was heated to reflux temperature. $H_2O$ produced in the reaction process was collected with a water separator, and the reaction was stopped when the actual water output was identical to the theoretical value. The crude product was washed with a base to remove the catalyst and washed with water until neutral, and then the reaction solvent was removed to obtain an ester compound II-B-1. It was confirmed by $^1$H-NMR to have the following structure.

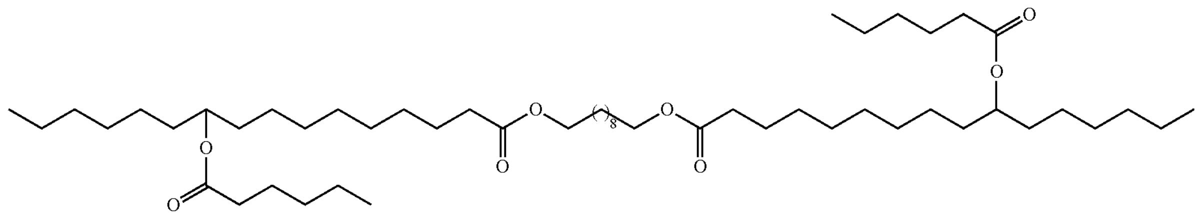 [SMILES: CCCCCCC(CCCCCCCCC(=O)OCCCOC(=O)CCCCCCCCC(CCCCCC)OC(=O)CCCCC)OC(=O)CCCCC]

Example II-6: Preparation of Ester Compound II-B-2

370 g of isomeric acid II-B, 45 g of butanediol, 3 g of a concentrated sulfuric acid (catalyst) and a water-carrying agent (90-120° C. petroleum ether) were added to a 1000 mL three-neck glass flask. The reaction mixture was heated to reflux temperature. $H_2O$ produced in the reaction process was collected with a water separator, and the reaction was stopped when the actual water output was identical to the theoretical value. The crude product was washed with a base to remove the catalyst and washed with water until neutral, and then the reaction solvent was removed to obtain an ester compound II-B-2. It was confirmed by $^1H$-NMR to have the following structure.

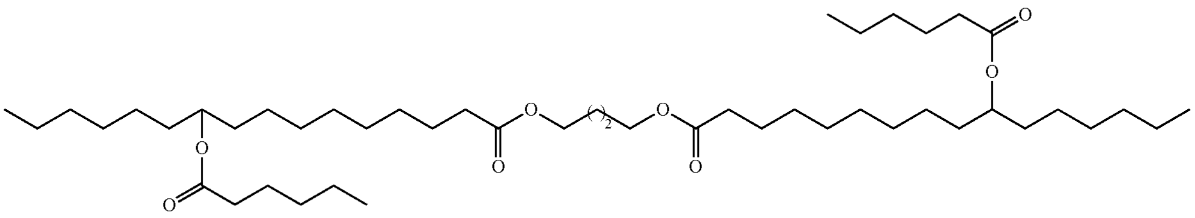 [SMILES: CCCCCCC(CCCCCCCCC(=O)OCCCOC(=O)CCCCCCCCC(CCCCCC)OC(=O)CCCCC)OC(=O)CCCCC]

Comparative Example II-3: Preparation of Ester Compound II-D-3

The preparation process of II-D-3 was identical to that of Example II-6 except that the isomeric acid II-B was replaced with equimolar palmitic acid to produce the ester compound II-D-3. It was confirmed by $^1H$-NMR to have the following structure.

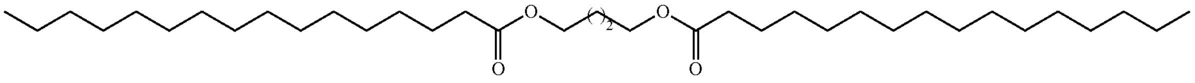 [SMILES: CCCCCCCCCCCCCCCC(=O)OCCCOC(=O)CCCCCCCCCCCCCCC]

The physical and chemical properties of ester compounds II-A-1, II-A-2, II-D-1, II-D-2, II-B-1, II-B-2, and II-D-3 were investigated, and the measurement methods were GB/T265 Petroleum products-determination of kinematic viscosity and calculation of dynamic viscosity, GB/T1995 Petroleum products-Calculation of viscosity index, GB/T3535 Petroleum products-Determination of pour point, and SH/T0074 Test method for oxidation stability of gasoline engine oils by thin-film oxygen uptake, SH/T0762 the test method for determination of the coefficient of friction of lubricants using the four-ball wear test machine. The measurement results were shown in Table II-1.

TABLE II-1

| Sample | Kinematic viscosity/($mm^2$/s) 40° C. | 100° C. | Viscosity index | Pour point/° C. | Oxidation induction period/min |
|---|---|---|---|---|---|
| II-A-1 | 31 | 6.0 | 143 | −51 | 223 |
| II-A-2 | 33 | 6.3 | 150 | −51 | 233 |
| II-D-1 | 27 | 5.7 | 159 | −27 | 114 |
| II-D-2 | 49 | 9.8 | 191 | −27 | 176 |
| II-B-1 | 46 | 7.9 | 143 | −54 | 214 |
| II-B-2 | 35 | 6.4 | 136 | −60 | 219 |
| II-D-3 | 28 | 5.8 | 163 | 15 | 268 |

Example II-7: Preparation of Isomeric Acid II-C

The reaction was carried out in a high-pressure reaction vessel equipped with a gas vent, a stirrer and a thermocouple. 280 g of linoleic acid was gradually pumped into a reaction vessel containing 600 g of acetic acid and 5 g of perchloric acid having a concentration of 70%. The reaction was carried out at 70° C. for 18 hours, and then the heating was stopped to finish the reaction. The residual acetic acid was removed by distillation. The resulting reaction product was cooled to room temperature, washed with a base, and washed with water. The resulting organic phase was washed three times with potassium dihydrogen phosphate at pH=3.7, dried over anhydrous sodium sulfate, and filtered. Finally, the unreacted linoleic acid was removed by molecular distillation to obtain an addition product of acetic acid-linoleic acid, an isomeric acid II-C, which was confirmed by $^1$H-NMR to have the following structure.

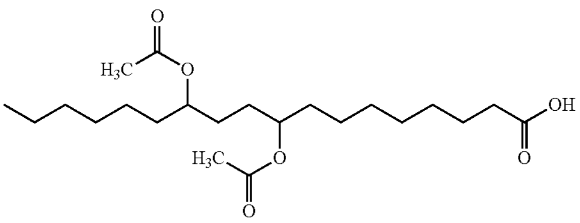 [SMILES: CCCCCCC(CCC(CCCCCCCC(=O)O)OC(C)=O)OC(C)=O]

Example II-8: Preparation of Ester Compound II-C-1

81 g of isomeric acid II-C, 12 g of hexanediol, 1.4 g of a concentrated sulfuric acid (catalyst) and a water-carrying agent (90-120° C. petroleum ether) were added to a 500 mL three-neck glass flask. The reaction mixture was heated to reflux temperature. $H_2O$ produced in the reaction process was collected with a water separator, and the reaction was stopped when the actual water output was identical to the theoretical value. The crude product was washed with a base to remove the catalyst and washed with water until neutral, and then the reaction solvent was removed to obtain an ester compound II-C-1. It was confirmed by $^1$H-NMR to have the following structure.

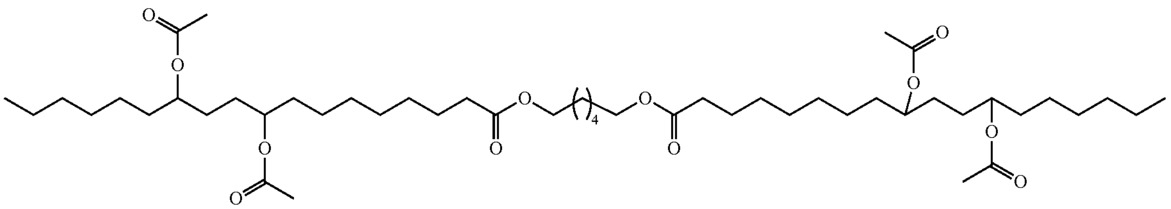

Comparative Example II-4: Preparation of Ester Compound II-D-4

The preparation process of 11-D-4 was identical to that of Example II-8 except that the isomeric acid C was replaced with equimolar linoleic acid to produce the ester compound II-D. It was confirmed by $^1$H-NMR to have the following structure.

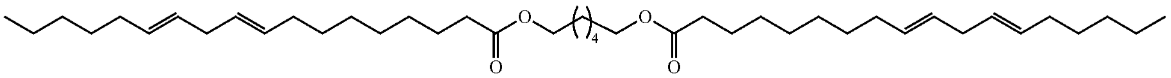

Example II-9: Preparation of Isomeric Acid II-E 10 g of a Strong Acid Ion Exchange Resin Treated by Washing with HCl was installed in a Fixed Bed reactor. The temperature of the reactor was controlled at 65° C. The weighed linoleic acid, hexanoic acid and butyric acid (molar ratio 1:5:5) were preheated to the same temperature, and pumped into the reactor. The reaction was performed at a space velocity of 0.3 $h^{-1}$. The discharged product was collected. The residual hexanoic acid and butyric acid were removed by preliminary distillation, and the unreacted linoleic acid was further removed by molecular distillation to produce an addition product of hexanoic acid/butyric acid-linoleic acid, an isomeric acid II-E, which was confirmed by $^1$H-NMR to have the following structure.

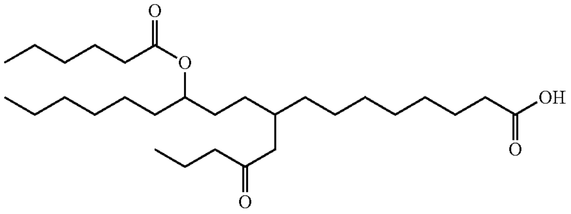

Example II-10: Preparation of Ester Compound II-E-1

242 g of isomeric acid II-E, 44 g of decanediol, 4.5 g of a concentrated sulfuric acid (catalyst) and a water-carrying agent (90-120° C. petroleum ether) were added to a 500 mL three-neck glass flask. The reaction mixture was heated to reflux temperature. $H_2O$ produced in the reaction process was collected with a water separator, and the reaction was stopped when the actual water output was identical to the theoretical value. The crude product was washed with a base to remove the catalyst and washed with water until neutral, and then the reaction solvent was removed to obtain an ester compound II-E-1. It was confirmed by $^1$H-NMR to have the following structure.

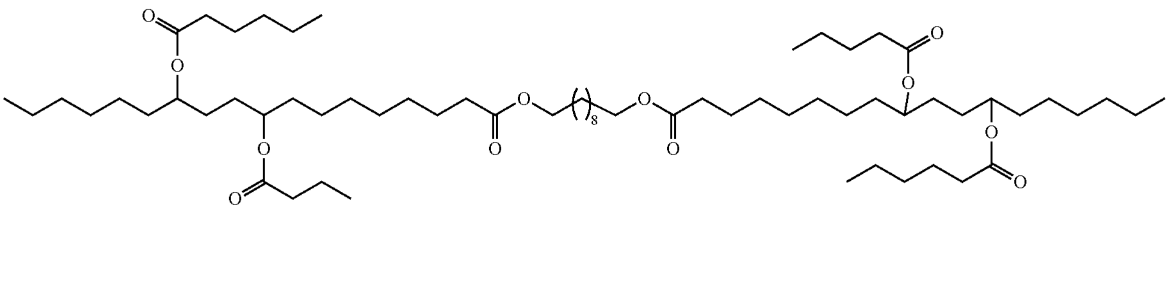

Example II-11: Preparation of Ester Compound II-E-2

242 g of isomeric acid II-E, 22.5 g of butanediol, 4.4 g of a concentrated sulfuric acid (catalyst) and a water-carrying agent (90-120° C. petroleum ether) were added to a 1000 mL three-neck glass flask. The reaction mixture was heated to reflux temperature. $H_2O$ produced in the reaction process was collected with a water separator, and the reaction was stopped when the actual water output was identical to the theoretical value. The crude product was washed with a base to remove the catalyst and washed with water until neutral, and then the reaction solvent was removed to obtain an ester compound II-E-2. It was confirmed by $^1$H-NMR to have the following structure.

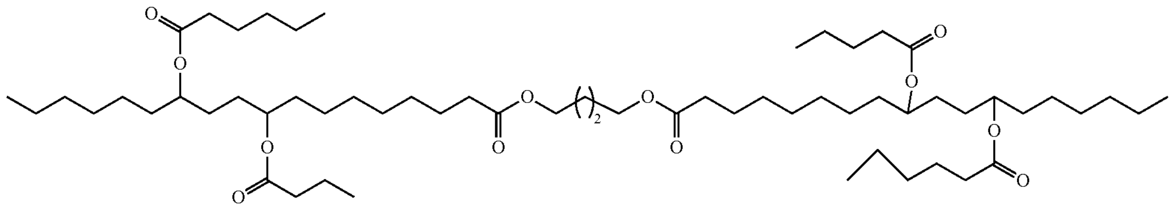

The physical and chemical properties of ester compounds IT-C-1, II-D-4, II-E-1, and II-E-2 were investigated, and the measurement methods were shown in Table II-2. The measurement methods were identical to those in Table II-1.

TABLE II-2

| Sample | Kinematic viscosity/(mm$^2$/ s) 40° C. | 100° C. | Viscosity index | Pour point/° C. | Oxidation induction period/min |
|---|---|---|---|---|---|
| II-C-3 | 36 | 6.6 | 145 | −57 | 218 |
| II-D-4 | 50 | 9.5 | 177 | −30 | 140 |
| II-E-1 | 51 | 8.4 | 139 | −54 | 224 |
| II-E-2 | 38 | 6.7 | 133 | <−60 | 209 |

Example III-1: Preparation of Isomeric Acid III-A

The reaction was carried out in a high-pressure reaction vessel equipped with a gas vent, a stirrer and a thermocouple. 565 g of oleic acid was gradually pumped into a reaction vessel containing 100% g of acetic acid and 10 g of perchloric acid having a concentration of 70%. The reaction was carried out at 70° C. for 24 hours, and then the heating was stopped to finish the reaction. The residual acetic acid was removed by distillation. The resulting reaction product was cooled to room temperature, washed with a base, and washed with water. The resulting organic phase was treated, for example, washed three times with potassium dihydrogen phosphate at pH=3.7, dried over anhydrous sodium sulfate, and filtered. The unreacted oleic acid was removed by molecular distillation to obtain an addition product of acetic acid-oleic acid, an isomeric acid III-A, which was confirmed by $^1$H-NMR to have the following structure.

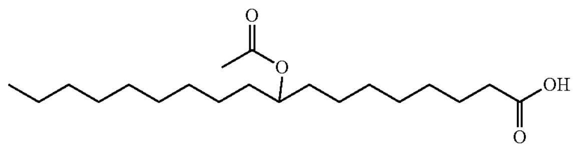 [SMILES: CCCCCCCCCC(CCCCCCCC(=O)O)OC(C)=O]

Example III-2: Preparation of Ester Compound III-A-1

29.2 g of hexanedioic acid, 53.6 g of trimethylolpropane, 0.3 g of a concentrated sulfuric acid (catalyst) and a water-carrying agent (90-120° C. petroleum ether) were added to a 500 mL three-necked glass flask. The reaction mixture was heated to reflux temperature. $H_2O$ produced in the reaction process was collected with a water separator, and the reaction was stopped when the actual water output was identical to the theoretical value to produce a composite polyhydroxyl compound. The crude product was not treated, and 274 g of isomeric acid III-A was added. The reaction mixture was heated to reflux temperature. $H_2O$ produced in the reaction process was collected with a water separator, and the reaction was stopped when the actual water output was identical to the theoretical value. The crude product was washed with a base to remove the catalyst and washed with water until neutral, and then the reaction solvent was removed to obtain a composite ester compound III-A-1. It was confirmed by $^1$H-NMR to have the following structure.

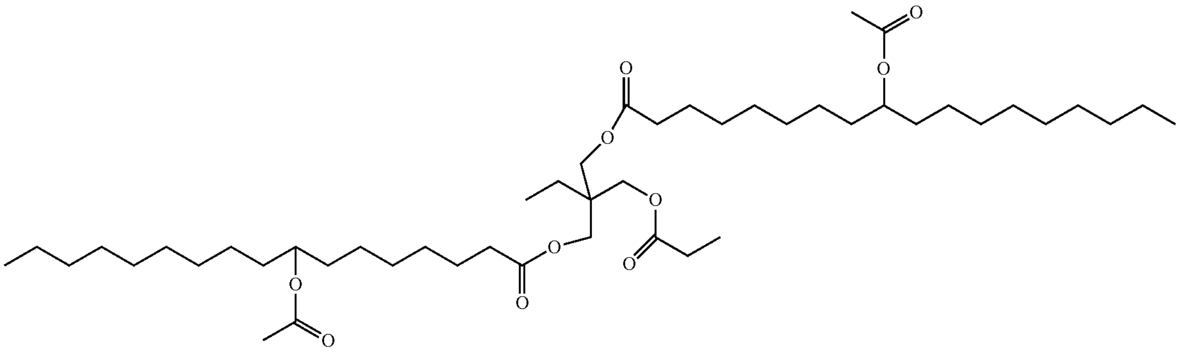

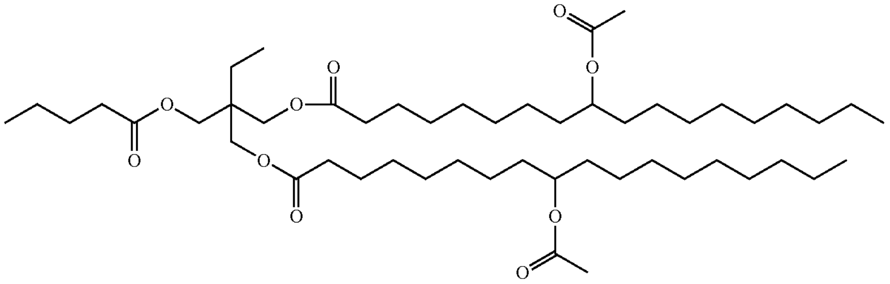

Example III-3: Preparation of Ester Compound III-A-2

23.6 g of butanedioic acid, 40.8 g of pentaerythritol, 0.3 g of a concentrated sulfuric acid (catalyst) and a water-carrying agent (90-120° C. petroleum ether) were added to a 500 mL three-necked glass flask. The reaction mixture was heated to reflux temperature. $H_2O$ produced in the reaction process was collected with a water separator, and the reaction was stopped when the actual water output was identical to the theoretical value to produce a composite polyhydroxyl compound. The crude product was not treated, and 272 g of isomeric acid III-A was added. The reaction mixture was heated to reflux temperature. $H_2O$ produced in the reaction process was collected with a water separator, and the reaction was stopped when the actual water output was identical to the theoretical value. The crude product was washed with a base to remove the catalyst and washed with water until neutral, and then the reaction solvent was removed to obtain a composite ester compound III-A-2. It was confirmed by $^1$H-NMR to have the following structure.

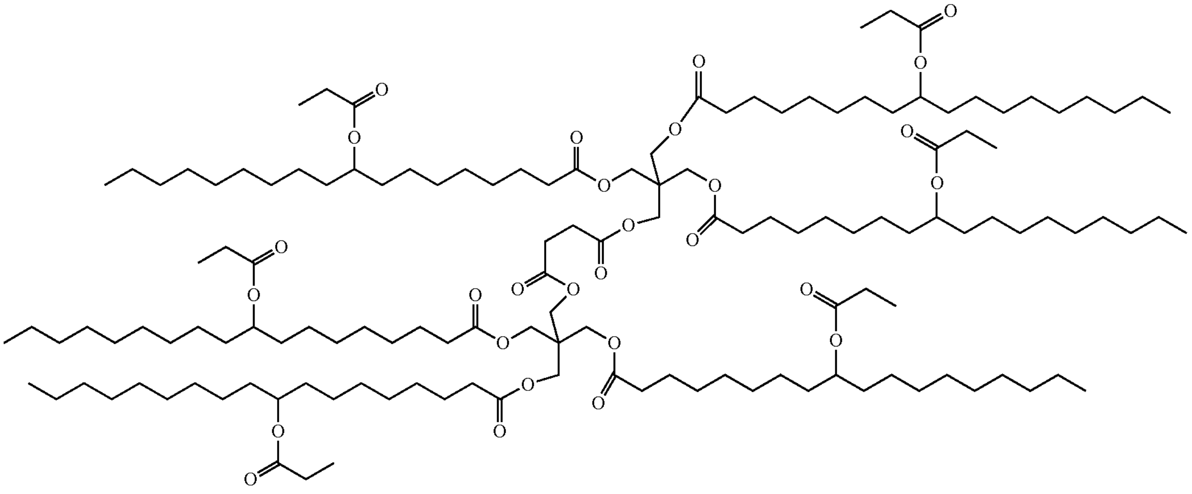

Comparative Example III-1: Preparation of Ester Compound III-D-1

The preparation process of the ester compound III-D-1 was identical to that of Example III-2 except that the isomeric acid III-A was replaced with equimolar oleic acid to produce the ester compound III-D-1. It was confirmed by $^1$H-NMR to have the following structure.

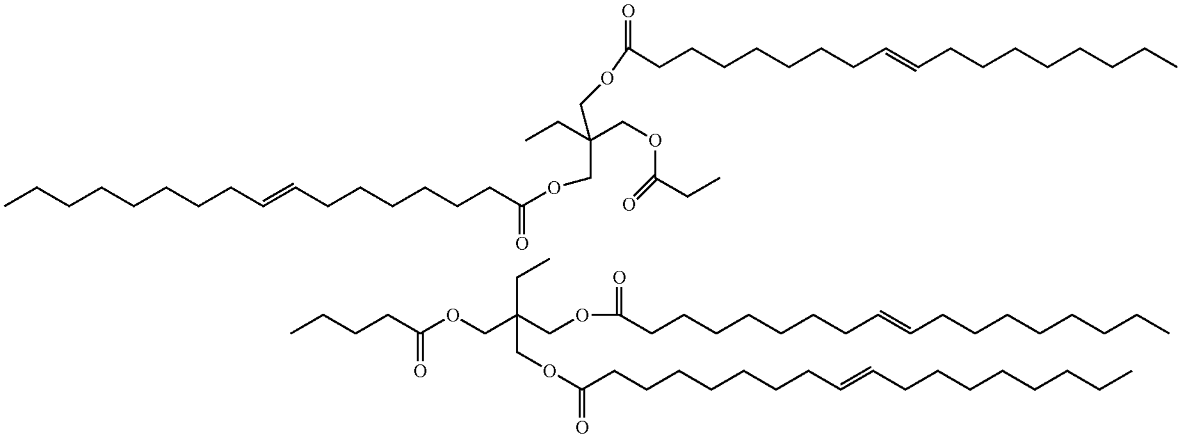

Example III-4: Preparation of Isomeric Acid III-BD 10 g of a strong acid ion exchange resin washed with HCl was installed in a fixed bed reactor. The temperature of the reactor was controlled at 60° C. The weighed hexadecylenic acid and hexanoic acid (molar ratio 1:20) were preheated to the same temperature, and pumped into the reactor. The reaction was performed at a space velocity of 0.4 $h^{-1}$. The discharged product was collected. The residual hexanoic acid was removed by preliminary distillation, and the unreacted hexadecylenic acid was further removed by molecular distillation to produce an addition product of hexanoic acid-hexadecylenic acid, an isomeric acid III-B, which was confirmed by $^1$H-NMR to have the following structure.

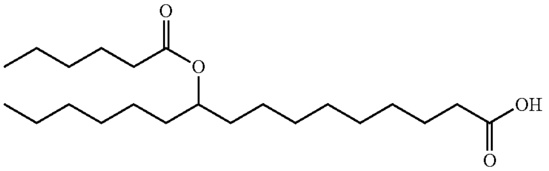 [SMILES: CCCCCCC(CCCCCCCCC(=O)O)OC(=O)CCCCC]

Example III-5: Preparation of Ester Compound III-B-1

40.4 g of decanedioic acid, 33.5 g of trimethylolpropane, 0.5 g of a concentrated sulfuric acid (catalyst) and a water-carrying, agent (90-120° C. petroleum ether) were added to a 500 mL, three-necked glass flask. The reaction mixture was heated to reflux temperature. $H_2O$ produced in the reaction process was collected with a water separator, and the reaction was stopped when the actual water output was identical to the theoretical value to produce a composite polyhydroxyl compound. The crude product was not treated, and 129.5 g of isomeric acid III-B was added. The reaction mixture was heated to reflux temperature. $H_2O$ produced in the reaction process was collected with a water separator, and the reaction was stopped when the actual water output was identical to the theoretical value. The crude product was washed with a base to remove the catalyst and washed with water until neutral, and then the reaction solvent was removed to obtain a composite ester compound III-B-1. It was confirmed by $^1$H-NMR to have the following structure.

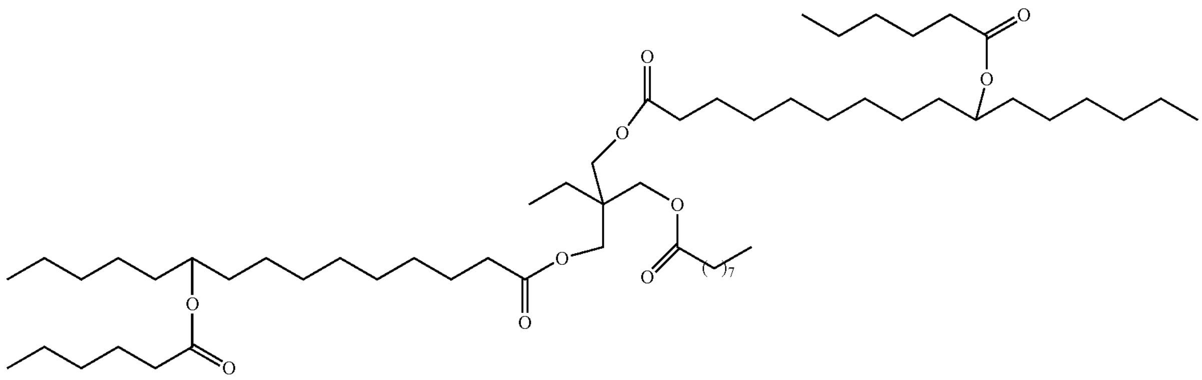

-continued

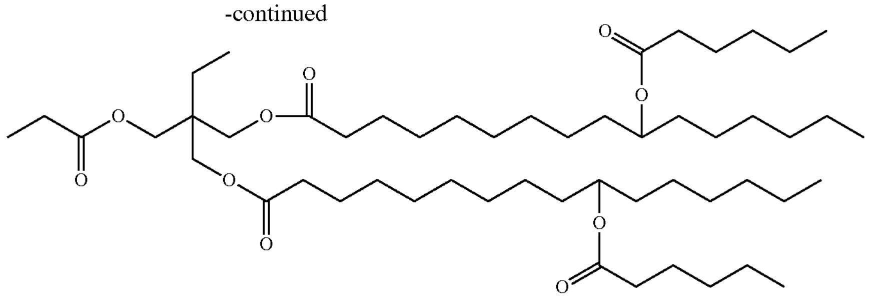

Example III-6: Preparation of Ester Compound III-B-2

37.6 g of nonandioic acid, 27.2 g of pentaerythritol, 0.2 g of a concentrated sulfuric acid (catalyst) and a water-carrying agent (90-120° C. petroleum ether) were added to a 500 mL three-necked glass flask. The reaction mixture was heated to reflux temperature. $H_2O$ produced in the reaction process was collected with a water separator, and the reaction was stopped when the actual water output was identical to the theoretical value to produce a composite polyhydroxyl compound. The crude product was not treated, and 162 g of isomeric acid III-B was added. The reaction mixture was heated to reflux temperature. $H_2O$ produced in the reaction process was collected with a water separator, and the reaction was stopped when the actual water output was identical to the theoretical value. The crude product was washed with a base to remove the catalyst and washed with water until neutral, and then the reaction solvent was removed to obtain a composite ester compound III-B-2. It was confirmed by $^1$H-NMR to have the following structure.

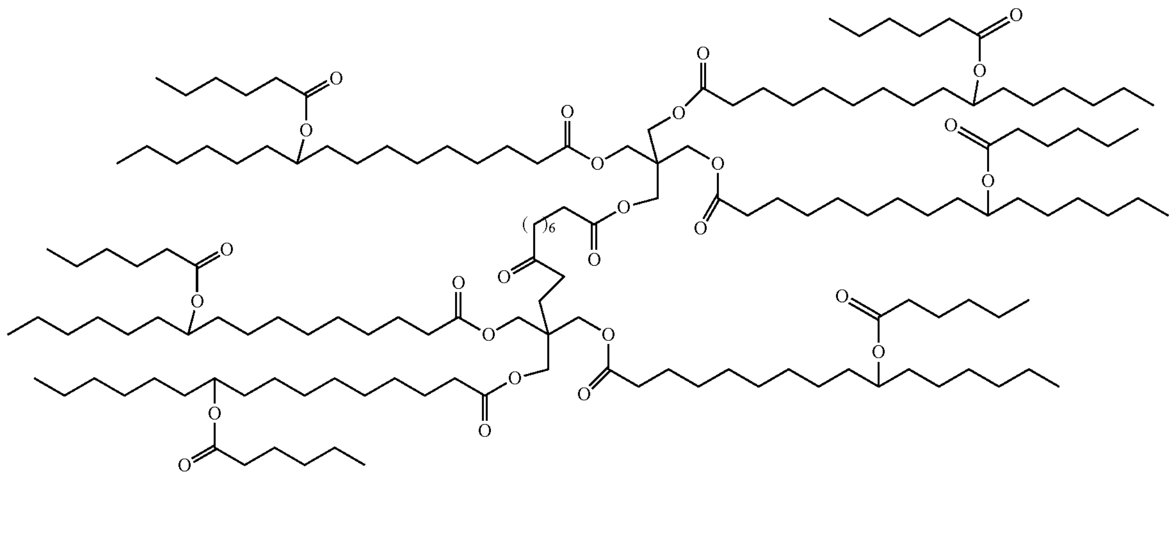

Comparative Example III-2: Preparation of Ester Compound III-D-2

The preparation process of the ester compound III-D-2 was identical to that of Example II-5 except that the isomeric acid 111-B was replaced with equimolar oleic acid to produce the ester compound III-D-2. It was confirmed by $^1$H-NMR to have the following structure.

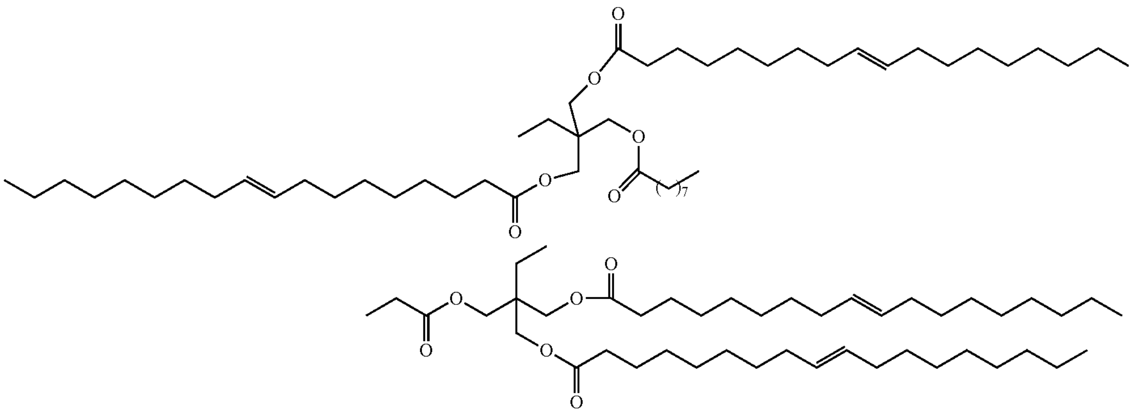

Example 111-7: Preparation of Isomeric Acid III-E 10 g of a strong acid ion exchange resin washed with HCl was installed in a fixed bed reactor. The temperature of the reactor was controlled at 65° C. The weighed linoleic acid, hexanoic acid and butyric acid (molar ratio 1:5:5) were preheated to the same temperature, and pumped into the reactor. The reaction was performed at a space velocity of 0.3 $h^{-1}$. The discharged product was collected. The residual hexanoic acid and butyric acid were removed by preliminary distillation, and the unreacted linoleic acid was further removed by molecular distillation to produce an addition product of butyric acid/hexanoic acid-linoleic acid, an isomeric acid III-E, which was confirmed by $^1$H-NMR to have the following structure.

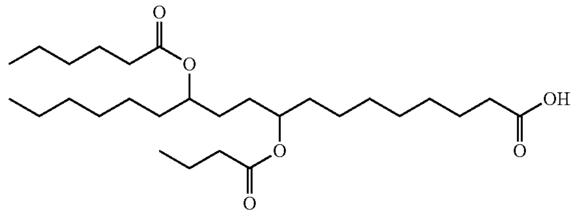 [SMILES: CCCCCCC(CCC(CCCCCCCC(=O)O)OC(=O)CCC)OC(=O)CCCCC]

Example III-8: Preparation of Ester Compound III-E-1

35.7 g of nonanedioic acid, 26.8 g of trimethylolpropane, 0.2 g of a concentrated sulfuric acid (catalyst) and a water-carrying agent (90-120° C. petroleum ether) were added to a 500 mL three-necked glass flask. The reaction mixture was heated to reflux temperature. $H_2O$ produced in the reaction process was collected with a water separator, and the reaction was stopped when the actual water output was identical to the theoretical value to produce a composite polyhydroxyl compound. The crude product was not treated, and 107 g of isomeric acid III-E was added. The reaction mixture was heated to reflux temperature. $H_2O$ produced in the reaction process was collected with a water separator, and the reaction was stopped when the actual water output was identical to the theoretical value. The crude product was washed with a base to remove the catalyst and washed with water until neutral, and then the reaction solvent was removed to obtain a composite ester compound III-E-1. It was confirmed by $^1$H-NMR to have the following structure.

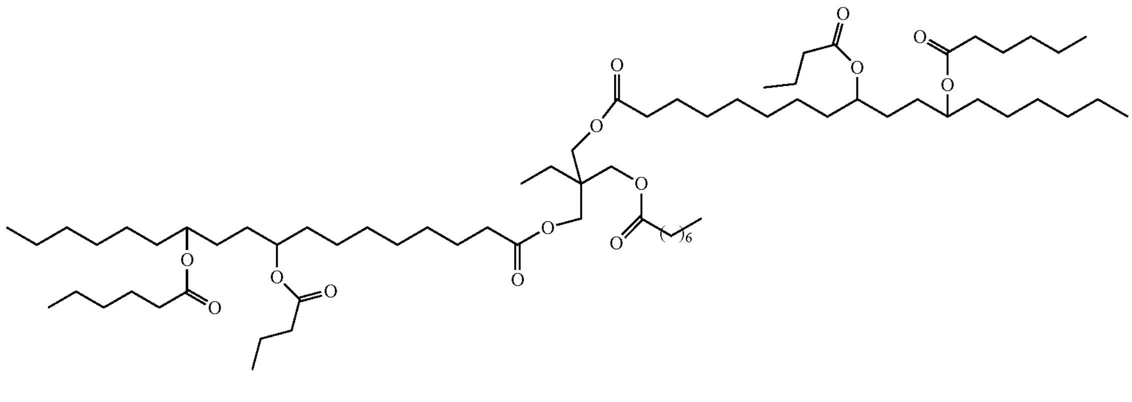

-continued

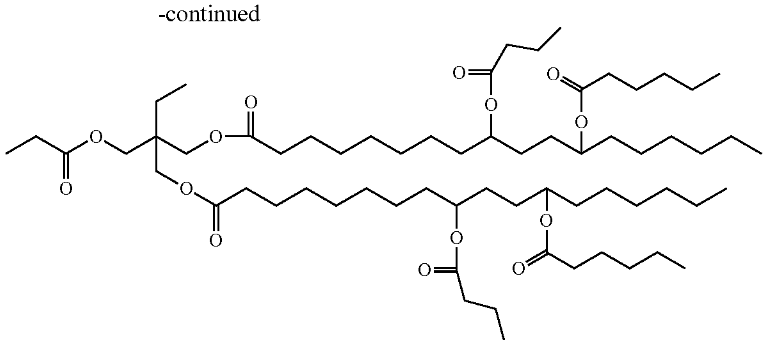

The physical and chemical properties of ester compounds of Examples III-2 to III-8 and Comparative Examples III-1 to 111-2 were investigated, and the measurement methods included GB/T265 Petroleum products-determination of kinematic viscosity and calculation of dynamic viscosity, GB/T1995 Petroleum products-Calculation of viscosity index, GB/T3535 Petroleum products-Determination of pour point, and SH/T0074 Test method for oxidation stability of gasoline engine oils by thin-film oxygen uptake. The measurement results were shown in Table Table III-1.

TABLE III-1

| | Kinematic viscosity/($mm^2$/s) | | Viscosity | Pour | Oxidation induction |
|---|---|---|---|---|---|
| Sample | 40° C. | 100° C. | index | point/° C. | period/min |
| III-A-1 | 65 | 11.2 | 169 | −51 | 211 |
| III-A-2 | 167 | 25.4 | 187 | −48 | 223 |
| III-D-1 | 119 | 18.7 | 177 | −21 | 118 |
| III-B-1 | 390 | 52.0 | 199 | −39 | 204 |
| III-B-2 | 756 | 94.8 | 217 | −33 | 220 |
| III-D-2 | 357 | 47.5 | 195 | −18 | 132 |
| III-E-1 | 9702 | 574.0 | 234 | −18 | 199 |

Example IV-1: Preparation of Epoxy Oleic Acid Methyl Ester IV-A

The reaction was carried out in a reaction vessel equipped with a gas vent, a stirrer and a thermocouple. 2000 g of oleic acid methyl ester, 158 g of formic acid and 15 g of sulfuric acid were added to the reaction vessel. The reaction mixture was warmed up to 60° C. 1150 g of hydrogen peroxide with a concentration of 30% was pumped into the reaction vessel, and the pumping time was 6 hours. After the completion of the reaction, the residual formic acid and water were removed by distillation. The reaction product was cooled to room temperature, and washed three times with deionized water to obtain the epoxy oleic acid methyl ester IV-A. It was confirmed by $^1$H-NMR to have the following structure.

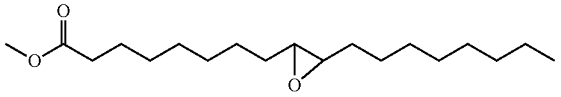 [SMILES: CCCCCCCCC1OC1CCCCCCCC(=O)OC]

Example IV-2: Preparation of Ester Compound IV-A-1

62 g of ethylene glycol and 1.5 g of p-toluenesulfonic acid (catalyst) were added to a 500 mL three-necked glass flask. The reaction mixture was heated to 100° C. 156 g of the epoxy oleic acid methyl ester IV-A was gradually added dropwise to the three-necked flask over 3 hours. After the completion of the dropwise addition, the temperature was maintained at 100° C. to continue the reaction for 2 hours. The excess ethylene glycol was removed by distillation. The crude product was washed with water to remove the catalyst and washed until neutral to obtain the ester compound IV-A-1, which was confirmed by $^1$H-NMR to have the following structure.

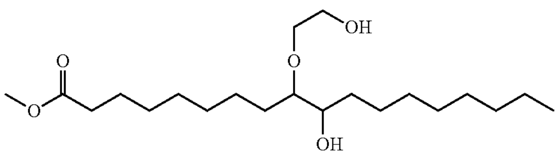 [SMILES: CCCCCCCCC(O)C(CCCCCCCC(=O)OC)OCCO]

Example IV-3: Preparation of Ester Compound IV-A-2

146 g of hexanedioic acid and 1.5 g of p-toluenesulfonic acid (catalyst) were added to a 500 mL three-necked glass flask. The reaction mixture was heated to 150° C. 156 g of the epoxy oleic acid methyl ester IV-A was gradually added dropwise to the three-necked flask over 3 hours. $H_2O$ produced in the reaction process was collected with a water separator. After the completion of the dropwise addition, the temperature was maintained at 100° C. to continue the reaction for 2 hours. The crude product was washed with water to remove the catalyst and washed until neutral to obtain the ester compound IV-A-2, which was confirmed by $^1$H-NMR to have the following structure.

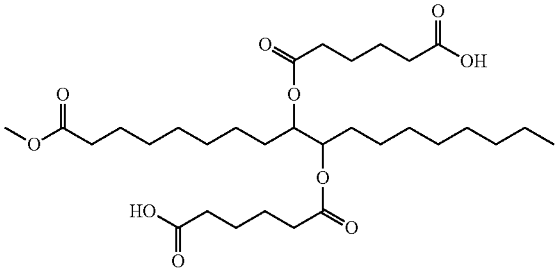 [SMILES: CCCCCCCCC(OC(=O)CCCCC(=O)O)C(CCCCCCCC(=O)OC)OC(=O)CCCCC(=O)O]

Comparative Example IV-1: Preparation of Ester Compound IV-D-1

The preparation process of IV-D-1 was identical to that of Example IV-2 except that ethylene glycol was replaced with equimolar ethanol to produce the ester compound IV-D-1. It was confirmed by $^{1}$H-NMR to have the following structure.

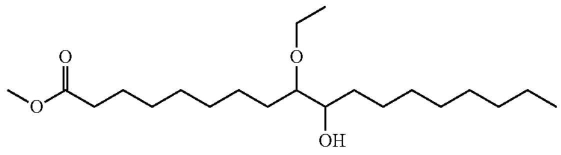 [SMILES: CCCCCCCCC(O)C(CCCCCCCC(=O)OC)OCC]

Comparative Example IV-2: Preparation of Ester Compound IV-D-2

The preparation process of IV-D-2 was identical to that of Example IV-3 except that hexanedioic acid was replaced with equimolar hexanoic acid to produce the ester compound IV-D-2. It was confirmed by $^{1}$H-NMR to have the following structure.

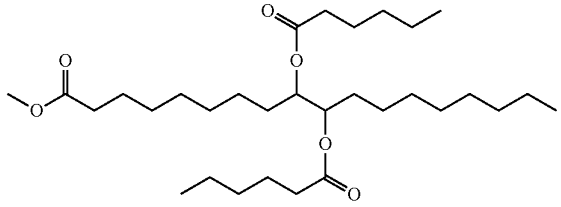 [SMILES: CCCCCCCCC(OC(=O)CCCCC)C(CCCCCCCC(=O)OC)OC(=O)CCCCC]

Example IV-4. Preparation of Epoxy Oleic Acid IV-B

The reaction was carried out in a reaction vessel equipped with a gas vent, a stirrer and a thermocouple. 1900 g of oleic acid, 158 g of formic acid and 15 g of sulfuric acid were added to the reaction vessel. The reaction mixture was warmed up to 60° C. 1150 g of hydrogen peroxide with a concentration of 30% was pumped into the reaction vessel, and the pumping time was 6 hours. After the completion of the reaction, the residual formic acid and water were removed by distillation. The reaction product was cooled to room temperature, and washed three times with deionized water to obtain the epoxy oleic acid IV-B. It was confirmed by $^{1}$H-NMR to have the following structure.

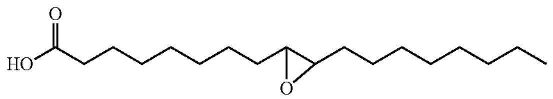 [SMILES: CCCCCCCCC1OC1CCCCCCCC(=O)O]

Example IV-5: Preparation of Ester Compound IV-B-1

76 g of 1,3-propylene glycol and 1.5 g of p-toluenesulfonic acid (catalyst) were added to a 500 mL three-necked glass flask. The reaction mixture was heated to 120° C. 150 g of the epoxy oleic acid IV-B was gradually added dropwise to the three-necked flask over 3 hours. $H_2O$ produced in the reaction process was collected with a water separator. After the completion of the dropwise addition, the temperature was maintained at 120° C. to continue the reaction for 5 hours. The excess propylene glycol was removed by distillation. The crude product was washed with water to remove the catalyst and washed until neutral to obtain the ester compound IV-B-1, which was confirmed by $^{1}$H-NMR to have the following structure.

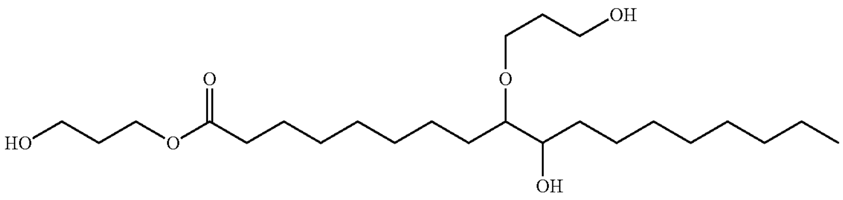 [SMILES: CCCCCCCCC(O)C(CCCCCCCC(=O)OCCCO)OCCCO]

Example IV-6. Preparation of Ester Compound IV-B-2

146 g of hexanedioic acid and 1.5 g of p-toluenesulfonic acid (catalyst) were added to a 500 mL three-necked glass flask. The reaction mixture was heated to 150° C. 150 g of the epoxy oleic acid IV-B was gradually added dropwise to the three-necked flask over 3 hours. $H_2O$ produced in the reaction process was collected with a water separator. After the completion of the dropwise addition, the temperature was maintained at 150° C. to continue the reaction for 2 hours. The crude product was washed with water to remove the catalyst and washed until neutral to obtain the ester compound IV-B-2, which was confirmed by $^1$H-NMR to have the following structure.

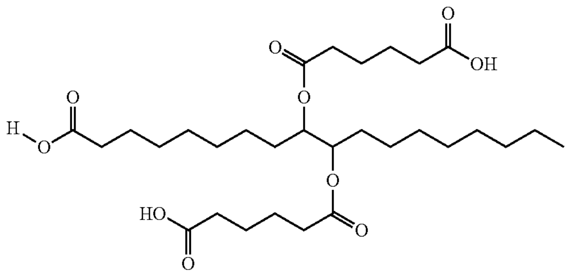 [SMILES: CCCCCCCCC(OC(=O)CCCCC(=O)O)C(CCCCCCCC(=O)O)OC(=O)CCCCC(=O)O]

Comparative Example IV-3: Preparation of Ester Compound IV-D-3

The preparation process of IV-D-3 was identical to that of Example IV-6 except that hexanedioic acid was replaced with equimolar methanol and the reaction temperature was controlled at 50° C. to produce the ester compound IV-D-3. It was confirmed by $^1$H-NMR to have the following structure.

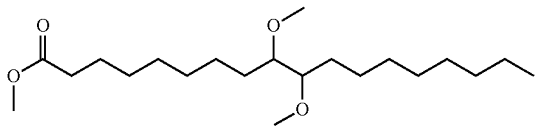 [SMILES: CCCCCCCCC(OC)C(CCCCCCCC(=O)OC)OC]

Example IV-7: Preparation of Epoxy Linoleic Acid IV-C

The reaction was carried out in a reaction vessel equipped with a gas vent, a stirrer and a thermocouple. 1900 g of linoleic acid, 300 g of formic acid and 15 g of sulfuric acid were added to the reaction vessel. The reaction mixture was warmed up to 60° C. 2300 g of hydrogen peroxide with a concentration of 30% was pumped into the reaction vessel, and the pumping time was 6 hours. After the completion of the reaction, the residual formic acid and water were removed by distillation. The reaction product was cooled to room temperature, and washed three times with deionized water to obtain the epoxy linoleic acid IV-C. It was confirmed by $^1$H-NMR to have the following structure.

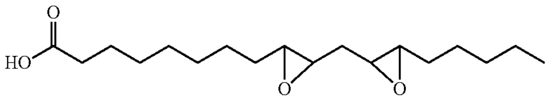 [SMILES: CCCCCC1OC1CC1OC1CCCCCCCC(=O)O]

Example IV-8: Preparation of Ester Compound IV-C-1

180 g of butanediol and 1.5 g of p-toluenesulfonic acid (catalyst) were added to a 500 mL three-necked glass flask. The reaction mixture was heated to 120° C. 156 g of the epoxy linoleic acid IV-C was gradually added dropwise to the three-necked flask over 3 hours. After the completion of the dropwise addition, the temperature was maintained at 120° C. to continue the reaction for 5 hours. The excess butanediol was removed by distillation. The crude product was washed with water to remove the catalyst and washed until neutral to obtain the ester compound IV-C-1. It was confirmed by $^1$H-NMR to have the following structure.

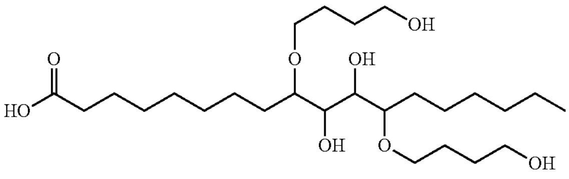 [SMILES: CCCCCCC(OCCCCO)C(O)C(O)C(CCCCCCCC(=O)O)OCCCCO]

Comparative Example IV-4: Preparation of Ester Compound IV-D-4

The preparation process of IV-D-4 was identical to that of Example IV-8 except that butanediol was replaced with equimolar butanol to produce the ester compound IV-D-4. It was confirmed by $^1$H-NMR to have the following structure.

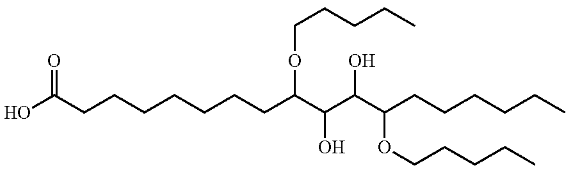 [SMILES: CCCCCCC(OCCCCC)C(O)C(O)C(CCCCCCCC(=O)O)OCCCCC]

The friction and wear properties of the ester compounds in Examples IV-2 to IV-8 and Comparative Examples IV-2 to IV-4 were investigated respectively, and the assessment of lubricity of diesel fuel is based on the method of ISO12156-1, using the high-frequency reciprocating rig (HFRR), and the assessment of lubricity of lubricating oil is based on SH/T0762 the test method for determination of the coefficient of friction of lubricants using the four-ball wear test machine. The measurement results were shown in Table IV-1.

TABLE IV-1

| Sample | Steel ball wear scar diameter/μm | Average friction coefficient |
|---|---|---|
| IV-A-1 | 301 | 0.065 |
| IV-A-2 | 254 | 0.062 |
| IV-D-1 | 531 | 0.089 |

TABLE IV-1-continued

| Sample | Steel ball wear scar diameter/μm | Average friction coefficient |
|---|---|---|
| IV-D-2 | 483 | 0.087 |
| IV-B-1 | 267 | 0.064 |
| IV-B-2 | 229 | 0.059 |
| IV-D-3 | 610 | 0.095 |
| IV-C-1 | 289 | 0.061 |
| IV-D-4 | 459 | 0.079 |

Example V-1: Preparation of Epoxy Oleic Acid Methyl Ester V-A

The reaction was carried out in a reaction vessel equipped with a gas vent, a stirrer and a thermocouple. 2000 g of oleic acid methyl ester, 158 g of formic acid and 15 g of sulfuric acid were added to the reaction vessel. The reaction mixture was warmed up to 60° C. 1150 g of hydrogen peroxide with a concentration of 30% was pumped into the reaction vessel, and the pumping time was 6 hours. After the completion of the reaction, the residual formic acid and water were removed by distillation. The reaction product was cooled to room temperature, and washed three times with deionized water to obtain the epoxy oleic acid methyl ester V-A. It was confirmed by $^1$H-NMR to have the following structure.

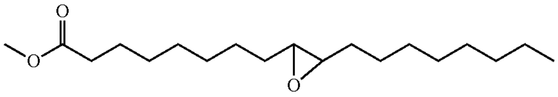 [SMILES: CCCCCCCCC1OC1CCCCCCCC(=O)OC]

Example V-2: Preparation of Ester Compound V-A-1

60 g of ethylene diamine and 150 g of the epoxy oleic acid methyl ester V-A were added to a 500 mL three-neck glass flask, and the mixture was heated to 80° C. The reaction was performed for 6 hours while the temperature was maintained at 80° C. The excess ethylene diamine was removed by distillation. The crude product was washed with water until neutral to obtain the ester compound V-A-1, which was confirmed by $^1$H-NMR to have the following structure.

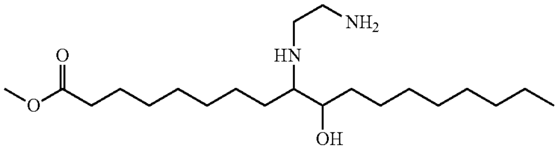 [SMILES: CCCCCCCCC(O)C(CCCCCCCC(=O)OC)NCCN]

Example V-3: Preparation of Ester Compound V-A-2

37 g of diethylamine and 150 g of the epoxy oleic acid methyl ester V-A were added to a 500 mL high-pressure reaction vessel, and the mixture was heated to 70° C. The reaction was performed for 5 hours while the temperature was maintained at 70° C. The excess diethylamine was removed by distillation. The crude product was washed with water until neutral to obtain the ester compound V-A-2, which was confirmed by $^1$H-NMR to have the following structure.

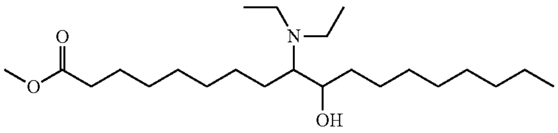 [SMILES: CCCCCCCCC(O)C(CCCCCCCC(=O)OC)N(CC)CC]

Example V-4: Preparation of Ester Compound V-A-3

60 g of benzamide, 2 g of sodium ethoxide, and 150 g of the epoxy oleic acid methyl ester V-A were added to a 500 mL reaction vessel, and the mixture was heated to 100° C. The reaction was performed for 7 hours while the temperature was maintained at 100° C. The excess benzamide was removed by distillation. The crude product was washed with water until neutral to obtain the ester compound V-A-3, which was confirmed by $^1$H-NMR to have the following structure.

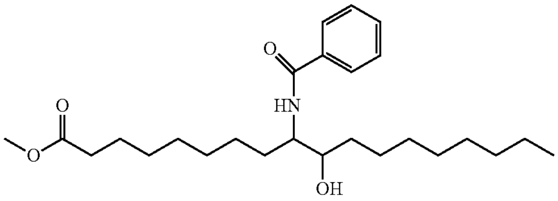 [SMILES: CCCCCCCCC(O)C(CCCCCCCC(=O)OC)NC(=O)c1ccccc1]

Comparative Example V-1: Preparation of Ester Compound V-D-1

The preparation process of V-D-1 was identical to that of Example V-2 except that ethylene diamine was replaced with equimolar ethanol to produce the ester compound V-D-1. It was confirmed by $^1$H-NMR to have the following structure.

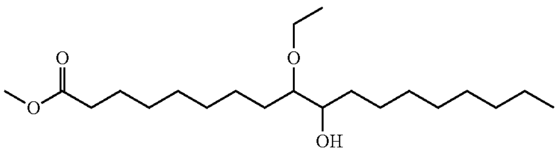 [SMILES: CCCCCCCCC(O)C(CCCCCCCC(=O)OC)OCC]

Example V-5: Preparation of Epoxy Linoleic Acid V-B

The reaction was carried out in a reaction vessel equipped with a gas vent, a stirrer and a thermocouple. 1900 g of linoleic acid methyl ester, 300 g of formic acid and 15 g of sulfuric acid were added to the reaction vessel. The reaction mixture was warmed up to 60° C. 2300 g of hydrogen peroxide with a concentration of 30% was pumped into the reaction vessel, and the pumping time was 6 hours. After the completion of the reaction, the residual formic acid and water were removed by distillation. The reaction product was cooled to room temperature, and washed three times with deionized water to obtain the epoxy linoleic acid methyl ester V-B. It was confirmed by $^1$H-NMR to have the following structure.

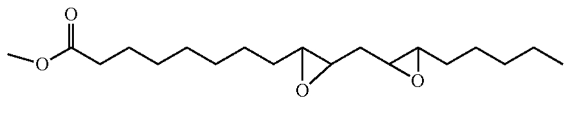 [SMILES: CCCCCC1OC1CC1OC1CCCCCCCC(=O)OC]

Example V-6: Preparation of Ester Compound V-B-1

90 g of ethylene diamine and 156 g of the epoxy linoleic acid methyl ester V-B were added to a 500 mL three-neck glass flask, and the mixture was heated to 80° C. The reaction was performed for 6 hours while the temperature was maintained at 80° C. The excess ethylene diamine was removed by distillation. The crude product was washed with water until neutral to obtain the ester compound V-B-1 which was confirmed by $^1$H-NMR to have the following structure.

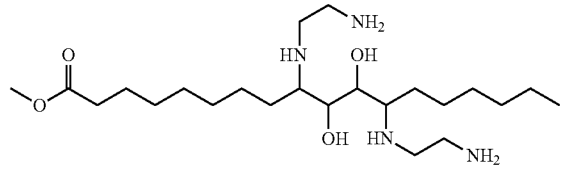 [SMILES: CCCCCCC(NCCN)C(O)C(O)C(CCCCCCCC(=O)OC)NCCN]

Example V-7: Preparation of Ester Compound V-B-2

37 g of diethylamine and 156 g of the epoxy linoleic acid methyl ester V-B were added to a 500 mL high-pressure reaction vessel, and the mixture was heated to 70° C. The reaction was performed for 5 hours while the temperature was maintained at 70° C. The excess diethylamine was removed by distillation. The crude product was washed with water until neutral to obtain the ester compound V-B-2, which was confirmed by $^1$H-NMR to have the following structure.

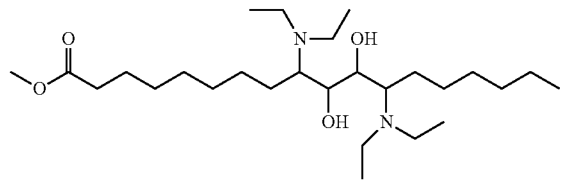 [SMILES: CCCCCCC(C(O)C(O)C(CCCCCCCC(=O)OC)N(CC)CC)N(CC)CC]

Comparative Example V-2: Preparation of Ester Compound V-D-2

The preparation process of V-D-2 was identical to that of Example V-7 except that diethylamine was replaced with equimolar ethanol to produce the ester compound V-D-2. It was confirmed by $^1$H-NMR to have the following structure.

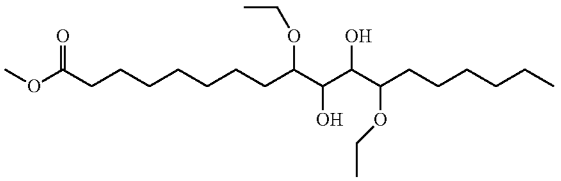 [SMILES: CCCCCCC(OCC)C(O)C(O)C(CCCCCCCC(=O)OC)OCC]

The friction and wear properties of the ester compounds in Examples V-2 to V-7 and Comparative Examples V-1 to V-2 were investigated respectively, and the assessment of lubricity of diesel fuel is based on the method of ISO12156-1, using the high-frequency reciprocating rig (HFRR), and the assessment of lubricity of lubricating oil is based on SH/T0762, the test method for determination of the coefficient of friction of lubricants using the four-ball wear test machine. The measurement results were shown in Table V-1.

TABLE V-1

| Sample | Steel ball wear scar diameter/μm | Average friction coefficient |
|---|---|---|
| V-A-1 | 221 | 0.061 |
| V-A-2 | 237 | 0.063 |
| V-A-3 | 259 | 0.067 |
| V-D-1 | 531 | 0.089 |
| V-D-2 | 465 | 0.080 |
| V-B-1 | 202 | 0.060 |
| V-B-2 | 219 | 0.061 |

Example VI-1: Preparation of Epoxy Oleic Acid Methyl Ester VI-A

The reaction was carried out in a reaction vessel equipped with a gas vent, a stirrer and a thermocouple. 2000 g of oleic acid methyl ester, 158 g of formic acid and 15 g of sulfuric acid were added to a reaction vessel. The reaction mixture was warmed up to 60° C. 1150 g of hydrogen peroxide with a concentration of 30% was pumped into the reaction vessel, and the pumping time was 6 hours. After the completion of the reaction, the residual formic acid and water were removed by distillation. The reaction product was cooled to room temperature, and washed three times with deionized water to obtain the epoxy oleic acid methyl ester VI-A. Tt was confirmed by $^1$H-NMR to have the following structure.

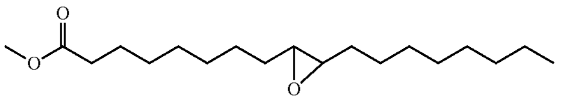 [SMILES: CCCCCCCCC1OC1CCCCCCCC(=O)OC]

Example VI-2: Ring Opening Compound VI-A-1

480 g of methanol, 624 g of the epoxy oleic acid methyl ester VI-A, and 5 g of p-toluenesulfonic acid (catalyst) were added to a 2000 mL three-neck glass flash, and the mixture was heated to 100° C. The reaction was performed for 5 hours while the temperature was maintained at 100° C. The excess methanol was removed by distillation. The crude product was washed with water to remove the catalyst and washed until neutral to obtain the ring-opening compound IV-A-1, which was confirmed by $^1$H-NMR to have the following structure.

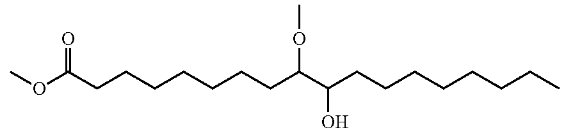 [SMILES: CCCCCCCCC(O)C(CCCCCCCC(=O)OC)OC]

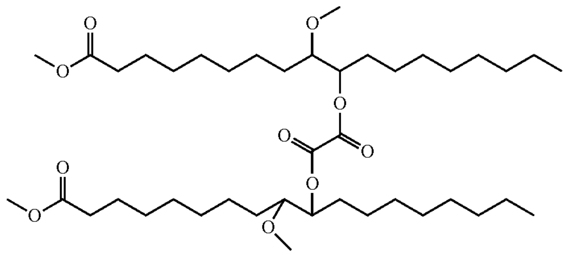 [SMILES: CCCCCCCCC(OC(=O)C(=O)OC(CCCCCCCC)C(CCCCCCCC(=O)OC)OC)C(CCCCCCCC(=O)OC)OC]

Example VI-3: Preparation of Ester Compound I-A-2

207 g of the ring-opening compound VI-A-1 and 3 g of p-toluenesulfonic acid (catalyst) were added to a 500 mL three-necked glass flask. The reaction mixture was heated to 100° C. 27 g of ethanedioic acid was gradually added dropwise to the three-necked flask over 3 hours. $H_2O$ produced in the reaction process was collected with a water separator. After the completion of the dropwise addition, the temperature was maintained at 100° C. to continue the reaction for 4 hours. The crude product was washed with water to remove the catalyst and washed until neutral to obtain the ester compound VI-A-2, which was confirmed by $^1$H-NMR to have the following structure.

Example VI-4: Preparation of Ester Compound I-A-3

207 g of the ring-opening compound VI-A-1 and 3.5 g of p-toluenesulfonic acid (catalyst) were added to a 500 mL three-necked glass flask. The reaction mixture was heated to 130° C. A mixture of 50 g of terephthalic acid and 100 g of xylene solution was gradually added dropwise to the three-necked flask over 3 hours. $H_2O$ produced in the reaction process was collected with a water separator. After the completion of the dropwise addition, the temperature was maintained at 130° C. to continue the reaction for 4 hours. The crude product was washed with water to remove the catalyst and washed until neutral, and xylene was removed by distillation to obtain the ester compound VI-A-3, which was confirmed by $^1$H-NMR to have the following structure.

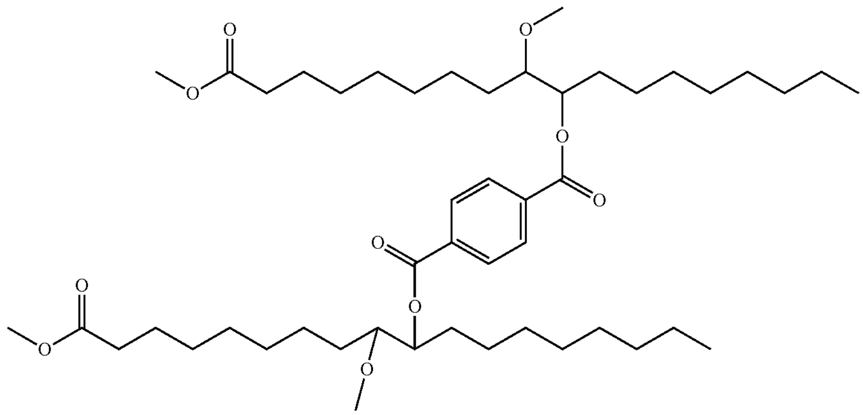 [SMILES: CCCCCCCCC(OC(=O)c1ccc(C(=O)OC(CCCCCCCC)C(CCCCCCCC(=O)OC)OC)cc1)C(CCCCCCCC(=O)OC)OC]

Comparative Example VI-1: Preparation of Ester Compound I-D-1

The preparation process of VI-D-1 was identical to that of Example VI-2 except that VI-A-1 was replaced with equimolar ricinoleic acid methyl ester to produce the ester compound VI-D-1. It was confirmed by $^1$H-NMR to have the following structure.

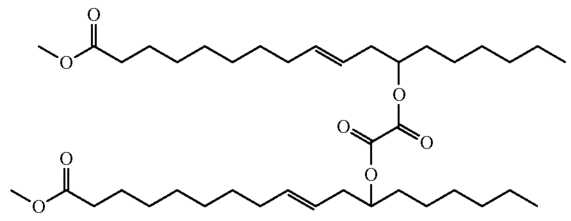 [SMILES: CCCCCCC(C/C=C/CCCCCCCC(=O)OC)OC(=O)C(=O)OC(C/C=C/CCCCCCCC(=O)OC)CCCCCC]

Comparative Example VI-2: Preparation of Ester Compound I-D-2

The preparation process of VI-D-2 was identical to that of Example VI-4 except that VI-A-1 was replaced with equimolar octadecanol to produce the ester compound VI-D-2. It was confirmed by $^1$H-NMR to have the following structure.

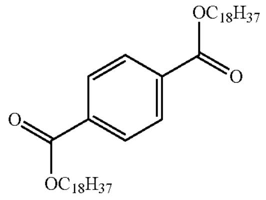

Example VI-5: Preparation of Ring Opening Compound VI-B-1

624 g of the epoxy oleic acid methyl ester VI-A and 5 g of p-toluenesulfonic acid (catalyst) were added to a 2000 mL three-necked glass flask. The reaction mixture was heated to 100° C. 880 g of butyric acid was gradually added dropwise to the three-necked flask over 3 hours. The temperature was maintained at 100° C. to continue the reaction for 5 hours. The crude product was washed with water to remove the catalyst and washed until neutral to obtain the ring-opening compound IV-B-1, which was confirmed by $^1$H-NMR to have the following structure.

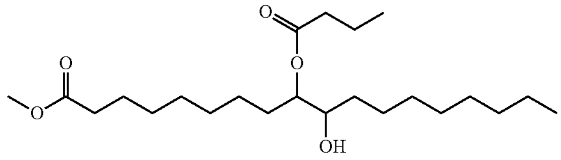 [SMILES: CCCCCCCCC(O)C(CCCCCCCC(=O)OC)OC(=O)CCC]

Example VI-6: Preparation of Ester Compound I-B-2

241 g of the ester compound VI-B-1 and 5 g of p-toluenesulfonic acid (catalyst) were added to a 500 mL three-necked glass flask. The reaction mixture was heated to 110° C. A solvent mixture of 44 g of hexanedioic acid and 100 g of toluene was gradually added dropwise to the three-necked flask over 3 hours. $H_2O$ produced in the reaction process was collected with a water separator. After the completion of the dropwise addition, the temperature was maintained at 130° C. to continue the reaction for 3 hours. The crude product was washed with water to remove the catalyst and washed until neutral to obtain the ester compound VI-B-2, which was confirmed by $^1$H-NMR to have the following structure.

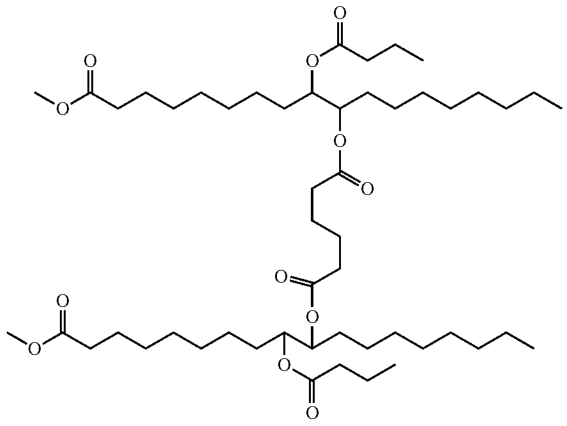 [SMILES: CCCCCCCCC(OC(=O)CCCCC(=O)OC(CCCCCCCC)C(CCCCCCCC(=O)OC)OC(=O)CCC)C(CCCCCCCC(=O)OC)OC(=O)CCC]

Example VI-7: Preparation of ester compound I-B-3 241 g of the ester compound VI-B-1 and 1.5 g of p-toluenesulfonic acid (catalyst) were added to a 500 mL three-necked glass flask. The reaction mixture was heated to 110° C. 52 g of 1, 4-cyclohexanedioic acid was gradually added dropwise to the three-necked flask over 3 hours. $H_2O$ produced in the reaction process was collected with a water separator. After the completion of the dropwise addition, the temperature was maintained at 110° C. to continue the reaction for 3 hours. The crude product was washed with water to remove the catalyst and washed until neutral to obtain the ester compound VI-B-3, which was confirmed by $^1$H-NMR to have the following structure.

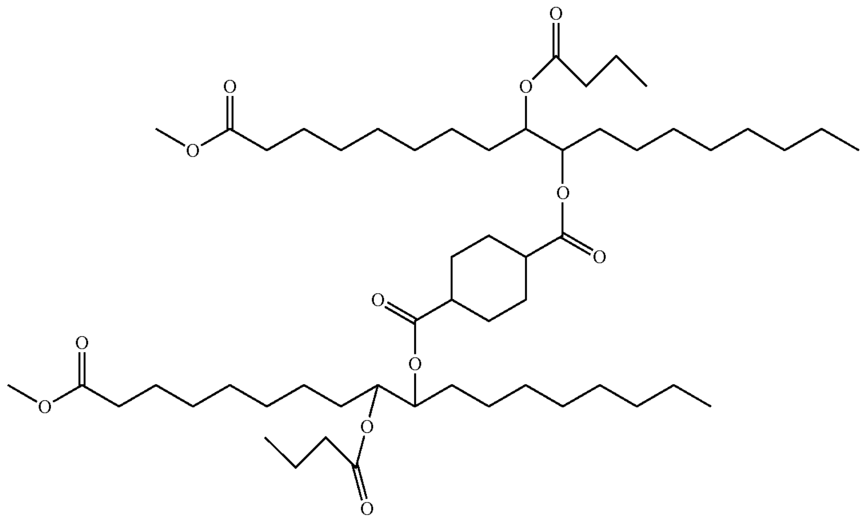 [SMILES: CCCCCCCCC(OC(=O)C1CCC(C(=O)OC(CCCCCCCC)C(CCCCCCCC(=O)OC)OC(=O)CCC)CC1)C(CCCCCCCC(=O)OC)OC(=O)CCC]

Comparative Example VI-3: Preparation of Ester Compound I-D-3

The preparation process of VI-D-3 was identical to that of Example VI-6 except that VI-B-1 was replaced with equimolar ricinoleic acid methyl ester to produce the ester compound VI-D-3. It was confirmed by $^1$H-NMR to have the following structure.

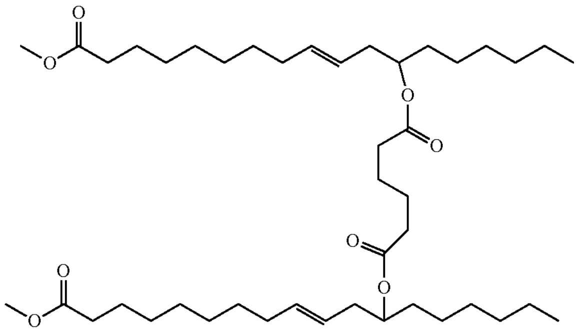 [SMILES: CCCCCCC(C/C=C/CCCCCCCC(=O)OC)OC(=O)CCCCC(=O)OC(C/C=C/CCCCCCCC(=O)OC)CCCCCC]

The physical and chemical properties of ester compounds of Examples VI-3 to VI-7 and Comparative Examples VI-1 to VI-3 were investigated, and the measurement methods included GB/T265 Petroleum products-determination of kinematic viscosity and calculation of dynamic viscosity, GB/T1995 Petroleum products-Calculation of viscosity index, GB/T3535 Petroleum products-Determination of pour point, and SH/T0074 Test method for oxidation stability of gasoline engine oils by thin-film oxygen uptake. The measurement results were shown in Table VI-1.

TABLE VI-1

| | Kinematic viscosity/(mm$^2$/s) | | Viscosity | Pour | Oxidation induction |
|---|---|---|---|---|---|
| Sample | 40° C. | 100° C. | index | point/° C. | period/min |
| VI-A-2 | 77 | 12 2 | 158 | −39 | 215 |
| VI-A-3 | 85 | 13.9 | 168 | −42 | 198 |
| VI-D-1 | 71 | 12.0 | 166 | −24 | 183 |
| VI-D-2 | 63 | 11.5 | 179 | 18 | 227 |
| VI-B-2 | 78 | 13.1 | 172 | −42 | 229 |
| VI-B-3 | 80 | 13.3 | 169 | −45 | 241 |
| VI-D-3 | 73 | 12.4 | 169 | −27 | 199 |

The above examples are only used to illustrate the technical solutions of the examples of the present disclosure, but not to limit them. Although the present invention has been described in detail with reference to the aforementioned examples, those of ordinary skill in the art should understand that they can still modify the technical solutions described in the examples or equivalently replace some technical features; and these modifications or replacements do not make the essence of the corresponding technical solutions deviate from the spirit and scope of the technical solutions in the examples of the present disclosure.

The invention claimed is:

1. An ester compound of formula (I):

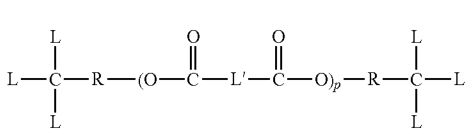

(I)

wherein, the plural L' groups, identical to or different from each other, are each independently selected from $C_{1-16}$ linear or branched alkylene;

the plural R groups, identical to or different from each other, are each independently selected from a single bond, a $C_{1-20}$ linear or branched alkylene;

p is 1, 2, or 3;

the plural L groups, identical to or different from each other, are each independently selected from a hydrogen atom, an optionally substituted $C_{1-10}$ linear or branched alkyl, a group of formula (II), a group of formula (III), with the proviso that at least two L groups are selected from a group of formula (III), $$-R'-OH, \quad \text{(II)}$$

(III)

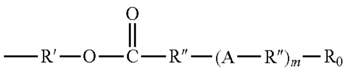

wherein, the R' group is selected from a single bond, a $C_{1-10}$ linear or branched alkylene, and the carbon atoms bonded to L are at most directly bonded to one oxygen atom, the plural R" groups, identical to or different from each other, are each independently selected from a single bond and a $C_{1-10}$ linear or branched alkylene;

the $R_0$ group is selected from H, an optionally substituted $C_{1-10}$ linear or branched alkyl;

m is 1;

the plural A groups, identical to or different from each other, are each independently selected from a group of formula (III-A), methylene and ethylene, with the proviso that at least one A group is selected from a group of formula (III-A); and (III-A)

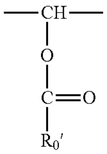

wherein the plural $R_0$' groups are each independently an optionally substituted $C_{1-15}$ linear or branched alkyl, said substituents are selected from halogen atoms, hydroxy, amino, $C_{1-6}$ linear or branched alkyl, $C_{6-10}$ aryl, and $C_{3-10}$ cycloalkyl.

2. The ester compound according to claim 1, wherein when p is not 0, the L groups, identical to or different from each other, are each independently selected from a group of formula (III).

3. The ester compound according to claim 1, wherein, when none of three L groups connected to one terminal carbon atom is a group of formula (III) or formula (II), three L groups connected to the other terminal carbon atom are each independently selected from a group of formula (III).

4. The ester compound according to claim 1, wherein, of three L groups connected to each terminal carbon atom, if two L groups are not a group of formula (III), the remaining one L group is each independently selected from a group of formula (III).

5. A lubricating oil composition, which comprises the ester compound according to claim 1, and a lubricating base oil, relative to the total mass of the lubricating oil composition, the content of said ester compound is 0.01%-50%.

6. The ester compound according to claim 1, wherein the L' groups, identical to or different from each other, are each independently selected from $C_{2-10}$ linear or branched alkylene.

7. The ester compound according to claim 1, wherein the R groups, identical to or different from each other, are each independently selected from a single bond, a $C_{1-6}$ linear or branched alkylene.

8. The ester compound according to claim 1, wherein the L groups, identical to or different from each other, are each independently selected from a hydrogen atom, an optionally substituted $C_{1-6}$ linear or branched alkyl, a group of formula (II), a group of formula (III).

9. The ester compound according to claim 1, wherein the R' group is selected from a single bond, a $C_{1-6}$ linear or branched alkylene.

10. The ester compound according to claim 1, wherein the R" groups, identical to or different from each other, are each independently selected from a single bond, a $C_{1-6}$ linear or branched alkylene.

11. The ester compound according to claim 1, wherein the $R_0$ group is selected from H, an optionally substituted $C_{1-6}$ linear or branched alkyl.

12. The ester compound according to claim 1, wherein the $R_0$' groups, at each occurrence, are each independently selected from an optionally substituted $C_{1-11}$ linear or branched alkyl.

13. The lubricating oil composition according to claim 5, wherein the content of said ester compound is 0.5%-20%.

* * * * *